US007175999B2

(12) United States Patent
Ruvkun et al.

(10) Patent No.: US 7,175,999 B2
(45) Date of Patent: Feb. 13, 2007

(54) POLYNUCLEOTIDE AND POLYPEPTIDE FAT METABOLISM REGULATORS AND USES THEREOF

(75) Inventors: Gary Ruvkun, Newton, MA (US); Kaveh Ashrafi, San Francisco, CA (US)

(73) Assignee: The General Hospital Corporation, Boston, MA (US)

(*) Notice: Subject to any disclaimer, the term of this patent is extended or adjusted under 35 U.S.C. 154(b) by 295 days.

(21) Appl. No.: 10/617,351

(22) Filed: Jul. 10, 2003

(65) Prior Publication Data

US 2004/0158879 A1 Aug. 12, 2004

Related U.S. Application Data

(60) Provisional application No. 60/395,159, filed on Jul. 11, 2002.

(51) Int. Cl.
*C12N 15/09* (2006.01)

(52) U.S. Cl. ............................ 435/69.2; 435/4; 435/6; 530/300; 530/350

(58) Field of Classification Search .................... 435/4, 435/6, 69.2; 530/300, 350
See application file for complete search history.

(56) References Cited

U.S. PATENT DOCUMENTS

2004/0197766 A1* 10/2004 Gu et al. ....................... 435/4

OTHER PUBLICATIONS

Yip et al. Life Sciences (2000) 66(2): 91-103.*

Adibi, "The Oligopeptide Transporter (Pept-1) in Human Intestine: Biology and Function," *Gastroenterology* 113:332-340 (1997).

Adibi, "Regulation of Expression of the Intestinal Oligopeptide Transporter (Pept-1) in Health and Disease," *Am. J. Physiol. Gastrointest. Liver Physiol.* 285: G779-G788 (2003).

Aschenbach et al., "Effect of AICAR Treatment on Glycogen Metabolism in Skeletal Muscle," *Diabetes* 51:567-573 (2002).

Brown et al., "Calcium Cages, Acid Baths and Recycling Receptors," *Nature* 388:629-630 (1997).

Chawla et al., "Nuclear Receptors and Lipid Physiology: Opening the X-Files," *Science* 294:1866-1870 (2001).

Chin, "On the Preparation and Utilization of Isolated and Purified Oligonucleotides," Description of CD-ROM deposited in the public collection of the Kathrine R. Everett Law Library of the University of North Carolina, Mar. 14, 2002.

Chin, "On the Preparation and Utilization of Isolated and Purified Oligonucleotides," Copy of CD-ROM deposited in the public collection of the Kathrine R. Everett Law Library of the University of North Carolina, Mar. 14, 2002.

Comings et al., "The Dopamine $D_2$ Receptor (DRD2) as a Major Gene in Obesity and Height," *Biochem Med Metab. Biol.* 50:176-185 (1993).

Contreras et al., "Dopamine, Hypertension and Obesity," *J. Hum. Hypertens.* 16 Suppl 1:S13-17 (2002).

Friedman et al., "Phosphoenolpyruvate Carboxykinase (GTP) Gene Transcription and Hyperglycemia are Regulated by Glucocorticoids in Genetically Obese *db/db* Transgenic Mice," *J. Biol. Chem.* 272:31475-31481 (1997).

Frykman et al., "Normal Plasma Lipoproteins and Fertility in Gene-Targeted Mice Homozygous for a Disruption in the Gene Encoding Very Low Density Lipoprotein Receptor," *Proc. Natl. Acad. Sci. USA* 92:8453-8457 (1995).

GenBank Accession No. C62139.

Geourjon et al., "A Common Mechanism for ATP Hydrolysis in ABC Transporter and Helicase Superfamilies," *Trends Biochem. Sci.* 26:539-544 (2001).

Good et al., "Hypogonadism and Obesity in Mice with a Targeted Deletion of the *Nhlh2* Gene," *Nat. Genet.* 15:397-401 (1997).

Gottlieb and Ruvkun, "daf-2, daf-16 and daf-23: Genetically Interacting Genes Controlling Dauer Formation in *Caenorhabditis elegans,*" *Genetics* 137:107-120 (1994).

Grant et al., "Evidence that RME-1, a Conserved *C. elegans* EH-Domain Protein, Functions in Endocytic Recycling," *Nat. Cell. Biol.* 3:573-579 (2001).

Greenspan et al., "Nile Red: a Selective Fluorescent Stain for Intracellular Lipid Droplets," *J. Cell. Biol.* 100:965-973 (1985).

Greenspan and Fowler, "Spectrofluorometric Studies of the Lipid Probe, Nile Red," *J. Lipid. Res.* 26:781-789 (1985).

Hanson and Reshef, "Regulation of Phosphoenolpyruvate Carboxykinase (GTP) Gene Expression," *Ann. Rev. Biochem.* 66:581-611 (1997).

Hardie and Carling, "The AMP-Activated Protein Kinase—Fuel Gauge of the Mammalian Cell?" *Eur. J. Biochem.* 246:259-273 (1997).

Hardie et al., "The AMP-Activated/SNF1 Protein Kinase Subfamily: Metabolic Sensors of the Eukaryotic Cell?," *Ann. Rev. Biochem.* 67:821-855 (1998).

Holland and Blight, ABC-ATPases, Adaptable Energy Generators Fuelling Transmembrane Movement of a Variety of Molecules in Organisms from Bacteria to Humans, *J. Mol. Biol.* 293:381-399 (1999).

Ioannou, "Multidrug Permeases and Subcellular Cholesterol Transport," *Nature Reviews* 2:657-668 (2001).

Lazar, "Becoming Fat," *Genes Dev.* 16:1-5 (2002).

Lin et al., "Rme-1 Regulates the Distribution and Function of the Endocytic Recycling Compartment in Mammalian Cells," *Nat. Cell. Biol.* 3:567-572 (2001).

McKenna and O'Malley, "Combinatorial Control of Gene Expression by Nuclear Receptors and Coregulators," *Cell* 108:465-474 (2002).

Nimpf and Schneider, "The VLDL Receptor: an LDL Receptor Relative with Eight Ligand Binding Repeats, LR8," *Atherosclerosis* 141:191-202 (1998).

(Continued)

*Primary Examiner*—Tekchand Saidha
(74) *Attorney, Agent, or Firm*—Clark & Elbing LLP

(57) ABSTRACT

In general, this invention relates to nucleic acid and amino acid sequences involved in fat metabolism regulation and the use of these sequences as targets for the diagnosis, treatment, and prevention of obesity and obesity-related diseases. In addition, the invention relates to screening methods for identifying modulators of body fat metabolism and the development of treatments for obesity and obesity-related diseases.

3 Claims, 28 Drawing Sheets

OTHER PUBLICATIONS

Noben-Trauth et al., "A Candidate Gene for the Mouse Mutation Tubby," *Nature* 380:534-538 (1996).

Olswang et al., "A Mutation in the Peroxisome Proliferator-Activated Receptor γ-Binding Site in the Gene for the Cytosolic Form of Phosphoenolpyruvate Carboxykinase Reduces Adipose Tissue Size and Fat Content in Mice," *Proc. Natl. Acad. Sci. USA* 99:625-630 (2002).

Ogg et al., "The Fork Head Transcription Factor DAF-16 Transduces Insulin-Like Metabolic and Longevity Signals in *C. elegans,*" *Nature* 389:994-999 (1997).

Pages et al., "LPA as a Paracrine Mediator of Adipocyte Growth and Function," *Ann. NY Acad. Sci.* 905:159-164 (2000).

Paradis et al., "A PDK1 Homolog is Necessary and Sufficient to Transduce AGE-1 PI3 Kinase Signals that Regulate Diapause in *Caenorhabditis elegans,*" *Genes Dev.* 13:1438-1452 (1999).

Patterson et al., "The DAF-3 Smad Protein Antagonizes TGF-β-Related Receptor Signaling in the *Caenorhabditis elegans* Dauer Pathway," *Genes Dev.* 11:2679-2690 (1997).

Rolland et al., "Evidence of Increased Glyceraldehyde-3-Phosphate Dehydrogenase and Fatty Acid Synthetase Promoter Activities in Transiently Transfected Adipocytes from Genetically Obese Rats," *J. Biol. Chem.* 270:1102-1106 (1995).

Sze et al., "Food and Metabolic Signalling Defects in a *Caenorhabditis elegans* Serotonin-Synthesis Mutant," *Nature* 403:560-564 (200).

Tacken et al., "Living up to a Name: the Role of the VLDL Receptor in Lipid Metabolism," *Curr. Opin. Lipidol.* 12:275-279 (2001).

Tecott et al., "Eating Disorder and Epilepsy in Mice Lacking 5-$HT_{2c}$ Serotonin Receptors," *Nature* 374:542-546 (1995).

Tissenbaum and Ruvkun, "An Insulin-like Signaling Pathway Affects both Longevity and Reproduction in *Caenorhabditis elegans,*" *Genetics* 148:703-717 (1998).

Trommsdorff et al., "Reeler/Disabled-like Disruption of Neuronal Migration in Knockout Mice Lacking the VLDL Receptor and ApoE Receptor 2," *Cell* 97:689-701 (1999).

Van Helvoort et al., "MDR1 P-Glycoprotein is a Lipid Translocase of Broad Specificity, while MDR3 P-Glycoprotein Specifically Translocates Phosphatidylcholine," *Cell* 87:507-517 (1996).

Watts and Browse, "Isolation and Characterization of a $\Delta^5$-Fatty Acid Desaturase from *Caenorhabditis elegans,*" *Arch. Biochem. Biophys.* 362:175-182 (1999).

Watts and Browse, "Genetic Dissection of Polyunsaturated Fatty Acid Synthesis in *Caenorhabditis elegans,*" *Proc. Natl. Acad. Sci. USA* 99:5854-5859 (2002).

Willson et al., "Peroxisome Proliferator-Activated Receptor γ and Metabolic Disease," *Ann. Rev. Biochem.* 70:341-367 (2001).

Wolkow et al., "Regulation of *C. elegans* Life-Span by Insulinlike Signaling in the Nervous System," *Science* 290:147-150 (2000).

Yamagata et al., "Mutations in the Hepatocyte Nuclear Factor-4α Gene in Maturity-Onset Diabetes of the Young (MODY1)," *Nature* 384:458-460 (1996).

Yoon et al., "Control of Hepatic Gluconeogenesis Through the Transcriptional Coactivator PGC-1," *Nature* 413:131-138 (2001).

* cited by examiner $C_1$-BODIPY 500/510 $C_{12}$ $C_8$-BODIPY 500/510 $C_5$

WILD TYPE

WILD TYPE

AICAR

WILD TYPE

STARVED

*daf-2(e1370)*

*daf-2(e1370)*

AICAR

*daf-2(e1370)*

STARVED

C12-BODIPY

WILD TYPE

NILE RED

WILD TYPE

C12-BODIPY

*lpo-1*

NILE RED

*lpo-1*

C12-BODIPY

*lpo-2*

NILE RED

*lpo-2*

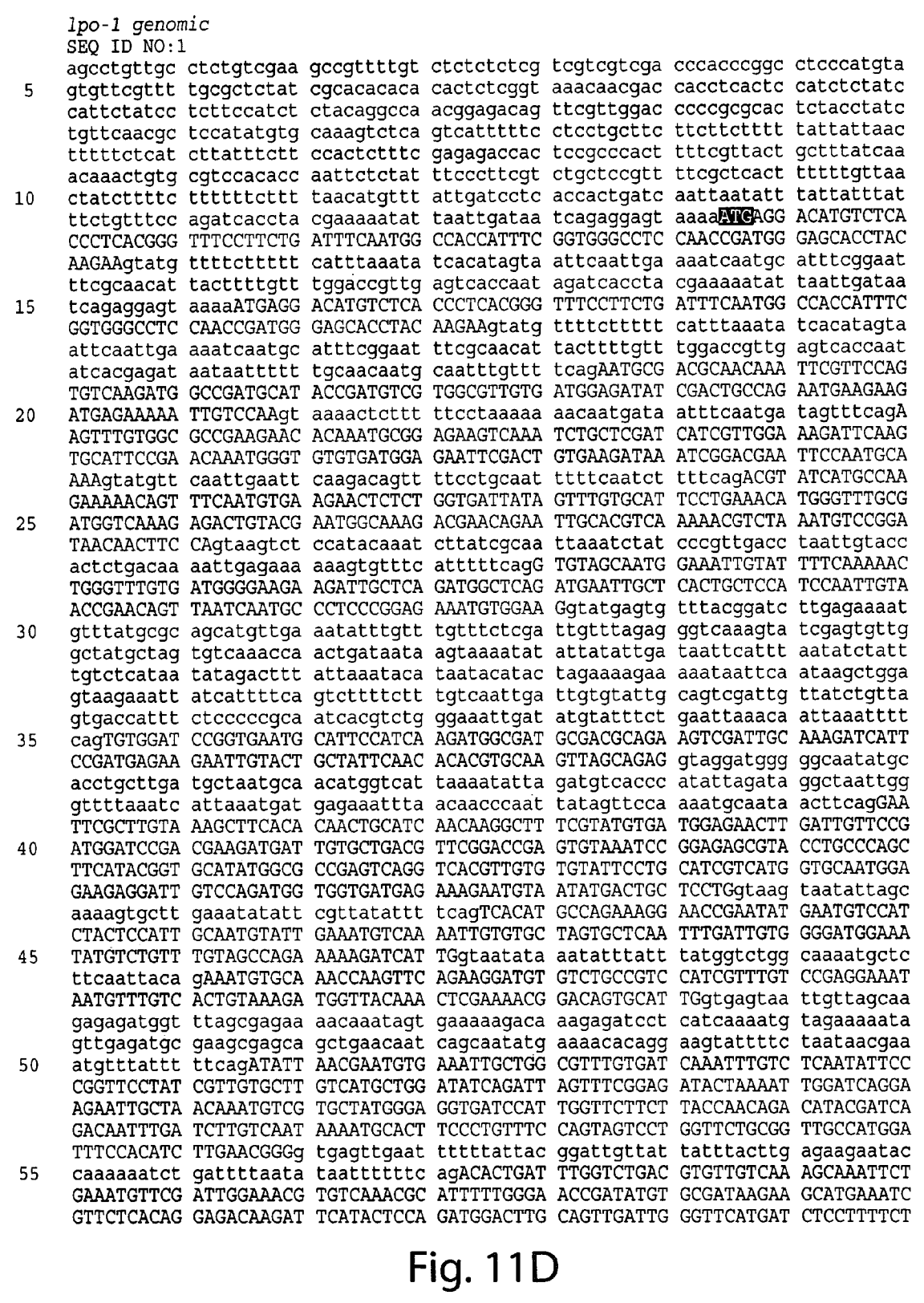

*lpo-1 genomic*
SEQ ID NO:1

```
agcctgttgc ctctgtcgaa gccgttttgt ctctctctcg tcgtcgtcga cccacccggc ctcccatgta
gtgttcgttt tgcgctctat cgcacacaca cactctcggt aaacaacgac cacctcactc catctctatc
cattctatcc tcttccatct ctacaggcca acggagacag ttcgttggac ccccgcgcac tctacctatc
tgttcaacgc tccatatgtg caaagtctca gtcatttttc ctcctgcttc ttcttctttt tattattaac
tttttctcat cttatttctt ccactctttc gagagaccac tccgcccact tttcgttact gctttatcaa
acaaactgtg cgtccacacc aattctctat ttcccttcgt ctgctccgtt ttcgctcact tttttgttaa
ctatcttttc tttttttcttt taacatgttt attgatcctc accactgatc aattaatatt tattatttat
ttctgtttcc agatcaccta cgaaaaatat taattgataa tcagaggagt aaaaATGAGG ACATGTCTCA
CCCTCACGGG TTTCCTTCTG ATTTCAATGG CCACCATTTC GGTGGGCCTC CAACCGATGG GAGCACCTAC
AAGAAgtatg ttttcttttt catttaaata tcacatagta attcaattga aaatcaatgc atttcggaat
ttcgcaacat tacttttgtt tggaccgttg agtcaccaat agatcaccta cgaaaaatat taattgataa
tcagaggagt aaaaATGAGG ACATGTCTCA CCCTCACGGG TTTCCTTCTG ATTTCAATGG CCACCATTTC
GGTGGGCCTC CAACCGATGG GAGCACCTAC AAGAAgtatg ttttcttttt catttaaata tcacatagta
attcaattga aaatcaatgc atttcggaat ttcgcaacat tacttttgtt tggaccgttg agtcaccaat
atcacgagat aataattttt tgcaacaatg caatttgttt tcagAATGCG ACGCAACAAA TTCGTTCCAG
TGTCAAGATG GCCGATGCAT ACCGATGTCG TGGCGTTGTG ATGGAGATAT CGACTGCCAG AATGAAGAAG
ATGAGAAAAA TTGTCCAAgt aaaactcttt ttcctaaaaa aacaatgata atttcaatga tagtttcagA
AGTTTGTGGC GCCGAAGAAC ACAAATGCGG AGAAGTCAAA TCTGCTCGAT CATCGTTGGA AAGATTCAAG
TGCATTCCGA ACAAATGGGT GTGTGATGGA GAATTCGACT GTGAAGATAA ATCGGACGAA TTCCAATGCA
AAAgtatgtt caattgaatt caagacagtt ttcctgcaat ttttcaatct tttcagACGT ATCATGCCAA
GAAAAACAGT TTCAATGTGA AGAACTCTCT GGTGATTATA GTTTGTGCAT TCCTGAAACA TGGGTTTGCG
ATGGTCAAAG AGACTGTACG AATGGCAAAG ACGAACAGAA TTGCACGTCA AAAACGTCTA AATGTCCGGA
TAACAACTTC CAgtaagtct ccatacaaat cttatcgcaa ttaaatctat cccgttgacc taattgtacc
actctgacaa aattgagaaa aaagtgtttc atttttcagG TGTAGCAATG GAAATTGTAT TTTCAAAAAC
TGGGTTTGTG ATGGGGAAGA AGATTGCTCA GATGGCTCAG ATGAATTGCT CACTGCTCCA TCCAATTGTA
ACCGAACAGT TAATCAATGC CCTCCCGGAG AAATGTGGAA Ggtatgagtg tttacggatc ttgagaaaat
gtttatgcgc agcatgttga aatatttgtt tgtttctcga ttgtttagag ggtcaaagta tcgagtgttg
gctatgctag tgtcaaacca actgataata agtaaaatat attatattga taattcattt aatatctatt
tgtctcataa tatagacttt attaaataca taatacatac tagaaaagaa aaataattca ataagctgga
gtaagaaatt atcattttca gtcttttctt tgtcaattga ttgtgtattg cagtcgattg ttatctgtta
gtgaccattt ctcccccgca atcacgtctg ggaaattgat atgtatttct gaattaaaca attaaatttt
cagTGTGGAT CCGGTGAATG CATTCCATCA AGATGGCGAT GCGACGCAGA AGTCGATTGC AAAGATCATT
CCGATGAGAA GAATTGTACT GCTATTCAAC ACACGTGCAA GTTAGCAGAG gtaggatggg ggcaatatgc
acctgcttga tgctaatgca acatggtcat taaaatatta gatgtcaccc atattagata ggctaattgg
gttttaaatc attaaatgat gagaaattta acaacccaat tatagttcca aaatgcaata acttcagGAA
TTCGCTTGTA AAGCTTCACA CAACTGCATC AACAAGGCTT TCGTATGTGA TGGAGAACTT GATTGTTCCG
ATGGATCCGA CGAAGATGAT TGTGCTGACG TTCGGACCGA GTGTAAATCC GGAGAGCGTA CCTGCCCAGC
TTCATACGGT GCATATGGCG CCGAGTCAGG TCACGTTGTG TGTATTCCTG CATCGTCATG GTGCAATGGA
GAAGAGGATT GTCCAGATGG TGGTGATGAG AAAGAATGTA ATATGACTGC TCCTGgtaag taatattagc
aaaagtgctt gaaatatatt cgttatattt tcagTCACAT GCCAGAAAGG AACCGAATAT GAATGTCCAT
CTACTCCATT GCAATGTATT GAAATGTCAA AATTGTGTGC TAGTGCTCAA TTTGATTGTG GGGATGGAAA
TATGTCTGTT TGTAGCCAGA AAAAGATCAT TGgtaatata aatatttatt tatggtctgg caaaatgctc
ttcaattaca gAAATGTGCA AACCAAGTTC AGAAGGATGT GTCTGCCGTC CATCGTTTGT CCGAGGAAAT
AATGTTTGTC ACTGTAAAGA TGGTTACAAA CTCGAAAACG GACAGTGCAT TGgtgagtaa ttgttagcaa
gagagatggt ttagcgagaa aacaaatagt gaaaaagaca aagagatcct catcaaaatg tagaaaaata
gttgagatgc gaagcgagca gctgaacaat cagcaatatg aaaacacagg aagtattttc taataacgaa
atgtttattt ttcagATATT AACGAATGTG AAATTGCTGG CGTTTGTGAT CAAATTTGTC TCAATATTCC
CGGTTCCTAT CGTTGTGCTT GTCATGCTGG ATATCAGATT AGTTTCGGAG ATACTAAAAT TGGATCAGGA
AGAATTGCTA ACAAATGTCG TGCTATGGGA GGTGATCCAT TGGTTCTTCT TACCAACAGA CATACGATCA
GACAATTTGA TCTTGTCAAT AAAATGCACT TCCCTGTTTC CAGTAGTCCT GGTTCTGCGG TTGCCATGGA
TTTCCACATC TTGAACGGGg tgagttgaat tttttattac ggattgttat tatttacttg agaagaatac
caaaaaatct gattttaata taatttttttc agACACTGAT TTGGTCTGAC GTGTTGTCAA AGCAAATTCT
GAAATGTTCG ATTGGAAACG TGTCAAACGC ATTTTTGGGA ACCGATATGT GCGATAAGAA GCATGAAATC
GTTCTCACAG GAGACAAGAT TCATACTCCA GATGGACTTG CAGTTGATTG GGTTCATGAT CTCCTTTTCT
```

Fig. 11D

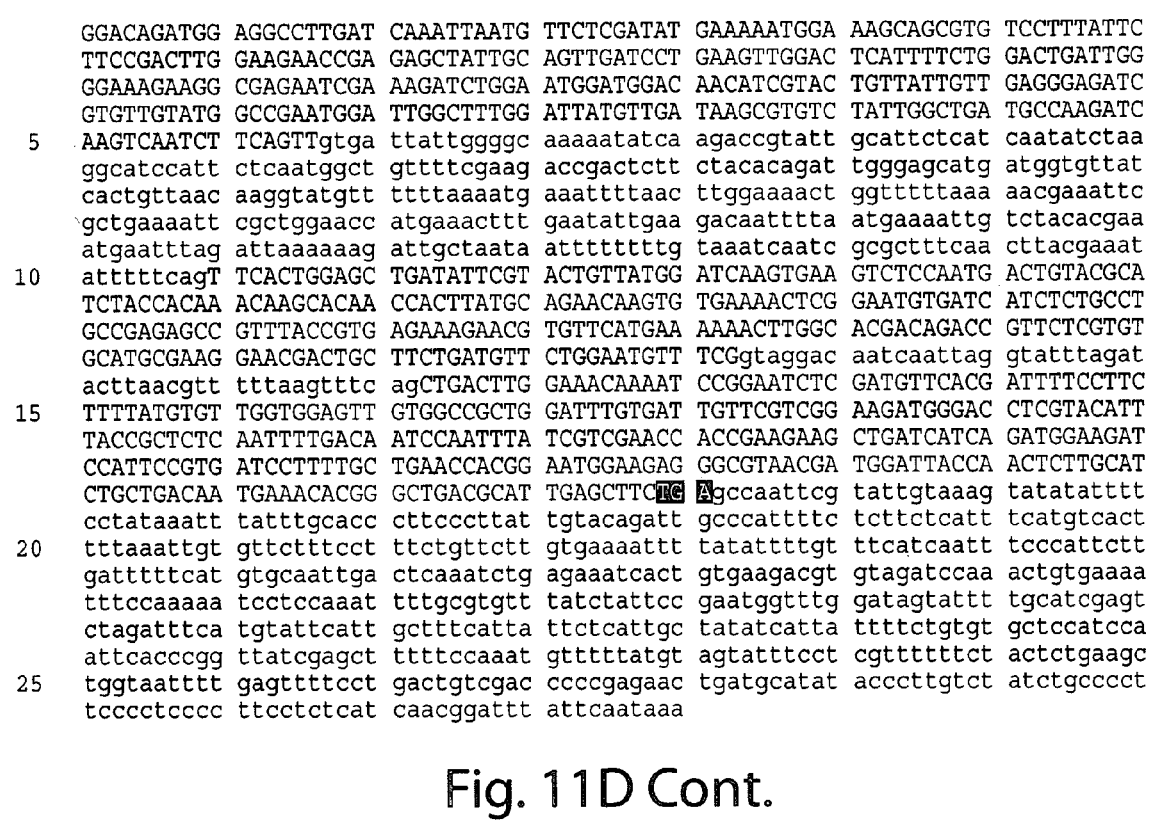

GGACAGATGG AGGCCTTGAT CAAATTAATG TTCTCGATAT GAAAAATGGA AAGCAGCGTG TCCTTTATTC
TTCCGACTTG GAAGAACCGA GAGCTATTGC AGTTGATCCT GAAGTTGGAC TCATTTTCTG GACTGATTGG
GGAAAGAAGG CGAGAATCGA AAGATCTGGA ATGGATGGAC AACATCGTAC TGTTATTGTT GAGGGAGATC
GTGTTGTATG GCCGAATGGA TTGGCTTTGG ATTATGTTGA TAAGCGTGTC TATTGGCTGA TGCCAAGATC
AAGTCAATCT TCAGTTgtga ttattggggc aaaaatatca agaccgtatt gcattctcat caatatctaa
ggcatccatt ctcaatggct gttttcgaag accgactctt ctacacagat tgggagcatg atggtgttat
cactgttaac aaggtatgtt ttttaaaatg aaattttaac ttggaaaact ggtttttaaa aacgaaattc
gctgaaaatt cgctggaacc atgaaacttt gaatattgaa gacaatttta atgaaaattg tctacacgaa
atgaatttag attaaaaaag attgctaata attttttttg taaatcaatc gcgctttcaa cttacgaaat
atttttcagT TCACTGGAGC TGATATTCGT ACTGTTATGG ATCAAGTGAA GTCTCCAATG ACTGTACGCA
TCTACCACAA ACAAGCACAA CCACTTATGC AGAACAAGTG TGAAAACTCG GAATGTGATC ATCTCTGCCT
GCCGAGAGCC GTTTACCGTG AGAAAGAACG TGTTCATGAA AAAACTTGGC ACGACAGACC GTTCTCGTGT
GCATGCGAAG GAACGACTGC TTCTGATGTT CTGGAATGTT TCGgtaggac aatcaattag gtatttagat
acttaacgtt tttaagtttc agCTGACTTG GAAACAAAAT CCGGAATCTC GATGTTCACG ATTTTCCTTC
TTTTATGTGT TGGTGGAGTT GTGGCCGCTG GATTTGTGAT TGTTCGTCGG AAGATGGGAC CTCGTACATT
TACCGCTCTC AATTTTGACA ATCCAATTTA TCGTCGAACC ACCGAAGAAG CTGATCATCA GATGGAAGAT
CCATTCCGTG ATCCTTTTGC TGAACCACGG AATGGAAGAG GGCGTAACGA TGGATTACCA ACTCTTGCAT
CTGCTGACAA TGAAACACGG GCTGACGCAT TGAGCTTCTG Agccaattcg tattgtaaag tatatatttt
cctataaatt tatttgcacc cttcccttat tgtacagatt gcccattttc tcttctcatt tcatgtcact
tttaaattgt gttctttcct ttctgttctt gtgaaaattt tatattttgt ttcatcaatt tcccattctt
gatttttcat gtgcaattga ctcaaatctg agaaatcact gtgaagacgt gtagatccaa actgtgaaaa
tttccaaaaa tcctccaaat tttgcgtgtt tatctattcc gaatggtttg gatagtattt tgcatcgagt
ctagatttca tgtattcatt gctttcatta ttctcattgc tatatcatta ttttctgtgt gctccatcca
attcacccgg ttatcgagct ttttccaaat gtttttatgt agtatttcct cgtttttttct actctgaagc
tggtaatttt gagttttcct gactgtcgac ccccgagaac tgatgcatat acccttgtct atctgcccct
tcccctcccc ttcctctcat caacggattt attcaataaa

Fig. 11D Cont.

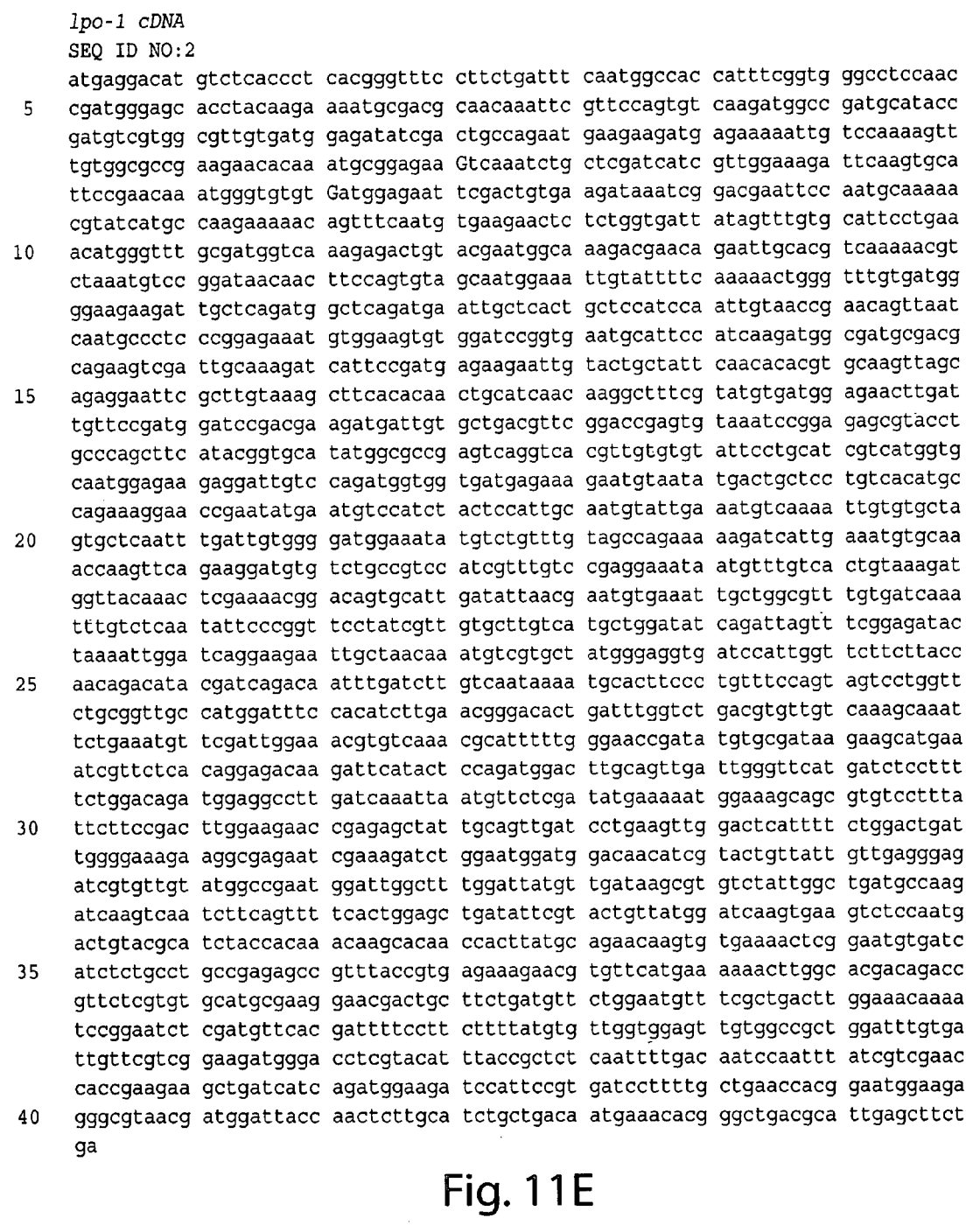

*lpo-1 cDNA*
SEQ ID NO:2

```
atgaggacat gtctcaccct cacgggtttc cttctgattt caatggccac catttcggtg ggcctccaac
cgatgggagc acctacaaga aaatgcgacg caacaaattc gttccagtgt caagatggcc gatgcatacc
gatgtcgtgg cgttgtgatg gagatatcga ctgccagaat gaagaagatg agaaaaattg tccaaaagtt
tgtggcgccg aagaacacaa atgcggagaa Gtcaaatctg ctcgatcatc gttggaaaga ttcaagtgca
ttccgaacaa atgggtgtgt Gatggagaat tcgactgtga agataaatcg gacgaattcc aatgcaaaaa
cgtatcatgc caagaaaaac agtttcaatg tgaagaactc tctggtgatt atagtttgtg cattcctgaa
acatgggttt gcgatggtca aagagactgt acgaatggca aagacgaaca gaattgcacg tcaaaaacgt
ctaaatgtcc ggataacaac ttccagtgta gcaatggaaa ttgtattttc aaaaactggg tttgtgatgg
ggaagaagat tgctcagatg gctcagatga attgctcact gctccatcca attgtaaccg aacagttaat
caatgccctc ccggagaaat gtggaagtgt ggatccggtg aatgcattcc atcaagatgg cgatgcgacg
cagaagtcga ttgcaaagat cattccgatg agaagaattg tactgctatt caacacacgt gcaagttagc
agaggaattc gcttgtaaag cttcacacaa ctgcatcaac aaggctttcg tatgtgatgg agaacttgat
tgttccgatg gatccgacga agatgattgt gctgacgttc ggaccgagtg taaatccgga gagcgtacct
gcccagcttc atacggtgca tatggcgccg agtcaggtca cgttgtgtgt attcctgcat cgtcatggtg
caatggagaa gaggattgtc cagatggtgg tgatgagaaa gaatgtaata tgactgctcc tgtcacatgc
cagaaaggaa ccgaatatga atgtccatct actccattgc aatgtattga aatgtcaaaa ttgtgtgcta
gtgctcaatt tgattgtggg gatggaaata tgtctgtttg tagccagaaa aagatcattg aaatgtgcaa
accaagttca gaaggatgtg tctgccgtcc atcgtttgtc cgaggaaata atgtttgtca ctgtaaagat
ggttacaaac tcgaaaacgg acagtgcatt gatattaacg aatgtgaaat tgctggcgtt tgtgatcaaa
tttgtctcaa tattcccggt tcctatcgtt gtgcttgtca tgctggatat cagattagtt tcggagatac
taaaattgga tcaggaagaa ttgctaacaa atgtcgtgct atgggaggtg atccattggt tcttcttacc
aacagacata cgatcagaca atttgatctt gtcaataaaa tgcacttccc tgtttccagt agtcctggtt
ctgcggttgc catggatttc cacatcttga acgggacact gatttggtct gacgtgttgt caaagcaaat
tctgaaatgt tcgattggaa acgtgtcaaa cgcatttttg ggaaccgata tgtgcgataa gaagcatgaa
atcgttctca caggagacaa gattcatact ccagatggac ttgcagttga ttgggttcat gatctccttt
tctggacaga tggaggcctt gatcaaatta atgttctcga tatgaaaaat ggaaagcagc gtgtccttta
ttcttccgac ttggaagaac cgagagctat tgcagttgat cctgaagttg gactcatttt ctggactgat
tggggaaaga aggcgagaat cgaaagatct ggaatggatg gacaacatcg tactgttatt gttgagggag
atcgtgttgt atggccgaat ggattggctt tggattatgt tgataagcgt gtctattggc tgatgccaag
atcaagtcaa tcttcagttt tcactggagc tgatattcgt actgttatgg atcaagtgaa gtctccaatg
actgtacgca tctaccacaa acaagcacaa ccacttatgc agaacaagtg tgaaaactcg gaatgtgatc
atctctgcct gccgagagcc gtttaccgtg agaaagaacg tgttcatgaa aaaacttggc acgacagacc
gttctcgtgt gcatgcgaag gaacgactgc ttctgatgtt ctggaatgtt tcgctgactt ggaaacaaaa
tccggaatct cgatgttcac gattttcctt cttttatgtg ttggtggagt tgtggccgct ggatttgtga
ttgttcgtcg gaagatggga cctcgtacat ttaccgctct caattttgac aatccaattt atcgtcgaac
caccgaagaa gctgatcatc agatggaaga tccattccgt gatccttttg ctgaaccacg gaatggaaga
gggcgtaacg atggattacc aactcttgca tctgctgaca atgaaacacg ggctgacgca ttgagcttct
ga
```

Fig. 11E

LPO-1
SEQ ID NO:3
MRTCLTLTGF LLISMATISV GLQPMGAPTR KCDATNSFQC QDGRCIPMSW RCDGDIDCQN EEDEKNCPKV
CGAEEHKCGE VKSARSSLER FKCIPNKWVC DGEFDCEDKS DEFQCKNVSC QEKQFQCEEL SGDYSLCIPE
TWVCDGQRDC TNGKDEQNCT SKTSKCPDNN FQCSNGNCIF KNWVCDGEED CSDGSDELLT APSNCNRTVN
QCPPGEMWKC GSGECIPSRW RCDAEVDCKD HSDEKNCTAI QHTCKLAEEF ACKASHNCIN KAFVCDGELD
CSDGSDEDDC ADVRTECKSG ERTCPASYGA YGAESGHVVC IPASSWCNGE EDCPDGGDEK ECNMTAPVTC
QKGTEYECPS TPLQCIEMSK LCASAQFDCG DGNMSVCSQK KIIEMCKPSS EGCVCRPSFV RGNNVCHCKD
GYKLENGQCI DINECEIAGV CDQICLNIPG SYRCACHAGY QISFGDTKIG SGRIANKCRA MGGDPLVLLT
NRHTIRQFDL VNKMHFPVSS SPGSAVAMDF HILNGTLIWS DVLSKQILKC SIGNVSNAFL GTDMCDKKHE
IVLTGDKIHT PDGLAVDWVH DLLFWTDGGL DQINVLDMKN GKQRVLYSSD LEEPRAIAVD PEVGLIFWTD
WGKKARIERS GMDGQHRTVI VEGDRVVWPN GLALDYVDKR VYWLMPRSSQ SSVFTGADIR TVMDQVKSPM
TVRIYHKQAQ PLMQNKCENS ECDHLCLPRA VYREKERVHE KTWHDRPFSC ACEGTTASDV LECFADLETK
SGISMFTIFL LLCVGGVVAA GFVIVRRKMG PRTFTALNFD NPIYRRTTEE ADHQMEDPFR DPFAEPRNGR
GRNDGLPTLA SADNETRADA LSF

Fig. 11F

```
RAT     MGTSARWALWLLLALCWAPRDSGATASGKKAKCDSSQFQCTNGRCITLLWKCDGDEDCTD 60  (SEQ ID NO:10)
human   MGTSALWALWLLLALCWAPRESGATGTGRKAKCEPSQFQCTNGRCITLLWKCDGDEDCVD 60  (SEQ ID NO:9)
lpo-1   MRTCLTLTGFLLISMATISVGLQPMGAPTRKCDATNSFQCQDGRCIPMSWRCDGDIDCQN 60  (SEQ ID NO:3)
        * *.   : :**:::.  .     . .:  :     ...*** :****.: *:**** ** :

RAT     GSDEKNCVKKTCAESDFVCKNG---------QCVPNRWQCDGDPDCEDGSDESPEQCHMR 111
human   GSDEKNCVKKTCAESDFVCNNG---------QCVPSRWKCDGDPDCEDGSDESPEQCHMR 111
lpo-1   EEDEKNCPKVCGAEEHKCGEVKSARSSLERFKCIPNKWVCDGEFDCEDKSDE--FQCKNV 118
         .***** *   **..   :  :: :: .  :*:*.:* ***: **** ***   **:

RAT     TCRINEISCGARS---TQCIPESWRCDGENDCDNGEDEENCGNIT--CSADEFTCSSGRC 166
human   TCRIHEISCGAHS---TQCIPVSWRCDGENDCDSGEDEENCGNIT--CSPDEFTCSSGRC 166
lpo-1   SCQEKQFQCEELSGDYSLCIPETWVCDGQRDCTNGKDEQNCTSKTSKCPDNNFQCSNGNC 178
        :*: :::.*   *.. : *** :* ***:.** .*:**:** . *:.*. ::* **.*.*

RAT     VSRNFVCNGQDDCDDGSDELDCAPPTCG--------AHEFQCRTSSCIPLSWVCDDDADC 218
human   ISRNFVCNGQDDCSDGSDELDCAPPTCG--------AHEFQCSTSSCIPISWVCDDDADC 218
lpo-1   IFKNWVCDGEEDCSDGSDELLTAPSNCNRTVNQCPPGEMWKCGSGECIPSRWRWCDAEVDC 238
        : :*:**:*::**.******  **..*. : ....... ::* :..***  * ** :.**

RAT     SDQSDESLEQCGRQPVIHTKCPTSEIQCGSGE-CIHKKWRCDGDPDCKDGSDEVNCPSR- 276
human   SDQSDESLEQCGRQPVIHTKCPASEIQCGSGE-CIHKKWRCDGDPDCKDGSDEVNCPSR- 276
lpo-1   KDHSDE----KNCTAIQHTCKLAEEFACKASHNCINKAFVCDGELDCSDGSDEDDCADVR 294
        .*:***       .   .: **   :.*: * :...**:* : ***: **.***** :*..

RAT     -TCRPDQFECEDGS-----------CIHGSRQCNGIRDCVDGSDEVNCKNVN--QCLGPG 322
human   -TCRPDQFECEDGS-----------CIHGSRQCNGIRDCVDGSDEVNCKNVN--QCLGPG 322
lpo-1   TECKSGERTCPASYGAYGAESGHVVCIPASSWCNGEEDCPDGGDEKECNMTAPVTCQKGT 354
        : *:..:  *  . .: .:.:.   ** .*  *** .** **.** :*: . .   *

RAT     KFKCRSG--ECIDITKVCD-QEQDCRDWSDEPLKECHINECLVNNGGCSHICKDLVIG-Y 378
human   KFKCRSG--ECIDISKVCN-QEQDCRDWSDEPLKECHINECLVNNGGCSHICKDLVIG-Y 378
lpo-1   EYECPSTPLQCIEMSKLCASAQFDCGDGNMSVCSQKKIIEMCKPSSEGCVCRPSFVRGNN 414
        :::* * . :**:::*:* : : ** * .  . .: :* *    .. .    .:* *.

RAT     ECDCAAGFELIDRKTCGDIDECQNPGICSQICINLKGGYKCECSRGYQMDLATG------ 432
human   ECDCAAGFELIDRKTCGDIDECQNPGICSQICINLKGGYKCECSRGYQMDLATG------ 432
lpo-1   VCHCKDGYKLEN-GQCIDINECEIAGVCDQICLNIPGSYRCACHAGYQISFGDTKIGSGR 473
         *.*  *:.* :    * **:**: .*:*.***:*: *.*:* * ***:.:.  . .:.

RAT     ---VCKAVGKEPSLIFTNRRDIRKIGLERKEYIQLVEQLRNTVALDADIAAQKLFWADLS 489
human   ---VCKAVGKEPSLIFTNRRDIRKIGLERKEYIQLVEQLRNTVALDADIAAQKLFWADLS 489
lpo-1   IANKCRAMGGDPLVLLTNRHTIRQFDLVNKMHFPVSSSPGSAVAMDFHILNGTLIWSDVL 533
          :. *:*:* :* :::***: **::.* .* :: : ..  .:**:* .*    .*:*:*:

RAT     QKAIFSASID------------DKVGRHFKMIDNVYNPAAIAVDWVYKTIYWTDAASKTI 537
human   QKAIFSASID------------DKVGRHVKMIDNVYNPAAIAVDWVYKTIYWTDAASKTI 537
lpo-1   SKQILKCSIGNVSNAFLGTDMCDKKHEIVLTGDKIHTPDGLAVDWVHDLLFWTDGGLDQI 593
        .* *:..**..  :.:   .:. .**  . .    *:::.* .:*****:. ::***.. . *
```

Fig. 11G

```
RAT       SVATLDGTKRKFLFNSDLREPASIAVDPLSGFVYWSDWGEPAKIEKAGMNGFDRRPLVTE 597
human     SVATLDGTKRKFLFNSDLREPASIAVDPLSGFVYWSDWGEPAKIEKAGMNGFDRRPLVTA 597
lpo-1     NVLDMKNGKQRVLYSSDLEEPRAIAVDPEVGLIFWTDWGKKARIERSGMDGQHRTVIVEG 653
          .*  :.. *::.*:.***.** :*****  *:::*:***: *:**::**:* .*  :*

RAT       D-IQWPNGITLDLVKSRLYWLDSKLHMLSSVDLNGQDRRIVLKSLEFLAHPLALTIFEDR 656
human     D-IQWPNGITLDLIKSRLYWLDSKLHMLSSVDLNGQDRRIVLKSLEFLAHPLALTIFEDR 656
lpo-1     DRVVWPNGLALDYVDKRVYWLMPRSSQSS------------------------------- 682
          * : ****::** :..*:*** .:    *

RAT       VYWIDGENEAVYGANKFTGSELATLVNNLNDAQDIIIYHELVQPSGKNWCEEDMENGGCE 716
human     VYWIDGENEAVYGANKFTGSELATLVNNLNDAQDIIVYHELVQPSGKNWCEEDMENGGCE 716
lpo-1     ---------------VFTGADIRTVMDQVKSPMTVRIYHKQAQPLMQNKCENSE----CD 723
                         ***::: *:::::::..  : :**: .**  :* **:.     *:

RAT       YLCLPAPQINDHSPKYTCSCPNGYNLEENGRECQSTSTPVTYSETKDVNTTDILRTSGLV 776
human     YLCLPAPQINDHSPKYTCSCPSGYNVEENGRDCQSTATTVTYSETKDTNTTEISATSGLV 776
lpo-1     HLCLPRAVYREKE------------RVHEKTWHDRPFSCACEGTTASDVLECFADLETK 770
          :**** .  .::.              . : :  :. . . : . *.  :. :

RAT       PGGINVTTAVSEVSVPPKGTSAAWAILPLLLLVMAAVGGYLMWRNWQHKNMKSMNFDNPV 836
human     PGGINVTTAVSEVSVPPKGTSAAWAILPLLLLVMAAVGGYLMWRNWQHKNMKSMNFDNPV 836
lpo-1     SG-----------------ISMFTIFLLLCVGGVVAAGFVIVRRKMGPRTFTALNFDNPI 813
          .*                 *    :* * :  :.*.*  :: *:   :.:.::*****:

RAT       YLKTTEEDLSIDIG---------RHSASVGHTYPAISVVSTDDDLA---- 873
human     YLKTTEEDLSIDIG---------RHSASVGHTYPAISVVSTDDDLA---- 873
lpo-1     YRRTTEEADHQMEDPFRDPFAEPRNGRGRNDGLPTLASADNETRADALSF 863
          * :
```

Fig. 11G Cont.

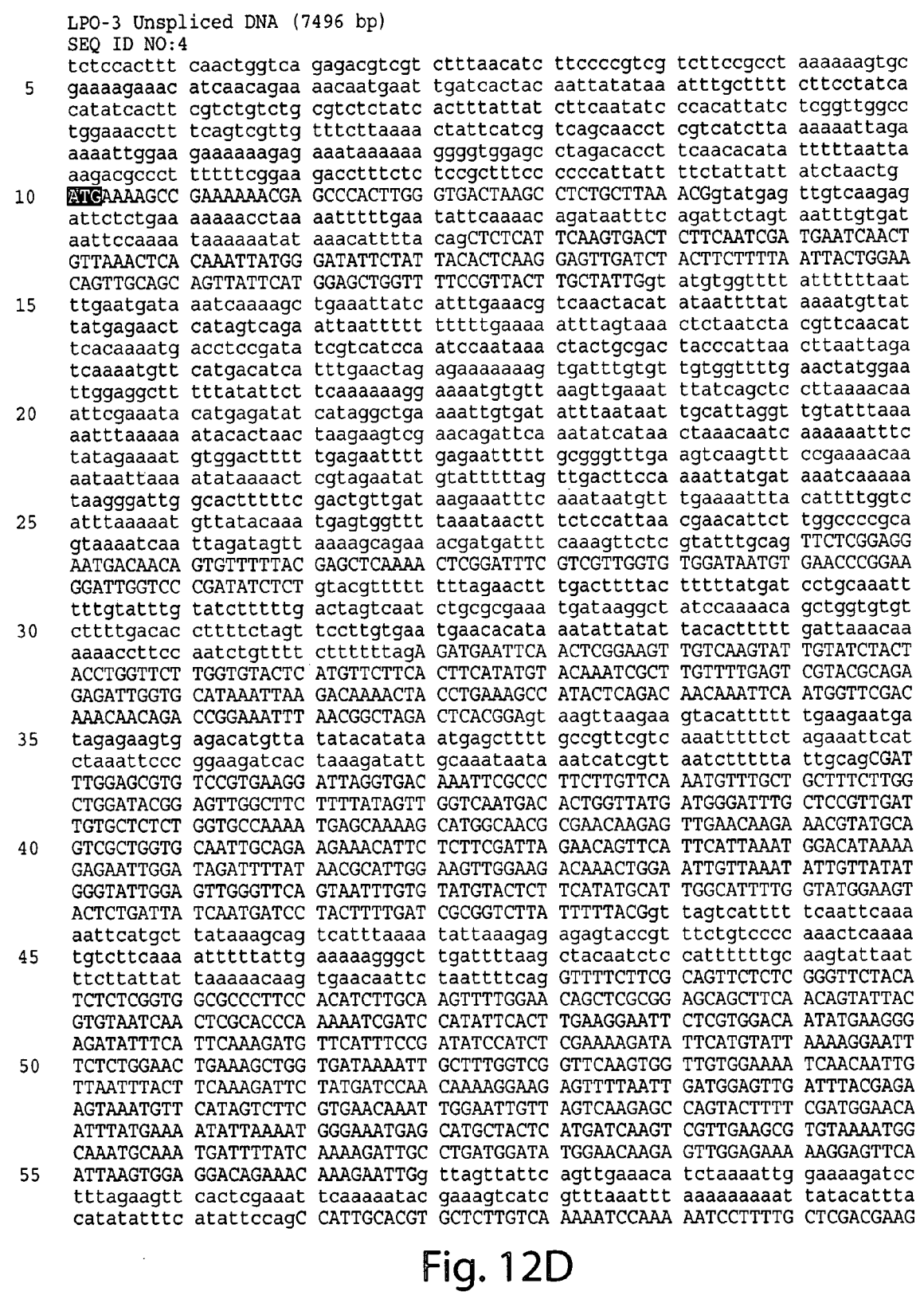

LPO-3 Unspliced DNA (7496 bp)
SEQ ID NO:4

```
tctccacttt caactggtca gagacgtcgt ctttaacatc ttccccgtcg tcttccgcct aaaaaagtgc
gaaaagaaac atcaacagaa aacaatgaat tgatcactac aattatataa atttgctttt cttcctatca
catatcactt cgtctgtctg cgtctctatc actttattat cttcaatatc ccacattatc tcggttggcc
tggaaacctt tcagtcgttg tttcttaaaa ctattcatcg tcagcaacct cgtcatctta aaaaattaga
aaaattggaa gaaaaaagag aaataaaaaa ggggtggagc ctagacacct tcaacacata tttttaatta
aagacgccct tttttcggaa gacctttctc tccgctttcc ccccattatt ttctattatt atctaactg
ATGAAAAGCC GAAAAAACGA GCCCACTTGG GTGACTAAGC CTCTGCTTAA ACGgtatgag ttgtcaagag
attctctgaa aaaaacctaa aatttttgaa tattcaaaac agataatttc agattctagt aatttgtgat
aattccaaaa taaaaaatat aaacatttta cagCTCTCAT TCAAGTGACT CTTCAATCGA TGAATCAACT
GTTAAACTCA CAAATTATGG GATATTCTAT TACACTCAAG GAGTTGATCT ACTTCTTTTA ATTACTGGAA
CAGTTGCAGC AGTTATTCAT GGAGCTGGTT TTCCGTTACT TGCTATTGgt atgtggtttt atttttttaat
ttgaatgata aatcaaaagc tgaaattatc atttgaaacg tcaactacat ataattttat aaaatgttat
tatgagaact catagtcaga attaattttt tttttgaaaa atttagtaaa ctctaatcta cgttcaacat
tcacaaaatg acctccgata tcgtcatcca atccaataaa ctactgcgac tacccattaa cttaattaga
tcaaaatgtt catgacatca tttgaactag agaaaaaaag tgatttgtgt tgtggttttg aactatggaa
ttggaggctt tttatattct tcaaaaaagg aaaatgtgtt aagttgaaat ttatcagctc cttaaaacaa
attcgaaata catgagatat cataggctga aaattgtgat atttaataat tgcattaggt tgtatttaaa
aatttaaaaa atacactaac taagaagtcg aacagattca aatatcataa ctaaacaatc aaaaaatttc
tatagaaaat gtggactttt tgagaatttt gagaattttt gcgggtttga agtcaagttt ccgaaaacaa
aataattaaa atataaaact cgtagaatat gtatttttag ttgacttcca aaattatgat aaatcaaaaa
taagggattg gcactttttc gactgttgat aagaaatttc aaataatgtt tgaaaattta cattttggtc
atttaaaaat gttatacaaa tgagtggttt taaataactt tctccattaa cgaacattct tggccccgca
gtaaaatcaa ttagatagtt aaaagcagaa acgatgattt caaagttctc gtatttgcag TTCTCGGAGG
AATGACAACA GTGTTTTTAC GAGCTCAAAA CTCGGATTTC GTCGTTGGTG TGGATAATGT GAACCCGGAA
GGATTGGTCC CGATATCTCT gtacgttttt tttagaactt tgacttttac tttttatgat cctgcaaatt
tttgtatttg tatcttttttg actagtcaat ctgcgcgaaa tgataaggct atccaaaaca gctggtgtgt
cttttgacac cttttctagt tccttgtgaa tgaacacata aatattatat tacacttttt gattaaacaa
aaaaccttcc aatctgtttt ctttttttagA GATGAATTCA ACTCGGAAGT TGTCAAGTAT TGTATCTACT
ACCTGGTTCT TGGTGTACTC ATGTTCTTCA CTTCATATGT ACAAATCGCT TGTTTTGAGT CGTACGCAGA
GAGATTGGTG CATAAATTAA GACAAAACTA CCTGAAAGCC ATACTCAGAC AACAAATTCA ATGGTTCGAC
AAACAACAGA CCGGAAATTT AACGGCTAGA CTCACGGAgt aagttaagaa gtacattttt tgaagaatga
tagagaagtg agacatgtta tatacatata atgagctttt gccgttcgtc aaatttttct agaaattcat
ctaaattccc ggaagatcac taaagatatt gcaaataata aatcatcgtt aatcttttta ttgcagCGAT
TTGGAGCGTG TCCGTGAAGG ATTAGGTGAC AAATTCGCCC TTCTTGTTCA AATGTTTGCT GCTTTCTTGG
CTGGATACGG AGTTGGCTTC TTTTATAGTT GGTCAATGAC ACTGGTTATG ATGGGATTTG CTCCGTTGAT
TGTGCTCTCT GGTGCCAAAA TGAGCAAAAG CATGGCAACG CGAACAAGAG TTGAACAAGA AACGTATGCA
GTCGCTGGTG CAATTGCAGA AGAAACATTC TCTTCGATTA GAACAGTTCA TTCATTAAAT GGACATAAAA
GAGAATTGGA TAGATTTTAT AACGCATTGG AAGTTGGAAG ACAAACTGGA ATTGTTAAAT ATTGTTATAT
GGGTATTGGA GTTGGGTTCA GTAATTTGTG TATGTACTCT TCATATGCAT TGGCATTTTG GTATGGAAGT
ACTCTGATTA TCAATGATCC TACTTTTGAT CGCGGTCTTA TTTTTACGGt tagtcatttt tcaattcaaa
aattcatgct tataaagcag tcatttaaaa tattaaagag agagtaccgt ttctgtcccc aaactcaaaa
tgtcttcaaa atttttattg aaaaagggct tgattttaag ctacaatctc catttttttgc aagtattaat
ttcttattat taaaaacaag tgaacaattc taattttcag GTTTTCTTCG CAGTTCTCTC GGGTTCTACA
TCTCTCGGTG GCGCCCTTCC ACATCTTGCA AGTTTTGGAA CAGCTCGCGG AGCAGCTTCA ACAGTATTAC
GTGTAATCAA CTCGCACCCA AAAATCGATC CATATTCACT TGAAGGAATT CTCGTGGACA ATATGAAGGG
AGATATTTCA TTCAAAGATG TTCATTTCCG ATATCCATCT CGAAAAGATA TTCATGTATT AAAAGGAATT
TCTCTGGAAC TGAAAGCTGG TGATAAAATT GCTTTGGTCG GTTCAAGTGG TTGTGGAAAA TCAACAATTG
TTAATTTACT TCAAAGATTC TATGATCCAA CAAAAGGAAG AGTTTTAATT GATGGAGTTG ATTTACGAGA
AGTAAATGTT CATAGTCTTC GTGAACAAAT TGGAATTGTT AGTCAAGAGC CAGTACTTTT CGATGGAACA
ATTTATGAAA ATATTAAAAT GGGAAATGAG CATGCTACTC ATGATCAAGT CGTTGAAGCG TGTAAAATGG
CAAATGCAAA TGATTTTATC AAAAGATTGC CTGATGGATA TGGAACAAGA GTTGGAGAAA AAGGAGTTCA
ATTAAGTGGA GGACAGAAAC AAAGAATTGg ttagttattc agttgaaaca tctaaaattg gaaaagatcc
tttagaagtt cactcgaaat tcaaaaatac gaaagtcatc gtttaaattt aaaaaaaaat tatacattta
catatatttc atattccagC CATTGCACGT GCTCTTGTCA AAAATCCAAA AATCCTTTTG CTCGACGAAG
```

Fig. 12D

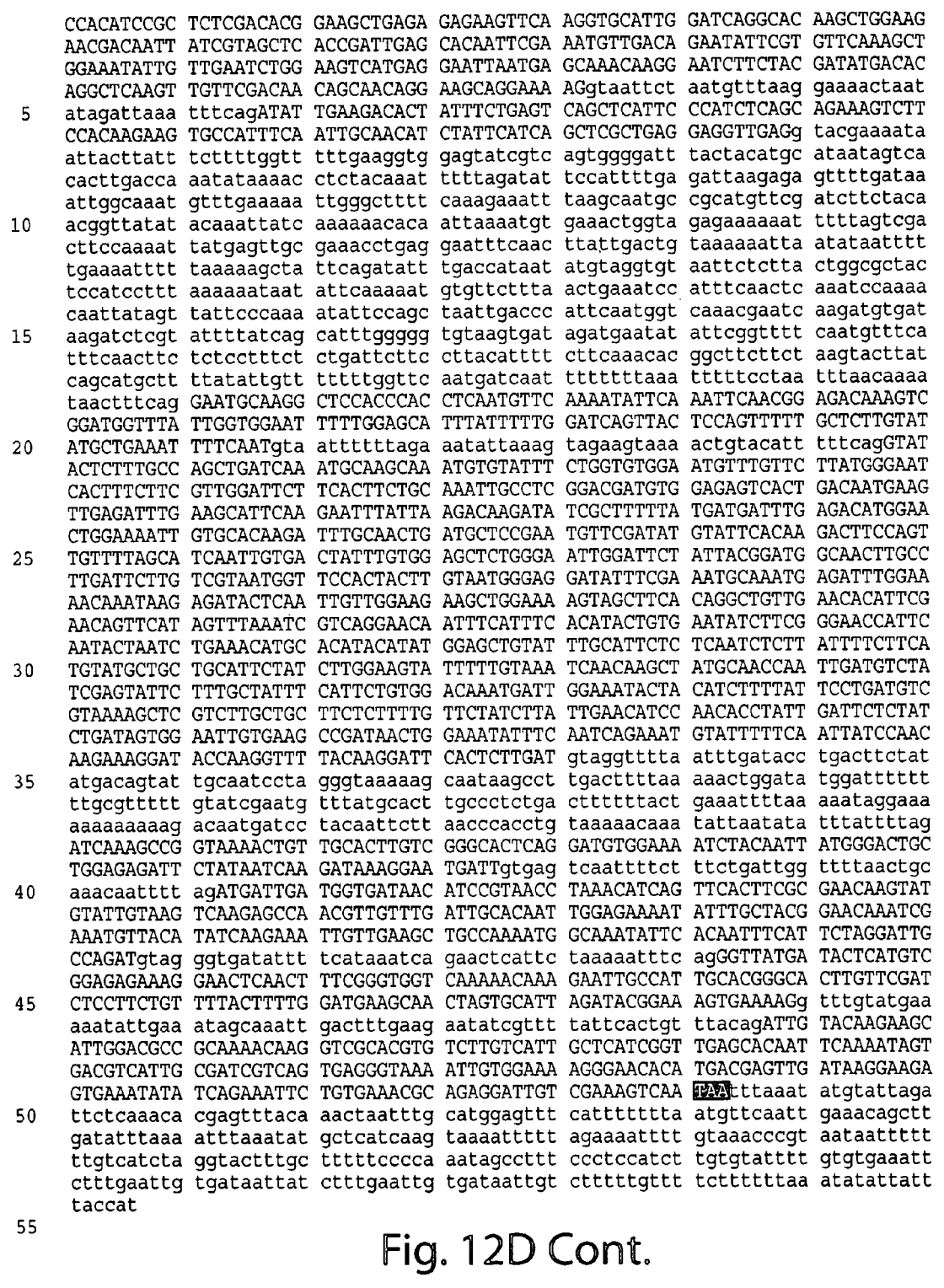

```
CCACATCCGC TCTCGACACG GAAGCTGAGA GAGAAGTTCA AGGTGCATTG GATCAGGCAC AAGCTGGAAG
AACGACAATT ATCGTAGCTC ACCGATTGAG CACAATTCGA AATGTTGACA GAATATTCGT GTTCAAAGCT
GGAAATATTG TTGAATCTGG AAGTCATGAG GAATTAATGA GCAAACAAGG AATCTTCTAC GATATGACAC
AGGCTCAAGT TGTTCGACAA CAGCAACAGG AAGCAGGAAA AGgtaattct aatgtttaag gaaaactaat
atagattaaa tttcagATAT TGAAGACACT ATTTCTGAGT CAGCTCATTC CCATCTCAGC AGAAAGTCTT
CCACAAGAAG TGCCATTTCA ATTGCAACAT CTATTCATCA GCTCGCTGAG GAGGTTGAGg tacgaaaata
attacttatt tcttttggtt tttgaaggtg gagtatcgtc agtggggatt tactacatgc ataatagtca
cacttgacca aatataaaac ctctacaaat ttttagatat tccattttga gattaagaga gttttgataa
attggcaaat gtttgaaaaa ttgggctttt caaagaaatt taagcaatgc cgcatgttcg atcttctaca
acggttatat acaaattatc aaaaaacaca attaaaatgt gaaactggta gagaaaaaat ttttagtcga
cttccaaaat tatgagttgc gaaacctgag gaatttcaac ttattgactg taaaaaatta atataatttt
tgaaaatttt taaaaagcta ttcagatatt tgaccataat atgtaggtgt aattctctta ctggcgctac
tccatccttt aaaaaataat attcaaaaat gtgttcttta actgaaatcc atttcaactc aaatccaaaa
caattatagt tattcccaaa atattccagc taattgaccc attcaatggt caaacgaatc aagatgtgat
aagatctcgt attttatcag catttggggg tgtaagtgat agatgaatat attcggtttt caatgtttca
tttcaacttc tctcctttct ctgattcttc cttacatttt cttcaaacac ggcttcttct aagtacttat
cagcatgctt ttatattgtt tttttggttc aatgatcaat ttttttttaaa tttttcctaa tttaacaaaa
taactttcag GAATGCAAGG CTCCACCCAC CTCAATGTTC AAAATATTCA AATTCAACGG AGACAAAGTC
GGATGGTTTA TTGGTGGAAT TTTTGGAGCA TTTATTTTTG GATCAGTTAC TCCAGTTTTT GCTCTTGTAT
ATGCTGAAAT TTTCAATgta atttttttaga aatattaaag tagaagtaaa actgtacatt tttcagGTAT
ACTCTTTGCC AGCTGATCAA ATGCAAGCAA ATGTGTATTT CTGGTGTGGA ATGTTTGTTC TTATGGGAAT
CACTTTCTTC GTTGGATTCT TCACTTCTGC AAATTGCCTC GGACGATGTG GAGAGTCACT GACAATGAAG
TTGAGATTTG AAGCATTCAA GAATTTATTA AGACAAGATA TCGCTTTTTA TGATGATTTG AGACATGGAA
CTGGAAAATT GTGCACAAGA TTTGCAACTG ATGCTCCGAA TGTTCGATAT GTATTCACAA GACTTCCAGT
TGTTTTAGCA TCAATTGTGA CTATTTGTGG AGCTCTGGGA ATTGGATTCT ATTACGGATG GCAACTTGCC
TTGATTCTTG TCGTAATGGT TCCACTACTT GTAATGGGAG GATATTTCGA AATGCAAATG AGATTTGGAA
AACAAATAAG AGATACTCAA TTGTTGGAAG AAGCTGGAAA AGTAGCTTCA CAGGCTGTTG AACACATTCG
AACAGTTCAT AGTTTAAATC GTCAGGAACA ATTTCATTTC ACATACTGTG AATATCTTCG GGAACCATTC
AATACTAATC TGAAACATGC ACATACATAT GGAGCTGTAT TTGCATTCTC TCAATCTCTT ATTTTCTTCA
TGTATGCTGC TGCATTCTAT CTTGGAAGTA TTTTTGTAAA TCAACAAGCT ATGCAACCAA TTGATGTCTA
TCGAGTATTC TTTGCTATTT CATTCTGTGG ACAAATGATT GGAAATACTA CATCTTTTAT TCCTGATGTC
GTAAAAGCTC GTCTTGCTGC TTCTCTTTTG TTCTATCTTA TTGAACATCC AACACCTATT GATTCTCTAT
CTGATAGTGG AATTGTGAAG CCGATAACTG GAAATATTTC AATCAGAAAT GTATTTTTCA ATTATCCAAC
AAGAAAGGAT ACCAAGGTTT TACAAGGATT CACTCTTGAT gtaggtttta atttgatacc tgacttctat
atgacagtat tgcaatccta gggtaaaaag caataagcct tgacttttaa aaactggata tggatttttt
ttgcgttttt gtatcgaatg tttatgcact tgccctctga ctttttttact gaaattttaa aaataggaaa
aaaaaaaaag acaatgatcc tacaattctt aacccacctg taaaaacaaa tattaatata tttattttag
ATCAAAGCCG GTAAAACTGT TGCACTTGTC GGGCACTCAG GATGTGGAAA ATCTACAATT ATGGGACTGC
TGGAGAGATT CTATAATCAA GATAAAGGAA TGATTgtgag tcaattttct ttctgattgg ttttaactgc
aaacaatttt agATGATTGA TGGTGATAAC ATCCGTAACC TAAACATCAG TTCACTTCGC GAACAAGTAT
GTATTGTAAG TCAAGAGCCA ACGTTGTTTG ATTGCACAAT TGGAGAAAAT ATTTGCTACG GAACAAATCG
AAATGTTACA TATCAAGAAA TTGTTGAAGC TGCCAAAATG GCAAATATTC ACAATTTCAT TCTAGGATTG
CCAGATgtag ggtgatattt tcataaatca gaactcattc taaaaatttc agGGTTATGA TACTCATGTC
GGAGAGAAAG GAACTCAACT TTCGGGTGGT CAAAAACAAA GAATTGCCAT TGCACGGGCA CTTGTTCGAT
CTCCTTCTGT TTTACTTTTG GATGAAGCAA CTAGTGCATT AGATACGGAA AGTGAAAAGg tttgtatgaa
aaatattgaa atagcaaatt gactttgaag aatatcgttt tattcactgt ttacagATTG TACAAGAAGC
ATTGGACGCC GCAAAACAAG GTCGCACGTG TCTTGTCATT GCTCATCGGT TGAGCACAAT TCAAAATAGT
GACGTCATTG CGATCGTCAG TGAGGGTAAA ATTGTGGAAA AGGGAACACA TGACGAGTTG ATAAGGAAGA
GTGAAATATA TCAGAAATTC TGTGAAACGC AGAGGATTGT CGAAAGTCAA TAAtttaaat atgtattaga
ttctcaaaca cgagtttaca aactaatttg catggagttt cattttttta atgttcaatt gaaacagctt
gatatttaaa atttaaatat gctcatcaag taaaattttt agaaaatttt gtaaacccgt aataattttt
ttgtcatcta ggtactttgc tttttcccca aatagccttt ccctccatct tgtgtatttt gtgtgaaatt
ctttgaattg tgataattat ctttgaattg tgataattgt ctttttgttt tctttttttaa atatattatt
taccat
```

Fig. 12D Cont.

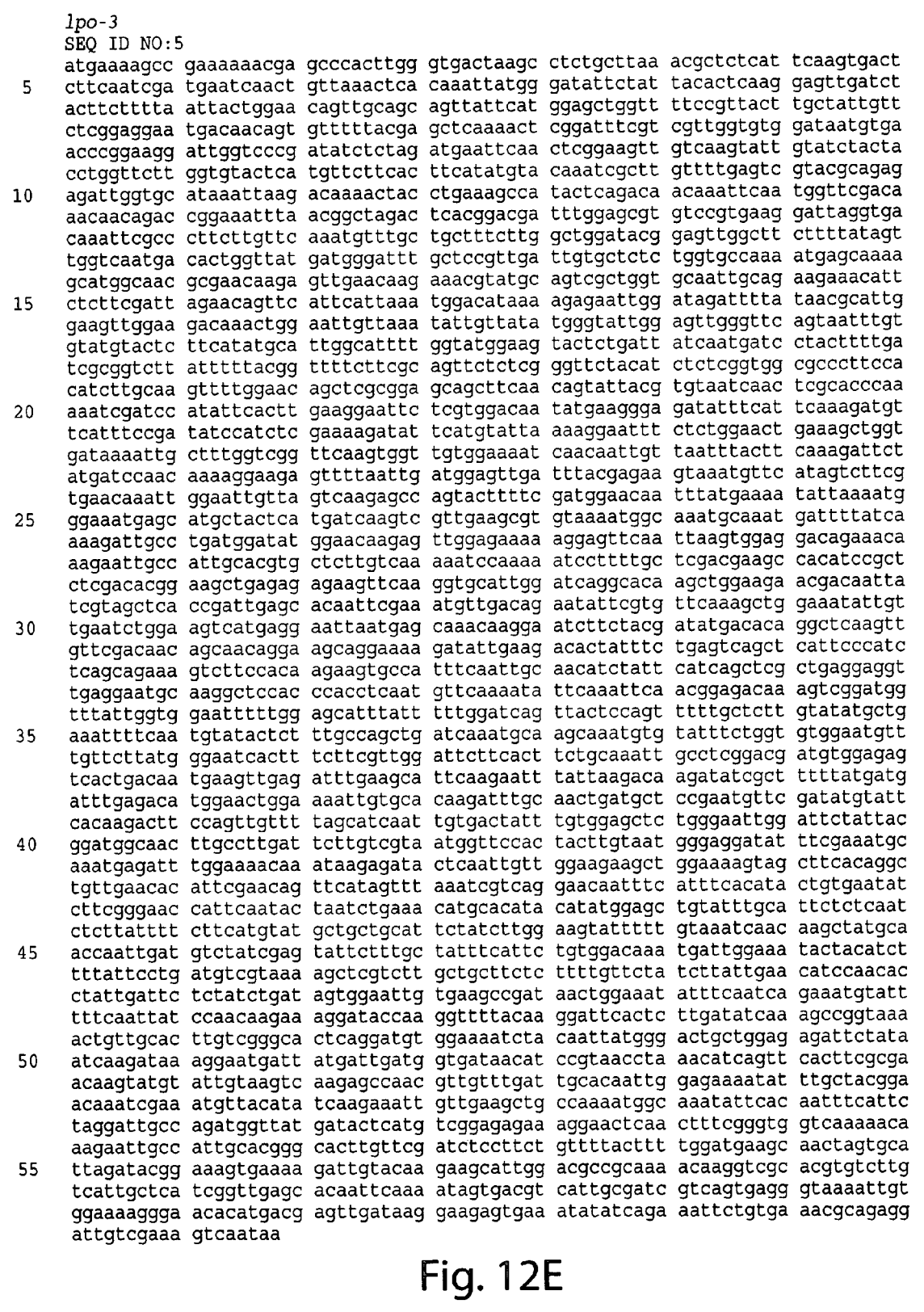

*lpo-3*
SEQ ID NO:5
atgaaaagcc gaaaaaacga gcccacttgg gtgactaagc ctctgcttaa acgctctcat tcaagtgact
cttcaatcga tgaatcaact gttaaactca caaattatgg gatattctat tacactcaag gagttgatct
acttctttta attactggaa cagttgcagc agttattcat ggagctggtt ttccgttact tgctattgtt
ctcggaggaa tgacaacagt gtttttacga gctcaaaact cggatttcgt cgttggtgtg gataatgtga
acccggaagg attggtcccg atatctctag atgaattcaa ctcggaagtt gtcaagtatt gtatctacta
cctggttctt ggtgtactca tgttcttcac ttcatatgta caaatcgctt gttttgagtc gtacgcagag
agattggtgc ataaattaag acaaaactac ctgaaagcca tactcagaca acaaattcaa tggttcgaca
aacaacagac cggaaattta acggctagac tcacggacga tttggagcgt gtccgtgaag gattaggtga
caaattcgcc cttcttgttc aaatgtttgc tgctttcttg gctggatacg gagttggctt cttttatagt
tggtcaatga cactggttat gatgggattt gctccgttga ttgtgctctc tggtgccaaa atgagcaaaa
gcatggcaac gcgaacaaga gttgaacaag aaacgtatgc agtcgctggt gcaattgcag aagaaacatt
ctcttcgatt agaacagttc attcattaaa tggacataaa agagaattgg atagatttta taacgcattg
gaagttggaa gacaaactgg aattgttaaa tattgttata tgggtattgg agttgggttc agtaatttgt
gtatgtactc ttcatatgca ttggcatttt ggtatggaag tactctgatt atcaatgatc ctacttttga
tcgcggtctt atttttacgg ttttcttcgc agttctctcg ggttctacat ctctcggtgg cgcccttcca
catcttgcaa gttttggaac agctcgcgga gcagcttcaa cagtattacg tgtaatcaac tcgcacccaa
aaatcgatcc atattcactt gaaggaattc tcgtggacaa tatgaaggga gatatttcat tcaaagatgt
tcatttccga tatccatctc gaaaagatat tcatgtatta aaaggaattt ctctggaact gaaagctggt
gataaaattg ctttggtcgg ttcaagtggt tgtggaaaat caacaattgt taatttactt caaagattct
atgatccaac aaaaggaaga gttttaattg atggagttga tttacgagaa gtaaatgttc atagtcttcg
tgaacaaatt ggaattgtta gtcaagagcc agtacttttc gatggaacaa tttatgaaaa tattaaaatg
ggaaatgagc atgctactca tgatcaagtc gttgaagcgt gtaaaatggc aaatgcaaat gattttatca
aaagattgcc tgatggatat ggaacaagag ttggagaaaa aggagttcaa ttaagtggag gacagaaaca
aagaattgcc attgcacgtg ctcttgtcaa aaatccaaaa atcctttttgc tcgacgaagc cacatccgct
ctcgacacgg aagctgagag agaagttcaa ggtgcattgg atcaggcaca agctggaaga acgacaatta
tcgtagctca ccgattgagc acaattcgaa atgttgacag aatattcgtg ttcaaagctg gaaatattgt
tgaatctgga agtcatgagg aattaatgag caaacaagga atcttctacg atatgacaca ggctcaagtt
gttcgacaac agcaacagga agcaggaaaa gatattgaag acactatttc tgagtcagct cattcccatc
tcagcagaaa gtcttccaca agaagtgcca tttcaattgc aacatctatt catcagctcg ctgaggaggt
tgaggaatgc aaggctccac ccacctcaat gttcaaaata ttcaaattca acggagacaa agtcggatgg
tttattggtg gaatttttgg agcatttatt tttggatcag ttactccagt ttttgctctt gtatatgctg
aaattttcaa tgtatactct ttgccagctg atcaaatgca agcaaatgtg tatttctggt gtggaatgtt
tgttcttatg ggaatcactt tcttcgttgg attcttcact tctgcaaatt gcctcggacg atgtggagag
tcactgacaa tgaagttgag atttgaagca ttcaagaatt tattaagaca agatatcgct tttttatgatg
atttgagaca tggaactgga aaattgtgca caagatttgc aactgatgct ccgaatgttc gatatgtatt
cacaagactt ccagttgttt tagcatcaat tgtgactatt tgtggagctc tgggaattgg attctattac
ggatggcaac ttgccttgat tcttgtcgta atggttccac tacttgtaat gggaggatat ttcgaaatgc
aaatgagatt tggaaaacaa ataagagata ctcaattgtt ggaagaagct ggaaaagtag cttcacaggc
tgttgaacac attcgaacag ttcatagttt aaatcgtcag gaacaatttc atttcacata ctgtgaatat
cttcgggaac cattcaatac taatctgaaa catgcacata catatggagc tgtatttgca ttctctcaat
ctcttatttt cttcatgtat gctgctgcat tctatcttgg aagtattttt gtaaatcaac aagctatgca
accaattgat gtctatcgag tattctttgc tatttcattc tgtggacaaa tgattggaaa tactacatct
tttattcctg atgtcgtaaa agctcgtctt gctgcttctc ttttgttcta tcttattgaa catccaacac
ctattgattc tctatctgat agtggaattg tgaagccgat aactggaaat atttcaatca gaaatgtatt
tttcaattat ccaacaagaa aggataccaa ggttttacaa ggattcactc ttgatatcaa agccggtaaa
actgttgcac ttgtcgggca ctcaggatgt ggaaaatcta caattatggg actgctggag agattctata
atcaagataa aggaatgatt atgattgatg gtgataacat ccgtaaccta aacatcagtt cacttcgcga
acaagtatgt attgtaagtc aagagccaac gttgtttgat tgcacaattg gagaaaatat ttgctacgga
acaaatcgaa atgttacata tcaagaaatt gttgaagctg ccaaaatggc aaatattcac aatttcattc
taggattgcc agatggttat gatactcatg tcggagagaa aggaactcaa ctttcgggtg gtcaaaaaca
aagaattgcc attgcacggg cacttgttcg atctccttct gttttacttt tggatgaagc aactagtgca
ttagatacgg aaagtgaaaa gattgtacaa gaagcattgg acgccgcaaa acaaggtcgc acgtgtcttg
tcattgctca tcggttgagc acaattcaaa atagtgacgt cattgcgatc gtcagtgagg gtaaaattgt
ggaaaaggga acacatgacg agttgataag gaagagtgaa atatatcaga aattctgtga aacgcagagg
attgtcgaaa gtcaataa

Fig. 12E

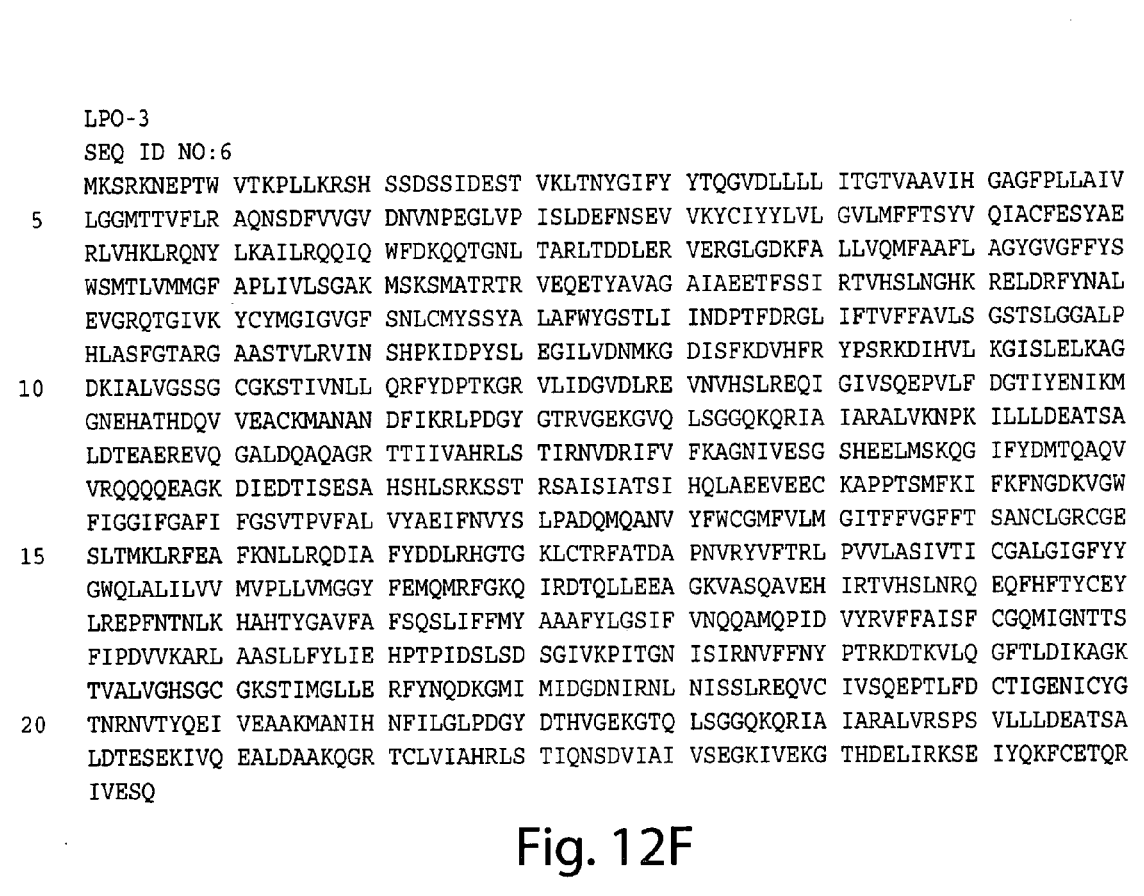

LPO-3
SEQ ID NO:6

```
MKSRKNEPTW VTKPLLKRSH SSDSSIDEST VKLTNYGIFY YTQGVDLLLL ITGTVAAVIH GAGFPLLAIV
LGGMTTVFLR AQNSDFVVGV DNVNPEGLVP ISLDEFNSEV VKYCIYYLVL GVLMFFTSYV QIACFESYAE
RLVHKLRQNY LKAILRQQIQ WFDKQQTGNL TARLTDDLER VERGLGDKFA LLVQMFAAFL AGYGVGFFYS
WSMTLVMMGF APLIVLSGAK MSKSMATRTR VEQETYAVAG AIAEETFSSI RTVHSLNGHK RELDRFYNAL
EVGRQTGIVK YCYMGIGVGF SNLCMYSSYA LAFWYGSTLI INDPTFDRGL IFTVFFAVLS GSTSLGGALP
HLASFGTARG AASTVLRVIN SHPKIDPYSL EGILVDNMKG DISFKDVHFR YPSRKDIHVL KGISLELKAG
DKIALVGSSG CGKSTIVNLL QRFYDPTKGR VLIDGVDLRE VNVHSLREQI GIVSQEPVLF DGTIYENIKM
GNEHATHDQV VEACKMANAN DFIKRLPDGY GTRVGEKGVQ LSGGQKQRIA IARALVKNPK ILLLDEATSA
LDTEAEREVQ GALDQAQAGR TTIIVAHRLS TIRNVDRIFV FKAGNIVESG SHEELMSKQG IFYDMTQAQV
VRQQQQEAGK DIEDTISESA HSHLSRKSST RSAISIATSI HQLAEEVEEC KAPPTSMFKI FKFNGDKVGW
FIGGIFGAFI FGSVTPVFAL VYAEIFNVYS LPADQMQANV YFWCGMFVLM GITFFVGFFT SANCLGRCGE
SLTMKLRFEA FKNLLRQDIA FYDDLRHGTG KLCTRFATDA PNVRYVFTRL PVVLASIVTI CGALGIGFYY
GWQLALILVV MVPLLVMGGY FEMQMRFGKQ IRDTQLLEEA GKVASQAVEH IRTVHSLNRQ EQFHFTYCEY
LREPFNTNLK HAHTYGAVFA FSQSLIFFMY AAAFYLGSIF VNQQAMQPID VYRVFFAISF CGQMIGNTTS
FIPDVVKARL AASLLFYLIE HPTPIDSLSD SGIVKPITGN ISIRNVFFNY PTRKDTKVLQ GFTLDIKAGK
TVALVGHSGC GKSTIMGLLE RFYNQDKGMI MIDGDNIRNL NISSLREQVC IVSQEPTLFD CTIGENICYG
TNRNVTYQEI VEAAKMANIH NFILGLPDGY DTHVGEKGTQ LSGGQKQRIA IARALVRSPS VLLLDEATSA
LDTESEKIVQ EALDAAKQGR TCLVIAHRLS TIQNSDVIAI VSEGKIVEKG THDELIRKSE IYQKFCETQR
IVESQ
```

Fig. 12F

```
human   MDLEGDRNGGAKKKNFFKLNNKSEKDKKEKKPTVSVFSMFRYSNWLDKLYMVVGTLAAII 60   SEQ ID NO:11
MOUSE   MEFEENLKGRADK-NFSKMGKKSKKEKKEKKPAVGVFGMFRYADWLDKLCMILGTLAAII 59   SEQ ID NO:12
LPO-3   MKSRKNEPTWVTK-PLLKRSHSSDSSIDESTVKLTNYGIFYYTQGVDLLLLITGTVAAVI 59   SEQ ID NO:6
        *. . :     . *. : * .:.*... .*..  :  :.:* *:: :* * :: **:**:*

human   HGAGLPLMMLVFGEMTDIFANAGNLEDLMSNITNRSDINDTGFFMN--LEEDMTRYAYYY 118
MOUSE   HGTLLPLLMLVFGNMTDSFTKA--EASILPSITNQSGPNSTLIISNSSLEEEMAIYAYYY 117
LPO-3   HGAGFPLLAIVLGGMTTVFLRAQ-NSDFVVGVDN-VNPEGLVPISLDEFNSEVVKYCIYY 117
        **: :**: :*:* **  * .* .  .:: .: *  . :.   :    ::.::. *. **

human   SGIGAGVLVAAYIQVSFWCLAAGRQIHKIRKQFFHAIMRQEIGWFDVHDVGELNTRLTDD 178
MOUSE   TGIGAGVLIVAYIQVSLWCLAAGRQIHKIRQKFFHAIMNQEIGWFDVHDVGELNTRLTDD 177
LPO-3   LVLGVLMFFTSYVQIACFESYAERLVHKLRQNYLKAILRQQIQWFDKQQTGNLTARLTDD 177
          :*. ::..:*:*:: :   * * :**:*:::::**:.*:* *** ::.*:*.:*****

human   VSKINEGIGDKIGMFFQSMATFFTGFIVGFTRGWKLTLVILAISPVLGLSAAVWAKILSS 238
MOUSE   VSKINDGIGDKIGMFFQSITTFLAGFIIGFISGWKLTLVILAVSPLIGLSSALWAKVLTS 237
LPO-3   LERVREGLGDKFALLVQMFAAFLAGYGVGFFYSWSMTLVMMGFAPLIVLSGAKMSKSMAT 237
        :.::.:*:***:.::.* :::*::*: :**  .*.:***::..:*:: **.*  :* :::

human   FTDKELLAYAKAGAVAEEVLAAIRTVIAFGGQKKELERYNKNLEEAKRIGIKKAITANIS 298
MOUSE   FTNKELQAYAKAGAVAEEVLAAIRTVIAFGGQQKELERYNKNLEEAKNVGIKKAITASIS 297
LPO-3   RTRVEQETYAVAGAIAEETFSSIRTVHSLNGHKRELDRFYNALEVGRQTGIVKYCYMGIG 297
         *  *  :** ***:***.:::**** ::.*:::**:*: : ** .:. ** *    .*.

human   IGAAFLLIYASYALAFWYGTTLVLSG-EYSIGQVLTVFFSVLIGAFSVGQASPSIEAFAN 357
MOUSE   IGIAYLLVYASYALAFWYGTSLVLSN-EYSIGEVLTVFFSILLGTFSIGHLAPNIEAFAN 356
LPO-3   VGFSNLCMYSSYALAFWYGSTLIINDPTFDRGLIFTVFFAVLSGGSTSLGGALPHLASFGT 357
        :* : * :*:*********::*::..  :. * ::****::* *: *:*   * : :*..

human   ARGAAYEIFKIIDNKPSIDSYSKSGHKPDNIKGNLEFRNVHFSYPSRKEVKILKGLNLKV 417
MOUSE   ARGAAFEIFKIIDNEPSIDSFSTKGYKPDSIMGNLEFKNVHFNYPSRSEVQILKGLNLKV 416
LPO-3   ARGAASTVLRVINSHPKIDPYSLEGILVDNMKGDISFKDVHFRYPSRKDIHVLKGISLEL 417
        *****  ::::*:..*.**.:* .*   *.: *::.*::*** ****.::::***:.*::

human   QSGQTVALVGNSGCGKSTTVQLMQRLYDPTEGMVSVDGQDIRTINVRFLREIIGVVSQEP 477
MOUSE   KSGQTVALVGNSGCGKSTTVQLMQRLYDPLEGVVSIDGQDIRTINVRYLREIIGVVSQEP 476
LPO-3   KAGDKIALVGSSGCGKSTIVNLLQRFYDPTKGRVLIDGVDLREVNVHSLREQIGIVSQEP 477
        ::*:.:****.******* *:*:**:*** :* :** *:* :**: *** **:*****

human   VLFATTIAENIRYGRENVTMDEIEKAVKEANAYDFIMKLPHKFDTLVGERGAQLSGGQKQ 537
MOUSE   VLFATTIAENIRYGREDVTMDEIEKAVKEANAYDFIMKLPHQFDTLVGERGAQLSGGQKQ 536
LPO-3   VLFDGTIYENIKMGNEHATHDQVVEACKMANANDFIKRLPDGYGTRVGEKGVQLSGGQKQ 537
        ***  ** ***: *.*..* *:: :* * *** *** :**. :.* ***:*.********

human   RIAIARALVRNPKILLLDEATSALDTESEAVVQVALDKARKGRTTIVIAHRLSTVRNADV 597
MOUSE   RIAIARALVRNPKILLLDEATSALDTESEAVVQAALDKAREGRTTIVIAHRLSTVRNADV 596
LPO-3   RIAIARALVKNPKILLLDEATSALDTEAEREVQGALDQAQAGRTTIIVAHRLSTIRNVDR 597
        *********:*****************:*  ** ***:*: *****::******:**.*

human   IAGFDDGVIVEKGNHDELMKEKGIYFKLVTMQTAGNEVELENAADESKSEIDALEMSSND 657
MOUSE   IAGFDGGVIVEQGNHDELMREKGIYFKLVMTQTRGNEIEPGNNAYGSQSDTDASELTSEE 656
LPO-3   IFVFKAGNIVESGSHEELMSKQGIFYDMTQAQVVRQQQQ--------EAGKDIEDTISES 649
        *  *. * ***.*.*:*** ::**::.:.  *.  :: :  . :  ::: *  :  *:.
```

Fig. 12G

```
human    SRSSLIRKRSTRRSVRGSQAQDRKLSTKEALDESIPPVSFWRIMKLNLTEWPYFVVGVFC 717
MOUSE    SKSPLIR-RSIYRSVHRKQDQERRLSMKEAVDEDVPLVSFWRILNLNLSEWPYLLVGVLC 715
LPO-3    AHSHLSRKSSTRSAIS--IATSIHQLAEEVEECKAPPTSMFKIFKFNGDKVGWFIGGIFG 707
         ::* * *. *   ::  .   . :   :*. : . * .*:::*:::*  :  ::: *::

human    AIINGGLQPAFAIIFSKIIGVFTRIDDPETKRQNSNLFSLLFLALGIISFITFFLQGFTF 777
MOUSE    AVINGCIQPVFAIVFSRIVGVFSRDDDHETKRQNCNLFSLFFLVMGLISFVTYFFQGFTF 775
LPO-3    AFIFGSVTPVFALVYAEIFNVYSLPAD--QMQANVYFWCGMFVLMGITFFVGFFTSANCL 765
         *.* * : *.**::::.*..*::   * .  : *  ::. :*: :*:  *: :* ..  :

human    GKAGEILTKRLRYMVFRSMLRQDVSWFDDPKNTTGALTTRLANDAAQVKGAIGSRLAVIT 837
MOUSE    GKAGEILTKRVRYMVFKSMLRQDISWFDDHKNSTGSLTTRLASDASSVKGAMGARLAVVT 835
LPO-3    GRCGESLTMKLRFEAFKNLLRQDIAFYDDLRHGTGKLCTRFATDAPNVR-YVFTRLPVVL 824
         *:.** ** ::*: .*:.:****::::** :: ** * **:*.**..*:. : :**.*:

human    QNIANLGTGIIISFIYGWQLTLLLLAIVPIIAIAGVVEMKMLSGQALKDKKELEGAGKIA 897
MOUSE    QNVANLGTGVILSLVYGWQLTLLLVVIIPLIVLGGIIEMKLLSGQALKDKKQLEISGKIA 895
LPO-3    ASIVTICGALGIGFYYGWQLALILVVMVPLLVMGGYFEMQMRFGKQIRDTQLLEEAGKVA 884
          .:..:  .: :.: *****:*:*:.::*::.:.* .**::  *: ::*.: ** :**:*

human    TEAIENFRTVVSLTQEQKFEHMYAQSLQVPYRNSLRKAHIFGITFSFTQAMMYFSYAGCF 957
MOUSE    TEAIENFRTIVSLTREQKFETMYAQSLQVPYRNAMKKAHVFGITFSFTQAMMYFSYAACF 955
LPO-3    SQAVEHIRTVHSLNRQEQFHFTYCEYLREPFNTNLKHAHTYGAVFAFSQSLIFFMYAAAF 944
         ::*:*::**: **.::::*.  *.: *: *:.. :::** :* .*:*:*::::* **..*

human    RFGAYLVAHKLMSFEDVLLVFSAVVFGAMAVGQVSSFAPDYAKAKISAAHIIMIIEKTPL 1017
MOUSE    RFGAYLVAQQLMTFENVMLVFSAVVFGAMAAGNTSSFAPDYAKAKVSASHIIRIIEKTPE 1015
LPO-3    YLGSIFVNQQAMQPIDVYRVFFAISFCGQMIGNTTSFIPDVVKARLAASLLFYLIEHPTP 1004
          :*: :* :: *   :*  ** *: * .   *:.:** ** .**:::*: :: :**:..

human    IDSYSTEGLMPNTLEGNVTFGEVVFNYPTRPDIPVLQGLSLEVKKGQTLALVGSSGCGKS 1077
MOUSE    IDSYSTEGLKPTLLEGNVKFNGVQFNYPTRPNIPVLQGLSLEVKKGQTLALVGSSGCGKS 1075
LPO-3    IDSLSDSGIVK-PITGNISIRNVFFNYPTRKDTKVLQGFTLDIKAGKTVALVGHSGCGKS 1063
         *** * .*:  . : **:.: * ****** :  ****::*::* *:*:**** ******

human    TVVQLLERFYDPLAGKVLLDGKEIKRLNVQWLRAHLGIVSQEPILFDCSIAENIAYGDNS 1137
MOUSE    TVVQLLERFYDPMAGSVFLDGKEIKQLNVQWLRAHLGIVSQEPILFDCSIAENIAYGDNS 1135
LPO-3    TIMGLLERFYNQDKGMIMIDGDNIRNLNISSLREQVCIVSQEPTLFDCTIGENICYGTN- 1122
         *:: ******:   * :::**.:*:.**:. ** :: ****** ****:*.***.** *:

human    RVVSQEEIVRAAKEANIHAFIESLPNKYSTKVGDKGTQLSGGQKQRIAIARALVRQPHIL 1197
MOUSE    RAVSHEEIVRAAKEANIHQFIDSLPDKYNTRVGDKGTQLSGGQKQRIAIARALVRQPHIL 1195
LPO-3    RNVTYQEIVEAAKMANIHNFILGLPDGYDTHVGEKGTQLSGGQKQRIAIARALVRSPSVL 1182
         * *: :***.*** **** ** .**: *.*:**:*********************.* :*

human    LLDEATSALDTESEKVVQEALDKAREGRTCIVIAHRLSTIQNADLIVVFQNGRVKEHGTH 1257
MOUSE    LLDEATSALDTESEKVVQEALDKAREGRTCIVIAHRLSTIQNADLIVVIENGKVKEHGTH 1255
LPO-3    LLDEATSALDTESEKIVQEALDAAKQGRTCLVIAHRLSTIQNSDVIAIVSEGKIVEKGTH 1242
         ***************:****** *::****:***********:*:*.:..:*:: *:***

human    QQLLAQKGIYFSMVSVQAGTKRQ 1280
MOUSE    QQLLAQKGIYFSMV--QAGAKRS 1276
LPO-3    DELIRKSEIYQKFCETQRIVESQ 1265
         ::*: :.
```

Fig. 12G Cont.

SEQUENCE LISTING

```
<160> NUMBER OF SEQ ID NOS: 12

<210> SEQ ID NO 1
<211> LENGTH: 5570
<212> TYPE: DNA
<213> ORGANISM: Caenorhabditis elegans

<400> SEQUENCE: 1

agcctgttgc ctctgtcgaa gccgttttgt ctctctctcg tcgtcgtcga cccacccggc      60

ctcccatgta gtgttcgttt tgcgctctat cgcacacaca cactctcggt aaacaacgac     120

cacctcactc catctctatc cattctatcc tcttccatct ctacaggcca acggagacag     180

ttcgttggac ccccgcgcac tctacctatc tgttcaacgc tccatatgtg caaagtctca     240
```

-continued

```
gtcatttttc ctcctgcttc ttcttctttt tattattaac tttttctcat cttatttctt    300
ccactctttc gagagaccac tccgcccact tttcgttact gctttatcaa acaaactgtg    360
cgtccacacc aattctctat ttcccttcgt ctgctccgtt ttcgctcact tttttgttaa    420
ctatcttttc ttttttcttt taacatgttt attgatcctc accactgatc aattaatatt    480
tattatttat ttctgtttcc agatcaccta cgaaaaatat taattgataa tcagaggagt    540
aaaaatgagg acatgtctca ccctcacggg tttccttctg atttcaatgg ccaccatttc    600
ggtgggcctc caaccgatgg gagcacctac aagaagtatg ttttcttttt catttaaata    660
tcacatagta attcaattga aaatcaatgc atttcggaat ttcgcaacat tacttttgtt    720
tggaccgttg agtcaccaat agatcaccta cgaaaaatat taattgataa tcagaggagt    780
aaaaatgagg acatgtctca ccctcacggg tttccttctg atttcaatgg ccaccatttc    840
ggtgggcctc caaccgatgg gagcacctac aagaagtatg ttttcttttt catttaaata    900
tcacatagta attcaattga aaatcaatgc atttcggaat ttcgcaacat tacttttgtt    960
tggaccgttg agtcaccaat atcacgagat aataattttt tgcaacaatg caatttgttt   1020
tcagaatgcg acgcaacaaa ttcgttccag tgtcaagatg gccgatgcat accgatgtcg   1080
tggcgttgtg atggagatat cgactgccag aatgaagaag atgagaaaaa ttgtccaagt   1140
aaaactcttt ttcctaaaaa aacaatgata atttcaatga tagtttcaga agtttgtggc   1200
gccgaagaac acaaatgcgg agaagtcaaa tctgctcgat catcgttgga aagattcaag   1260
tgcattccga acaaatgggt gtgtgatgga gaattcgact gtgaagataa atcggacgaa   1320
ttccaatgca aaagtatgtt caattgaatt caagacagtt ttcctgcaat ttttcaatct   1380
tttcagacgt atcatgccaa gaaaaacagt ttcaatgtga agaactctct ggtgattata   1440
gtttgtgcat tcctgaaaca tgggtttgcg atggtcaaag agactgtacg aatggcaaag   1500
acgaacagaa ttgcacgtca aaaacgtcta aatgtccgga taacaacttc cagtaagtct   1560
ccatacaaat cttatcgcaa ttaaatctat cccgttgacc taattgtacc actctgacaa   1620
aattgagaaa aaagtgtttc atttttcagg tgtagcaatg gaaattgtat tttcaaaaac   1680
tgggtttgtg atggggaaga agattgctca gatggctcag atgaattgct cactgctcca   1740
tccaattgta accgaacagt taatcaatgc cctcccggag aaatgtggaa ggtatgagtg   1800
tttacggatc ttgagaaaat gtttatgcgc agcatgttga aatatttgtt tgtttctcga   1860
ttgtttagag ggtcaaagta tcgagtgttg gctatgctag tgtcaaacca actgataata   1920
agtaaaatat attatattga taattcattt aatatctatt tgtctcataa tatagacttt   1980
attaaataca taatacatac tagaaaagaa aaataattca ataagctgga gtaagaaatt   2040
atcattttca gtcttttctt tgtcaattga ttgtgtattg cagtcgattg ttatctgtta   2100
gtgaccattt ctccccgca atcacgtctg ggaaattgat atgtatttct gaattaaaca   2160
attaaatttt cagtgtggat ccggtgaatg cattccatca agatggcgat gcgacgcaga   2220
agtcgattgc aaagatcatt ccgatgagaa gaattgtact gctattcaac acacgtgcaa   2280
gttagcagag gtaggatggg ggcaatatgc acctgcttga tgctaatgca acatggtcat   2340
taaaatatta gatgtcaccc atattagata ggctaattgg gttttaaatc attaaatgat   2400
gagaaattta acaacccaat tatagttcca aaatgcaata acttcaggaa ttcgcttgta   2460
aagcttcaca caactgcatc aacaaggctt tcgtatgtga tggagaactt gattgttccg   2520
atggatccga cgaagatgat tgtgctgacg ttcggaccga gtgtaaatcc ggagagcgta   2580
```

-continued

```
cctgcccagc ttcatacggt gcatatggcg ccgagtcagg tcacgttgtg tgtattcctg   2640
catcgtcatg gtgcaatgga gaagaggatt gtccagatgg tggtgatgag aaagaatgta   2700
atatgactgc tcctggtaag taatattagc aaaagtgctt gaaatatatt cgttatattt   2760
tcagtcacat gccagaaagg aaccgaatat gaatgtccat ctactccatt gcaatgtatt   2820
gaaatgtcaa aattgtgtgc tagtgctcaa tttgattgtg gggatggaaa tatgtctgtt   2880
tgtagccaga aaaagatcat tggtaatata aatatttatt tatggtctgg caaaatgctc   2940
ttcaattaca gaaatgtgca aaccaagttc agaaggatgt gtctgccgtc catcgtttgt   3000
ccgaggaaat aatgtttgtc actgtaaaga tggttacaaa ctcgaaaacg gacagtgcat   3060
tggtgagtaa ttgttagcaa gagagatggt ttagcgagaa aacaaatagt gaaaaagaca   3120
aagagatcct catcaaaatg tagaaaaata gttgagatgc gaagcgagca gctgaacaat   3180
cagcaatatg aaaacacagg aagtattttc taataacgaa atgtttattt ttcagatatt   3240
aacgaatgtg aaattgctgg cgtttgtgat caaatttgtc tcaatattcc cggttcctat   3300
cgttgtgctt gtcatgctgg atatcagatt agtttcggag atactaaaat tggatcagga   3360
agaattgcta acaaatgtcg tgctatggga ggtgatccat tggttcttct taccaacaga   3420
catacgatca gacaatttga tcttgtcaat aaaatgcact tccctgtttc cagtagtcct   3480
ggttctgcgg ttgccatgga tttccacatc ttgaacgggg tgagttgaat tttttattac   3540
ggattgttat tatttacttg agaagaatac caaaaaatct gattttaata taattttttc   3600
agacactgat ttggtctgac gtgttgtcaa agcaaattct gaaatgttcg attggaaacg   3660
tgtcaaacgc atttttggga accgatatgt gcgataagaa gcatgaaatc gttctcacag   3720
gagacaagat tcatactcca gatggacttg cagttgattg ggttcatgat ctccttttct   3780
ggacagatgg aggccttgat caaattaatg ttctcgatat gaaaaatgga aagcagcgtg   3840
tcctttattc ttccgacttg gaagaaccga gagctattgc agttgatcct gaagttggac   3900
tcattttctg gactgattgg ggaaagaagg cgagaatcga aagatctgga atggatggac   3960
aacatcgtac tgttattgtt gagggagatc gtgttgtatg gccgaatgga ttggctttgg   4020
attatgttga taagcgtgtc tattggctga tgccaagatc aagtcaatct tcagttgtga   4080
ttattggggc aaaaatatca agaccgtatt gcattctcat caatatctaa ggcatccatt   4140
ctcaatggct gttttcgaag accgactctt ctacacagat tgggagcatg atggtgttat   4200
cactgttaac aaggtatgtt ttttaaaatg aaattttaac ttggaaaact ggtttttaaa   4260
aacgaaattc gctgaaaatt cgctggaacc atgaaacttt gaatattgaa gacaatttta   4320
atgaaaattg tctacacgaa atgaatttag attaaaaaag attgctaata attttttttg   4380
taaatcaatc gcgctttcaa cttacgaaat atttttcagt tcactggagc tgatattcgt   4440
actgttatgg atcaagtgaa gtctccaatg actgtacgca tctaccacaa acaagcacaa   4500
ccacttatgc agaacaagtg tgaaaactcg gaatgtgatc atctctgcct gccgagagcc   4560
gtttaccgtg agaaagaacg tgttcatgaa aaaacttggc acgacagacc gttctcgtgt   4620
gcatgcgaag gaacgactgc ttctgatgtt ctggaatgtt tcggtaggac aatcaattag   4680
gtatttagat acttaacgtt tttaagtttc agctgacttg gaaacaaaat ccggaatctc   4740
gatgttcacg attttccttc ttttatgtgt tggtggagtt gtggccgctg gatttgtgat   4800
tgttcgtcgg aagatgggac ctcgtacatt taccgctctc aattttgaca atccaattta   4860
tcgtcgaacc accgaagaag ctgatcatca gatggaagat ccattccgtg atccttttgc   4920
tgaaccacgg aatggaagag ggcgtaacga tggattacca actcttgcat ctgctgacaa   4980
```

-continued

```
tgaaacacgg gctgacgcat tgagcttctg agccaattcg tattgtaaag tatatatttt   5040

cctataaatt tatttgcacc cttcccttat tgtacagatt gcccattttc tcttctcatt   5100

tcatgtcact tttaaattgt gttctttcct ttctgttctt gtgaaaattt tatattttgt   5160

ttcatcaatt tcccattctt gatttttcat gtgcaattga ctcaaatctg agaaatcact   5220

gtgaagacgt gtagatccaa actgtgaaaa tttccaaaaa tcctccaaat tttgcgtgtt   5280

tatctattcc gaatggtttg gatagtattt tgcatcgagt ctagatttca tgtattcatt   5340

gctttcatta ttctcattgc tatatcatta ttttctgtgt gctccatcca attcacccgg   5400

ttatcgagct ttttccaaat gtttttatgt agtatttcct cgtttttttct actctgaagc   5460

tggtaatttt gagttttcct gactgtcgac ccccgagaac tgatgcatat acccttgtct   5520

atctgcccct tcccctcccc ttcctctcat caacggattt attcaataaa              5570
```

<210> SEQ ID NO 2
<211> LENGTH: 2592
<212> TYPE: DNA
<213> ORGANISM: Caenorhabditis elegans

<400> SEQUENCE: 2

```
atgaggacat gtctcaccct cacgggtttc cttctgattt caatggccac catttcggtg     60

ggcctccaac cgatgggagc acctacaaga aaatgcgacg caacaaattc gttccagtgt    120

caagatggcc gatgcatacc gatgtcgtgg cgttgtgatg gagatatcga ctgccagaat    180

gaagaagatg agaaaaattg tccaaaagtt tgtggcgccg aagaacacaa atgcggagaa    240

gtcaaatctg ctcgatcatc gttggaaaga ttcaagtgca ttccgaacaa atgggtgtgt    300

gatggagaat tcgactgtga agataaatcg gacgaattcc aatgcaaaaa cgtatcatgc    360

caagaaaaac agtttcaatg tgaagaactc tctggtgatt atagtttgtg cattcctgaa    420

acatgggttt gcgatggtca aagagactgt acgaatggca aagacgaaca gaattgcacg    480

tcaaaaacgt ctaaatgtcc ggataacaac ttccagtgta gcaatggaaa ttgtattttc    540

aaaaactggg tttgtgatgg ggaagaagat tgctcagatg gctcagatga attgctcact    600

gctccatcca attgtaaccg aacagttaat caatgccctc ccggagaaat gtggaagtgt    660

ggatccggtg aatgcattcc atcaagatgg cgatgcgacg cagaagtcga ttgcaaagat    720

cattccgatg agaagaattg tactgctatt caacacacgt gcaagttagc agaggaattc    780

gcttgtaaag cttcacacaa ctgcatcaac aaggctttcg tatgtgatgg agaacttgat    840

tgttccgatg gatccgacga agatgattgt gctgacgttc ggaccgagtg taaatccgga    900

gagcgtacct gcccagcttc atacggtgca tatggcgccg agtcaggtca cgttgtgtgt    960

attcctgcat cgtcatggtg caatggagaa gaggattgtc cagatggtgg tgatgagaaa   1020

gaatgtaata tgactgctcc tgtcacatgc cagaaaggaa ccgaatatga atgtccatct   1080

actccattgc aatgtattga aatgtcaaaa ttgtgtgcta gtgctcaatt tgattgtggg   1140

gatggaaata tgtctgtttg tagccagaaa aagatcattg aaatgtgcaa accaagttca   1200

gaaggatgtg tctgccgtcc atcgtttgtc cgaggaaata atgtttgtca ctgtaaagat   1260

ggttacaaac tcgaaaacgg acagtgcatt gatattaacg aatgtgaaat tgctggcgtt   1320

tgtgatcaaa tttgtctcaa tattcccggt tcctatcgtt gtgcttgtca tgctggatat   1380

cagattagtt tcggagatac taaaattgga tcaggaagaa ttgctaacaa atgtcgtgct   1440

atgggaggtg atccattggt tcttcttacc aacagacata cgatcagaca atttgatctt   1500
```

-continued

```
gtcaataaaa tgcacttccc tgtttccagt agtcctggtt ctgcggttgc catggatttc   1560

cacatcttga acgggacact gatttggtct gacgtgttgt caaagcaaat tctgaaatgt   1620

tcgattggaa acgtgtcaaa cgcatttttg ggaaccgata tgtgcgataa gaagcatgaa   1680

atcgttctca caggagacaa gattcatact ccagatggac ttgcagttga ttgggttcat   1740

gatctccttt tctggacaga tggaggcctt gatcaaatta atgttctcga tatgaaaaat   1800

ggaaagcagc gtgtccttta ttcttccgac ttggaagaac cgagagctat tgcagttgat   1860

cctgaagttg gactcatttt ctggactgat tggggaaaga aggcgagaat cgaaagatct   1920

ggaatggatg gacaacatcg tactgttatt gttgagggag atcgtgttgt atggccgaat   1980

ggattggctt tggattatgt tgataagcgt gtctattggc tgatgccaag atcaagtcaa   2040

tcttcagttt tcactggagc tgatattcgt actgttatgg atcaagtgaa gtctccaatg   2100

actgtacgca tctaccacaa acaagcacaa ccacttatgc agaacaagtg tgaaaactcg   2160

gaatgtgatc atctctgcct gccgagagcc gtttaccgtg agaaagaacg tgttcatgaa   2220

aaaacttggc acgacagacc gttctcgtgt gcatgcgaag gaacgactgc ttctgatgtt   2280

ctggaatgtt tcgctgactt ggaaacaaaa tccggaatct cgatgttcac gattttcctt   2340

cttttatgtg ttggtggagt tgtggccgct ggatttgtga ttgttcgtcg gaagatggga   2400

cctcgtacat ttaccgctct caattttgac aatccaattt atcgtcgaac caccgaagaa   2460

gctgatcatc agatggaaga tccattccgt gatccttttg ctgaaccacg gaatggaaga   2520

gggcgtaacg atggattacc aactcttgca tctgctgaca atgaaacacg ggctgacgca   2580

ttgagcttct ga                                                       2592
```

<210> SEQ ID NO 3
<211> LENGTH: 863
<212> TYPE: PRT
<213> ORGANISM: Caenorhabditis elegans

<400> SEQUENCE: 3

```
Met Arg Thr Cys Leu Thr Leu Thr Gly Phe Leu Leu Ile Ser Met Ala
 1               5                   10                  15

Thr Ile Ser Val Gly Leu Gln Pro Met Gly Ala Pro Thr Arg Lys Cys
            20                  25                  30

Asp Ala Thr Asn Ser Phe Gln Cys Gln Asp Gly Arg Cys Ile Pro Met
        35                  40                  45

Ser Trp Arg Cys Asp Gly Asp Ile Asp Cys Gln Asn Glu Glu Asp Glu
    50                  55                  60

Lys Asn Cys Pro Lys Val Cys Gly Ala Glu Glu His Lys Cys Gly Glu
65                  70                  75                  80

Val Lys Ser Ala Arg Ser Ser Leu Glu Arg Phe Lys Cys Ile Pro Asn
                85                  90                  95

Lys Trp Val Cys Asp Gly Glu Phe Asp Cys Glu Asp Lys Ser Asp Glu
            100                 105                 110

Phe Gln Cys Lys Asn Val Ser Cys Gln Glu Lys Gln Phe Gln Cys Glu
        115                 120                 125

Glu Leu Ser Gly Asp Tyr Ser Leu Cys Ile Pro Glu Thr Trp Val Cys
    130                 135                 140

Asp Gly Gln Arg Asp Cys Thr Asn Gly Lys Asp Glu Gln Asn Cys Thr
145                 150                 155                 160

Ser Lys Thr Ser Lys Cys Pro Asp Asn Asn Phe Gln Cys Ser Asn Gly
                165                 170                 175
```

-continued

```
Asn Cys Ile Phe Lys Asn Trp Val Cys Asp Gly Glu Glu Asp Cys Ser
            180                 185                 190

Asp Gly Ser Asp Glu Leu Leu Thr Ala Pro Ser Asn Cys Asn Arg Thr
        195                 200                 205

Val Asn Gln Cys Pro Pro Gly Glu Met Trp Lys Cys Gly Ser Gly Glu
    210                 215                 220

Cys Ile Pro Ser Arg Trp Arg Cys Asp Ala Glu Val Asp Cys Lys Asp
225                 230                 235                 240

His Ser Asp Glu Lys Asn Cys Thr Ala Ile Gln His Thr Cys Lys Leu
                245                 250                 255

Ala Glu Glu Phe Ala Cys Lys Ala Ser His Asn Cys Ile Asn Lys Ala
            260                 265                 270

Phe Val Cys Asp Gly Glu Leu Asp Cys Ser Asp Gly Ser Asp Glu Asp
        275                 280                 285

Asp Cys Ala Asp Val Arg Thr Glu Cys Lys Ser Gly Glu Arg Thr Cys
    290                 295                 300

Pro Ala Ser Tyr Gly Ala Tyr Gly Ala Glu Ser Gly His Val Val Cys
305                 310                 315                 320

Ile Pro Ala Ser Ser Trp Cys Asn Gly Glu Glu Asp Cys Pro Asp Gly
                325                 330                 335

Gly Asp Glu Lys Glu Cys Asn Met Thr Ala Pro Val Thr Cys Gln Lys
            340                 345                 350

Gly Thr Glu Tyr Glu Cys Pro Ser Thr Pro Leu Gln Cys Ile Glu Met
        355                 360                 365

Ser Lys Leu Cys Ala Ser Ala Gln Phe Asp Cys Gly Asp Gly Asn Met
    370                 375                 380

Ser Val Cys Ser Gln Lys Lys Ile Ile Glu Met Cys Lys Pro Ser Ser
385                 390                 395                 400

Glu Gly Cys Val Cys Arg Pro Ser Phe Val Arg Gly Asn Asn Val Cys
                405                 410                 415

His Cys Lys Asp Gly Tyr Lys Leu Glu Asn Gly Gln Cys Ile Asp Ile
            420                 425                 430

Asn Glu Cys Glu Ile Ala Gly Val Cys Asp Gln Ile Cys Leu Asn Ile
        435                 440                 445

Pro Gly Ser Tyr Arg Cys Ala Cys His Ala Gly Tyr Gln Ile Ser Phe
    450                 455                 460

Gly Asp Thr Lys Ile Gly Ser Gly Arg Ile Ala Asn Lys Cys Arg Ala
465                 470                 475                 480

Met Gly Gly Asp Pro Leu Val Leu Leu Thr Asn Arg His Thr Ile Arg
                485                 490                 495

Gln Phe Asp Leu Val Asn Lys Met His Phe Pro Val Ser Ser Ser Pro
            500                 505                 510

Gly Ser Ala Val Ala Met Asp Phe His Ile Leu Asn Gly Thr Leu Ile
        515                 520                 525

Trp Ser Asp Val Leu Ser Lys Gln Ile Leu Lys Cys Ser Ile Gly Asn
    530                 535                 540

Val Ser Asn Ala Phe Leu Gly Thr Asp Met Cys Asp Lys Lys His Glu
545                 550                 555                 560

Ile Val Leu Thr Gly Asp Lys Ile His Thr Pro Asp Gly Leu Ala Val
                565                 570                 575

Asp Trp Val His Asp Leu Leu Phe Trp Thr Asp Gly Gly Leu Asp Gln
            580                 585                 590

Ile Asn Val Leu Asp Met Lys Asn Gly Lys Gln Arg Val Leu Tyr Ser
```

-continued

```
        595                 600                 605

Ser Asp Leu Glu Glu Pro Arg Ala Ile Ala Val Asp Pro Glu Val Gly
    610                 615                 620

Leu Ile Phe Trp Thr Asp Trp Gly Lys Lys Ala Arg Ile Glu Arg Ser
625                 630                 635                 640

Gly Met Asp Gly Gln His Arg Thr Val Ile Val Glu Gly Asp Arg Val
                645                 650                 655

Val Trp Pro Asn Gly Leu Ala Leu Asp Tyr Val Asp Lys Arg Val Tyr
            660                 665                 670

Trp Leu Met Pro Arg Ser Ser Gln Ser Ser Val Phe Thr Gly Ala Asp
        675                 680                 685

Ile Arg Thr Val Met Asp Gln Val Lys Ser Pro Met Thr Val Arg Ile
    690                 695                 700

Tyr His Lys Gln Ala Gln Pro Leu Met Gln Asn Lys Cys Glu Asn Ser
705                 710                 715                 720

Glu Cys Asp His Leu Cys Leu Pro Arg Ala Val Tyr Arg Glu Lys Glu
                725                 730                 735

Arg Val His Glu Lys Thr Trp His Asp Arg Pro Phe Ser Cys Ala Cys
            740                 745                 750

Glu Gly Thr Thr Ala Ser Asp Val Leu Glu Cys Phe Ala Asp Leu Glu
        755                 760                 765

Thr Lys Ser Gly Ile Ser Met Phe Thr Ile Phe Leu Leu Leu Cys Val
    770                 775                 780

Gly Gly Val Val Ala Ala Gly Phe Val Ile Val Arg Arg Lys Met Gly
785                 790                 795                 800

Pro Arg Thr Phe Thr Ala Leu Asn Phe Asp Asn Pro Ile Tyr Arg Arg
                805                 810                 815

Thr Thr Glu Glu Ala Asp His Gln Met Glu Asp Pro Phe Arg Asp Pro
            820                 825                 830

Phe Ala Glu Pro Arg Asn Gly Arg Gly Arg Asn Asp Gly Leu Pro Thr
        835                 840                 845

Leu Ala Ser Ala Asp Asn Glu Thr Arg Ala Asp Ala Leu Ser Phe
    850                 855                 860


<210> SEQ ID NO 4
<211> LENGTH: 7495
<212> TYPE: DNA
<213> ORGANISM: Caenorhabditis elegans

<400> SEQUENCE: 4

tctccacttt caactggtca gagacgtcgt ctttaacatc ttccccgtcg tcttccgcct     60

aaaaaagtgc gaaaagaaac atcaacagaa aacaatgaat tgatcactac aattatataa    120

atttgctttt cttcctatca catatcactt cgtctgtctg cgtctctatc actttattat    180

cttcaatatc ccacattatc tcggttggcc tggaaacctt tcagtcgttg tttcttaaaa    240

ctattcatcg tcagcaacct cgtcatctta aaaaattaga aaaattggaa gaaaaaagag    300

aaataaaaaa ggggtggagc ctagacacct tcaacacata tttttaatta aagacgccct    360

tttttcggaa gacctttctc tccgctttcc ccccattatt ttctattatt atctaactga    420

tgaaaagccg aaaaaacgag cccacttggg tgactaagcc tctgcttaaa cggtatgagt    480

tgtcaagaga ttctctgaaa aaaacctaaa atttttgaat attcaaaaca gataatttca    540

gattctagta atttgtgata attccaaaat aaaaaatata aacattttac agctctcatt    600

caagtgactc ttcaatcgat gaatcaactg ttaaactcac aaattatggg atattctatt    660
```

-continued

```
acactcaagg agttgatcta cttcttttaa ttactggaac agttgcagca gttattcatg    720
gagctggttt tccgttactt gctattggta tgtggtttta ttttttaatt tgaatgataa    780
atcaaaagct gaaattatca tttgaaacgt caactacata taattttata aaatgttatt    840
atgagaactc atagtcagaa ttaatttttt ttttgaaaaa tttagtaaac tctaatctac    900
gttcaacatt cacaaaatga cctccgatat cgtcatccaa tccaataaac tactgcgact    960
acccattaac ttaattagat caaaatgttc atgacatcat ttgaactaga gaaaaaaagt   1020
gatttgtgtt gtggttttga actatggaat tggaggcttt ttatattctt caaaaaagga   1080
aaatgtgtta agttgaaatt tatcagctcc ttaaaacaaa ttcgaaatac atgagatatc   1140
ataggctgaa aattgtgata tttaataatt gcattaggtt gtatttaaaa atttaaaaaa   1200
tacactaact aagaagtcga acagattcaa atatcataac taaacaatca aaaaatttct   1260
atagaaaatg tggacttttt gagaattttg agaatttttg cgggtttgaa gtcaagtttc   1320
cgaaaacaaa ataattaaaa tataaaactc gtagaatatg tatttttagt tgacttccaa   1380
aattatgata aatcaaaaat aagggattgg cactttttcg actgttgata agaaatttca   1440
aataatgttt gaaaatttac attttggtca tttaaaaatg ttatacaaat gagtggtttt   1500
aaataacttt ctccattaac gaacattctt ggccccgcag taaaatcaat tagatagtta   1560
aaagcagaaa cgatgatttc aaagttctcg tatttgcagt tctcggagga atgacaacag   1620
tgtttttacg agctcaaaac tcggatttcg tcgttggtgt ggataatgtg aacccggaag   1680
gattggtccc gatatctctg tacgtttttt ttagaacttt gacttttact ttttatgatc   1740
ctgcaaattt ttgtatttgt atctttttga ctagtcaatc tgcgcgaaat gataaggcta   1800
tccaaaacag ctggtgtgtc ttttgacacc ttttctagtt ccttgtgaat gaacacataa   1860
atattatatt acacttttg attaaacaaa aaaccttcca atctgttttc ttttttagag   1920
atgaattcaa ctcggaagtt gtcaagtatt gtatctacta cctggttctt ggtgtactca   1980
tgttcttcac ttcatatgta caaatcgctt gttttgagtc gtacgcagag agattggtgc   2040
ataaattaag acaaaactac ctgaaagcca tactcagaca acaaattcaa tggttcgaca   2100
aacaacagac cggaaattta acggctagac tcacggagta agttaagaag tacatttttt   2160
gaagaatgat agagaagtga gacatgttat atacatataa tgagcttttg ccgttcgtca   2220
aatttttcta gaaattcatc taaattcccg gaagatcact aaagatattg caaataataa   2280
atcatcgtta atctttttat tgcagcgatt tggagcgtgt ccgtgaagga ttaggtgaca   2340
aattcgccct tcttgttcaa atgtttgctg ctttcttggc tggatacgga gttggcttct   2400
tttatagttg gtcaatgaca ctggttatga tgggatttgc tccgttgatt gtgctctctg   2460
gtgccaaaat gagcaaaagc atggcaacgc gaacaagagt tgaacaagaa acgtatgcag   2520
tcgctggtgc aattgcagaa gaaacattct cttcgattag aacagttcat tcattaaatg   2580
gacataaaag agaattggat agattttata acgcattgga agttggaaga caaactggaa   2640
ttgttaaata ttgttatatg ggtattggag ttgggttcag taatttgtgt atgtactctt   2700
catatgcatt ggcattttgg tatggaagta ctctgattat caatgatcct acttttgatc   2760
gcggtcttat ttttacggtt agtcattttt caattcaaaa attcatgctt ataaagcagt   2820
catttaaaat attaaagaga gagtaccgtt tctgtcccca aactcaaaat gtcttcaaaa   2880
tttttattga aaaagggctt gattttaagc tacaatctcc attttttgca agtattaatt   2940
tcttattatt aaaaacaagt gaacaattct aattttcagg ttttcttcgc agttctctcg   3000
```

-continued

```
ggttctacat ctctcggtgg cgcccttcca catcttgcaa gttttggaac agctcgcgga   3060
gcagcttcaa cagtattacg tgtaatcaac tcgcacccaa aaatcgatcc atattcactt   3120
gaaggaattc tcgtggacaa tatgaaggga gatatttcat tcaaagatgt tcatttccga   3180
tatccatctc gaaaagatat tcatgtatta aaaggaattt ctctggaact gaaagctggt   3240
gataaaattg ctttggtcgg ttcaagtggt tgtggaaaat caacaattgt taatttactt   3300
caaagattct atgatccaac aaaaggaaga gttttaattg atggagttga tttacgagaa   3360
gtaaatgttc atagtcttcg tgaacaaatt ggaattgtta gtcaagagcc agtacttttc   3420
gatggaacaa tttatgaaaa tattaaaatg ggaaatgagc atgctactca tgatcaagtc   3480
gttgaagcgt gtaaaatggc aaatgcaaat gattttatca aaagattgcc tgatggatat   3540
ggaacaagag ttggagaaaa aggagttcaa ttaagtggag gacagaaaca aagaattggt   3600
tagttattca gttgaaacat ctaaaattgg aaaagatcct ttagaagttc actcgaaatt   3660
caaaaatacg aaagtcatcg tttaaattta aaaaaaaatt atacatttac atatatttca   3720
tattccagcc attgcacgtg ctcttgtcaa aaatccaaaa atccttttgc tcgacgaagc   3780
cacatccgct ctcgacacgg aagctgagag agaagttcaa ggtgcattgg atcaggcaca   3840
agctggaaga acgacaatta tcgtagctca ccgattgagc acaattcgaa atgttgacag   3900
aatattcgtg ttcaaagctg gaaatattgt tgaatctgga agtcatgagg aattaatgag   3960
caaacaagga atcttctacg atatgacaca ggctcaagtt gttcgacaac agcaacagga   4020
agcaggaaaa ggtaattcta atgtttaagg aaaactaata tagattaaat ttcagatatt   4080
gaagacacta tttctgagtc agctcattcc catctcagca gaaagtcttc cacaagaagt   4140
gccatttcaa ttgcaacatc tattcatcag ctcgctgagg aggttgaggt acgaaaataa   4200
ttacttattt cttttggttt ttgaaggtgg agtatcgtca gtggggattt actacatgca   4260
taatagtcac acttgaccaa atataaaacc tctacaaatt tttagatatt ccattttgag   4320
attaagagag ttttgataaa ttggcaaatg tttgaaaaat tgggcttttc aaagaaattt   4380
aagcaatgcc gcatgttcga tcttctacaa cggttatata caaattatca aaaaacacaa   4440
ttaaaatgtg aaactggtag agaaaaaatt tttagtcgac ttccaaaatt atgagttgcg   4500
aaacctgagg aatttcaact tattgactgt aaaaaattaa tataattttt gaaaattttt   4560
aaaaagctat tcagatattt gaccataata tgtaggtgta attctcttac tggcgctact   4620
ccatccttta aaaaataata ttcaaaaatg tgttctttaa ctgaaatcca tttcaactca   4680
aatccaaaac aattatagtt attcccaaaa tattccagct aattgaccca ttcaatggtc   4740
aaacgaatca agatgtgata agatctcgta ttttatcagc atttgggggt gtaagtgata   4800
gatgaatata ttcggttttc aatgtttcat ttcaacttct ctcctttctc tgattcttcc   4860
ttacattttc ttcaaacacg gcttcttcta agtacttatc agcatgcttt tatattgttt   4920
ttttggttca atgatcaatt ttttttaaat ttttcctaat ttaacaaaat aactttcagg   4980
aatgcaaggc tccacccacc tcaatgttca aaatattcaa attcaacgga gacaaagtcg   5040
gatggtttat tggtggaatt tttggagcat ttatttttgg atcagttact ccagtttttg   5100
ctcttgtata tgctgaaatt ttcaatgtaa ttttttagaa atattaaagt agaagtaaaa   5160
ctgtacattt ttcaggtata ctctttgcca gctgatcaaa tgcaagcaaa tgtgtatttc   5220
tggtgtggaa tgtttgttct tatgggaatc actttcttcg ttggattctt cacttctgca   5280
aattgcctcg gacgatgtgg agagtcactg acaatgaagt tgagatttga agcattcaag   5340
aatttattaa gacaagatat cgctttttat gatgatttga gacatggaac tggaaaattg   5400
```

-continued

```
tgcacaagat ttgcaactga tgctccgaat gttcgatatg tattcacaag acttccagtt   5460
gttttagcat caattgtgac tatttgtgga gctctgggaa ttggattcta ttacggatgg   5520
caacttgcct tgattcttgt cgtaatggtt ccactacttg taatgggagg atatttcgaa   5580
atgcaaatga gatttggaaa acaaataaga gatactcaat tgttggaaga agctggaaaa   5640
gtagcttcac aggctgttga acacattcga acagttcata gtttaaatcg tcaggaacaa   5700
tttcatttca catactgtga atatcttcgg gaaccattca atactaatct gaaacatgca   5760
catacatatg gagctgtatt tgcattctct caatctctta ttttcttcat gtatgctgct   5820
gcattctatc ttggaagtat ttttgtaaat caacaagcta tgcaaccaat tgatgtctat   5880
cgagtattct ttgctatttc attctgtgga caaatgattg gaaatactac atcttttatt   5940
cctgatgtcg taaaagctcg tcttgctgct tctcttttgt tctatcttat tgaacatcca   6000
acacctattg attctctatc tgatagtgga attgtgaagc cgataactgg aaatatttca   6060
atcagaaatg tatttttcaa ttatccaaca agaaaggata ccaaggtttt acaaggattc   6120
actcttgatg taggttttaa tttgatacct gacttctata tgacagtagt gcaatcctag   6180
ggtaaaaagc aataagcctt gacttttaaa aactggatat ggattttttt tgcgtttttg   6240
tatcgaatgt ttatgcactt gccctctgac ttttttactg aaattttaaa aataggaaaa   6300
aaaaaaaaga caatgatcct acaattctta acccacctgt aaaaacaaat attaatatat   6360
ttattttaga tcaaagccgg taaaactgtt gcacttgtcg ggcactcagg atgtggaaaa   6420
tctacaatta tgggactgct ggagagattc tataatcaag ataaaggaat gattgtgagt   6480
caattttctt tctgattggt tttaactgca aacaatttta gatgattgat ggtgataaca   6540
tccgtaacct aaacatcagt tcacttcgcg aacaagtatg tattgtaagt caagagccaa   6600
cgttgtttga ttgcacaatt ggagaaaata tttgctacgg aacaaatcga aatgttacat   6660
atcaagaaat tgttgaagct gccaaaatgg caaatattca caatttcatt ctaggattgc   6720
cagatgtagg gtgatatttt cataaatcag aactcattct aaaaatttca gggttatgat   6780
actcatgtcg gagagaaagg aactcaactt tcgggtggtc aaaaacaaag aattgccatt   6840
gcacgggcac ttgttcgatc tccttctgtt ttacttttgg atgaagcaac tagtgcatta   6900
gatacggaaa gtgaaaaggt ttgtatgaaa aatattgaaa tagcaaattg actttgaaga   6960
atatcgtttt attcactgtt tacagattgt acaagaagca ttggacgccg caaaacaagg   7020
tcgcacgtgt cttgtcattg ctcatcggtt gagcacaatt caaaatagtg acgtcattgc   7080
gatcgtcagt gagggtaaaa ttgtggaaaa gggaacacat gacgagttga taaggaagag   7140
tgaaatatat cagaaattct gtgaaacgca gaggattgtc gaaagtcaat aatttaaata   7200
tgtattagat tctcaaacac gagtttacaa actaatttgc atggagtttc atttttttaa   7260
tgttcaattg aaacagcttg atatttaaaa tttaaatatg ctcatcaagt aaaattttta   7320
gaaaattttg taaacccgta ataatttttt tgtcatctag gtactttgct ttttccccaa   7380
atagcctttc cctccatctt gtgtattttg tgtgaaattc tttgaattgt gataattatc   7440
tttgaattgt gataattgtc tttttgtttt ctttttttaaa tatattattt accat       7495
```

<210> SEQ ID NO 5
<211> LENGTH: 3798
<212> TYPE: DNA
<213> ORGANISM: Caenorhabditis elegans

<400> SEQUENCE: 5

-continued

```
atgaaaagcc gaaaaaacga gcccacttgg gtgactaagc ctctgcttaa acgctctcat     60
tcaagtgact cttcaatcga tgaatcaact gttaaactca caaattatgg gatattctat    120
tacactcaag gagttgatct acttctttta attactggaa cagttgcagc agttattcat    180
ggagctggtt ttccgttact tgctattgtt ctcggaggaa tgacaacagt gtttttacga    240
gctcaaaact cggatttcgt cgttggtgtg gataatgtga acccggaagg attggtcccg    300
atatctctag atgaattcaa ctcggaagtt gtcaagtatt gtatctacta cctggttctt    360
ggtgtactca tgttcttcac ttcatatgta caaatcgctt gttttgagtc gtacgcagag    420
agattggtgc ataaattaag acaaaactac ctgaaagcca tactcagaca acaaattcaa    480
tggttcgaca aacaacagac cggaaattta acggctagac tcacggacga tttggagcgt    540
gtccgtgaag gattaggtga caaattcgcc cttcttgttc aaatgtttgc tgctttcttg    600
gctggatacg gagttggctt cttttatagt tggtcaatga cactggttat gatgggattt    660
gctccgttga ttgtgctctc tggtgccaaa atgagcaaaa gcatggcaac gcgaacaaga    720
gttgaacaag aaacgtatgc agtcgctggt gcaattgcag aagaaacatt ctcttcgatt    780
agaacagttc attcattaaa tggacataaa agagaattgg atagatttta taacgcattg    840
gaagttggaa gacaaactgg aattgttaaa tattgttata tgggtattgg agttgggttc    900
agtaatttgt gtatgtactc ttcatatgca ttggcatttt ggtatggaag tactctgatt    960
atcaatgatc ctacttttga tcgcggtctt atttttacgg ttttcttcgc agttctctcg   1020
ggttctacat ctctcggtgg cgcccttcca catcttgcaa gttttggaac agctcgcgga   1080
gcagcttcaa cagtattacg tgtaatcaac tcgcacccaa aaatcgatcc atattcactt   1140
gaaggaattc tcgtggacaa tatgaaggga gatatttcat tcaaagatgt tcatttccga   1200
tatccatctc gaaaagatat tcatgtatta aaaggaattt ctctggaact gaaagctggt   1260
gataaaattg ctttggtcgg ttcaagtggt tgtggaaaat caacaattgt taatttactt   1320
caaagattct atgatccaac aaaaggaaga gttttaattg atggagttga tttacgagaa   1380
gtaaatgttc atagtcttcg tgaacaaatt ggaattgtta gtcaagagcc agtacttttc   1440
gatggaacaa tttatgaaaa tattaaaatg ggaaatgagc atgctactca tgatcaagtc   1500
gttgaagcgt gtaaaatggc aaatgcaaat gattttatca aaagattgcc tgatggatat   1560
ggaacaagag ttggagaaaa aggagttcaa ttaagtggag gacagaaaca aagaattgcc   1620
attgcacgtg ctcttgtcaa aaatccaaaa atccttttgc tcgacgaagc cacatccgct   1680
ctcgacacgg aagctgagag agaagttcaa ggtgcattgg atcaggcaca agctggaaga   1740
acgacaatta tcgtagctca ccgattgagc acaattcgaa atgttgacag aatattcgtg   1800
ttcaaagctg gaaatattgt tgaatctgga agtcatgagg aattaatgag caaacaagga   1860
atcttctacg atatgacaca ggctcaagtt gttcgacaac agcaacagga agcaggaaaa   1920
gatattgaag acactatttc tgagtcagct cattcccatc tcagcagaaa gtcttccaca   1980
agaagtgcca tttcaattgc aacatctatt catcagctcg ctgaggaggt tgaggaatgc   2040
aaggctccac ccacctcaat gttcaaaata ttcaaattca acggagacaa agtcggatgg   2100
tttattggtg gaatttttgg agcatttatt tttggatcag ttactccagt ttttgctctt   2160
gtatatgctg aaattttcaa tgtatactct ttgccagctg atcaaatgca agcaaatgtg   2220
tatttctggt gtggaatgtt tgttcttatg ggaatcactt tcttcgttgg attcttcact   2280
tctgcaaatt gcctcggacg atgtggagag tcactgacaa tgaagttgag atttgaagca   2340
ttcaagaatt tattaagaca agatatcgct ttttatgatg atttgagaca tggaactgga   2400
```

-continued

```
aaattgtgca caagatttgc aactgatgct ccgaatgttc gatatgtatt cacaagactt   2460
ccagttgttt tagcatcaat tgtgactatt tgtggagctc tgggaattgg attctattac   2520
ggatggcaac ttgccttgat tcttgtcgta atggttccac tacttgtaat gggaggatat   2580
ttcgaaatgc aaatgagatt tggaaaacaa ataagagata ctcaattgtt ggaagaagct   2640
ggaaaagtag cttcacaggc tgttgaacac attcgaacag ttcatagttt aaatcgtcag   2700
gaacaatttc atttcacata ctgtgaatat cttcgggaac cattcaatac taatctgaaa   2760
catgcacata catatggagc tgtatttgca ttctctcaat ctcttatttt cttcatgtat   2820
gctgctgcat tctatcttgg aagtattttt gtaaatcaac aagctatgca accaattgat   2880
gtctatcgag tattctttgc tatttcattc tgtggacaaa tgattggaaa tactacatct   2940
tttattcctg atgtcgtaaa agctcgtctt gctgcttctc ttttgttcta tcttattgaa   3000
catccaacac ctattgattc tctatctgat agtggaattg tgaagccgat aactggaaat   3060
atttcaatca gaaatgtatt tttcaattat ccaacaagaa aggataccaa ggttttacaa   3120
ggattcactc ttgatatcaa agccggtaaa actgttgcac ttgtcgggca ctcaggatgt   3180
ggaaaatcta caattatggg actgctggag agattctata atcaagataa aggaatgatt   3240
atgattgatg gtgataacat ccgtaaccta aacatcagtt cacttcgcga acaagtatgt   3300
attgtaagtc aagagccaac gttgtttgat tgcacaattg gagaaaatat ttgctacgga   3360
acaaatcgaa atgttacata tcaagaaatt gttgaagctg ccaaaatggc aaatattcac   3420
aatttcattc taggattgcc agatggttat gatactcatg tcggagagaa aggaactcaa   3480
ctttcgggtg gtcaaaaaca aagaattgcc attgcacggg cacttgttcg atctccttct   3540
gttttacttt tggatgaagc aactagtgca ttagatacgg aaagtgaaaa gattgtacaa   3600
gaagcattgg acgccgcaaa acaaggtcgc acgtgtcttg tcattgctca tcggttgagc   3660
acaattcaaa atagtgacgt cattgcgatc gtcagtgagg gtaaaattgt ggaaaaggga   3720
acacatgacg agttgataag gaagagtgaa atatatcaga aattctgtga aacgcagagg   3780
attgtcgaaa gtcaataa                                                 3798
```

<210> SEQ ID NO 6
<211> LENGTH: 1265
<212> TYPE: PRT
<213> ORGANISM: Caenorhabditis elegans

<400> SEQUENCE: 6

```
Met Lys Ser Arg Lys Asn Glu Pro Thr Trp Val Thr Lys Pro Leu Leu
 1               5                  10                  15

Lys Arg Ser His Ser Ser Asp Ser Ser Ile Asp Glu Ser Thr Val Lys
            20                  25                  30

Leu Thr Asn Tyr Gly Ile Phe Tyr Tyr Thr Gln Gly Val Asp Leu Leu
        35                  40                  45

Leu Leu Ile Thr Gly Thr Val Ala Ala Val Ile His Gly Ala Gly Phe
    50                  55                  60

Pro Leu Leu Ala Ile Val Leu Gly Gly Met Thr Thr Val Phe Leu Arg
65                  70                  75                  80

Ala Gln Asn Ser Asp Phe Val Val Gly Val Asp Asn Val Asn Pro Glu
                85                  90                  95

Gly Leu Val Pro Ile Ser Leu Asp Glu Phe Asn Ser Glu Val Val Lys
            100                 105                 110

Tyr Cys Ile Tyr Tyr Leu Val Leu Gly Val Leu Met Phe Phe Thr Ser
```

-continued

```
        115                 120                 125

Tyr Val Gln Ile Ala Cys Phe Glu Ser Tyr Ala Glu Arg Leu Val His
    130                 135                 140

Lys Leu Arg Gln Asn Tyr Leu Lys Ala Ile Leu Arg Gln Gln Ile Gln
145                 150                 155                 160

Trp Phe Asp Lys Gln Gln Thr Gly Asn Leu Thr Ala Arg Leu Thr Asp
                165                 170                 175

Asp Leu Glu Arg Val Arg Glu Gly Leu Gly Asp Lys Phe Ala Leu Leu
            180                 185                 190

Val Gln Met Phe Ala Ala Phe Leu Ala Gly Tyr Gly Val Gly Phe Phe
        195                 200                 205

Tyr Ser Trp Ser Met Thr Leu Val Met Met Gly Phe Ala Pro Leu Ile
    210                 215                 220

Val Leu Ser Gly Ala Lys Met Ser Lys Ser Met Ala Thr Arg Thr Arg
225                 230                 235                 240

Val Glu Gln Glu Thr Tyr Ala Val Ala Gly Ala Ile Ala Glu Glu Thr
                245                 250                 255

Phe Ser Ser Ile Arg Thr Val His Ser Leu Asn Gly His Lys Arg Glu
            260                 265                 270

Leu Asp Arg Phe Tyr Asn Ala Leu Glu Val Gly Arg Gln Thr Gly Ile
        275                 280                 285

Val Lys Tyr Cys Tyr Met Gly Ile Gly Val Gly Phe Ser Asn Leu Cys
    290                 295                 300

Met Tyr Ser Ser Tyr Ala Leu Ala Phe Trp Tyr Gly Ser Thr Leu Ile
305                 310                 315                 320

Ile Asn Asp Pro Thr Phe Asp Arg Gly Leu Ile Phe Thr Val Phe Phe
                325                 330                 335

Ala Val Leu Ser Gly Ser Thr Ser Leu Gly Gly Ala Leu Pro His Leu
            340                 345                 350

Ala Ser Phe Gly Thr Ala Arg Gly Ala Ala Ser Thr Val Leu Arg Val
        355                 360                 365

Ile Asn Ser His Pro Lys Ile Asp Pro Tyr Ser Leu Glu Gly Ile Leu
    370                 375                 380

Val Asp Asn Met Lys Gly Asp Ile Ser Phe Lys Asp Val His Phe Arg
385                 390                 395                 400

Tyr Pro Ser Arg Lys Asp Ile His Val Leu Lys Gly Ile Ser Leu Glu
                405                 410                 415

Leu Lys Ala Gly Asp Lys Ile Ala Leu Val Gly Ser Ser Gly Cys Gly
            420                 425                 430

Lys Ser Thr Ile Val Asn Leu Leu Gln Arg Phe Tyr Asp Pro Thr Lys
        435                 440                 445

Gly Arg Val Leu Ile Asp Gly Val Asp Leu Arg Glu Val Asn Val His
    450                 455                 460

Ser Leu Arg Glu Gln Ile Gly Ile Val Ser Gln Glu Pro Val Leu Phe
465                 470                 475                 480

Asp Gly Thr Ile Tyr Glu Asn Ile Lys Met Gly Asn Glu His Ala Thr
                485                 490                 495

His Asp Gln Val Val Glu Ala Cys Lys Met Ala Asn Ala Asn Asp Phe
            500                 505                 510

Ile Lys Arg Leu Pro Asp Gly Tyr Gly Thr Arg Val Gly Glu Lys Gly
        515                 520                 525

Val Gln Leu Ser Gly Gly Gln Lys Gln Arg Ile Ala Ile Ala Arg Ala
    530                 535                 540
```

-continued

```
Leu Val Lys Asn Pro Lys Ile Leu Leu Leu Asp Glu Ala Thr Ser Ala
545                 550                 555                 560

Leu Asp Thr Glu Ala Glu Arg Glu Val Gln Gly Ala Leu Asp Gln Ala
                565                 570                 575

Gln Ala Gly Arg Thr Thr Ile Ile Val Ala His Arg Leu Ser Thr Ile
            580                 585                 590

Arg Asn Val Asp Arg Ile Phe Val Phe Lys Ala Gly Asn Ile Val Glu
        595                 600                 605

Ser Gly Ser His Glu Glu Leu Met Ser Lys Gln Gly Ile Phe Tyr Asp
    610                 615                 620

Met Thr Gln Ala Gln Val Val Arg Gln Gln Gln Glu Ala Gly Lys
625                 630                 635                 640

Asp Ile Glu Asp Thr Ile Ser Glu Ser Ala His Ser His Leu Ser Arg
                645                 650                 655

Lys Ser Ser Thr Arg Ser Ala Ile Ser Ile Ala Thr Ser Ile His Gln
            660                 665                 670

Leu Ala Glu Glu Val Glu Glu Cys Lys Ala Pro Pro Thr Ser Met Phe
        675                 680                 685

Lys Ile Phe Lys Phe Asn Gly Asp Lys Val Gly Trp Phe Ile Gly Gly
    690                 695                 700

Ile Phe Gly Ala Phe Ile Phe Gly Ser Val Thr Pro Val Phe Ala Leu
705                 710                 715                 720

Val Tyr Ala Glu Ile Phe Asn Val Tyr Ser Leu Pro Ala Asp Gln Met
                725                 730                 735

Gln Ala Asn Val Tyr Phe Trp Cys Gly Met Phe Val Leu Met Gly Ile
            740                 745                 750

Thr Phe Phe Val Gly Phe Phe Thr Ser Ala Asn Cys Leu Gly Arg Cys
        755                 760                 765

Gly Glu Ser Leu Thr Met Lys Leu Arg Phe Glu Ala Phe Lys Asn Leu
    770                 775                 780

Leu Arg Gln Asp Ile Ala Phe Tyr Asp Asp Leu Arg His Gly Thr Gly
785                 790                 795                 800

Lys Leu Cys Thr Arg Phe Ala Thr Asp Ala Pro Asn Val Arg Tyr Val
                805                 810                 815

Phe Thr Arg Leu Pro Val Val Leu Ala Ser Ile Val Thr Ile Cys Gly
            820                 825                 830

Ala Leu Gly Ile Gly Phe Tyr Tyr Gly Trp Gln Leu Ala Leu Ile Leu
        835                 840                 845

Val Val Met Val Pro Leu Leu Val Met Gly Gly Tyr Phe Glu Met Gln
    850                 855                 860

Met Arg Phe Gly Lys Gln Ile Arg Asp Thr Gln Leu Leu Glu Glu Ala
865                 870                 875                 880

Gly Lys Val Ala Ser Gln Ala Val Glu His Ile Arg Thr Val His Ser
                885                 890                 895

Leu Asn Arg Gln Glu Gln Phe His Phe Thr Tyr Cys Glu Tyr Leu Arg
            900                 905                 910

Glu Pro Phe Asn Thr Asn Leu Lys His Ala His Thr Tyr Gly Ala Val
        915                 920                 925

Phe Ala Phe Ser Gln Ser Leu Ile Phe Phe Met Tyr Ala Ala Ala Phe
    930                 935                 940

Tyr Leu Gly Ser Ile Phe Val Asn Gln Gln Ala Met Gln Pro Ile Asp
945                 950                 955                 960
```

-continued

```
Val Tyr Arg Val Phe Phe Ala Ile Ser Phe Cys Gly Gln Met Ile Gly
                965                 970                 975

Asn Thr Thr Ser Phe Ile Pro Asp Val Val Lys Ala Arg Leu Ala Ala
            980                 985                 990

Ser Leu Leu Phe Tyr Leu Ile Glu His Pro Thr Pro Ile Asp Ser Leu
        995                 1000                1005

Ser Asp Ser Gly Ile Val Lys Pro Ile Thr Gly Asn Ile Ser Ile Arg
    1010                1015                1020

Asn Val Phe Phe Asn Tyr Pro Thr Arg Lys Asp Thr Lys Val Leu Gln
1025                1030                1035                1040

Gly Phe Thr Leu Asp Ile Lys Ala Gly Lys Thr Val Ala Leu Val Gly
                1045                1050                1055

His Ser Gly Cys Gly Lys Ser Thr Ile Met Gly Leu Leu Glu Arg Phe
            1060                1065                1070

Tyr Asn Gln Asp Lys Gly Met Ile Met Ile Asp Gly Asp Asn Ile Arg
        1075                1080                1085

Asn Leu Asn Ile Ser Ser Leu Arg Glu Gln Val Cys Ile Val Ser Gln
    1090                1095                1100

Glu Pro Thr Leu Phe Asp Cys Thr Ile Gly Glu Asn Ile Cys Tyr Gly
1105                1110                1115                1120

Thr Asn Arg Asn Val Thr Tyr Gln Glu Ile Val Glu Ala Ala Lys Met
                1125                1130                1135

Ala Asn Ile His Asn Phe Ile Leu Gly Leu Pro Asp Gly Tyr Asp Thr
            1140                1145                1150

His Val Gly Glu Lys Gly Thr Gln Leu Ser Gly Gly Gln Lys Gln Arg
        1155                1160                1165

Ile Ala Ile Ala Arg Ala Leu Val Arg Ser Pro Ser Val Leu Leu Leu
    1170                1175                1180

Asp Glu Ala Thr Ser Ala Leu Asp Thr Glu Ser Glu Lys Ile Val Gln
1185                1190                1195                1200

Glu Ala Leu Asp Ala Ala Lys Gln Gly Arg Thr Cys Leu Val Ile Ala
                1205                1210                1215

His Arg Leu Ser Thr Ile Gln Asn Ser Asp Val Ile Ala Ile Val Ser
            1220                1225                1230

Glu Gly Lys Ile Val Glu Lys Gly Thr His Asp Glu Leu Ile Arg Lys
        1235                1240                1245

Ser Glu Ile Tyr Gln Lys Phe Cys Glu Thr Gln Arg Ile Val Glu Ser
    1250                1255                1260

Gln
1265


<210> SEQ ID NO 7
<211> LENGTH: 29
<212> TYPE: DNA
<213> ORGANISM: Caenorhabditis elegans

<400> SEQUENCE: 7

cacaacaagt cagcaagcaa tacaagtgg                                      29


<210> SEQ ID NO 8
<211> LENGTH: 28
<212> TYPE: DNA
<213> ORGANISM: Caenorhabditis elegans

<400> SEQUENCE: 8

gtaggagatg tgaccaatcg ttgaagtg                                       28
```

-continued

<210> SEQ ID NO 9
<211> LENGTH: 873
<212> TYPE: PRT
<213> ORGANISM: Homo sapiens

<400> SEQUENCE: 9

Met Gly Thr Ser Ala Leu Trp Ala Leu Trp Leu Leu Leu Ala Leu Cys
1 5 10 15

Trp Ala Pro Arg Glu Ser Gly Ala Thr Gly Thr Gly Arg Lys Ala Lys
20 25 30

Cys Glu Pro Ser Gln Phe Gln Cys Thr Asn Gly Arg Cys Ile Thr Leu
35 40 45

Leu Trp Lys Cys Asp Gly Asp Glu Asp Cys Val Asp Gly Ser Asp Glu
50 55 60

Lys Asn Cys Val Lys Lys Thr Cys Ala Glu Ser Asp Phe Val Cys Asn
65 70 75 80

Asn Gly Gln Cys Val Pro Ser Arg Trp Lys Cys Asp Gly Asp Pro Asp
85 90 95

Cys Glu Asp Gly Ser Asp Glu Ser Pro Glu Gln Cys His Met Arg Thr
100 105 110

Cys Arg Ile His Glu Ile Ser Cys Gly Ala His Ser Thr Gln Cys Ile
115 120 125

Pro Val Ser Trp Arg Cys Asp Gly Glu Asn Asp Cys Asp Ser Gly Glu
130 135 140

Asp Glu Glu Asn Cys Gly Asn Ile Thr Cys Ser Pro Asp Glu Phe Thr
145 150 155 160

Cys Ser Ser Gly Arg Cys Ile Ser Arg Asn Phe Val Cys Asn Gly Gln
165 170 175

Asp Asp Cys Ser Asp Gly Ser Asp Glu Leu Asp Cys Ala Pro Pro Thr
180 185 190

Cys Gly Ala His Glu Phe Gln Cys Ser Thr Ser Ser Cys Ile Pro Ile
195 200 205

Ser Trp Val Cys Asp Asp Asp Ala Asp Cys Ser Asp Gln Ser Asp Glu
210 215 220

Ser Leu Glu Gln Cys Gly Arg Gln Pro Val Ile His Thr Lys Cys Pro
225 230 235 240

Ala Ser Glu Ile Gln Cys Gly Ser Gly Glu Cys Ile His Lys Lys Trp
245 250 255

Arg Cys Asp Gly Asp Pro Asp Cys Lys Asp Gly Ser Asp Glu Val Asn
260 265 270

Cys Pro Ser Arg Thr Cys Arg Pro Asp Gln Phe Glu Cys Glu Asp Gly
275 280 285

Ser Cys Ile His Gly Ser Arg Gln Cys Asn Gly Ile Arg Asp Cys Val
290 295 300

Asp Gly Ser Asp Glu Val Asn Cys Lys Asn Val Asn Gln Cys Leu Gly
305 310 315 320

Pro Gly Lys Phe Lys Cys Arg Ser Gly Glu Cys Ile Asp Ile Ser Lys
325 330 335

Val Cys Asn Gln Glu Gln Asp Cys Arg Asp Trp Ser Asp Glu Pro Leu
340 345 350

Lys Glu Cys His Ile Asn Glu Cys Leu Val Asn Asn Gly Gly Cys Ser
355 360 365

His Ile Cys Lys Asp Leu Val Ile Gly Tyr Glu Cys Asp Cys Ala Ala

-continued

```
    370                 375                 380

Gly Phe Glu Leu Ile Asp Arg Lys Thr Cys Gly Asp Ile Asp Glu Cys
385                 390                 395                 400

Gln Asn Pro Gly Ile Cys Ser Gln Ile Cys Ile Asn Leu Lys Gly Gly
                405                 410                 415

Tyr Lys Cys Glu Cys Ser Arg Gly Tyr Gln Met Asp Leu Ala Thr Gly
            420                 425                 430

Val Cys Lys Ala Val Gly Lys Glu Pro Ser Leu Ile Phe Thr Asn Arg
        435                 440                 445

Arg Asp Ile Arg Lys Ile Gly Leu Glu Arg Lys Glu Tyr Ile Gln Leu
    450                 455                 460

Val Glu Gln Leu Arg Asn Thr Val Ala Leu Asp Ala Asp Ile Ala Ala
465                 470                 475                 480

Gln Lys Leu Phe Trp Ala Asp Leu Ser Gln Lys Ala Ile Phe Ser Ala
                485                 490                 495

Ser Ile Asp Asp Lys Val Gly Arg His Val Lys Met Ile Asp Asn Val
            500                 505                 510

Tyr Asn Pro Ala Ala Ile Ala Val Asp Trp Val Tyr Lys Thr Ile Tyr
        515                 520                 525

Trp Thr Asp Ala Ala Ser Lys Thr Ile Ser Val Ala Thr Leu Asp Gly
    530                 535                 540

Thr Lys Arg Lys Phe Leu Phe Asn Ser Asp Leu Arg Glu Pro Ala Ser
545                 550                 555                 560

Ile Ala Val Asp Pro Leu Ser Gly Phe Val Tyr Trp Ser Asp Trp Gly
                565                 570                 575

Glu Pro Ala Lys Ile Glu Lys Ala Gly Met Asn Gly Phe Asp Arg Arg
            580                 585                 590

Pro Leu Val Thr Ala Asp Ile Gln Trp Pro Asn Gly Ile Thr Leu Asp
        595                 600                 605

Leu Ile Lys Ser Arg Leu Tyr Trp Leu Asp Ser Lys Leu His Met Leu
    610                 615                 620

Ser Ser Val Asp Leu Asn Gly Gln Asp Arg Arg Ile Val Leu Lys Ser
625                 630                 635                 640

Leu Glu Phe Leu Ala His Pro Leu Ala Leu Thr Ile Phe Glu Asp Arg
                645                 650                 655

Val Tyr Trp Ile Asp Gly Glu Asn Glu Ala Val Tyr Gly Ala Asn Lys
            660                 665                 670

Phe Thr Gly Ser Glu Leu Ala Thr Leu Val Asn Asn Leu Asn Asp Ala
        675                 680                 685

Gln Asp Ile Ile Val Tyr His Glu Leu Val Gln Pro Ser Gly Lys Asn
    690                 695                 700

Trp Cys Glu Glu Asp Met Glu Asn Gly Gly Cys Glu Tyr Leu Cys Leu
705                 710                 715                 720

Pro Ala Pro Gln Ile Asn Asp His Ser Pro Lys Tyr Thr Cys Ser Cys
                725                 730                 735

Pro Ser Gly Tyr Asn Val Glu Glu Asn Gly Arg Asp Cys Gln Ser Thr
            740                 745                 750

Ala Thr Thr Val Thr Tyr Ser Glu Thr Lys Asp Thr Asn Thr Thr Glu
        755                 760                 765

Ile Ser Ala Thr Ser Gly Leu Val Pro Gly Gly Ile Asn Val Thr Thr
    770                 775                 780

Ala Val Ser Glu Val Ser Val Pro Pro Lys Gly Thr Ser Ala Ala Trp
785                 790                 795                 800
```

-continued

```
Ala Ile Leu Pro Leu Leu Leu Leu Val Met Ala Ala Val Gly Gly Tyr
                805                 810                 815

Leu Met Trp Arg Asn Trp Gln His Lys Asn Met Lys Ser Met Asn Phe
            820                 825                 830

Asp Asn Pro Val Tyr Leu Lys Thr Thr Glu Glu Asp Leu Ser Ile Asp
        835                 840                 845

Ile Gly Arg His Ser Ala Ser Val Gly His Thr Tyr Pro Ala Ile Ser
    850                 855                 860

Val Val Ser Thr Asp Asp Asp Leu Ala
865                 870


<210> SEQ ID NO 10
<211> LENGTH: 873
<212> TYPE: PRT
<213> ORGANISM: Rattus norvigicus

<400> SEQUENCE: 10

Met Gly Thr Ser Ala Arg Trp Ala Leu Trp Leu Leu Leu Ala Leu Cys
 1               5                  10                  15

Trp Ala Pro Arg Asp Ser Gly Ala Thr Ala Ser Gly Lys Lys Ala Lys
            20                  25                  30

Cys Asp Ser Ser Gln Phe Gln Cys Thr Asn Gly Arg Cys Ile Thr Leu
        35                  40                  45

Leu Trp Lys Cys Asp Gly Asp Glu Asp Cys Thr Asp Gly Ser Asp Glu
    50                  55                  60

Lys Asn Cys Val Lys Lys Thr Cys Ala Glu Ser Asp Phe Val Cys Lys
65                  70                  75                  80

Asn Gly Gln Cys Val Pro Asn Arg Trp Gln Cys Asp Gly Asp Pro Asp
                85                  90                  95

Cys Glu Asp Gly Ser Asp Glu Ser Pro Glu Gln Cys His Met Arg Thr
            100                 105                 110

Cys Arg Ile Asn Glu Ile Ser Cys Gly Ala Arg Ser Thr Gln Cys Ile
        115                 120                 125

Pro Glu Ser Trp Arg Cys Asp Gly Glu Asn Asp Cys Asp Asn Gly Glu
    130                 135                 140

Asp Glu Glu Asn Cys Gly Asn Ile Thr Cys Ser Ala Asp Glu Phe Thr
145                 150                 155                 160

Cys Ser Ser Gly Arg Cys Val Ser Arg Asn Phe Val Cys Asn Gly Gln
                165                 170                 175

Asp Asp Cys Asp Asp Gly Ser Asp Glu Leu Asp Cys Ala Pro Pro Thr
            180                 185                 190

Cys Gly Ala His Glu Phe Gln Cys Arg Thr Ser Ser Cys Ile Pro Leu
        195                 200                 205

Ser Trp Val Cys Asp Asp Asp Ala Asp Cys Ser Asp Gln Ser Asp Glu
    210                 215                 220

Ser Leu Glu Gln Cys Gly Arg Gln Pro Val Ile His Thr Lys Cys Pro
225                 230                 235                 240

Thr Ser Glu Ile Gln Cys Gly Ser Gly Glu Cys Ile His Lys Lys Trp
                245                 250                 255

Arg Cys Asp Gly Asp Pro Asp Cys Lys Asp Gly Ser Asp Glu Val Asn
            260                 265                 270

Cys Pro Ser Arg Thr Cys Arg Pro Asp Gln Phe Glu Cys Glu Asp Gly
        275                 280                 285

Ser Cys Ile His Gly Ser Arg Gln Cys Asn Gly Ile Arg Asp Cys Val
```

-continued

```
    290                 295                 300

Asp Gly Ser Asp Glu Val Asn Cys Lys Asn Val Asn Gln Cys Leu Gly
305                 310                 315                 320

Pro Gly Lys Phe Lys Cys Arg Ser Gly Glu Cys Ile Asp Ile Thr Lys
                325                 330                 335

Val Cys Asp Gln Glu Gln Asp Cys Arg Asp Trp Ser Asp Glu Pro Leu
            340                 345                 350

Lys Glu Cys His Ile Asn Glu Cys Leu Val Asn Asn Gly Gly Cys Ser
        355                 360                 365

His Ile Cys Lys Asp Leu Val Ile Gly Tyr Glu Cys Asp Cys Ala Ala
    370                 375                 380

Gly Phe Glu Leu Ile Asp Arg Lys Thr Cys Gly Asp Ile Asp Glu Cys
385                 390                 395                 400

Gln Asn Pro Gly Ile Cys Ser Gln Ile Cys Ile Asn Leu Lys Gly Gly
                405                 410                 415

Tyr Lys Cys Glu Cys Ser Arg Gly Tyr Gln Met Asp Leu Ala Thr Gly
            420                 425                 430

Val Cys Lys Ala Val Gly Lys Glu Pro Ser Leu Ile Phe Thr Asn Arg
        435                 440                 445

Arg Asp Ile Arg Lys Ile Gly Leu Glu Arg Lys Glu Tyr Ile Gln Leu
    450                 455                 460

Val Glu Gln Leu Arg Asn Thr Val Ala Leu Asp Ala Asp Ile Ala Ala
465                 470                 475                 480

Gln Lys Leu Phe Trp Ala Asp Leu Ser Gln Lys Ala Ile Phe Ser Ala
                485                 490                 495

Ser Ile Asp Asp Lys Val Gly Arg His Phe Lys Met Ile Asp Asn Val
            500                 505                 510

Tyr Asn Pro Ala Ala Ile Ala Val Asp Trp Val Tyr Lys Thr Ile Tyr
        515                 520                 525

Trp Thr Asp Ala Ala Ser Lys Thr Ile Ser Val Ala Thr Leu Asp Gly
    530                 535                 540

Thr Lys Arg Lys Phe Leu Phe Asn Ser Asp Leu Arg Glu Pro Ala Ser
545                 550                 555                 560

Ile Ala Val Asp Pro Leu Ser Gly Phe Val Tyr Trp Ser Asp Trp Gly
                565                 570                 575

Glu Pro Ala Lys Ile Glu Lys Ala Gly Met Asn Gly Phe Asp Arg Arg
            580                 585                 590

Pro Leu Val Thr Glu Asp Ile Gln Trp Pro Asn Gly Ile Thr Leu Asp
        595                 600                 605

Leu Val Lys Ser Arg Leu Tyr Trp Leu Asp Ser Lys Leu His Met Leu
    610                 615                 620

Ser Ser Val Asp Leu Asn Gly Gln Asp Arg Arg Ile Val Leu Lys Ser
625                 630                 635                 640

Leu Glu Phe Leu Ala His Pro Leu Ala Leu Thr Ile Phe Glu Asp Arg
                645                 650                 655

Val Tyr Trp Ile Asp Gly Glu Asn Glu Ala Val Tyr Gly Ala Asn Lys
            660                 665                 670

Phe Thr Gly Ser Glu Leu Ala Thr Leu Val Asn Asn Leu Asn Asp Ala
        675                 680                 685

Gln Asp Ile Ile Ile Tyr His Glu Leu Val Gln Pro Ser Gly Lys Asn
    690                 695                 700

Trp Cys Glu Glu Asp Met Glu Asn Gly Gly Cys Glu Tyr Leu Cys Leu
705                 710                 715                 720
```

-continued

```
Pro Ala Pro Gln Ile Asn Asp His Ser Pro Lys Tyr Thr Cys Ser Cys
                725                 730                 735

Pro Asn Gly Tyr Asn Leu Glu Glu Asn Gly Arg Glu Cys Gln Ser Thr
            740                 745                 750

Ser Thr Pro Val Thr Tyr Ser Glu Thr Lys Asp Val Asn Thr Thr Asp
        755                 760                 765

Ile Leu Arg Thr Ser Gly Leu Val Pro Gly Gly Ile Asn Val Thr Thr
    770                 775                 780

Ala Val Ser Glu Val Ser Val Pro Pro Lys Gly Thr Ser Ala Ala Trp
785                 790                 795                 800

Ala Ile Leu Pro Leu Leu Leu Leu Val Met Ala Ala Val Gly Gly Tyr
                805                 810                 815

Leu Met Trp Arg Asn Trp Gln His Lys Asn Met Lys Ser Met Asn Phe
            820                 825                 830

Asp Asn Pro Val Tyr Leu Lys Thr Thr Glu Glu Asp Leu Ser Ile Asp
        835                 840                 845

Ile Gly Arg His Ser Ala Ser Val Gly His Thr Tyr Pro Ala Ile Ser
    850                 855                 860

Val Val Ser Thr Asp Asp Asp Leu Ala
865                 870


<210> SEQ ID NO 11
<211> LENGTH: 1280
<212> TYPE: PRT
<213> ORGANISM: Homo sapiens

<400> SEQUENCE: 11

Met Asp Leu Glu Gly Asp Arg Asn Gly Gly Ala Lys Lys Lys Asn Phe
 1               5                  10                  15

Phe Lys Leu Asn Asn Lys Ser Glu Lys Asp Lys Lys Glu Lys Lys Pro
            20                  25                  30

Thr Val Ser Val Phe Ser Met Phe Arg Tyr Ser Asn Trp Leu Asp Lys
        35                  40                  45

Leu Tyr Met Val Val Gly Thr Leu Ala Ala Ile Ile His Gly Ala Gly
    50                  55                  60

Leu Pro Leu Met Met Leu Val Phe Gly Glu Met Thr Asp Ile Phe Ala
65                  70                  75                  80

Asn Ala Gly Asn Leu Glu Asp Leu Met Ser Asn Ile Thr Asn Arg Ser
                85                  90                  95

Asp Ile Asn Asp Thr Gly Phe Phe Met Asn Leu Glu Glu Asp Met Thr
            100                 105                 110

Arg Tyr Ala Tyr Tyr Tyr Ser Gly Ile Gly Ala Gly Val Leu Val Ala
        115                 120                 125

Ala Tyr Ile Gln Val Ser Phe Trp Cys Leu Ala Ala Gly Arg Gln Ile
    130                 135                 140

His Lys Ile Arg Lys Gln Phe Phe His Ala Ile Met Arg Gln Glu Ile
145                 150                 155                 160

Gly Trp Phe Asp Val His Asp Val Gly Glu Leu Asn Thr Arg Leu Thr
                165                 170                 175

Asp Asp Val Ser Lys Ile Asn Glu Gly Ile Gly Asp Lys Ile Gly Met
            180                 185                 190

Phe Phe Gln Ser Met Ala Thr Phe Phe Thr Gly Phe Ile Val Gly Phe
        195                 200                 205

Thr Arg Gly Trp Lys Leu Thr Leu Val Ile Leu Ala Ile Ser Pro Val
```

-continued

```
    210                 215                 220

Leu Gly Leu Ser Ala Ala Val Trp Ala Lys Ile Leu Ser Ser Phe Thr
225                 230                 235                 240

Asp Lys Glu Leu Leu Ala Tyr Ala Lys Ala Gly Ala Val Ala Glu Glu
                245                 250                 255

Val Leu Ala Ala Ile Arg Thr Val Ile Ala Phe Gly Gly Gln Lys Lys
            260                 265                 270

Glu Leu Glu Arg Tyr Asn Lys Asn Leu Glu Glu Ala Lys Arg Ile Gly
        275                 280                 285

Ile Lys Lys Ala Ile Thr Ala Asn Ile Ser Ile Gly Ala Ala Phe Leu
    290                 295                 300

Leu Ile Tyr Ala Ser Tyr Ala Leu Ala Phe Trp Tyr Gly Thr Thr Leu
305                 310                 315                 320

Val Leu Ser Gly Glu Tyr Ser Ile Gly Gln Val Leu Thr Val Phe Phe
                325                 330                 335

Ser Val Leu Ile Gly Ala Phe Ser Val Gly Gln Ala Ser Pro Ser Ile
            340                 345                 350

Glu Ala Phe Ala Asn Ala Arg Gly Ala Ala Tyr Glu Ile Phe Lys Ile
        355                 360                 365

Ile Asp Asn Lys Pro Ser Ile Asp Ser Tyr Ser Lys Ser Gly His Lys
    370                 375                 380

Pro Asp Asn Ile Lys Gly Asn Leu Glu Phe Arg Asn Val His Phe Ser
385                 390                 395                 400

Tyr Pro Ser Arg Lys Glu Val Lys Ile Leu Lys Gly Leu Asn Leu Lys
                405                 410                 415

Val Gln Ser Gly Gln Thr Val Ala Leu Val Gly Asn Ser Gly Cys Gly
            420                 425                 430

Lys Ser Thr Thr Val Gln Leu Met Gln Arg Leu Tyr Asp Pro Thr Glu
        435                 440                 445

Gly Met Val Ser Val Asp Gly Gln Asp Ile Arg Thr Ile Asn Val Arg
    450                 455                 460

Phe Leu Arg Glu Ile Ile Gly Val Val Ser Gln Glu Pro Val Leu Phe
465                 470                 475                 480

Ala Thr Thr Ile Ala Glu Asn Ile Arg Tyr Gly Arg Glu Asn Val Thr
                485                 490                 495

Met Asp Glu Ile Glu Lys Ala Val Lys Glu Ala Asn Ala Tyr Asp Phe
            500                 505                 510

Ile Met Lys Leu Pro His Lys Phe Asp Thr Leu Val Gly Glu Arg Gly
        515                 520                 525

Ala Gln Leu Ser Gly Gly Gln Lys Gln Arg Ile Ala Ile Ala Arg Ala
    530                 535                 540

Leu Val Arg Asn Pro Lys Ile Leu Leu Leu Asp Glu Ala Thr Ser Ala
545                 550                 555                 560

Leu Asp Thr Glu Ser Glu Ala Val Val Gln Val Ala Leu Asp Lys Ala
                565                 570                 575

Arg Lys Gly Arg Thr Thr Ile Val Ile Ala His Arg Leu Ser Thr Val
            580                 585                 590

Arg Asn Ala Asp Val Ile Ala Gly Phe Asp Asp Gly Val Ile Val Glu
        595                 600                 605

Lys Gly Asn His Asp Glu Leu Met Lys Glu Lys Gly Ile Tyr Phe Lys
    610                 615                 620

Leu Val Thr Met Gln Thr Ala Gly Asn Glu Val Glu Leu Glu Asn Ala
625                 630                 635                 640
```

-continued

```
Ala Asp Glu Ser Lys Ser Glu Ile Asp Ala Leu Glu Met Ser Ser Asn
                645                 650                 655

Asp Ser Arg Ser Ser Leu Ile Arg Lys Arg Ser Thr Arg Arg Ser Val
            660                 665                 670

Arg Gly Ser Gln Ala Gln Asp Arg Lys Leu Ser Thr Lys Glu Ala Leu
        675                 680                 685

Asp Glu Ser Ile Pro Pro Val Ser Phe Trp Arg Ile Met Lys Leu Asn
    690                 695                 700

Leu Thr Glu Trp Pro Tyr Phe Val Val Gly Val Phe Cys Ala Ile Ile
705                 710                 715                 720

Asn Gly Gly Leu Gln Pro Ala Phe Ala Ile Ile Phe Ser Lys Ile Ile
                725                 730                 735

Gly Val Phe Thr Arg Ile Asp Asp Pro Glu Thr Lys Arg Gln Asn Ser
            740                 745                 750

Asn Leu Phe Ser Leu Leu Phe Leu Ala Leu Gly Ile Ile Ser Phe Ile
        755                 760                 765

Thr Phe Phe Leu Gln Gly Phe Thr Phe Gly Lys Ala Gly Glu Ile Leu
    770                 775                 780

Thr Lys Arg Leu Arg Tyr Met Val Phe Arg Ser Met Leu Arg Gln Asp
785                 790                 795                 800

Val Ser Trp Phe Asp Asp Pro Lys Asn Thr Thr Gly Ala Leu Thr Thr
                805                 810                 815

Arg Leu Ala Asn Asp Ala Ala Gln Val Lys Gly Ala Ile Gly Ser Arg
            820                 825                 830

Leu Ala Val Ile Thr Gln Asn Ile Ala Asn Leu Gly Thr Gly Ile Ile
        835                 840                 845

Ile Ser Phe Ile Tyr Gly Trp Gln Leu Thr Leu Leu Leu Leu Ala Ile
    850                 855                 860

Val Pro Ile Ile Ala Ile Ala Gly Val Val Glu Met Lys Met Leu Ser
865                 870                 875                 880

Gly Gln Ala Leu Lys Asp Lys Lys Glu Leu Glu Gly Ala Gly Lys Ile
                885                 890                 895

Ala Thr Glu Ala Ile Glu Asn Phe Arg Thr Val Val Ser Leu Thr Gln
            900                 905                 910

Glu Gln Lys Phe Glu His Met Tyr Ala Gln Ser Leu Gln Val Pro Tyr
        915                 920                 925

Arg Asn Ser Leu Arg Lys Ala His Ile Phe Gly Ile Thr Phe Ser Phe
    930                 935                 940

Thr Gln Ala Met Met Tyr Phe Ser Tyr Ala Gly Cys Phe Arg Phe Gly
945                 950                 955                 960

Ala Tyr Leu Val Ala His Lys Leu Met Ser Phe Glu Asp Val Leu Leu
                965                 970                 975

Val Phe Ser Ala Val Val Phe Gly Ala Met Ala Val Gly Gln Val Ser
            980                 985                 990

Ser Phe Ala Pro Asp Tyr Ala Lys Ala Lys Ile Ser Ala Ala His Ile
        995                 1000                1005

Ile Met Ile Ile Glu Lys Thr Pro Leu Ile Asp Ser Tyr Ser Thr Glu
    1010                1015                1020

Gly Leu Met Pro Asn Thr Leu Glu Gly Asn Val Thr Phe Gly Glu Val
1025                1030                1035                1040

Val Phe Asn Tyr Pro Thr Arg Pro Asp Ile Pro Val Leu Gln Gly Leu
                1045                1050                1055
```

-continued

```
Ser Leu Glu Val Lys Lys Gly Gln Thr Leu Ala Leu Val Gly Ser Ser
            1060                1065                1070

Gly Cys Gly Lys Ser Thr Val Val Gln Leu Leu Glu Arg Phe Tyr Asp
        1075                1080                1085

Pro Leu Ala Gly Lys Val Leu Leu Asp Gly Lys Glu Ile Lys Arg Leu
    1090                1095                1100

Asn Val Gln Trp Leu Arg Ala His Leu Gly Ile Val Ser Gln Glu Pro
1105                1110                1115                1120

Ile Leu Phe Asp Cys Ser Ile Ala Glu Asn Ile Ala Tyr Gly Asp Asn
                1125                1130                1135

Ser Arg Val Val Ser Gln Glu Glu Ile Val Arg Ala Ala Lys Glu Ala
            1140                1145                1150

Asn Ile His Ala Phe Ile Glu Ser Leu Pro Asn Lys Tyr Ser Thr Lys
        1155                1160                1165

Val Gly Asp Lys Gly Thr Gln Leu Ser Gly Gly Gln Lys Gln Arg Ile
    1170                1175                1180

Ala Ile Ala Arg Ala Leu Val Arg Gln Pro His Ile Leu Leu Leu Asp
1185                1190                1195                1200

Glu Ala Thr Ser Ala Leu Asp Thr Glu Ser Glu Lys Val Val Gln Glu
                1205                1210                1215

Ala Leu Asp Lys Ala Arg Glu Gly Arg Thr Cys Ile Val Ile Ala His
            1220                1225                1230

Arg Leu Ser Thr Ile Gln Asn Ala Asp Leu Ile Val Val Phe Gln Asn
        1235                1240                1245

Gly Arg Val Lys Glu His Gly Thr His Gln Gln Leu Leu Ala Gln Lys
    1250                1255                1260

Gly Ile Tyr Phe Ser Met Val Ser Val Gln Ala Gly Thr Lys Arg Gln
1265                1270                1275                1280


<210> SEQ ID NO 12
<211> LENGTH: 1276
<212> TYPE: PRT
<213> ORGANISM: Mus musculus

<400> SEQUENCE: 12

Met Glu Phe Glu Glu Asn Leu Lys Gly Arg Ala Asp Lys Asn Phe Ser
 1               5                  10                  15

Lys Met Gly Lys Lys Ser Lys Lys Glu Lys Lys Glu Lys Lys Pro Ala
            20                  25                  30

Val Gly Val Phe Gly Met Phe Arg Tyr Ala Asp Trp Leu Asp Lys Leu
        35                  40                  45

Cys Met Ile Leu Gly Thr Leu Ala Ala Ile Ile His Gly Thr Leu Leu
    50                  55                  60

Pro Leu Leu Met Leu Val Phe Gly Asn Met Thr Asp Ser Phe Thr Lys
65                  70                  75                  80

Ala Glu Ala Ser Ile Leu Pro Ser Ile Thr Asn Gln Ser Gly Pro Asn
                85                  90                  95

Ser Thr Leu Ile Ile Ser Asn Ser Ser Leu Glu Glu Glu Met Ala Ile
            100                 105                 110

Tyr Ala Tyr Tyr Tyr Thr Gly Ile Gly Ala Gly Val Leu Ile Val Ala
        115                 120                 125

Tyr Ile Gln Val Ser Leu Trp Cys Leu Ala Ala Gly Arg Gln Ile His
    130                 135                 140

Lys Ile Arg Gln Lys Phe Phe His Ala Ile Met Asn Gln Glu Ile Gly
145                 150                 155                 160
```

-continued

```
Trp Phe Asp Val His Asp Val Gly Glu Leu Asn Thr Arg Leu Thr Asp
                165                 170                 175

Asp Val Ser Lys Ile Asn Asp Gly Ile Gly Asp Lys Ile Gly Met Phe
            180                 185                 190

Phe Gln Ser Ile Thr Thr Phe Leu Ala Gly Phe Ile Ile Gly Phe Ile
        195                 200                 205

Ser Gly Trp Lys Leu Thr Leu Val Ile Leu Ala Val Ser Pro Leu Ile
    210                 215                 220

Gly Leu Ser Ser Ala Leu Trp Ala Lys Val Leu Thr Ser Phe Thr Asn
225                 230                 235                 240

Lys Glu Leu Gln Ala Tyr Ala Lys Ala Gly Ala Val Ala Glu Glu Val
                245                 250                 255

Leu Ala Ala Ile Arg Thr Val Ile Ala Phe Gly Gly Gln Gln Lys Glu
            260                 265                 270

Leu Glu Arg Tyr Asn Lys Asn Leu Glu Glu Ala Lys Asn Val Gly Ile
        275                 280                 285

Lys Lys Ala Ile Thr Ala Ser Ile Ser Ile Gly Ile Ala Tyr Leu Leu
    290                 295                 300

Val Tyr Ala Ser Tyr Ala Leu Ala Phe Trp Tyr Gly Thr Ser Leu Val
305                 310                 315                 320

Leu Ser Asn Glu Tyr Ser Ile Gly Glu Val Leu Thr Val Phe Phe Ser
                325                 330                 335

Ile Leu Leu Gly Thr Phe Ser Ile Gly His Leu Ala Pro Asn Ile Glu
            340                 345                 350

Ala Phe Ala Asn Ala Arg Gly Ala Ala Phe Glu Ile Phe Lys Ile Ile
        355                 360                 365

Asp Asn Glu Pro Ser Ile Asp Ser Phe Ser Thr Lys Gly Tyr Lys Pro
    370                 375                 380

Asp Ser Ile Met Gly Asn Leu Glu Phe Lys Asn Val His Phe Asn Tyr
385                 390                 395                 400

Pro Ser Arg Ser Glu Val Gln Ile Leu Lys Gly Leu Asn Leu Lys Val
                405                 410                 415

Lys Ser Gly Gln Thr Val Ala Leu Val Gly Asn Ser Gly Cys Gly Lys
            420                 425                 430

Ser Thr Thr Val Gln Leu Met Gln Arg Leu Tyr Asp Pro Leu Glu Gly
        435                 440                 445

Val Val Ser Ile Asp Gly Gln Asp Ile Arg Thr Ile Asn Val Arg Tyr
    450                 455                 460

Leu Arg Glu Ile Ile Gly Val Val Ser Gln Glu Pro Val Leu Phe Ala
465                 470                 475                 480

Thr Thr Ile Ala Glu Asn Ile Arg Tyr Gly Arg Glu Asp Val Thr Met
                485                 490                 495

Asp Glu Ile Glu Lys Ala Val Lys Glu Ala Asn Ala Tyr Asp Phe Ile
            500                 505                 510

Met Lys Leu Pro His Gln Phe Asp Thr Leu Val Gly Glu Arg Gly Ala
        515                 520                 525

Gln Leu Ser Gly Gly Gln Lys Gln Arg Ile Ala Ile Ala Arg Ala Leu
    530                 535                 540

Val Arg Asn Pro Lys Ile Leu Leu Leu Asp Glu Ala Thr Ser Ala Leu
545                 550                 555                 560

Asp Thr Glu Ser Glu Ala Val Val Gln Ala Ala Leu Asp Lys Ala Arg
                565                 570                 575
```

-continued

```
Glu Gly Arg Thr Thr Ile Val Ile Ala His Arg Leu Ser Thr Val Arg
            580                 585                 590

Asn Ala Asp Val Ile Ala Gly Phe Asp Gly Gly Val Ile Val Glu Gln
        595                 600                 605

Gly Asn His Asp Glu Leu Met Arg Glu Lys Gly Ile Tyr Phe Lys Leu
    610                 615                 620

Val Met Thr Gln Thr Arg Gly Asn Glu Ile Glu Pro Gly Asn Asn Ala
625                 630                 635                 640

Tyr Gly Ser Gln Ser Asp Thr Asp Ala Ser Glu Leu Thr Ser Glu Glu
                645                 650                 655

Ser Lys Ser Pro Leu Ile Arg Arg Ser Ile Tyr Arg Ser Val His Arg
            660                 665                 670

Lys Gln Asp Gln Glu Arg Arg Leu Ser Met Lys Glu Ala Val Asp Glu
        675                 680                 685

Asp Val Pro Leu Val Ser Phe Trp Arg Ile Leu Asn Leu Asn Leu Ser
    690                 695                 700

Glu Trp Pro Tyr Leu Leu Val Gly Val Leu Cys Ala Val Ile Asn Gly
705                 710                 715                 720

Cys Ile Gln Pro Val Phe Ala Ile Val Phe Ser Arg Ile Val Gly Val
                725                 730                 735

Phe Ser Arg Asp Asp Asp His Glu Thr Lys Arg Gln Asn Cys Asn Leu
            740                 745                 750

Phe Ser Leu Phe Phe Leu Val Met Gly Leu Ile Ser Phe Val Thr Tyr
        755                 760                 765

Phe Phe Gln Gly Phe Thr Phe Gly Lys Ala Gly Glu Ile Leu Thr Lys
    770                 775                 780

Arg Val Arg Tyr Met Val Phe Lys Ser Met Leu Arg Gln Asp Ile Ser
785                 790                 795                 800

Trp Phe Asp Asp His Lys Asn Ser Thr Gly Ser Leu Thr Thr Arg Leu
                805                 810                 815

Ala Ser Asp Ala Ser Ser Val Lys Gly Ala Met Gly Ala Arg Leu Ala
            820                 825                 830

Val Val Thr Gln Asn Val Ala Asn Leu Gly Thr Gly Val Ile Leu Ser
        835                 840                 845

Leu Val Tyr Gly Trp Gln Leu Thr Leu Leu Leu Val Val Ile Ile Pro
    850                 855                 860

Leu Ile Val Leu Gly Gly Ile Ile Glu Met Lys Leu Leu Ser Gly Gln
865                 870                 875                 880

Ala Leu Lys Asp Lys Lys Gln Leu Glu Ile Ser Gly Lys Ile Ala Thr
                885                 890                 895

Glu Ala Ile Glu Asn Phe Arg Thr Ile Val Ser Leu Thr Arg Glu Gln
            900                 905                 910

Lys Phe Glu Thr Met Tyr Ala Gln Ser Leu Gln Val Pro Tyr Arg Asn
        915                 920                 925

Ala Met Lys Lys Ala His Val Phe Gly Ile Thr Phe Ser Phe Thr Gln
    930                 935                 940

Ala Met Met Tyr Phe Ser Tyr Ala Ala Cys Phe Arg Phe Gly Ala Tyr
945                 950                 955                 960

Leu Val Ala Gln Gln Leu Met Thr Phe Glu Asn Val Met Leu Val Phe
                965                 970                 975

Ser Ala Val Val Phe Gly Ala Met Ala Ala Gly Asn Thr Ser Ser Phe
            980                 985                 990

Ala Pro Asp Tyr Ala Lys Ala Lys Val Ser Ala Ser His Ile Ile Arg
```

-continued

```
        995                 1000                1005

Ile Ile Glu Lys Thr Pro Glu Ile Asp Ser Tyr Ser Thr Glu Gly Leu
    1010                1015                1020

Lys Pro Thr Leu Leu Glu Gly Asn Val Lys Phe Asn Gly Val Gln Phe
1025                1030                1035                1040

Asn Tyr Pro Thr Arg Pro Asn Ile Pro Val Leu Gln Gly Leu Ser Leu
                1045                1050                1055

Glu Val Lys Lys Gly Gln Thr Leu Ala Leu Val Gly Ser Ser Gly Cys
            1060                1065                1070

Gly Lys Ser Thr Val Val Gln Leu Leu Glu Arg Phe Tyr Asp Pro Met
        1075                1080                1085

Ala Gly Ser Val Phe Leu Asp Gly Lys Glu Ile Lys Gln Leu Asn Val
    1090                1095                1100

Gln Trp Leu Arg Ala His Leu Gly Ile Val Ser Gln Glu Pro Ile Leu
1105                1110                1115                1120

Phe Asp Cys Ser Ile Ala Glu Asn Ile Ala Tyr Gly Asp Asn Ser Arg
                1125                1130                1135

Ala Val Ser His Glu Glu Ile Val Arg Ala Ala Lys Glu Ala Asn Ile
            1140                1145                1150

His Gln Phe Ile Asp Ser Leu Pro Asp Lys Tyr Asn Thr Arg Val Gly
        1155                1160                1165

Asp Lys Gly Thr Gln Leu Ser Gly Gly Gln Lys Gln Arg Ile Ala Ile
    1170                1175                1180

Ala Arg Ala Leu Val Arg Gln Pro His Ile Leu Leu Leu Asp Glu Ala
1185                1190                1195                1200

Thr Ser Ala Leu Asp Thr Glu Ser Glu Lys Val Val Gln Glu Ala Leu
                1205                1210                1215

Asp Lys Ala Arg Glu Gly Arg Thr Cys Ile Val Ile Ala His Arg Leu
            1220                1225                1230

Ser Thr Ile Gln Asn Ala Asp Leu Ile Val Val Ile Glu Asn Gly Lys
        1235                1240                1245

Val Lys Glu His Gly Thr His Gln Gln Leu Leu Ala Gln Lys Gly Ile
    1250                1255                1260

Tyr Phe Ser Met Val Gln Ala Gly Ala Lys Arg Ser
1265                1270                1275
```

POLYNUCLEOTIDE AND POLYPEPTIDE FAT METABOLISM REGULATORS AND USES THEREOF

CROSS-REFERENCE TO RELATED APPLICATION

This application claims the benefit of U.S. provisional application No. 60/395,159, filed on Jul. 11, 2002.

BACKGROUND OF THE INVENTION

In general, this invention relates to nucleic acid and amino acid sequences involved in fat metabolism regulation and the use of these sequences as targets for the diagnosis, treatment, and prevention of obesity and obesity-related diseases. In addition, the invention relates to screening methods for identifying modulators of body fat metabolism and the development of treatments for obesity and obesity-related diseases.

Fat metabolism is controlled by a regulatory loop that exists between the central nervous system (CNS) and adipocytes. Adipocytes are specialized cells that store energy in the form of fat droplets, composed primarily of triglycerides. These fat droplets are thought to form by pinching off from membranes of the endoplasmic reticulum. Access to these fat stores is regulated by a protective protein coat, which limits their exposure to cellular lipases, enzymes that break-down fat. Adipocytes communicate with the CNS via peptide and hormonal signals that carry information regarding the peripheral energy state. In response to these signals, the CNS controls food seeking or satiety behaviors in order to maintain energy homeostasis.

Large gaps remain in our understanding of the cell biology of fat storage, fat droplet biogenesis, and fat droplet size regulation. Moreover, the global regulators of fat metabolism, the interplay of food signals and hormones, and the genetic and environmental factors that influence body weight are still poorly understood. Addressing these deficits is crucial given the devastating impact of obesity on human health throughout the developed world. The dysregulation of body weight is associated with obesity, atherosclerosis, type II diabetes mellitus, and osteoarthritis of body joints. Conservative estimates of economic costs associated with the adverse health effects of obesity range between 2% to 7% of total health costs in the developed world. In the United States, for example, diabetes, one of the diseases associated and exacerbated by obesity, is thought to affect over 16 million individuals at an annual cost of over 92 billion dollars.

As current therapies offer limited effectiveness in treating obesity and obesity-related disease, a need exists for new therapeutic targets.

SUMMARY OF THE INVENTION

As described below, the present invention features nucleic acids and polypeptides that regulate fat metabolism.

In a first aspect, the invention generally features a method for identifying a nucleic acid molecule encoding a fat metabolism regulator polypeptide whose inactivation results in an alteration in nematode fat content or localization. The method includes the steps of: (a) providing a mutagenized nematode; (b) contacting the nematode with a dye that stains body fat (e.g., Nile Red); and (c) comparing the body fat staining of the mutagenized nematode to a control nematode, where a mutation in a nucleic acid molecule encoding a fat metabolism regulator polypeptide is identified by an alteration in nematode fat content or localization. In one embodiment of this method, the mutagenized nematode includes a mutation, prior to mutagenesis, in a fat metabolism regulator nucleic acid molecule.

In a second aspect, the invention generally features a method for identifying a nucleic acid molecule that encodes a fat metabolism regulator polypeptide whose inactivation results in an alteration in nematode fat content or localization. The method includes the steps of: (a) contacting a nematode with a candidate inhibitory nucleic acid molecule (e.g., dsRNA, siRNA, or antisense); (b) contacting the nematode with a dye that stains body fat (e.g., Nile Red); and (c) comparing the body fat staining of the nematode contacted with the inhibitory nucleic acid molecule (e.g., dsRNA, siRNA, or antisense) to a control nematode, where an alteration in body fat staining identifies the sense nucleic acid molecule corresponding to an antisense strand of the inhibitory nucleic acid molecule (e.g., dsRNA, siRNA, or antisense), as a nucleic acid molecule encoding a fat metabolism regulator polypeptide whose inactivation results in an alteration in nematode fat content or localization. In one embodiment, the nematode includes a mutation in rrf-3. In another embodiment, the nematode includes a mutation in a fat metabolism regulator nucleic acid molecule (e.g., lpo-1, lpo-2, lpo-3, lpo-4, lpo-5, lpo-6, and lpo-7).

In a third aspect, the invention generally features a method for identifying a candidate compound that modulates fat metabolism. The method includes the steps of: (a) providing a cell (e.g., a nematode cell or a mammalian cell) expressing a fat metabolism regulator nucleic acid molecule selected from the group consisting of those encoding a polypeptide listed in Tables V, VI, VII, XII, XIII, or XIV; (b) contacting the cell with a candidate compound; and (c) comparing the expression of the nucleic acid molecule in the cell contacted with the candidate compound with the expression of the nucleic acid molecule in a control cell, where an alteration in the expression identifies the candidate compound as a candidate compound that modulates fat metabolism.

In a fourth aspect, the invention generally features a method for identifying a candidate compound that modulates fat metabolism. The method includes the steps of: (a) providing a nematode cell expressing a fat metabolism regulator nucleic acid molecule; (b) contacting the nematode cell with a candidate compound; and (c) comparing the expression of the nucleic acid molecule in the cell contacted with the candidate compound with the expression of the nucleic acid molecule in a control cell, where an alteration in the expression identifies the candidate compound as a candidate compound that modulates fat metabolism.

In one embodiment of the third or fourth aspects, the screening method identifies a compound that increases or decreases the transcription of the fat metabolism regulator nucleic acid molecule. In another embodiment, the screening method identifies a compound that increases or decreases translation of an mRNA transcribed from the fat metabolism regulator nucleic acid molecule. In vet another embodiment the compound is a member of a chemical library. In yet another embodiment, the nematode cell is in a nematode. In yet other embodiments, one or more of the fat metabolism regulator nucleic acids are selected from the group consisting of those listed in Tables V, VI, VII, XII, XIII, and XIV.

In a fifth aspect, the invention generally features a method for identifying a candidate compound that modulates fat metabolism. The method includes the steps of: (a) providing a cell (e.g., a nematode cell or a mammalian cell) expressing a fat metabolism regulator polypeptide selected from the group consisting of one or more of those listed in Table V, VI, VII, XII, XIII, and XIV; (b) contacting the cell with a candidate compound; and (c) comparing the biological activity of the fat metabolism regulator polypeptide in the cell contacted with the candidate compound to a control cell, where an alteration in the biological activity of the fat metabolism regulator polypeptide identifies the candidate compound as a candidate compound that modulates fat metabolism.

In a sixth aspect, the invention generally features a method for identifying a candidate compound that modulates fat metabolism. The method includes the steps of: (a) providing a nematode cell expressing a fat metabolism regulator polypeptide; (b) contacting the nematode cell with a candidate compound; and (c) comparing the biological activity of the fat metabolism regulator polypeptide in the nematode cell contacted with the candidate compound to a control cell, where an alteration in the biological activity of the fat metabolism regulator polypeptide identifies the candidate compound as a candidate compound that modulates fat metabolism.

In one embodiment, the fat metabolism regulator polypeptide is an endogenous regulator polypeptide. In another embodiment, the fat metabolism regulator polypeptide is a polypeptide selected from the group consisting of one or more of those listed in Tables XII, XIII, and XIV. In yet another embodiment, biological activity is monitored with an enzymatic assay, an immunological assay, or by detecting fat levels. In yet another embodiment, the nematode cell is in a nematode.

In a seventh aspect, the invention generally features a method for identifying a candidate compound that modulates fat metabolism. The method includes the steps of: (a) contacting a nematode with a candidate compound and a dye that stains body fat; and (b) comparing staining by the dye in the nematode contacted with a candidate compound to a control nematode, where an alteration in the staining identifies the candidate compound as a candidate compound that modulates fat metabolism. In one embodiment, the nematode includes a mutation in a fat metabolism regulator nucleic acid molecule (e.g., lpo-1, lpo-2, lpo-3, lpo-4, lpo-5, lpo-6, and lpo-7).

In an eighth aspect, the invention generally features a microarray consisting of at least two fat metabolism regulator nucleic acids or fragments thereof, where inactivation of each of the fat metabolism regulator nucleic acids results in a decrease in fat content of an organism (e.g., *C. elegans*, a mammal, or a human) compared to a control organism. In one embodiment, at least one of the fat metabolism regulator nucleic acids is chosen from the group consisting of one or more of the nucleic acids that encode polypeptides listed in Tables V, VI, IX, X, XII, and XIII. In another embodiment, the inactivation does not reduce the viability of an organism.

In a ninth aspect, the invention generally features a microarray consisting of at least two fat metabolism regulator nucleic acids or fragments thereof, where inactivation of each of the fat metabolism regulator nucleic acids results in an increase in fat content of an organism (e.g., *C. elegans*, a mammal, or a human) compared to a control organism. In one embodiment, at least one of the fat metabolism regulator nucleic acids is chosen from the group consisting of one or more of the nucleic acids that encode polypeptides listed in Tables VII, XI, and XIV.

In a tenth aspect, the invention generally features a microarray consisting of at least two of the fat metabolism regulator polypeptide molecules or fragments thereof, where inactivation of each of the fat metabolism regulator polypeptides results in a decrease in fat content of an organism compared to a control organism (e.g., *C. elegans*, a mammal, or a human). In one embodiment, the polypeptides are chosen from the group consisting of one or more of those listed in Tables V, VI, IX, X, XII, and XIII.

In an eleventh aspect, the invention generally features a microarray consisting of at least two of the fat metabolism regulator polypeptides of an organism or fragments thereof, where inactivation of the fat metabolism regulator polypeptides results in an increase in fat content of an organism (e.g., *C. elegans*, a mammal, or a human) compared to a control organism. In one embodiment, at least one of the polypeptides is chosen from the group consisting of one or more of the polypeptides listed in Tables VII, XI, and XIV.

In a twelfth aspect, the invention generally features a method of identifying a candidate compound that modulates fat metabolism. The method includes (a) contacting a cell with a candidate compound; (b) obtaining mRNA from said cell; (c) contacting a microarray of the invention with a candidate compound; and (d) detecting an alteration in cellular mRNA levels of a fat metabolism regulator nucleic acid molecule in said cell contacted with said candidate compound compared to a control cell; where the alteration identifies the candidate compound as a candidate compound that modulates fat metabolism.

In a thirteenth aspect, the invention generally features a method of identifying a candidate compound that modulates fat metabolism. The method includes (a) contacting the microarray of the invention with a candidate compound; and (b) detecting binding of the candidate compound to a fat metabolism regulator polypeptide; where the binding identifies the compound as a candidate compound that modulates fat metabolism.

In a fourteenth aspect, the invention generally features a purified nucleic acid library, where at least 3%, 5%, 10%, 20%, 30%, 40%, 50%, 60%, 70%, 80%, 90%, or even 95–99% of the total nucleic acids in the library encode fat metabolism regulator polypeptides. In one embodiment, the nucleic acids in the library are carried in a vector. In another embodiment, each of the nucleic acids in the library is fused to a reporter gene. In yet another embodiment, the library includes at least one of the fat metabolism regulator nucleic acids selected from the nucleic acids that encode the polypeptides consisting of one or more of those listed in Tables XII, XIII, or XIV.

In a fifteenth aspect, the invention generally features a method of identifying a candidate compound that modulates fat metabolism. The method includes the steps of: a) contacting a cell including one member of the library of described above; and b) measuring the expression of the reporter gene; and c) comparing the level of reporter gene expression in the cell contacted with the candidate compound with a control cell not contacted with the candidate compound, where an alteration in the level of the reporter gene expression identifies the candidate compound as a compound that modulates fat metabolism.

In a sixteenth aspect, the invention generally features an isolated polypeptide including an amino acid sequence having at least 40%, 50%, 60%, 70%, 80%, 90%, or even 95–99% identity to the amino acid sequence of a polypeptide selected from the group consisting of one or more of those listed in Tables XV, XVI, and XVII, where expression of the polypeptide in an organism affects the regulation of fat metabolism in the organism. In one embodiment, the isolated polypeptide of this aspect includes the amino acid sequence of a polypeptide selected from the group consisting of those listed in Tables XV, XVI, and XVII.

In a seventeenth aspect, the invention generally features an isolated nucleic acid molecule including a nucleotide sequence having at least 40%, 50%, 60%, 70%, 80%, 90%, or even 95–99% identity to the nucleotide sequence of a nucleic acid molecule selected from the group consisting of one or more of those that encode the polypeptides listed in Tables XV, XVI, and XVII, where expression of the nucleic acid molecule in an organism affects the regulation of fat metabolism in the organism. In one embodiment of this aspect, the nucleic acid molecule includes the nucleotide sequence of a nucleic acid molecule selected from the group consisting of those that encode the polypeptides listed in Tables XV, XVI, and XVII or a complement thereof, or a fragment having the biological activity thereof. In addition, the invention includes a vector or a host cell including the isolated nucleic acid molecule of this aspect.

In an eighteenth aspect, the invention generally features a transgenic animal (e.g., a *C. elegans*, mammal, or rodent) expressing a fat metabolism regulator nucleic acid sequence, the nucleic acid sequence being selected from the group consisting of those that encode the polypeptides listed in Tables XV, XVI, and XVII.

In a nineteenth aspect, the invention generally features an organism (e.g., a *C. elegans*, mammal, or rodent) including a mutation in a fat metabolism regulator nucleic acid sequence the nucleic acid sequence being selected from the group consisting of those that encode the polypeptides listed in Tables XV, XVI, and XVII.

In a twentieth aspect, the invention generally features a double-stranded RNA (e.g., siRNA) corresponding to at least a portion of a fat metabolism regulator nucleic acid molecule of an organism the nucleic acid molecule being selected from the group consisting of those that encode the polypeptides listed in Tables XV, XVI, and XVII, where the double-stranded RNA is capable of decreasing the level of protein encoded by the fat metabolism regulator nucleic acid molecule.

In a twenty-first aspect, the invention generally features an antisense nucleic acid molecule, where the nucleic acid molecule is complementary to at least six nucleotides of a nucleic acid molecule selected from the group consisting of those that encode the polypeptides listed in Tables XV, XVI, and XVII, and where the antisense nucleic acid is capable of decreasing expression from the nucleic acid molecule to which it is complementary.

In a twenty-second aspect, the invention generally features an isolated polypeptide including an amino acid sequence having at least 35%, 40%, 50%, 60%, 70%, 80%, 90%, or even 95–99% identity to the amino acid sequence of LPO-1 (SEQ ID NO.:2), where expression of the polypeptide in an organism (e.g., a *C. elegans*, mammal, rodent, or human) affects the regulation of fat metabolism in the organism. In one embodiment, the polypeptide includes the amino acid sequence of LPO-1 (SEQ ID NO:2).

In a twenty-third aspect, the invention generally features an isolated nucleic acid molecule having at least 35%, 40%, 50%, 60%, 70%, 80%, 90%, or even 95–99% identity to the nucleotide sequence of lpo-1 (SEQ ID NO:1), where expression of the nucleic acid molecule in an organism (e.g., a *C. elegans*, mammal, or human) affects the regulation of fat metabolism in the organism. In one embodiment, the nucleic acid molecule includes the nucleotide sequence of lpo-1 (SEQ ID NO:1) or a complement thereof. In another embodiment the invention features a vector or host cell including the isolated nucleic acid molecule of the twenty-third aspect.

In a twenty-fourth aspect, the invention generally features an antibody that specifically binds to the LPO-1 (SEQ ID NO:2) polypeptide.

In a twenty-fifth aspect, the invention generally features an isolated polypeptide including an amino acid sequence having at least 45%, 50%, 60%, 70%, 80%, 90%, or even 95–99% identity to the amino acid sequence of LPO-3 (SEQ ID NO:4), where expression of the polypeptide in an organism (e.g., a *C. elegans*, mammal, or human) affects the regulation of fat metabolism in the organism.

In a twenty-sixth aspect, the invention generally features an isolated nucleic acid molecule having at least 45%, 50%, 60%, 70%, 80%, 90%, or even 95–99% % identity to the nucleotide sequence of lpo-3 (SEQ ID NO:3), where expression of the nucleic acid molecule in an organism affects the regulation of fat metabolism in the organism. In one embodiment, the nucleic acid molecule includes the nucleotide sequence of lpo-3 or a complement thereof. In another embodiment of this aspect, the nucleic acids are included in a vector or a host cell.

In a twenty-seventh aspect, the invention generally features a method for diagnosing an organism (e.g., a human) having, or having a propensity to develop, a disease associated with fat metabolism regulation, obesity, or obesity-related diseases. The method includes detecting an alteration in the sequence of a fat metabolism regulator nucleic and molecule relative to a wild-type sequence of said fat metabolism regulator nucleic acid molecule, the molecule being selected from the group consisting of one or more of those that encode the polypeptides listed in Tables XII, XIII, and XIV.

In a twenty-eighth aspect, the invention generally features a method for diagnosing an organism (e.g., a human) having, or having a propensity to develop, a disease associated with fat metabolism regulation, obesity, or an obesity-related disease. The method includes detecting an alteration in the expression of a fat metabolism regulator nucleic acid molecule or polypeptide relative to the wild type level of expression of said fat metabolism regulator nucleic acid molecule or polypeptide, the nucleic acid or polypeptide being selected from the group consisting of those listed in Tables XII, XIII, and XIV.

In a twenty-ninth aspect, the invention generally features a method for diagnosing an organism (e.g., a human) having, or having a propensity to develop, a disease associated with fat metabolism regulation, obesity, or an obesity-related disease. The method includes detecting an alteration in the biological activity of a fat metabolism regulator polypeptide relative to the wild-type level of activity.

In a thirtieth aspect, the invention generally features a collection of primer sets, each of the primer sets including at least two primers that bind to a fat metabolism regulator nucleic acid molecule that encodes a polypeptide selected from the group consisting of those listed in Tables IX, X, XI, XII, XIII, and IV under high stringency conditions, the collection including at least two primer sets. In one embodiment, the binding detects an alteration in a fat metabolism regulator nucleic acid molecule. In another embodiment, the primer sets can be used to amplify a fat metabolism regulator nucleic acid molecule.

In a thirty-first aspect, the invention generally features a method for ameliorating or delaying a fat metabolism or obesity disorder in an organism (e.g., a human). The method includes contacting the organism with an inhibitory nucleic acid molecule (e.g., dsRNA, siRNA, or antisense) whose antisense strand complements a portion of a fat metabolism regulator nucleic acid molecule selected from the group consisting of those that encode the polypeptides listed in Tables XII, XIII, and IV.

In a thirty-second aspect, the invention generally features a method for ameliorating or delaying a fat metabolism or obesity disorder in an organism (e.g., a human). The method includes contacting the organism with a fat metabolism regulator nucleic acid molecule selected from the group consisting of those that encode the polypeptides listed in Tables XII, XIII, and IV.

In a thirty-third aspect, the invention generally features a pharmaceutical composition including fat metabolism regulator polypeptides or portions thereof, selected from the group consisting of those that encode the polypeptides listed in Tables XII, XIII, and IV, that treat a fat metabolism or obesity disorder.

In a thirty-fourth aspect, the invention generally features a pharmaceutical composition including a fat metabolism regulator nucleic acid molecule or portion thereof, selected from the group consisting of those that encode the polypeptides listed in Tables XII, XIII, and IV, that treats a fat metabolism or obesity disorder.

In preferred embodiments of any of the above aspects, any one or more of the nucleic acids or polypeptides selected from the group consisting of those listed in Tables V, VI, VII, IX, X, XI, XII, XIII, XIV, XV, XVI, XVII, XVIII, XIX, and XX may be used.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule which is transcribed from a DNA molecule, as well as a recombinant DNA which is part of a hybrid gene encoding additional polypeptide sequence.

By "polypeptide" is meant any chain of amino acids, regardless of length or post-translational modification (for example, glycosylation or phosphorylation).

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel clectrophoresis, or by HPLC analysis.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80%, and most preferably 90% or even 95% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "transformed cell" is meant a cell into which (or into an ancestor of which) has been introduced, by means of recombinant DNA techniques, a polynucleotide molecule encoding (as used herein) a polypeptide of the invention.

By "positioned for expression" is meant that the polynucleotide of the invention (e.g., a DNA molecule) is positioned adjacent to a DNA sequence which directs transcription and translation of the sequence (i.e., facilitates the production of, for example, a recombinant polypepetide of the invention, or an RNA molecule).

By "purified antibody" is meant an antibody which is at least 60%, by weight, free from proteins and naturally-occurring organic molecules with which it is naturally associated. Preferably, the preparation is at least 75%, more preferably 90%, and most preferably at least 99%, by weight, antibody. A purified antibody of the invention may be obtained, for example, by affinity chromatography using a recombinantly-produced polypeptide of the invention and standard techniques.

By "specifically binds" is meant a compound or antibody which recognizes and binds a polypeptide of the invention but which does not substantially recognize and bind other molecules in a sample, for example, a biological sample, which naturally includes a polypeptide of the invention.

By "derived from" is meant isolated from or having the sequence of a naturally-occurring sequence (e.g., a cDNA, genomic DNA, synthetic, or combination thereof).

By "immunological assay" is meant an assay that relies on an immunological reaction, for example, antibody binding to an antigen. Examples of immunological assays include ELISAs, Western blots, immunoprecipitations, and other assays known to the skilled artisan.

By "inhibitory nucleic acid" is meant a nucleic acid that reduces or eliminates expression or biological activity of a gene or protein of interest. "Inhibitory nucleic acids" include, without limitation, antisense nucleic acids, double stranded RNAs (dsRNA), or small interfering RNAs (siRNA), or analogs thereof.

By "anti-sense" is meant a nucleic acid, or analog thereof, regardless of length, that is complementary to the coding strand or mRNA of a nucleic acid sequence. In one embodiment, an antisense RNA is introduced to an individual cell, tissue, organ, or to a whole animals. Desirably the anti-sense nucleic acid is capable of decreasing the expression or biological activity of a nucleic acid or amino acid sequence. In one embodiment, the decrease in expression or biological activity is at least 10%, relative to a control, more desirably 25%, and most desirably 50%, 60%, 70%, 80%, 90%, or more. The anti-sense nucleic acid may contain a modified backbone, for example, phosphorothioate, phosphorodithioate, or other modified backbones known in the art, or may contain non-natural internucleoside linkages.

By "double stranded RNA" is meant a complementary pair of sense and antisense RNAs regardless of length. In one embodiment, these dsRNAs are introduced to an individual cell, tissue, organ, or to a whole animals. For example, they may be introduced systemically via the bloodstream. Desirably, the double stranded RNA is capable of decreasing the expression or biological activity of a nucleic acid or amino acid sequence. In one embodiment, the decrease in expression or biological activity is at least 10%, relative to a control, more desirably 25%, and most desirably 50%, 60%, 70%, 80%, 90%, or more. The anti-sense nucleic acid may contain a modified backbone, for example, phosphorothioate, phosphorodithioate, or other modified backbones known in the art, or may contain non-natural internucleoside linkages.

By "siRNA" is meant a double stranded RNA that complements a region of an mRNA. Optimally, an siRNA is 22–24 nucleotides in length and has a 2 base overhang at its 3' end. These dsRNAs can be introduced to an individual cell or to a whole animal, for example, they may be introduced systemically via the bloodstream. Such siRNAs are used to down-regulate mRNA levels or promoter activity. In one embodiment, the decrease in expression or biological activity is at least 10%, relative to a control, more desirably 25%, and most desirably 50%, 60%, 70%, 80%, 90%, or more. The siRNA may contain a modified backbone, for example, phosphorothioate, phosphorodithioate, or other modified backbones known in the art, or may contain non-natural internucleoside linkages.

By "hybridize" is meant pair to form a double-stranded molecule between complementary polynucleotide sequences (e.g., genes listed in Tables 1–4 and 7), or portions thereof, under various conditions of stringency. (See, e.g., Wahl, G. M. and S. L. Berger (1987) *Methods Enzymol.* 152:399; Kimmel, A. R. (1987) *Methods Enzymol.* 152:507) For example, stringent salt concentration will ordinarily be less than about 750 mM NaCl and 75 mM trisodium citrate, preferably less than about 500 mM NaCl and 50 mM trisodium citrate, and most preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and most preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 μg/ml denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and most preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a most preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (*Science* 196: 180, 1977); Grunstein and Hogness (*Proc. Natl. Acad. Sci.,* USA 72:3961, 1975); Ausubel et al. (*Current Protocols in Molecular Biology*, Wiley Interscience, New York, 2001); Berger and Kimmel (*Guide to Molecular Cloning Techniques,* 1987, Academic Press, New York); and Sambrook et al., *Molecular Cloning: A Laboratory Manual*, Cold Spring Harbor Laboratory Press, New York.

By "binds" is meant a compound or antibody which recognizes and binds a polypeptide of the invention but which does not substantially recognize and bind other different molecules in a sample, for example, a biological sample, which naturally includes a polypeptide of the invention.

By "ortholog" is meant a polypeptide or nucleic acid molecule of an organism that is highly related to a reference protein, or nucleic acid sequence, from another organism. An ortholog is functionally related to the reference protein or nucleic acid sequence. In other words, the ortholog and its reference molecule would be expected to fulfill similar, if not equivalent, functional roles in their respective organisms. For example, a *C. elegans* lipase and its mammalian ortholog would both be expected to fulfill the enzymatic function of lipases in their respective organisms. It is not required that an ortholog, when aligned with a reference sequence, have a particular degree of amino acid sequence identity to the reference sequence. A protein ortholog might share significant amino acid sequence identity over the entire length of the protein, for example, or, alternatively, might share significant amino acid sequence identity over only a single functionally important domain of the protein. Orthologs may be identified using methods provided herein. The functional role of an ortholog may be assayed using methods well known to the skilled artisan, and described herein. For example, function might be assayed in vivo or in vitro using a biochemical, immunological, or enzymatic assays; transformation rescue, Nile Red or BODIPY assays for the effect of gene inactivation on fat content, storage, or mobilization; such fat content assays, as described herein, may be carried out in a whole animal (e.g., *C. elegans*) or in tissue culture; function may also be assayed by gene inactivation (e.g., by RNAi, siRNA, or gene knockout), or gene over-expression, as well as by other methods.

By "fat metabolism" is meant, for example, fat storage, fat deposition, fat breakdown, fat droplet biogenesis, fat mobilization, or the increase, decrease, or maintenance of the fat content of an organism.

By "fat metabolism regulator polypeptide" is meant a polypeptide that modulates fat metabolism, for example, fat storage, fat deposition, fat breakdown, fat droplet biogenesis, fat mobilization, or the fat content of an organism. A fat metabolism regulator polypeptide has at least 50%, 60%, 70% amino acid sequence identity to the proteins encoded by the nucleic acid sequences listed in, for example, Tables V, VI, VII, IX, X, XI, XII, XIII, XIV, XV, XVI, and XVII. More desirably, a fat metabolism regulator polypeptide would have at least 75%, 80%, 85% amino acid sequence identity to the proteins encoded by the nucleic acid sequences listed in, for example, Tables V, VI, VII, IX, X, XI, XII, XIII, XIV, XV, XVI, and XVII. A fat metabolism regulator polypeptide could have at least 90%, 95%, or even 97% identity with polypeptide encoded by a nucleic acid sequence listed in, for example, Tables V, VI, VII, IX, X, XI, XII, XIII, XIV, XV, XVI, and XVII.

By "fat metabolism regulator nucleic acid" is meant a nucleic acid that encodes a fat metabolism regulator polypeptide. Such polypeptides are encoded by the nucleic acid sequences listed in, for example, Tables V, VI, VII, IX, X, XI, XII, XIII, XIV, XV, XVI, and XVII.

By "transgene" is meant any piece of DNA which is inserted by artifice into a cell and typically becomes part of the genome of the organism which develops from that cell. Such a transgene may include a gene which is partly or entirely heterologous (i.e., foreign) to the transgenic organism, or may represent a gene homologous to an endogenous gene of the organism.

By "transgenic" is meant any cell which includes a DNA sequence which is inserted by artifice into a cell and becomes part of the genome of the organism which develops from that cell. As used herein, the transgenic organisms are generally transgenic vertebrates, such as, zebrafish, mice, and rats, and the DNA (transgene) is inserted by artifice into the nuclear genome.

"Cell" as used herein may be a single-cellular organism, cell from a multi-cellular organism, or it may be a cell contained in a multi-cellular organism.

"Differentially expressed" means a difference in the expression level of a nucleic acid.

This difference may be either an increase or a decrease in expression, when compared to control conditions.

"Microarray" means a collection of nucleic acids or polypeptides from one or more organisms arranged on a solid support (for example, a chip, plate, or bead). These nucleic acids or polypeptides may be arranged in a grid where the location of each nucleic acid or polypeptide remains fixed to aid in identification of the individual nucleic acids or polypeptides. A microarray may include, for example, nucleic acids representing all, or a subset, of the open reading frames of an organism, or of the polypeptides that those open reading frames encode. In one embodiment, the nucleic acids of the array are defined as having a common region of the genome having limited homology to other regions of an organism's genome. A microarray may also be enriched for a particular type of gene. In one example, a "microarray of fat metabolism regulator nucleic acids or polypeptides" may be enriched for fat metabolism regulator nucleic acids or polypeptides so that, for example, it comprises at least 5%, 10%, 15%, 20%, 22%, 25%, 30%, 40%, 50%, 60%, 70%, 80%, 90%, 95%, 97% or even 99% fat metabolism regulator genes or their encoded fat metabolism regulator polypeptides. In one example, a "microarray of fat metabolism regulator nucleic acids or polypeptides" comprises the *C. elegans* nucleic acids listed in Tables V, VI, VII, IX, X, XI, XII, XIII, XIV, XV, XVI, and XVII; or the mammalian nucleic acids listed in Table IX, X, XI, XII, XIII, XIV, XV, XVI, or XVII, or the polypeptides they encode.

"Primer set" means a set of oligonucleotides that may be used, for example, for PCR. A primer set would consist of at least 2, 4, 6, 8, 10, 12, 14, 16, 18, 20, 30, 40, 50, 60, 80, 100, 200, 250, 300, 400, 500, 600, or more primers.

"Therapeutic compound" means a substance that has the potential of affecting the function of an organism. Such a compound may be, for example, a naturally occurring, semi-synthetic, or synthetic agent. For example, the test compound may be a drug that targets a specific function of an organism. A test compound may also be an antibiotic or a nutrient. A therapeutic compound may decrease, suppress, attenuate, diminish, arrest, or stabilize the development or progression of disease, disorder, or infection in a eukaryotic host organism.

The invention provides a number of targets that are useful for the development of drugs to treat obesity and the dysregulation of fat metabolism. In addition, the methods of the invention provide a facile means to identify therapies that are safe for use in eukaryotic host organisms (i.e., compounds which do not adversely affect the normal development, physiology, or fertility of the organism). In addition, the methods of the invention provide a route for analyzing virtually any number of compounds for effects on fat metabolism with high-volume throughput, high sensitivity, and low complexity. The methods are also relatively inexpensive to perform and enable the analysis of small quantities of active substances found in either purified or crude extract form.

Other features and advantages of the invention will be apparent from the detailed description, and from the claims.

BRIEF DESCRIPTION OF THE DRAWINGS

FIG. 4A is a photomicrograph showing Nile Red staining in a wild-type nematode. FIG. 4B is a photomicrograph showing Nile Red staining in a tph-1 (mg280)II (Sze et al., *Nature* 403:560–4, 2000) (serotonin-deficient) nematode. FIG. 4C is a photomicrograph showing Nile Red staining in a tub-1(nr2004) nematode.

FIGS. 6A and 6C show corresponding rhodamine and Nomarski images, respectively, of a daf-2(e1370) animal grown at 25° C. to induce dauer formation. FIGS. 6B and 6D show corresponding rhodamine and Nomarski images, respectively, of a daf-2(e1370) animal grown at 15° C. to bypass dauer entry.

FIG. 8A shows Nile Red staining in a wild-type untreated nematode. FIG. 8B shows Nile Red staining in a wild-type nematode treated with 5-aminoimidazole-4-carbozamide ribonucleoside (AICAR). FIG. 8C shows Nile Red staining in a wild-type starved nematode. FIG. 8D shows Nile Red staining in an adult daf-2(e1370) mutant nematode grown at the permissive temperature of 15° C. past the dauer decision stage and then shifted to the non-permissive temperature of 25° C. This nematode has increased fat content relative to a wild-type nematode. FIG. 8E shows Nile Red staining in a daf-2(e1370) mutant nematode treated with AICAR. FIG. 8F shows Nile Red staining in a starved adult daf-2(e1370) mutant nematode grown at 15° C. past the dauer decision stage and then shifted to the non-permissive temperature, 25° C. This nematode has increased fat content relative to a wild-type nematode.

FIG. 11D shows the genomic nucleic acid sequence of lpo-1 (Genomic Position: chromosome II: 6783394-6787620) (SEQ ID NO:1). The 5,570 nucleic acid sequence includes 545 basepairs upstream of the start codon. ATG (which is highlighted); 4,228 nucleotides of predicted exons (which are shown in upper-case letters) and introns (which are shown in lower case) and 558 basepairs downstream of the stop codon, TGA (which is highlighted).

FIG. 11E shows the nucleic acid sequence (SEQ ID NO:2) (2592 nucleotides) of the lpo-1 open reading frame.

FIG. 11F shows the predicted amino acid sequence (SEQ ID NO:3) of the LPO-1 protein.

FIG. 11G shows an alignment of LPO-1 and the human (accession number: 4507901) (SEQ ID NO:9) and rat (accession number: 6981706) (SEQ ID NO:10) very low density lipoprotein (VLDL) receptors. Identical amino acids are denoted with an asterisk (*). Conservative substitutions are denoted with a period (.), and substitutions that conserve the charge of the amino acid residues are denoted with a colon (:).

FIG. 12D shows the genomic nucleic acid sequence (SEQ ID NO:4) of lpo-3 (Genomic Position: chromosome I: 5897000-5903772). The 7,496 nucleotide sequence includes 420 nucleotides upstream of the start codon, ATG (which is highlighted); 6,774 nucleotides of predicted exons (which are shown in capitol letters) and introns (which are shown in lower case letters); and 304 nucleotides downstream of the stop codon, TGA (which is highlighted).

FIG. 12E shows the nucleic acid sequence (SEQ ID NO:5) of the lpo-3 open reading frame.

FIG. 12F shows the amino acid sequence (SEQ ID NO:6) of LPO-3.

FIG. 12G shows an amino acid sequence alignment of the LPO-3 with the human (Human Multidrug resistance protein 1 (P-glycoprotein-1), accession number:2506118) (SEQ ID NO:11) and mouse (ATP-binding cassette (P glycoprotein 1), accession number: 6755046) (SEQ ID NO:12) ATP-binding cassette (ABC)-type transporters. The glycine at position 1163, denoted in red, is mutated to aspartic acid in lpo-3. Identical amino acids are denoted with an asterisk (*). Conservative substitutions are denoted with a period (.), and substitutions that conserve the charge of the amino acid residues are denoted with a colon (:).

FIG. 13A shows a nematode grown on L4440 vector control RNAi bacteria. FIG. 13B shows reduced straining in a nematode grown on Y49A3A.1 (choline/ethanolamine phosphotransferase) RNAi bacteria. FIG. 13C shows reduced staining in a nematode grown on F08F8.2 (HMG-CoA reductase) RNAi bacteria. FIG. 13D shows reduced staining in a nematode grown on Y47D3B.7 (Sterol Response Element Binding Protein (SREBP), a transcription factor required for endogenous sterol synthesis) RNAi bacteria. FIG. 13E shows mislocalized staining in a nematode grown on K02D3.2 (steroidegenic acute regulatory related protein (StAr)) RNAi bacteria. FIG. 13F shows increased staining in a nematode grown on NHLH2 (neurogenic transcription factor) RNAi bacteria.

DESCRIPTION OF THE INVENTION

Figure 1A:
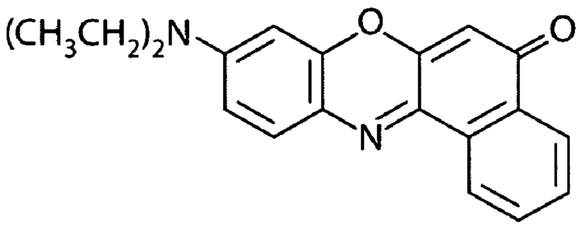
FIG. 1A shows the chemical structure of Nile Red.

The present invention features *C. elegans* fat metabolism regulator genes and polypeptides. Mammalian orthologs of these *C. elegans* genes have also been identified. Because pathways that regulate fat cell biology are likely to be evolutionarily conserved between mammals and nematodes, these mammalian genes provide new targets for the treatment of obesity and obesity-related disease, and the invention also features such methods.

As reported in more detail below, a systematic survey of the *C. elegans* genome using RNAi has identified nematode (and mammalian) genes that regulate fat storage. These fat metabolism regulator genes have been characterized in *C. elegans* and found to define two sets. A first set of fat metabolism regulator genes was defined by those whose inactivation caused a reduced fat (50% or less of wild-type fat level) or altered fat deposition phenotype. A large subset of these fat metabolism regulator genes included those whose inactivation did not result in significant viability, growth, or fertility defects. The mammalian orthologs of these *C. elegans* genes provide attractive therapeutic targets whose inactivation is unlikely to result in adverse side effects. Another attractive subset of therapeutic targets are those *C. elegans* genes and their mammalian orthologs whose inactivation results in a much reduced fat phenotype (20% or less of wild-type fat level) and whose inactivation does not significantly interfere with viability, growth, or fertility defects. Activating mutations in the human orthologs of these genes are likely to underlie human obesity or fat metabolism disorders.

A second useful set of *C. elegans* genes is defined by those whose inactivation results in an increase in nematode fat content. Loss of function or dominant negative mutations in these genes are likely to underlie human obesity or fat metabolism disorders.

A systematic method of identifying fat metabolism regulator genes was used that provides unique advantages over existing methods of gene identification, such as transcriptional profiling studies. In particular, the approach described herein assigns a genetic function in fat metabolism to genes identified in a genome-wide RNAi screen. In contrast, gene array based gene identification implicates a gene in a process by its transcriptional regulation, but fails to assign a function to that gene. The genetic and RNAi approaches described herein test whether a particular gene is required for fat accumulation, thus characterizing the function of the identified gene in *C. elegans* fat metabolism and predicting its role in mammalian fat metabolism. Many of the genes identified (e.g., phosphoenolpyruvate carboxykinase (PEPCK), 3-hydroxyacyl-CoA dehydrogenase, choline/ethanolamine kinase, and sterol response element binding protein, a transcription factor required for endogenous sterol synthesis (SREBP)) are focal points of regulation for their respective multicomponent metabolic pathways (gluconeogenesis, β-oxidation, phospholipid biosynthesis, and sterol metabolism, respectively). The fat phenotypes produced by their inactivation are likely due to significant shifts in metabolism resulting from the perturbation of key regulatory components. Given this identification of known, important components of fat metabolism, it is reasonable to conclude that other metabolic genes identified by this assay also serve as key regulated components of their particular pathways.

*C. elegans* Strains

All strains were maintained as described by Brenner (Brenner, *Genetics* 77:71–94, 1974) at 25° C., except when noted. The *E. coli* used for feeding *C. elegans* was strain OP50. The wild-type reference strain was N2 Bristol. The mutant strains used herein were as follows: tub-1(nr2004)II (kindly provided by Carl D. Johnson), tph-1(mg280)II (Sze et al., *Nature* 403:560–4, 2000), pgp-1(pk17)IV, pgp-3 (pk18)X, mrp-1(pk89)X; pgp-1(pk17)IV; pgp-3(pk18)X; mrp-1(pk89) (Broeks et al., *Embo J.* 14:1858–66, 1995).

The following strains were hatched and grown at the permissive temperature 15° C. until the L2 stage and then transferred to 25° C.: daf-2(e1370) III, daf-2(e1370) III; daf-1(m40) IV, daf-2(e1370) III; daf-3(mgDf90) X, daf-2 (e1370) III; daf-12(sa204) X, daf-16(mgDf47) I; daf-2 (e1370) III, daf-2(e1370) III; daf-18(mg198) IV, daf-16 (mgDf47) I, pdk-1(sa680) X, daf-16(mgDf47) I, daf-3 (mgDf90) X, daf-12(m20) X, daf-7(e1372) III, daf-7(e1372) III, daf-12(m20) X, daf-7(e1372) III; daf-3(mgDf90) X, (Paradis et al., *Genes Dev.* 13:1438–52, 1999; Tissenbaum et al., *Genetics* 148:703–17,1998; Patterson et al., *Genes Dev.* 11:2679–90, 1997; Gottlieb et al., *Genetics* 137:107–20, 1994); many of these strains were provided by the Caenorhabditis Genetic Center.

Detection of Nematode Fat by Nile Red

Figure 1B:
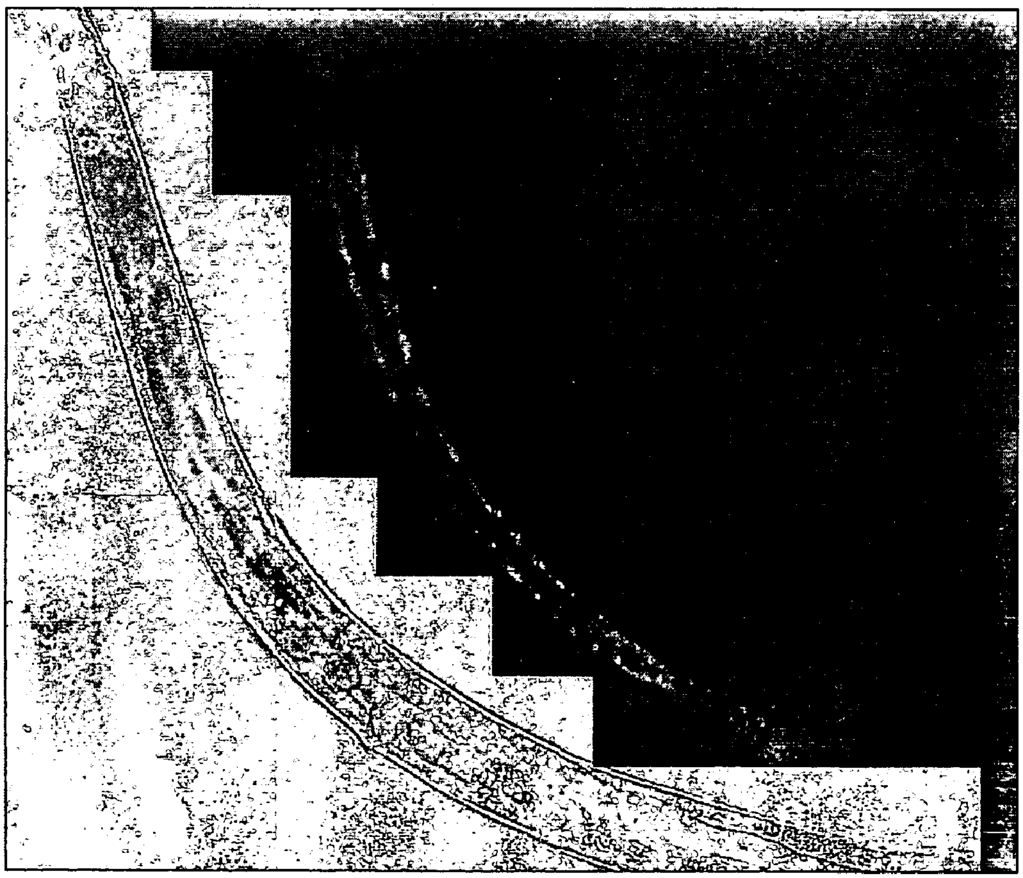
FIG. 1B is a Nomarski photomicrograph showing a wild-type nematode grown on Nile Red, and a photomicrograph showing Nile Red staining in a wild-type nematode grown on Nile Red.

The vital dye, 9-diethylamino-5H-benzo[α]phenoxazine-5-one (Nile Red) (FIG. 1A), was used to visualize fat droplets in living nematodes (FIG. 1B). Nile Red had previously been used as a vital stain for the detection of intracellular lipid droplets by fluorescence microscopy in cell culture models of fat accumulation (Greenspan et al., *J. Lipid. Res.* 26:781–9, 1985; Greenspan et al., *J. Cell. Biol.* 100:965–73, 1985). Nile Red is non-fluorescent in an aqueous environment, but undergoes a spectral shift in the presence of hydrophobic lipid.

Nile Red was adapted for use in a *C. elegans* in vivo genetic screen. Nile Red powder (N-1142 Molecular Probes) was dissolved in acetone at 500 μg/ml. It was then diluted in 1× phosphate buffered saline (PBS) and added to nematode growth media (NGM) plates, with lawns of OP50 or RNAi bacteria. The final Nile Red concentration in plates was 0.05 μg/ml. Nematodes were cultured on plates containing *E. coli* OP50 mixed with Nile Red. While no Nile Red fat staining was observed in nematodes maintained on agar plates containing Nile Red in the absence of *E. coli, C. elegans* feeding on the Nile Red *E. coli* mixture incorporated the dye specifically into lipid droplets within intestinal cells. No adverse effects on *C. elegans* growth rate, brood-size, pharyngeal pumping, dauer formation, dauer recovery, or lifespan was observed at Nile Red concentrations between 0.001 μg/ml and 25 μg/ml. The growth rate, brood-size, pharyngeal pumping, dauer formation, dauer recovery, and lifespan assays were carried out as follows. The mutant nematodes were compared to wild-type control nematodes.

To assay growth rate, nematode eggs were hatched in M9 buffer for twelve hours to obtain synchronized L1 progeny. The L1 progeny were then transferred to NGM/OP50 plates and maintained at 25° C. The period of time required for the population to reach the L4 stage was recorded.

To assay brood size, at least three L4 hermaphrodites were transferred to individual NGM/OP50 plates and allowed to lay eggs for forty-eight hours. The parents were then removed and the number of progeny on each plate was scored within twenty-four hours (prior to the time at which the F1 progeny reached the egg-laying adult stage). All experiments were done at 25° C.

To assay pharyngeal pumping, nematodes are placed on NGM plates with OP50 bacteria at 25° C., and observed under a dissection scope. The number of times the terminal bulb of the pharynx opens and closes per minute in the presence of bacteria is then determined.

Dauer formation, dauer recovery, and life span were assayed using standard methods known to the skilled artisan, and described, for example, in Malone, et al. (*Genetics* 143, 1193–1205, 1996).

To assay lifespan, nematodes were grown on NGM plates with OP50 bacteria at 25° C. until the L4 stage (t=0). At least 50 nematodes were then transferred to NGM/OP50 plates containing 0.1 mg/ml 5-fluorodeoxyuridine to prevent growth of progeny. Nematodes were then observed every one to two days, and scored as dead when no longer responsive to gentle prodding with a platinum wire.

The specificity of Nile Red staining was confirmed using Sudan Black B, a dye that had previously been shown to specifically stain *C. elegans* fat (Sze et al., *Nature* 403: 560–4, 2000; Wolkow, *Science* 290:147–50, 2000). For Sudan Black B staining, L4 or young adult nematodes were grown at 25° C. and fixed in 1% paraformaldehyde. While in fixative, the nematodes were subjected to three freeze-thaws in dry-ice/ethanol. The nematodes were then incubated on ice for ten minutes. The fixed nematodes were washed and dehydrated through a 25%, 50%, and 70% ethanol series of baths. The fixed and dehydrated nematodes were then stained in a saturated Sudan Black B solution (in 70% ethanol) for four hours.

Figure 2A:
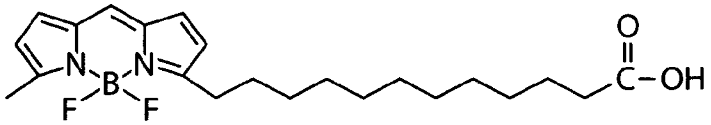
FIG. 2A shows the chemical structure of C1 and C5 BODIPY fluorophore (Molecular Probes, D-3823 and D-3825) labeled fatty acids.
Figure 2A:
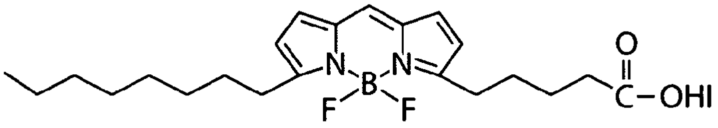
Figure 2B:
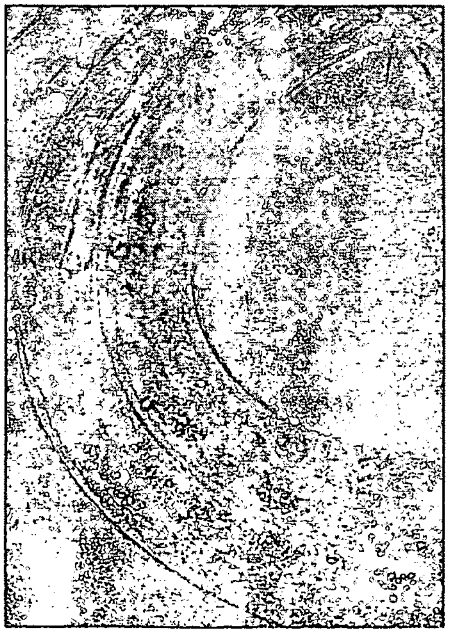
FIG. 2B is a Nomarski photomicrograph showing a wild-type nematode grown on C1 BODIPY fat.
Figure 2C:
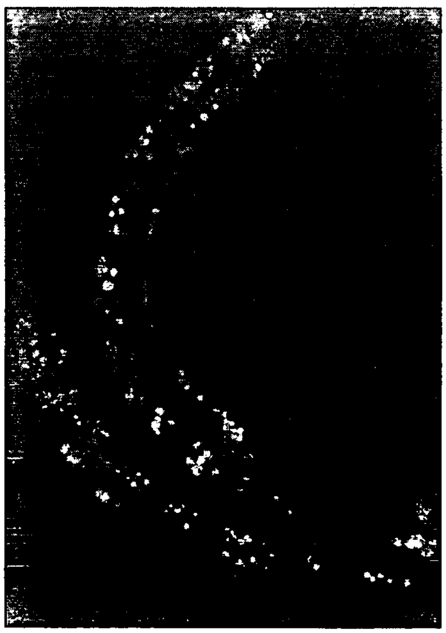
FIG. 2C is a photomicrograph showing GFP fluorescence in a wild-type nematode grown on C1 BODIPY fat.
Figure 2D:
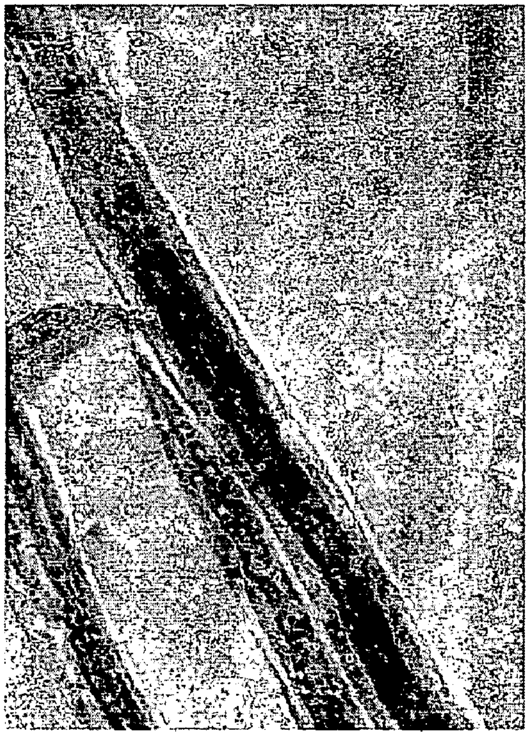
FIG. 2D is a photomicrograph showing Sudan black staining in a wild-type nematode.
Figure 3A:
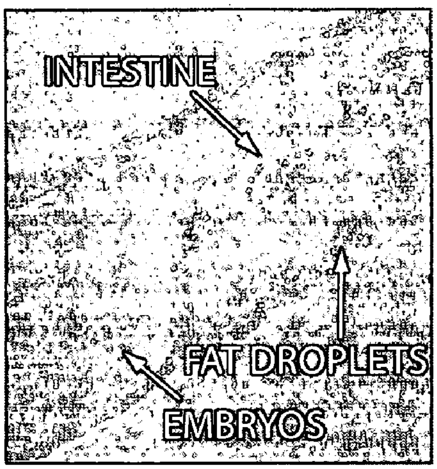
FIG. 3A is a photomicrograph showing a nematode co-stained with Nile Red and BODIPY-labeled fatty acids. In this image a rhodamine overlay (visualizing Nile Red) is superimposed on a Nomarski image (400× mag). The anterior of the animal is at the upper right hand corner of the panel.
Figure 3B:
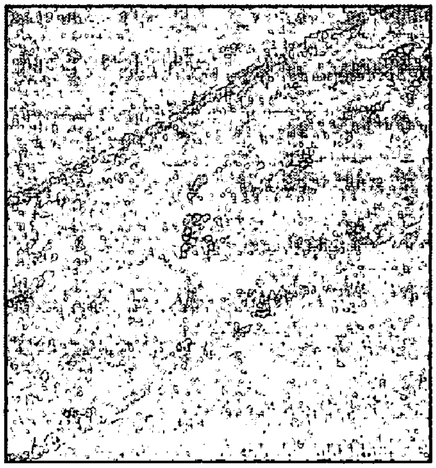
FIG. 3B is a photomicrograph showing $C_1$-BODIPY 500/510 $C_{12}$ fatty acid staining of the same nematode pictured in FIG. 3A. In this image a GFP overlay is superimposed on a Nomarski image. An identical staining pattern was observed when $C_8$-BODIPY 500/510 $C_5$ was used.

Nile Red staining specificity was also confirmed by feeding nematodes BODIPY-labeled fatty acids (FIG. 2A). $C_1$-BODIPY 500/510 $C_{12}$(4,4-difluoro-5-methyl-4-bora-3a, 4a-diaza-s-indace-3-dodecanoic acid), and $C_8$-BODIPY 500/510 $C_5$ (4,4-difluoro-5-octoyl-4-bora-3a,4a-diaza-s-indacene-3-pentanoic acid) were purchased from Molecular Probes (D-3823 and D-3825). 1 mg/ml stock solutions of the BODIPY-labeled fatty acids were made in dimethyl sulfoxide (DMSO). The stocks were diluted 1:10,000 or 1:100,000 in PBS containing 20 μM bovine serum albumin. The diluted BODIPY-labeled fatty acid solutions were added to plates containing lawns of *E. coli* OP50. Nematodes were placed on these plates as eggs or L1s and the incorporation of BODIPY-labelled fatty acids was assessed in L4 or non-starved young adult nematodes. The incorporated fatty acids were visualized using UV fluorescence, and found to co-localize with Sudan Black staining (FIGS. 2B, 2C, 2D, 3A, and 3B).

Nile Red Staining Detects Quantitative Differences in Fat Accumulation

To determine whether Nile Red staining could be used to detect differences in nematode body fat accumulation, previously identified mutant nematodes having defects in fat accumulation were stained with Nile Red, as described herein.

Figure 4A:
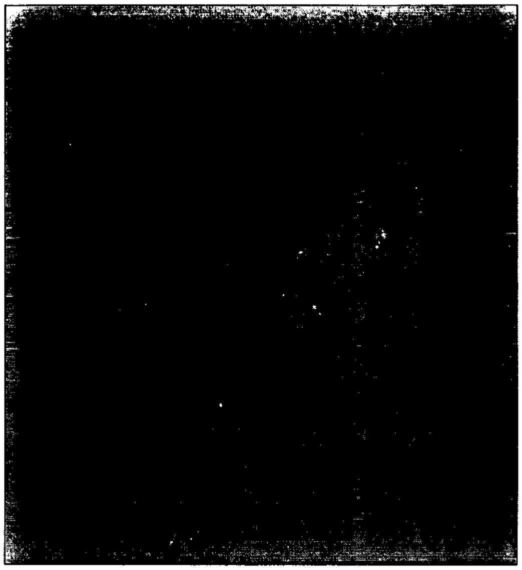
FIGS. 4A–4C show nematodes photographed under equal exposure conditions.
Figure 4B:
Figure 4C:
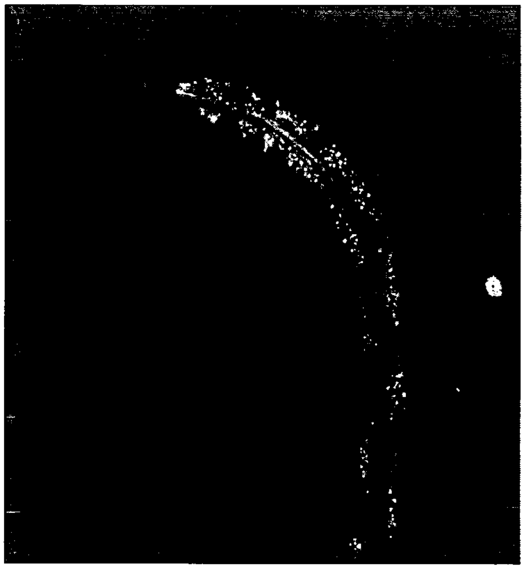

Nile Red staining revealed increased fat stores in serotonin-deficient tph-1(mg280) mutant nematodes when compared to wild-type nematodes (FIGS. 4A and 4B). Nematodes containing a deletion in the tub-1 locus, the nematode ortholog of the murine mutant tubby, also displayed increased Nile Red staining (FIG. 4C). Nile Red was also used to stain *C. elegans* daf-2(e1370); daf-2(e1370); daf-16 (mgDf37); and daf-2(e1370); daf-3(mgDf90) mutant nematodes (FIGS. 5A–5D). The number and pixel intensities of Nile Red staining droplets were quantitated using an imaging quantitation software package. All images were captured using the Openlab software (Improvision Inc. Lexington, Mass.) on a Zeiss Axioplan II microscope equipped with rhodamine (emission 560–590 nm) and FITC/GFP (emission 500–515 nm) filters and a digital CCD camera (Hamamatsu C4742-95-12ER). All Nile Red images were acquired using equal exposure times such that the maximum pixel intensity of any image would be below the maximal intensity recordable by the CCD camera. To quantitate pixel intensities and total pixel numbers, equal planes and regions of the nematode body were selected and the selection tool was used to shrink the region of interest to include only Nile Red Staining droplets. The total fluorescence of a selected area was calculated as the product of area multiplied by the mean fluorescence. At least three nematodes were quantitated for each condition and their average was recorded. Similar results were found in multiple independent experiments. For each independent experiment, nematodes were compared to the reference N2 strain grown, stained, and then photographed under the exact same conditions.

Figure 5A:
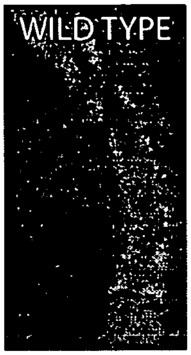
FIG. 5A is a photomicrograph showing Nile Red fat staining in non-starved young adult wild-type *C. elegans* (160× mag).
Figure 5B:
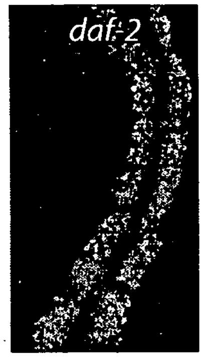
FIG. 5B is a photomicrograph showing Nile Red fat staining in a non-starved young adult insulin receptor daf-2(e1370) mutant nematode (160× mag).
Figure 5C:
FIG. 5C is a photomicrograph showing Nile Red fat staining in a daf-16(mgDf47);daf-2(e1370) mutant nematode (160× mag).
Figure 5D:
FIG. 5D is a photomicrograph showing Nile Red fat staining in a daf-2(e1370);daf-3(mgDf90) mutant nematode (160× mag).
Figure 5E:
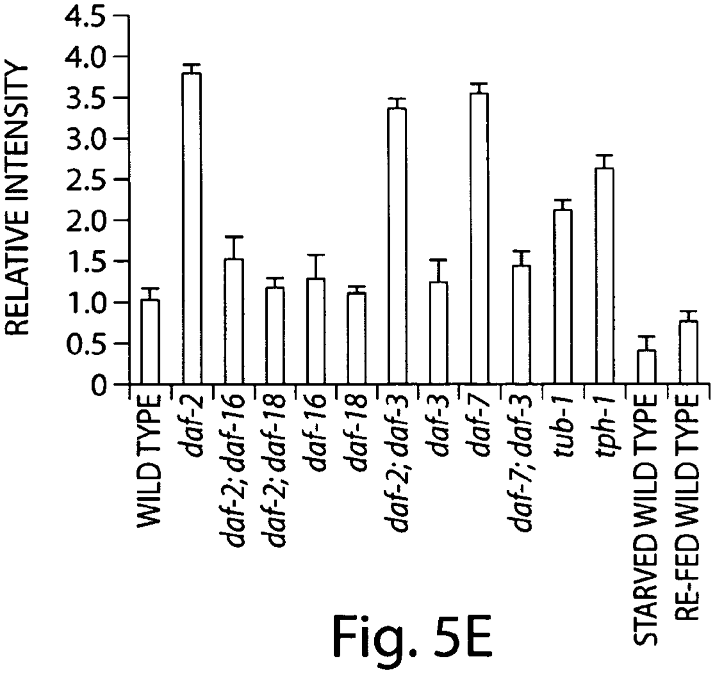
FIG. 5E is a bar graph showing quantitation of fat staining in indicated mutant nematodes by measuring pixel intensity and number of Nile Red stained droplets (n=10 nematodes in at least 2 independent experiments. Standard deviation is given as error bars).

Quantitation of Nile Red staining in wild-type and mutant nematodes is shown in FIG. 5E. Nematodes with a deletion in a key biosynthetic serotonin enzyme, tph-1(ng280) (Sze, et al., *Nature* 403:560–4, 2000), or in the tubby homolog, tub-1(nr2004)II (kindly provided by Carl D. Johnson), exhibited increased fat content detectable by Nile Red. tub-1(nr2004) mutant nematodes have ~2 fold increased fat content while tph-1(mg280) mutant nematodes accumulate ~2.5 fold greater fat levels than wild-type nematodes (FIG. 5E). These *C. elegans* fat phenotypes are reminiscent of what has been seen in mammals, where serotonin and tubby signalling pathways affect body fat. Mice deficient either in Tubby, a novel gene product, or in HTR2C, a serotonin receptor, are obese (Noben-Trauth, et al., *Nature* 380:534–8, 1996; Tecott, et al., *Nature* 374:542–6, 1995).

Visualization of fat droplets by BODIPY-labeled fat compounds in tph-1(mg280), tub-1 (nr2004), insulin, or TGF-β pathway mutant nematodes closely matched the patterns and intensities observed by Nile Red staining.

Figure 6A:
FIGS. 6A–6D are photomicrographs showing that increased fat stores in dauers are detectable by Nile Red staining.
Figure 6B:
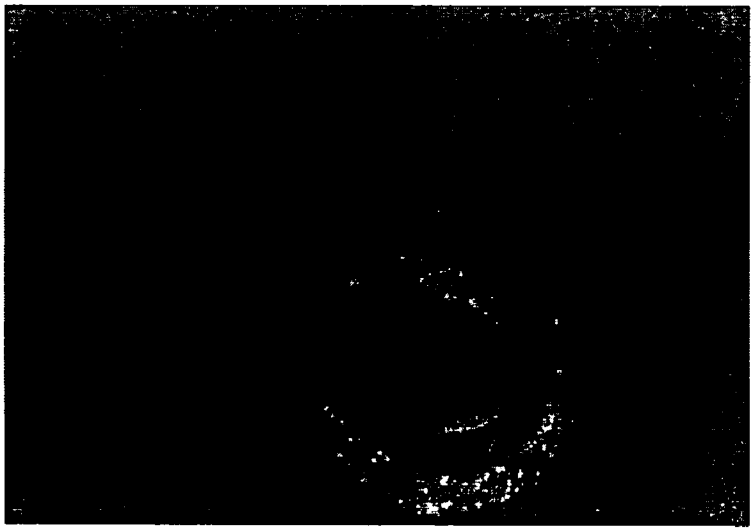
Figure 6C:
Figure 6D:
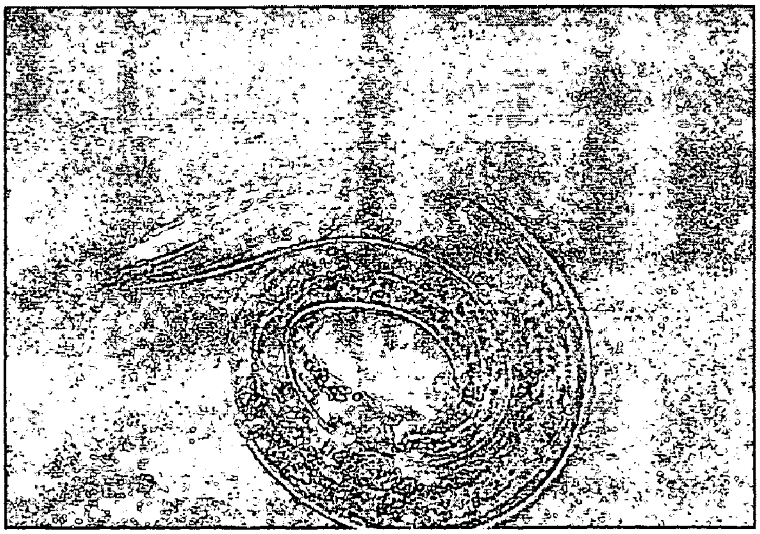

Temperature-sensitive daf-2(e1370) mutant nematodes, containing a mutation in the insulin-like receptor, DAF-2, form dauers at the restrictive temperature (25° C.) (FIGS. 6A and 6C). daf-2(e1370) were grown at the permissive temperature (15° C.) past the developmental stage at which the shift to the alternative dauer developmental stage is initiated. The non-dauer daf-2(e1370) nematodes were then shifted to the non-permissive temperature. These temperature-shifted daf-2(e1370) non-dauers showed increased fat accumulation when stained with Nile Red (FIGS. 6B and 6D). The average number and pixel intensities of Nile Red staining fat droplets were calculated as described herein. daf-2(e1370) and daf-7(e1372) *C. elegans* staining is increased nearly 3-fold compared to wild-type *C. elegans*.

This result was consistent with results by Ogg et al. and Wolkow et al. showing that under these conditions daf-2 (e1370) grow to be long-lived adults with increased fat stores (Ogg et al., *Nature* 389:994–9, 1997; Wolkow et al., *Science* 290:147–50, 2000).

Nematodes containing mutations in genes encoding components of the insulin-like and TGF-β signaling pathways were also stained with Nile Red. Genetic analysis had previously shown that daf-16(mgDf47) suppressed the dauer and longevity phenotypes of daf-2(e1370). Nile Red staining of daf-16(mgDf47) daf-2(e1370) double mutant nematodes revealed that daf-16 also suppressed the daf-2(e1370) fat accumulation phenotype. Genetic analysis had previously shown that mutations in the TGF-β pathway, such as DAF-1, a type I receptor, or DAF-3, a SMAD like transcription factor, fail to suppress daf-2(e1370) dauer and longevity phenotypes. Nile Red staining of daf-2(e1370); daf-1(m40) or daf-2(e1370), daf-3(mgDf90) double mutant nematodes also failed to suppress the daf-2(e1370) fat accumulation phenotype. Thus, previously characterized epistatic relationships among the components of these signaling pathways were recapitulated by Nile Red fat staining (FIGS. 5A–5D).

Figure 7:
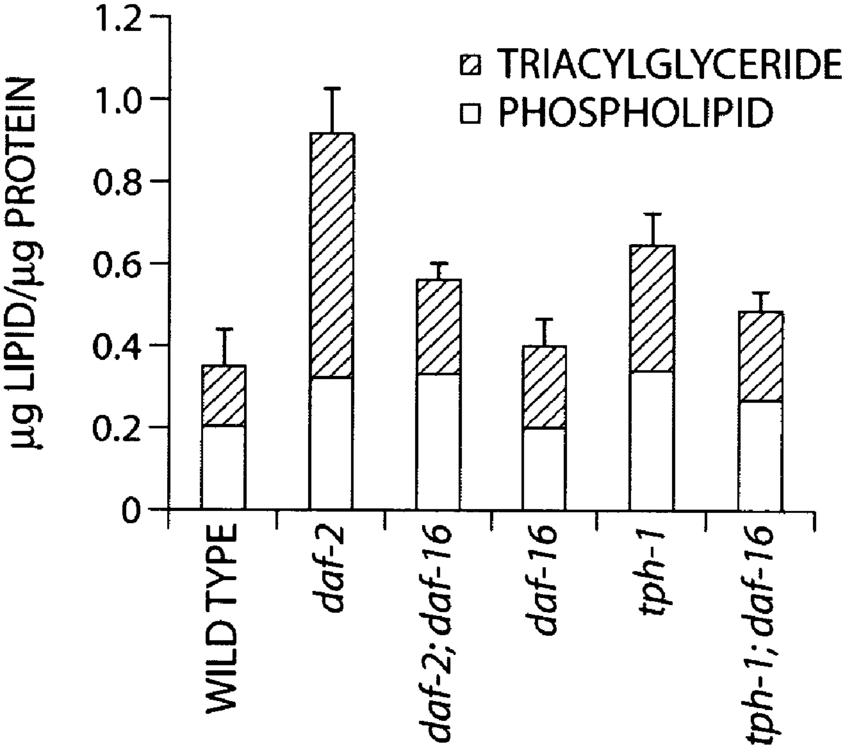
FIG. 7 is a bar graph showing that differences in Nile Red staining correspond to actual fat content. Total *C. elegans* lipid extracts were separated into triacylglyceride and phospholipid components and their respective constituents were identified and quantitated by gas chromatography. Reported numbers have been normalized to protein content extracted from the same *C. elegans* (n=2 measurements from two independent extractions; standard deviation is given as error bars).

Differences in body fat as visualized by Nile Red were correlated with actual fat content (FIG. 7). Total lipids were extracted from wild-type, tph-1(mg280), daf-2(e1370), daf-2(e1370); daf-16(mgDf47), daf-16(mgDf47), tph-1 (mg280); daf-16 (mgDf47) nematodes as follows. L1 synchronized nematodes were grown on four 6-cm plates at 15° C. past the L2 stage of development, and then shifted to 25° C. Non-starved, young adult nematodes were washed off the plates with water, and placed into 15 ml polypropylene screw-capped centrifuge tubes. The tubes were spun at 1,000×g for 1 minute. The pelleted nematodes were washed five times with water and then, after the final wash, the water was removed.

A 100 mg nematode pellet was required for each assay. Each pellet was split into two equal portions. Each portion was flash frozen in dry ice/ethanol and maintained at −80° C. degrees until analyzed. One portion of each sample was used for fatty acid extraction while the other portion was used for protein extraction as described by Watts and Browse (Watts et al., *Arch. Biochem. Biophys.* 362:175–82, 1999; Watts et al., *Proc Natl Acad Sci USA* 99:5854–9, 2002). Briefly, after extraction and transmethylation of total lipids, phospholipids were separated on Thin Layer Chromatography plates (TLC) using chloroform:methanol: acetic acid (25:15:4). Triacylglycerides, diacylglycerides and phospholipids were separated from each other on TLC plates using hexane:diethyether:acetic acid (75:25:2). Separated samples were then analyzed by Gas Chromatography using an Agilent 6890 series machine equipped with a 30×0.25-mm SP-2380 column (Supelco) (Watts et al., *Arch. Biochem. Biophys.* 362:175–82, 1999; Watts et al., *Proc. Natl. Acad. Sci. USA* 99:5854–9, 2002).

As expected, tph-1(mg280) and daf-2(e1370) nematodes have greater total fat content than wild-type nematodes (FIG. 7). Moreover, as in mammals, the daf-2(e1370) excess fat is generally stored as triacylglycerides (FIG. 7).

Nile Red Staining Detected Fat Mobilization

Mobilization of fat stores in response to starvation can be monitored by Nile Red staining. When grown on Nile Red plus bacterial food plates, larval stage or adult wild-type nematodes increase their fat content as they near starvation. When maintained in the starved state, they then undergo a progressive loss of Nile Red stained fat droplets. Furthermore, the loss of Nile red stained fat droplets is reversible when food is reintroduced to starved nematodes. daf-2 (e1370), tph-1(mg280), or tub-1(nr2004) nematodes undergo similar alterations in fat content in response to starvation.

Nile Red staining can also be used to detect the mobilization of fat droplets in response to fat mobilizing agents, for example, 5-aminoimidazole-4-carbozamide ribonucleoside (AICAR). AICAR is an adenosine analog that activates AMP-activated protein kinase (AMPK), a putative cellular energy sensor and metabolic master switch. Activation of AMPK results in the mobilization of fat stores (Hardie et al., *Eur. J. Biochem.* 246:259–73, 1997; Hardie et al., *Ann. Rev. Biochem.* 37:821–55, 1998; Aschenbach et al., *Diabetes* 51:567–73, 2002; Corton et al., *Eur. J. Biochem.* 229: 558–65, 1995).

Figure 8A:
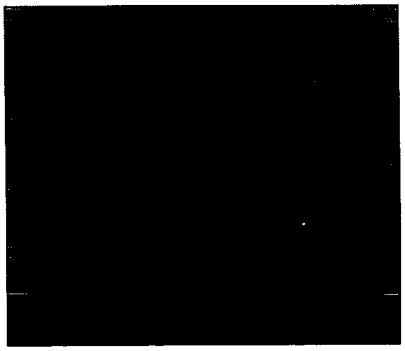
FIGS. 8A–8F are photomicrographs showing that mobilization of fat droplets in a nematode can be monitored by Nile Red staining.
Figure 8B:
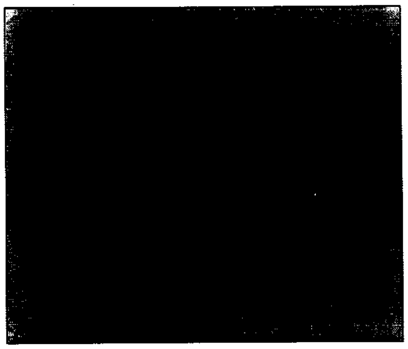
Figure 8C:
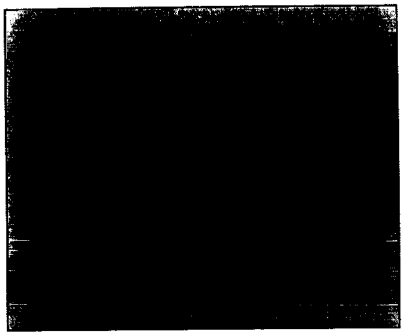
Figure 8D:
Figure 8E:
Figure 8F:
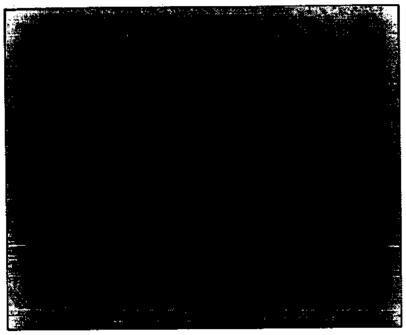

Adult wild-type nematodes, daf-2 (e1370), tph-1(mg280), and tub-1(nr2004) mutant nematodes were treated with 500 μM AICAR, and their fat content was detected using Nile Red as described above. Wild-type nematodes (FIGS. 8A and 8B), daf-2 e1370) (FIGS. 8D and 8E), tph-1(mg280), and tub-1(nr2004) mutant nematodes all displayed a progressive reduction in fat content relative to untreated control nematodes, and this reduction in fat content was detectable within twenty-four hours. To determine whether the effects of AICAR were reversible, AICAR-treated nematodes were then moved to culture plates without AICAR. Without continued AICAR treatment, these nematodes regained their fat content. The effect of continuous AICAR treatment was tested by seeding AICAR plates with five hermaphrodites, and then monitoring the effect of AICAR on the growth and development of nematode progeny relative to untreated control progeny Continuous AICAR treatment resulted in a dramatic retardation of larval growth accompanied by depleted fat stores. These results indicated that Nile Red staining provides a sensitive, reproducible, and convenient method for assaying the body fat of living *C. elegans*. The result of AICAR treatment was also compared to the effect of starvation on wild-type (FIGS. 8A–8C) and daf-2(e1370) mutant nematodes (FIGS. 8D–8F). This comparison showed that the mobilization of fat stores in response to starvation or treatment with fat mobilizing agents can be monitored using Nile Red staining.

Genetic Screen for Fat Mutant Nematodes

To identify mutant nematodes that display perturbations in fat content, droplet size, or localization, wild-type (N2) *C. elegans* were mutagenized with ethylmethanesulfonate (Brenner, *Genetics* 77:71–94, 1974). Synchronized populations of F1 and F2 progeny were then grown on Nile Red plates and examined for their fat staining.

Mutagenesis screens were conducted on plates containing 0.005 μg/ml Nile Red. The screen and subsequent manipulations were conducted at 25° C. (to reduce the number of fat accumulating daf-c mutant nematodes present in the F1 and F2 progeny).

*C. elegans* were placed on Nile Red plates either as eggs or starved L1s, and their Nile Red staining phenotype was assessed when they reached the L4 stage and/or the young adult stage, prior to starvation, unless specified. Nile Red fluorescence was visualized under a Zeiss SV11 M2-bio microscope equipped with a rhodamine filter (emission 565–590 nm). For studying the impact of starvation on fat content, nematodes were grown to the L4 or young adult stage on Nile Red plates. They were washed five time in M9 media and maintained either in M9 media or transferred to NGM plates without OP50. They were then monitored as described herein for their fat content.

The recovered nematode mutants defined several distinct classes: i) nematodes with increased fat, ii) nematodes with decreased fat, iii) nematodes with altered fat droplet morphology, and iv) nematodes with grossly distorted fat deposits accompanied by an altered Nile Red emission profile. These mutant nematodes displayed a variety of lipophilic dye staining phenotypes (FIGS. 9A–9G) and thus were designated as lpo mutants. The Nile Red staining phenotype of each mutant was confirmed by BODIPY labeled fatty acid visualization and Sudan Black B staining. BODIPY-labeled fatty acids and Nile Red staining results in wild-type nematodes (FIGS. 10A and 10B), lpo-1 (FIGS. 10C and 10D) and lpo-2 (FIGS. 10E and 10F) mutant nematodes are shown.

The fat contents of tph-1(mg280), tub-1(nr2004), daf-2 (e1370), lpo-1, and lpo-6 mutant nematodes were assayed by Nile Red staining. The results of this staining are shown in Table 1.

TABLE I

Fat Content Assayed by Nile Red

| STRAIN | STRAIN DESCRIPTION | FAT CONTENT ASSAYED BY NILE RED STAINING |
|---|---|---|
| Wild-type | | wild-type |
| tph-1(mg280) | deletion in serotonin biosynthetic enzyme | increased fat compared to wild-type |
| tub-1(nr2004) | deletion of nematode tubby locus | increased fat compared to wild-type |
| daf-2(e1370) | insulin receptor mutant | increased fat compared to wild-type |
| lpo-1 | VLDL receptor mutant | increased fat compared to wild-type |
| lpo-6 | identity of molecular lesion unknown | increased fat compared to wild-type and enlarged fat droplets |

lpo-1, lpo-2, lpo-3, lpo-4, lpo-5, lpo-6, and lpo-7 were each back crossed four times to wild-type (N2) nematodes. Standard genetic techniques were used to determine that lpo-1, lpo-2, lpo-3, lpo-4, lpo-5, lpo-6, and lpo-7 represented distinct complementation groups. All of the lpo mutations were recessive with fully penetrant phenotypes. While the fat staining patterns were most dramatic in adult nematodes, the phenotypes were also detectable at all larval stages. The characterization of lpo-1 through lpo-7 is summarized in Table II.

TABLE II

Characterization of LPO mutant nematodes

| | lpo-1 | Lpo-2 | lpo-3 | lpo-4 | lpo-5 | lpo-6 | lpo-7 |
|---|---|---|---|---|---|---|---|
| Fat content relative to wild-type | Increased | Reduced | Reduced | Reduced (green) | Reduced (green) | Enlarged Droplets | Reduced |
| Growth rate | 115% of wt | Wt | wt | wt | wt | 75% of wt | 50% of wt |
| Adult body Length | wt | Wt | wt | wt | wt | wt | wt |
| Adult body Width | wt | Wt | wt | wt | wt | 20% smaller than wt | wt |
| Brood size | wt | Wt | wt | wt | wt | less than wt | Much less than wt |
| Lifespan | wt | Wt | wt | wt | wt | 1.7 fold greater than wt | wt |
| Survival rate when starved | 120% of wt | 30% of wt | wt | wt | wt | 30% of wt | 10% of wt |
| Dye filling | wt | Wt | wt | wt | wt | wt | wt |

Table Legend
wt = wild-type

As indicated in Table II, lpo-1 nematodes had a slightly increased growth rate (~15% faster than wild-type nematodes). In contrast, lpo-6 nematodes, which have enlarged fat droplets, exhibited a reduced growth rate (~25% slower than wild-type).

All lpo mutant nematodes were able to form dauers, recovered from the dauer stage, and developed into reproductive adults. Response to starvation was assayed as follows. Eggs were hatched in M9 buffer and equal numbers of nematodes (~100) were aliquoted into individual test tubes containing 1 ml of M9 media. Twice daily, during the first forty-eight hours after transfer to M9, and once a day during for next eight days, nematodes in each aliquot were plated on NMG plates with lawns of OP50. Forty-eight hours after transfer to plates, the number of viable nematodes was scored. The reported results in Table II were the average of two independent experiments.

The reduced fat mutant nematodes, lpo-2 and lpo-3, accumulated fat when they formed dauers. Inspite of this increase, lpo-2 and lpo-3 dauers failed to accumulate the fat levels typical of wild-type dauers. When high fat lpo-1 mutant nematodes formed dauers, lpo-1 dauers had increased fat levels as compared to wild-type dauers.

These results indicate the lpo mutant nematodes may be used to identify genes that encode polypeptides that regulate feeding and metabolism (e.g., neuropeptides), hormonal response pathways, subcellular fat trafficking, or fat droplet mobilization.

lpo-1 Cloning

For mapping each mutant, the mutant nematode was crossed to *C. elegans* strain CB4856. F2 hermaphrodite progeny of the cross, displaying the appropriate Nile Red phenotype (e.g. increased staining for lpo-1, reduced staining for lpo-3), were then picked onto individual Nile Red plates, and allowed to self-fertilize. The Nile Red staining phenotype of F3 progeny was checked to ensure that the recombinants had been accurately picked. Once plates starved out, several hundred nematodes from each plate were pooled and their DNA was extracted as described by Williams (*Methods Cell. Biol.* 48:81–96, 1995). Using snip-SNP mapping (Wicks et al., *Nat Genet* 28:160–4, 2001) the mutant loci were assigned chromosomal positions.

The lpo-1 mutation was mapped using single nucleotide polymorphisms (SNP). The lpo-1 mutation was generated in an N2-Bristol parental strain. This lpo-1 mutant was then crossed with Hawaiian strain CB4856, a highly polymorphic *C. elegans* strain. lpo-1 was mapped to a genomic region covered by the cosmid T13C2 as shown in Table III.

TABLE III lpo-1 SNP mapping (A) Chromosomal Linkage

| Chromosome | I | II | III | IV | V | X |
|---|---|---|---|---|---|---|
| SNP clone | T22A3 | T13C2 | F10E9 | C09G12 | AC3 | F45E1 |
| allele | pkP1075 | pkP2107 | pkP3049 | pkP4032 | pkP5064 | PkP6110 |
| map position | +4.47 | +0.08 | −0.32 | −3.64 | +2.53 | −0.83 |
| # F2 recombinants with lpo-1 phenotype tested | 32 | 32 | 15 | 30 | 33 | 32 |
| % CB4856 | 75% | 0% | 73% | 86% | 82% | 82% |

(B) Mapping within Chromosome II

| SNP clone | C16C8 | C01F1 | T13C2 | ZK666 |
|---|---|---|---|---|
| allele | pkP2115 | pkP2051 | pkP2107 | pkP2070 |
| map position | −6.47 | −3.95 | +0.08 | +2.57 |
| # F2 recombinants with lpo-1 phenotype tested | 80 | 80 | 558 | 80 |
| % CB4856 | 14% | 10% | 0% | 10% |
| # homozygous wild-type F2 recombinants tested | 0 | 0 | 51 | 0 |
| % CB4856 | | | 100% | |

Table IIIA shows that lpo-1 was mapped to chromosome II. Table IIIB shows that lpo-1 was mapped to a region of chromosome II.

After lpo-1 was mapped to cosmid T13C2, the open reading frames on that cosmid were analyzed for likely lpo-1 candidates. An open reading frame, T13C2.6, which encodes Very Low Density Lipoprotein (VLDL) receptor, was selected for further analysis. PCR primers were designed to amplify not only T13C2.6, but also several kilobases of flanking DNA. The nucleic acid sequence of the forward and reverse primers, respectively, were 5'CACAACAAGT-CAGCAAGCAATACAAGTGG 3' (SEQ ID NO: 7) and 5' GTAGGAGATGTGACCAATCGTTGAAGTG (SEQ ID NO:8). The purified 9.5-kb PCR fragment consisting of the complete T13C2.6 coding sequence, and 2604 basepairs (bp) upstream and 2674 base pairs of downstream sequence was injected into lpo-1 nematodes at 1.5, 3, 5, and 15 ng/μl, in combination with a nucleic acid encoding a visible marker, SUR-5::GFP (Yochem et al., *Genetics* 149:1323–34, 1998) at 80 ng/μl. Stable lines were maintained by picking green nematodes. No other predicted full length or partial ORFs were contained in this 9.5 kb fragment.

Figure 11A:
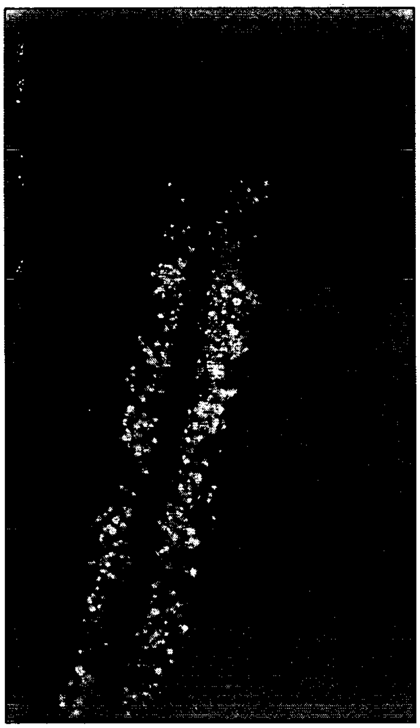
FIG. 11A is a photomicrograph showing Nile Red staining in a lpo-1 nematode.
Figure 11B:
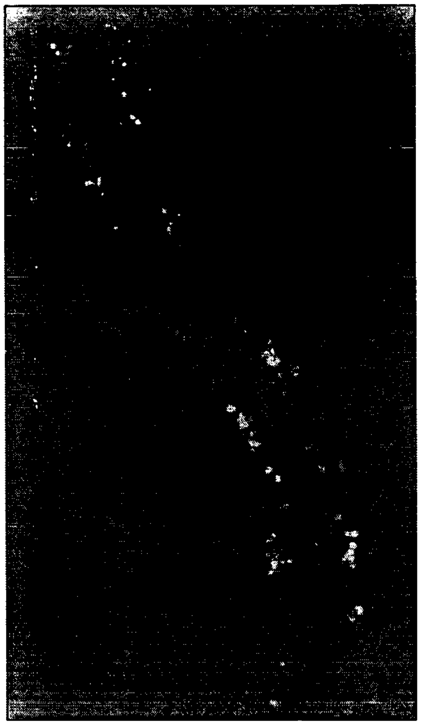
FIG. 11B is a photomicrograph showing Nile Red staining in a lpo-1 nematode transformation rescued by expression of wild-type lpo-1.
Figure 11C:
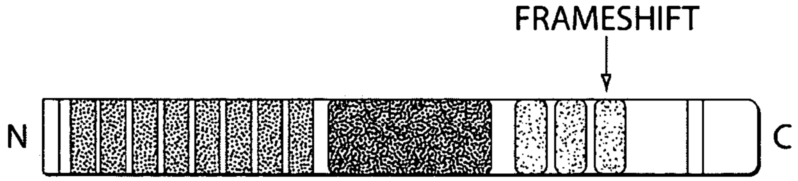
FIG. 11C is a schematic diagram showing the structure of the LPO-1 polypeptide.

The T13C2.6 containing fragment rescued the lpo-1 fat phenotype (FIGS. 11A and 11B).

lpo-1 Encodes a VLDL Receptor Homolog lpo-1 encodes a predicted 863 amino acid protein that has 35% amino acid sequence identity to human (SEQ ID NO:9) and rat (SEQ ID NO:10) very low density lipoprotein (VLDL) receptors. An alignment of the *C. elegans*, human, and rat VLDL amino acid sequences is shown in FIG. 11G. Mammalian VLDL receptors contain eight adjacent LDL type A domains, which are ligand binding repeats stabilized by three cysteine disulfide bonds. The A domains are followed by an epidermal growth factor (EGF) homology domain, modules of type B LDL repeats (including the YWTD consensus tetrapeptide), a single pass transmembrane domain, and a short cytosolic tail. The amino acid sequence, NPXY, which is thought to be the receptor internalization signal, resides in the VLDL receptor's short cytosolic tail (Brown et al., *Nature* 388:629–30, 1997; Nimpf et al., *Atherosclerosis* 141:191–202, 1998; Trommsdorff et al., *Cell* 97:689–701, 1999). The predicted topology of LPO-1 closely matches the described domain structure of VLDL-receptors (FIG. 11C). The lpo-1 genomic nucleic acid sequence (SEQ ID NO:1) is shown in FIG. 11D. The nucleic acid sequence (SEQ ID NO:2) of the lpo-1 open reading frame is shown in FIG. 11E. The LPO-1 amino acid sequence (SEQ ID NO:3) is shown in FIG. 11F.

The LDL receptor gene family comprises five mammalian and several invertebrate members that are predicted to mediate extracellular ligand endocytosis. The role of LDL receptors in cholesterol endocytosis, trafficking, and homeostasis is well established. The major structural difference between mammalian LDL and VLDL receptors is the number of ligand binding repeats. LDL receptors contain seven type A repeats, while VLDL receptors contain eight type A repeats (Nimpf et al., *Atherosclerosis* 141:191–202, 1998). Chickens lacking VLDL receptor are obese and sterile, due to defective yolk deposition. In contrast, mice lacking the VLDL receptor do not gain excess weight and appear to be protected from obesity (Frykman et al., *Proc. Natl. Acad. Sci. USA* 92:8453–7, 1995; Tacken et al., *Curr. Opin. Lipidol.* 12:275–9, 2001). Interestingly, mice lacking two LDLR superfamily members, VLDLR and ApoE receptor 2 (ApoER2) have neuronal migration defects (Trommsdorff et al., *Cell* 97:689–701, 1999). VLDLR and ApoER2 are predicted to be cell surface receptors for Reelin, a guidance molecule associated with neuronal migration (Trommsdorff et al., *Cell* 97:689–701, 1999).

In light of the yolk abnormalities observed in VLDL-receptor deficient chickens, vitellogenin deposit was examined in lpo-1 mutant nematodes. Vitellogenins are yolk proteins that are synthesized and secreted by nematode intestinal cells. RME-2, a member of the LDL receptor superfamily, is predicted to be the egg yolk receptor that mediates yolk deposit in *C. elegans* (Grant et al., *Nat. Cell. Biol.* 3:573–9, 2001; Lin et al., *Nat. Cell. Biol.* 3:567–72, 2001). This prediction is based on the observation that vitellogenin:GFP (YP170::GFP) accumulated in eggs of wild-type nematodes, but was mislocalized in rme-2 mutant nematodes (Grant et al., *Nat. Cell Biol.* 3:573–9, 2001; Lin et al., *Nat. Cell Biol.* 3:567–72, 2001). The YP170::GFP reporter construct was crossed into lpo-1 mutant nematodes, and used to study egg yolk accumulation. The localization of YP170::GFP in lpo-1 mutant nematodes was indistinguishable from that observed in wild-type nematodes. Thus, LPO-1 did not affect egg yolk receptor-mediated endocytosis.

Next, inhibitors of HMG-CoA reductase (e.g., lovastatin) were tested to assess whether they affected the fat content of lpo-1 mutant nematodes. Hydroxymethylglutary-CoA (HMG-CoA) reductase is an enzyme that functions in a key regulatory step of cholesterol biosynthesis. Inhibitors of HMG-CoA reductase have been commonly used to lower human cholesterol levels. The high fat content of lpo-1 mutant nematodes was reduced when they were grown on plates containing 200 μg/ml mevinolin, an HMG-CoA reductase inhibitor.

lpo-3 Cloning

Another exemplary gene identified by the method described above, termed lpo-3, was also mapped and cloned. Genetic mapping using SNP polymorphisms placed lpo-3 between cosmids C18E3 and K04F10 on chromosome I as shown in Table IV.

TABLE IV lpo-3 SNP mapping (A) Chromosomal designation

| Chromosome | I | II | III | IV | V | X |
|---|---|---|---|---|---|---|
| SNP clone | T22A3 | T13C2 | F10E9 | C09G12 | AC3 | F45E1 |
| allele | pkP1075 | pkP2107 | pkP3049 | pkP4032 | pkP5064 | PkP6110 |
| map position | +4.47 | +0.08 | −0.32 | −3.64 | +2.53 | −0.83 |
| # F2 recombinants with lpo-3 phenotype tested | 40 | 38 | 39 | 35 | 40 | 38 |
| % CB4856 | 15% | 76% | 72% | 85% | 83% | 71% |

(B) Chromosome I mapping

| SNP clone | C18E3 | C09D4 | T22A3 | ZK1025 |
|---|---|---|---|---|
| allele | pkP2115 | PkP1055 | PkP1075 | PkP1066 |
| map position | −1.49 | +0.09 | +4.74 | +8.84 |
| # F2 recombinants with lpo-3 phenotype tested | 247 | 48 | 254 | 48 |
| % CB4856 | 5.6% | 0% | 9.4% | 19% |

(C) Establishment of mapping boundaries

| SNP: | C18E3 | C09D4 | K04F10 | D2030 | T23G11 | F18C12 | VF3H21 | Y67A6A | T22A3 |
|---|---|---|---|---|---|---|---|---|---|
| Map: | (−1.49) | (+0.09) | (+0.92) | (+2.12) | (+2.23) | (+2.46) | (+2.94) | (+3.99) | (+4.78) |
| recombinants | | | | | | | | | |
| #1 | N/N | N/N | N/N | N/C | N/C | N/C | N/C | N/C | N/C |
| #6 | N/N | N/N | N/N | N/N | N/N | N/C | N/C | N/C | N/C |
| #8 | N/N | N/N | N/N | N/C | N/C | N/C | N/C | N/C | N/C |
| #17 | N/N | N/N | N/N | N/N | N/N | N/N | N/C | N/C | N/C |
| #24 | N/C | N/N | N/N | N/N | N/N | N/N | N/N | N/N | N/N |
| #39 | N/C | N/N | N/N | N/N | N/N | N/N | N/N | N/N | N/N |
| #121 | N/N | N/N | N/C | N/C | N/C | N/C | N/C | N/C | N/C |
| #127 | N/N | N/N | — | — | — | N/N | N/N | N/N | N/C |
| #132 | N/N | N/N | — | — | — | N/N | N/N | N/C | N/C |
| #156 | N/N | N/N | — | — | — | N/C | N/C | N/C | N/C |
| #167 | N/C | N/N | — | — | — | N/N | N/N | N/N | N/N |
| #176 | N/C | N/N | — | — | — | N/N | N/N | N/N | N/N |
| #209 | N/C | N/N | — | — | — | N/N | N/N | N/N | N/N |
| #244 | N/N | N/N | — | — | — | N/C | N/C | N/C | N/C |

Table Legend
N: N2 Bristol, wild-type chromosomal SNP detected
C: CB4856 recombinant SNP detected Table IVA shows that lpo-3 was mapped to chromosome I. Table IVB shows that lpo-3 was mapped to a specific region of chromosome I. Table IVC shows that mapping boundaries were established using F2 recombinant progeny (of an lpo-3 mutant nematode crossed to *C. elegans* strain CB4856) that displayed an lpo-3 mutant phenotype.

Figure 12A:
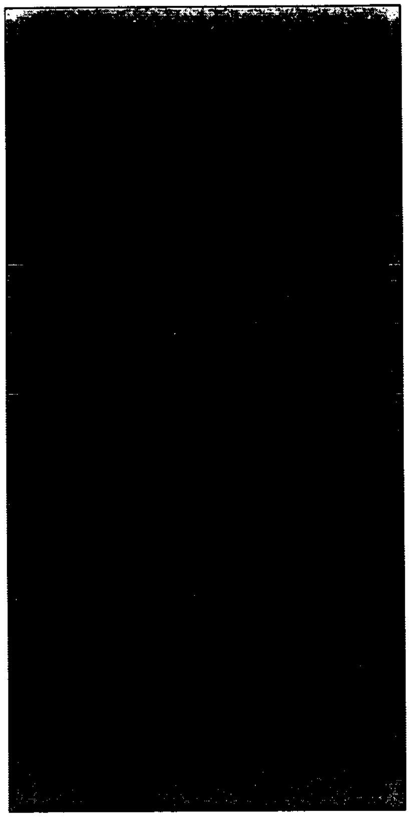
FIG. 12A is a photomicrograph showing Nile Red staining in an lpo-3 mutant nematode.
Figure 12B:
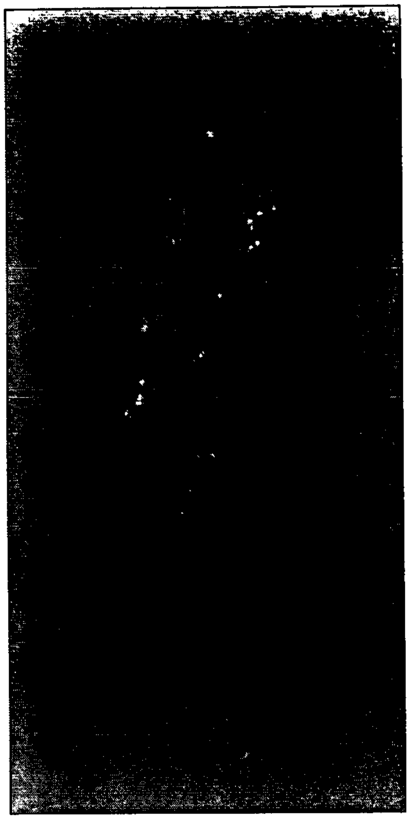
FIG. 12B is a photomicrograph showing Nile Red staining in a lpo-3 nematode transformation rescued by expression of wild-type lpo-3.
Figure 12C:
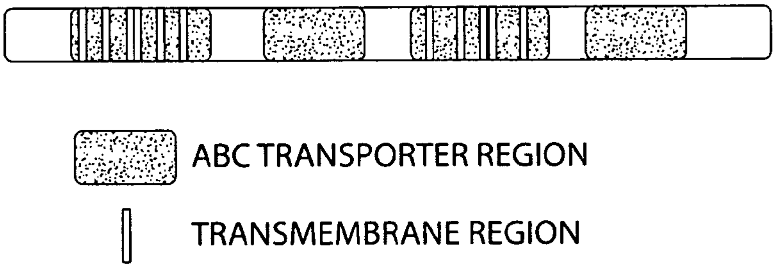
FIG. 12C is a schematic diagram showing the structure of the LPO-3 polypeptide.
Figure 13A:
FIGS. 13A–13F are photomicrographs showing Nile Red staining superimposed on a Nomarski image in wild-type nematodes grown on *E. coli* carrying an RNA interference (RNAi) clone.
Figure 13B:
Figure 13C:
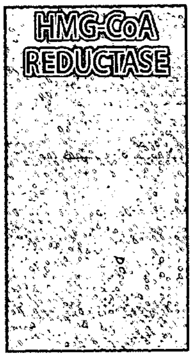
Figure 13D:
Figure 13E:
Figure 13F:

Having mapped lpo-3 to a relatively small interval, a set of RNAi-expressing bacteria was screened. These bacteria were described by Fraser et al. and Kamath et al (Fraser et al., *Nature* 408:325–30, 2000; Kamath et al., *Genome Biol.* 2:RESEARCH0002). The nematodes cultured on these RNAi-expressing bacteria were then analysed using Nile Red fat staining, as described herein. This analysis identified C34G6.4 as an lpo-3 candidate. When wild-type nematodes were fed C34G6.4 RNAi-expressing bacteria, they mimicked the low fat phenotype of lpo-3. To test whether C34G6.4 could rescue the lpo-3 phenotype, a genomic region flanking the open reading frame was amplified by PCR. 10 kb and 7.8 kb PCR fragments (with 1 kb overlap) were used to cover the entire C34G6.4 coding sequence, including 9,051 base pairs of upstream and 1,367 base pairs of downstream sequence. The 10 kb fragment contained the upstream sequences plus 1,244 base pairs of C34G6.4 coding sequence, while the 7.8 kb fragment contained 300 nucleotides downstream of the C34G6.4 ATG codon, and extended to 1,367 base pairs downstream of the C34G6.4 stop codon. lpo-3 mutant nematodes injected with these overlapping PCR fragments displayed wild-type fat staining (FIGS. 12A and 12B) only when both fragments were injected into lpo-3 mutant nematodes at 2.5, 5, or 7.5 ng/μl. No rescue was noted when the PCR fragments were injected individually into lpo-3 mutant nematodes at 5 ng/μl. (These injections were carried out using the visible co-injection marker *SUR*-5*::GFP* (80 ng/μl)). The topology of the predicted LPO-3 protein is shown in FIG. 12C.

This result suggested that C34G6.4 was lpo-3. No other predicated full length or partial ORFs were contained in the two overlapping PCR fragments. Sequencing of the C34G6.4 genomic fragment identified a G to A transition in exon 12, which caused a Glycine (G) to Aspartic acid (D) change at position 1163 of the predicted protein. Thus lpo-3 is C34G6.4. The genomic nucleic acid sequence (SEQ ID NO:4) of lpo-3 is shown in FIG. 12D. The lpo-3 open reading frame is shown in FIG. 12E. The amino acid sequence of LPO-3 is shown in FIG. 12F.

lpo-3 Encodes an ABC-Type Transporter Homolog lpo-3 encodes a predicted protein of 1,265 amino acids that is a P-glycoprotein family member with 45% and 44% amino acid identity to human (SEQ ID NO:11) and mouse (SEQ ID NO:12) ATP-Binding Cassette (ABC)-type transporters, respectively. An alignment of the *C. elegans*, mouse and human ABC transporter proteins is shown in FIG. 12G. In humans, ABC-type transporter molecular lesions cause cholesterol and lipid homeostasis disorders, such as Tangier disease, familial HDL deficiency, progressive familial intrahepatic cholestasis type 2 and type 3, adrenoleukodystrophy, and sitosterolaemia (Ioannou, *Nat. Rev. Mol. Cell Biol.* 2:657–68, 2001). At least ten ABC-type transporters have previously been shown to facilitate cholesterol and lipid flux across membrane bilayers (Geourjon et al., *Trends Biochem. Sci.* 26:539–44, 2001; Holland et al., *J. Mol. Biol.* 293:381–99, 1999). lpo-3 contains a pair of ATP-binding domains and two sets of transmembrane domains that are characteristic of ABC-type transporters. A comparison of the lpo-3 encoded protein with other ABC-type transporters indicated that the G to D mutation occurred in a functionally important conserved LSGGQ nucleotide binding domain (Geourjon et al., *Trends Biochem. Sci.* 26:539–44, 2001; Holland et al., *J. Mol. Biol.* 293:381–99, 1999). These results indicated that lpo-3 regulates fat dynamics in *C. elegans*. A schematic diagram depicting the structure of lpo-3 is shown in FIG. 11C.

The *C. elegans* genome contains three other P-glycoprotein family members: pgp-1, pgp-3, and mrp-1. To test whether the proteins encoded by these genes are involved in *C. elegans* fat dynamics, the following strains were obtained: pgp-1(pk17) IV, pgp-3(pk18) X, mrp-1(pk89) X; pgp-1(pk17) IV; pgp-3(pk18) X; mrp-1(pk89) (Broeks et al., *EMBO J.* 14:1858–66, 1995).

Three of these previously described nematode deletion mutants, pgp-1(pk17), pgp-3(pk18), and mrp-1(pk89) were stained with Nile Red. Relative to wild-type nematodes, pgp-3(pk18) nematodes displayed slightly increased fat content; pgp-1(pk17) mutant nematodes displayed reduced fat content during adulthood, particularly when starved, but their fat content appeared wild-type during larval stages; and mrp-1(pk89) staining was indistinguishable from wild-type nematode staining. Nematodes having deletions in all three genes, pgp-1(pk17); pgp-3(pk18); mrp-1(pk89), were viable and had normal fat content. Feeding-mediated RNAi was used to inactivate lpo-3 in the individual P-glycoprotein deletion mutant nematodes as well as in the triple mutant (i.e., pgp-1(pk17); pgp-3(pk18); mrp-1(pk89)). Inactivation of lpo-3 in the individual P-glycoprotein mutant nematodes, pgp-1, pgp-3, mrp-1, or in the triple mutant, resulted in a low fat phenotype. Fat levels in these lpo-3 RNAi mutant nematodes were comparable to those observed in the original lpo-3 mutant nematode.

lpo-1 and lpo-3 therefore encode polypeptides whose human homologs are critical regulators of cholesterol and lipid homeostasis. Their identification in an unbiased screen for *C. elegans* fat metabolism regulators provides proof that the methods of the invention are useful not only for the identification of *C. elegans* fat metabolism regulator genes, but also for the identification of their human homologs. These working examples demonstrate that human fat/sterol disease genes can be identified and studied in *C. elegans* using the methods of the invention.

Feeding-Mediated RNAi is Useful for Studying Fat Metabolism Regulator Genes

In *C. elegans* many expressed genes are subject to inactivation by RNAi (Fire et al., *Nature* 391:806–11, 1998; Fraser et al., *Nature* 408:325–30, 2000). RNAi may be accomplished by growing *C. elegans* on plates of *E. coli* expressing double stranded RNA. The nematodes feed on RNA-expressing bacteria, and this feeding is sufficient to cause the inactivation of specific target genes (Fraser et al., *Nature* 408:325–30, 2000; Kamath et al., *Genome Biol* 2, 2001). To test whether RNAi feeding could be used to study fat metabolism regulator genes, high fat daf-2(e1370) nematodes were fed daf-16 or daf-12 RNA-expressing bacteria. These nematodes were then analyzed using Nile Red, as previously described. The RNAi assays were carried out as follows.

Bacteria containing each RNAi clone were cultured in 300 μl Luria Broth (LB) media containing 50 μg/ml ampicillin for six to fourteen hours. 40 μl of each culture was then spotted in a single well of a 24-well plate containing NGM agar, 6 mM IPTG, and 25 μg/ml carbenicillin. After overnight induction with IPTG, Nile Red was added to each well to a final concentration of 0.05 μg/ml. Five to ten synchronized L1 nematodes were then added to each well and incubated at 20° C. Growth conditions and Nile Red staining of nematodes were assessed after forty-eight, seventy-two, and ninety-six hours using light phase and UV fluorescence microscopy. For each batch of RNAi clones tested, L4440 (vector control) and OP50 control wells were included. At forty-eight hours, nematodes in control wells would be expected to have reached the L4 or young adult stage. By seventy-two hours, nematodes in control wells were at or near starvation. A fat metabolism phenotype was assigned to an RNAi well only if a majority of the nematodes in that well displayed a fat metabolism phenotype. Wells producing a fat metabolism phenotype were then re-tested in at least two independent trials. In all cases, the fat metabolism phenotype was scored blind, i.e. the investigator was unaware of the identity of the target RNAi clone while scoring the phenotype.

Results with feeding-mediated RNAi paralleled previous results obtained with genetic analysis, showing that mutations in the forkhead transcription factor gene, daf-16, and in the nuclear hormone receptor gene, daf-12, suppressed daf-2's high fat phenotype. These results indicated that feeding-mediated RNAi is useful for the analysis of fat metabolism regulator genes.

Feeding-mediated RNAi was then used to study lpo-1 nematodes. lpo-1 mutant nematodes were fed RNAi bacteria expressing daf-16, daf-12, or daf-3, and then the lpo-1 mutant nematodes were analyzed using Nile Red, as described herein. While daf-16 and daf-12 suppressed the high fat phenotype of daf-2, lpo-1 nematodes high fat phenotype remained unchanged when grown on daf-16, daf-12, or daf-3 RNAi bacteria. This indicated that lpo-1's high fat phenotype was not caused by defects in insulin or TGF-β signaling.

Systematic Identification of Fat Metabolism Regulator Genes Using RNAi

To identify additional fat metabolism regulator genes, a double stranded RNAi bacterial library with a coverage of greater than 80% of the 19,000 known and predicted *C. elegans* ORFs was utilized (Fraser, et al., *Nature* 408: 325–30, 2000; Kameth et al., *Genome Biol.* 2; 2001). The potency and specificity of this library was demonstrated by studies showing that 90% of genes identified by classical genetics as causing embryonic lethality when disrupted also cause embryonic lethality when inactivated by feeding RNAi (Fraser, et al., *Nature* 408:325–30, 2000). Combining the Nile Red fat content assay with the bacterial feeding RNAi strategy, a systematic analysis of genes that regulate fat content, fat droplet morphology, and pattern of fat droplet deposition was conducted.

For each targeted open reading frame, a plate of bacteria expressing the corresponding double stranded RNA was cultured. *C. elegans* L1 larva were then transferred to the plate and allowed to feed on the RNAi-expressing bacteria. Nile Red was also present on the plate, as described herein. The fat phenotype of non-starved adults was then analyzed. RNAi clones producing an increased or reduced fat phenotype were confirmed by re-testing in at least 2 independent experiments. Of 16,757 genes tested by RNAi, 2% (325 genes) (Table V) (a) caused reduced fat content or distorted fat deposition pattern, while 0.7% (116 genes) (Table VII) resulted in nematodes with increased fat content or enlarged fat droplet size. RNAi inactivation of another 240 genes produced reduced fat accompanied by larval arrest, embryonic lethality, or sterility (Table VI).

RNAi Clones that Reduce Fat without Interfering with Growth or Development

Figure 9A:
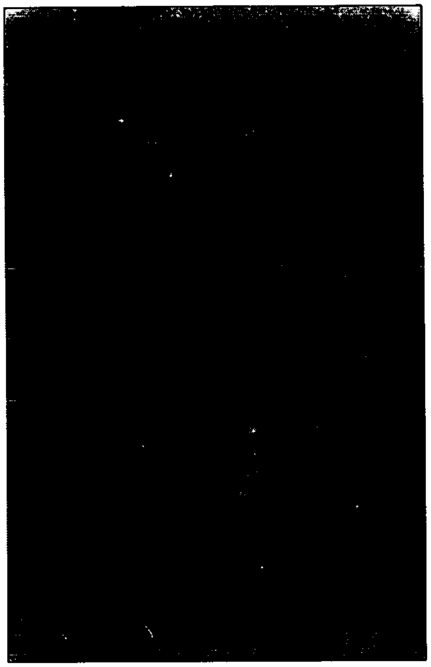
FIG. 9A is a photomicrograph showing Nile Red staining in a wild-type nematode.
Figure 9B:
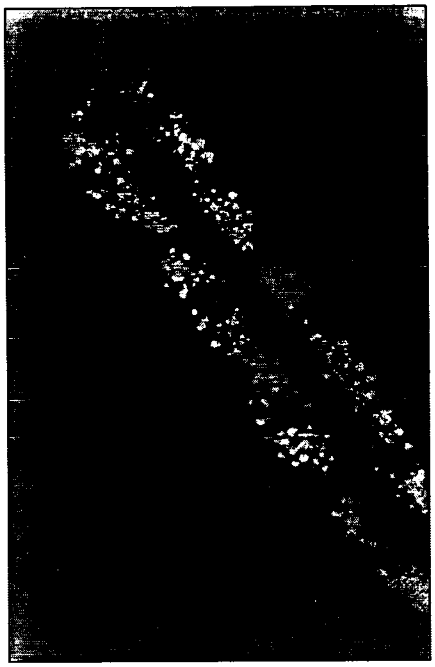
FIG. 9B is a photomicrograph showing Nile Red staining in an lpo-1 mutant nematode with increased fat staining.
Figure 9C:
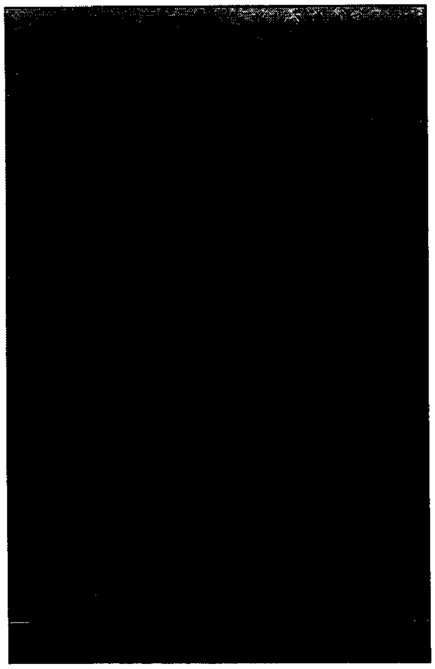
FIG. 9C is a photomicrograph showing Nile Red staining in an lpo-2 mutant nematode with reduced fat staining.
Figure 9D:
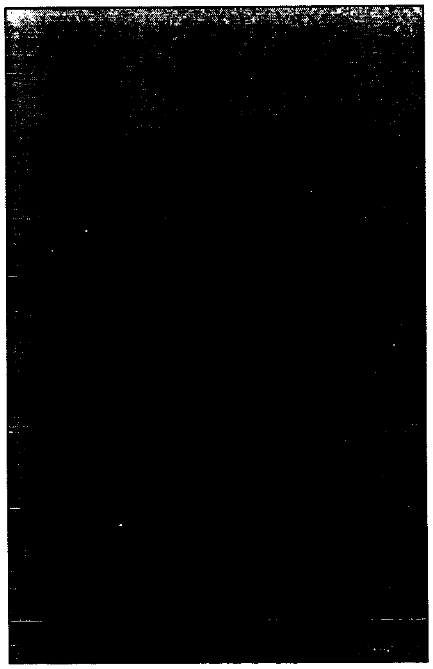
FIG. 9D is a photomicrograph showing Nile Red staining in an lpo-3 mutant nematode with reduced fat staining.
Figure 9E:
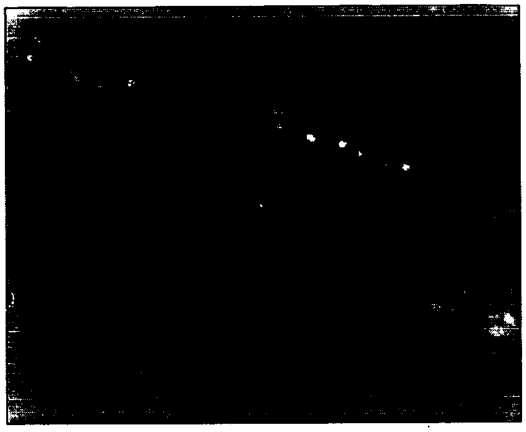
FIG. 9E is a photomicrograph showing Nile Red staining in a wild-type nematode (400× magnification).
Figure 9F:
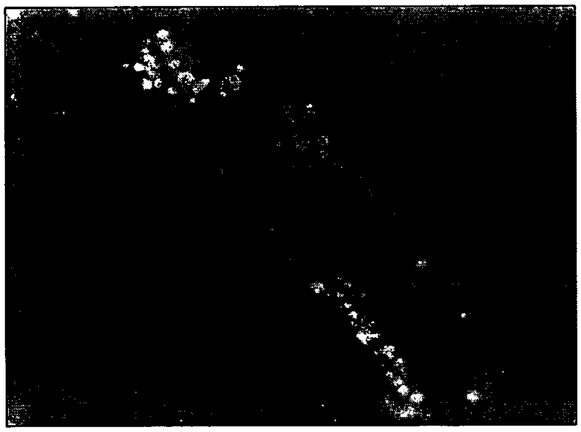
FIG. 9F is a photomicrograph showing Nile Red staining in an lpo-6 mutant nematode with increased fat droplets (400× magnification).
Figure 9G:
FIG. 9G is a photomicrograph showing Nile Red staining in an lpo-4 mutant nematode with reduced fat staining (400× magnification) and altered Nile Red emission profile. Green emission is observed instead of red.
Figure 10A:
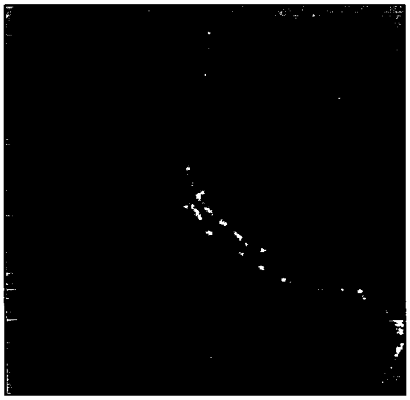
FIG. 10A is a photomicrograph showing C12-BODIPY-labelled fatty acid staining in a wild-type nematode.
Figure 10B:
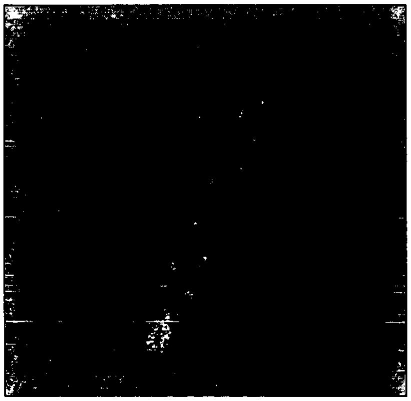
FIG. 10B is a photomicrograph showing Nile Red staining in a wild-type nematode.
Figure 10C:
FIG. 10C is a photomicrograph showing C12-BODIPY-labelled fatty acid staining in a lpo-1 nematode.
Figure 10D:
FIG. 10D is a photomicrograph showing Nile Red staining in a lpo-1 nematode.
Figure 10E:
FIG. 10E is a photomicrograph showing C12-BODIPY-labelled fatty acid staining in a lpo-2 nematode.
Figure 10F:
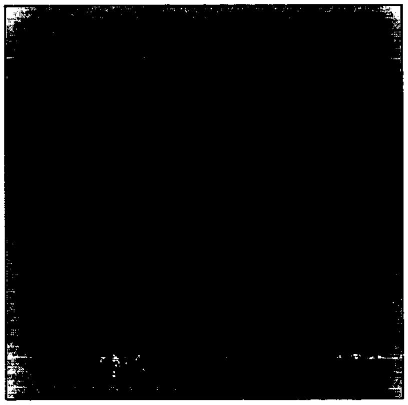
FIG. 10F is a photomicrograph showing Nile Red staining in a lpo-2 nematode.

This analysis identified three hundred twenty-five genes whose inactivation caused a reduction in fat content or fat mislocalization, but did not interfere with growth or development. These RNAi clones produced fat phenotypes that ranged from dramatic alterations in fat content or deposition pattern to more subtle changes. For the most part, fat droplets remained confined to intestinal cells even in mutant nematodes in which the distinct rows of intestinal fat droplets were distorted (these mutant nematodes are designated as distorted in Table V, an example of this phenotype is shown in FIG. 9G).

Inspection of the list of the genes whose inactivation caused altered fat content in fertile adults revealed a wide range of biological molecules including metabolic enzymes, signal transduction factors, transcription factors, receptors, channels, transporters, adhesion molecules, vesicular transport molecules, structural proteins, general cellular maintenance components and a significant number of genes with previously uncharacterised functions (Tables V, VI and VII). Some of the genes on these lists are known to be key players in mammalian fat or lipid metabolism. For example, reduced levels of stored fat resulted from RNAi of genes encoding nematode homologs of enzymatic components of membrane lipid biosynthetic machinery (such as choline/ethanolamine phosphotransferase, and CDP-alcohol phosphatidyltransferase), β-oxidation (Δ2, Δ4, dienoylCoA reductase, 3-hydroxyacyl-CoA dehydrogenase, long chain acyl-CoA thioesterase), fatty acid elongation enzymes, and cytosolic fatty acid and acyl-CoA binding proteins. Similarly, reduced fat content or distorted deposits resulted from RNAi of several known components of sterol metabolism, for example nematode homologs of HMG-CoA reductase (catalyzing the conversion of hydroxymethylgutaryl-CoA to mevalonate, the committed step of cholesterol biosynthesis), SREBP, LCAT (Lecitin-cholesterol acyltransferase, a facilitator of reverse cholesterol transport and modifier of ApoB-containing lipoproteins), and Steroidogenic acute regulatory (StAR—responsible for the transport of cholesterol from the outer to the inner mitochondrial membrane, the rate-limiting step in steroidogenesis) related protein (FIG. 13).

RNAi inactivation of glyceraldehyde-3-phosphate-dehydrogenase (GAPDH, an insulin regulated glycolytic enzyme) and phosphoenolpyruvate carboxykinase ((PEPCK), an enzyme which catalyses a regulated step of gluconeogenesis in adipose tissue (Hanson, et al., *Ann. Rev. Biochem.* 66:581–611, 1997)) reduced body fat content. GAPDH mRNA upregulation is associated with fat storage and lipogenesis in adipocytes of obese Zucker rats (Rolland, et al., *J. Biol. Chem.* 270:1102–6, 1995). Similarly, PEPCK expression is upregulated in several animal models of obesity and type II diabetes (Friedman, et al., *J. Biol. Chem.* 272:31475–81, 1997; Yoon, et al., *Nature* 413:131–8, 2001), while selective down regulation of PEPCK expression in mouse adipocytes correlates with reduced adipose tissue size and fat content (Olswang, et al., *Proc. Natl. Acad. Sci. USA* 99:625–30, 2002).

RNAi of *C. elegans* homologs of genes that function in gastrointestinal digestion and uptake of food in mammals also affect fat phenotype. In humans, PepT-1 is an insulin responsive transporter of dipeptide and tripeptides that is located in the intestinal brush border and provides a mechanism for protein absorption (Adibi, *Gastroenterology* 113: 332–40, 1997). RNAi down regulation of *C. elegans* ptr-2 locus, the PepT-1 homolog, produced a reduction in fat content as did the inactivations of ZK6.7 and R07B7.9, which encode two lipases most similar to mammalian gastric and brush-border lipases, respectively.

In mammals, CNS control of satiety is fundamental to the regulation of mammalian appetite and weight control. RNAi inactivation of a number of *C. elegans* genes that may function in food sensation and neuroendocrine signaling resulted in aberrant fat content. RNAi targeting of C43H6.9, for example, a putative glutamate receptor, and F56B6.5, a putative G-coupled protein with homology to rat hippocampal somatostatin receptor, lead to increased fat storage. Reduced fat content resulted from RNAi inactivation of R11A5.1, a homolog of neuronal β-adaptin, H27A22.1, encoding the potential ortholog of glutaminyl cyclase (required for biosynthesis of pyroglutamyl peptides), and several chemoreceptor and nematode olfactory receptors.

RNAi of specific nuclear hormone receptor genes produced nematodes with reduced or increased fat content. Nuclear hormone receptors regulate fat and sterol metabolism either by modulating transcription of metabolic genes or by initiating organelle or cellular differentiation cascades, notably peroxisomes and adipocytes, or by modulating transcription of sterol modifying and transport enzymes (Chawla, et al., *Science* 294:1866–70, 2001; Lazar, *Genes Dev.* 16:1–5, 2002; McKenna, et al., *Cell* 108:465–74, 2002; Willson, et al., *Ann. Rev. Biochem.* 70:341–67, 2001).

Although *C. elegans* lack dedicated adipocytes, their intestinal cells function as a major site of fat storage. Interestingly, several genes found to affect fat levels in *C. elegans* are homologs of mammalian proteins that function in adipocyte recruitment, growth, and differentiation. Adipocytes produce and secrete lysophosphatidic acid (LPA) among other peptidic and lipid factors. Paracrine regulation of preadipocyte growth is thought to be one of the biological activities mediated by LPA (Pages, et al., *Ann. NY Acad. Sci.* 905:159–64, 2000). G-protein coupled receptors ($LPA_1$/EDG-2) have been identified as potential transducers of the LPA signal (Pages, et al., *Ann. NY Acad. Sci.* 905:159–64, 2000). Inactivation of nematode homolog of $LPA_{R1}$/Edg-2 receptor results in reduced fat.

The reduced fat phenotypes were categorized as (i) much reduced (i.e., less than 20% of the fat content present in wild-type nematodes; fat content in these nematodes was reduced by at least 80%, 85%, 90%, 95%, 97%, 99% or 100%); (ii) reduced and/or distorted (i.e., less than 50% of the fat content present in wild-type nematodes; fat content in these nematodes was reduced by at least 50%, 55%, 60%, 70%, 75%, or 79%); (iii) moderately reduced (i.e., less than 75% of the fat content present in wild-type nematodes; fat content in these nematodes was reduced by at least 25%, 30%, 35%, 40%, 45%, or 49%); or (iv) slightly reduced (i.e., less than 97.5% of the fat content of wild-type nematodes; fat content in these nematodes was reduced by at least 2.5%, 5%, 10%, 15%, 20%, or 24%). The percentages of the 325 genes falling into each of these categories were 15%, 61%, 19%, and 5%, respectively. The list of target genes identified was annotated using BlastP searches against Genbank mammalian databases. This list identifies the target genes by *C. elegans* cosmid name and open reading frame number. In addition, information available at nematodebase (www.nematodebase.org), a central repository of data on *C. elegans* was also used.

TABLE V

RNAi Clones that Reduce Fat Content or Alter Fat Deposition Pattern without Reducing Viability

| *C. elegans* Gene | Brief Description | Nile Red Fat Phenotype |
|---|---|---|
| METABOLIC ENZYME (38) | | |
| C36A4.9 | acetyl-CoA synthetase | reduced |
| AH10.1 | medium-chain acyl-CoA synthetase | reduced |
| C17C3.1 | peroxisomal long-chain acyl-coA thioesterase | reduced |
| K05F1.3 | acyl-coA dehydrogenase | distorted, reduced |
| T08B2.7 | gastrin-binding/3-hydroxyacyl-Coenzyme A dehydrogenase | much reduced |
| W01C9.4 | mitochondrial Δ2,Δ4-dienoyl-CoA reductase | distorted |
| T02G5.4 | acyl-CoA thiolase | slightly reduced |
| F14H8.1 | long chain fatty acyl elongase | reduced |
| F11E6.5 | fatty acid elongase | reduced |
| B0285.8 | choline/ethanolamine kinase | distorted, reduced |
| Y49A3A.1 | choline/ethanolamine phosphotransferase | much reduced |
| F23H11.9 | CDP-alcohol phosphatidyltransferas | moderately reduced |
| C01C10.3 | phospholipid and glycerol acyltransferase | slightly reduced |
| F08F8.2 | 3-hydroxymethyglutary-CoA (HMG-CoA) reductase | reduced |
| F15A8.6 | cholesterol esterase | reduced |
| K02D3.2 | steroidogenic acute regulatory (StAR) related | distorted |
| M05B5.4 | LCAT-like lysophospholipase | distorted |
| K10B3.7 | glyceraldehyde 3-phosphate dehydrogenase (GAPDH) | reduced |
| H04M03.1 | phosphoenolpyruvate carboxykinase (PEPCK-C) | reduced |
| F43H9.2 | serine palmitoyltransferase II | reduced |
| Y6B3B.10 | lag1 (ceramide synthesis) | distorted |
| K09D9.2 | cytochrome P450 | much reduced |
| K07C6.4 | cytochrome P450 2C2 (P450 PBC2) | moderately reduced |
| K07C6.5 | cytochrome P450 2C2 (P450 PBC2) | much reduced |
| T04A8.16 | calpain-type cysteine-protease | moderately reduced |
| F28H6.3 | 1-aminocyclopropane-1-carboxylic acid synthase | reduced |
| C06E7.3 | S-adenosylmethionine synthetase | reduced |
| F13D11.1 | lysosomal acid phosphatase precursor | much reduced |
| F52B11.2 | phosphomannomutase 2 | reduced |
| K03B8.3 | neutral zinc metallopeptidases | distorted |
| C24A11.9 | trans-prenyltransferase | reduced, slow growth |
| T09B4.8 | alanine-glyoxylate aminotransferase 2 | reduced |
| Y55F3C.c | putative thioredoxin | distorted, few droplets |
| T12A2.1 | chlorohydrolase/histidine degradation | distorted |
| C31H2.3 | 4-hydroxyphenylpyruvate dioxygenase | moderately reduced |
| E01A2.i | glutamate-cysteine ligase/oxidative stress | reduced |

TABLE V-continued

RNAi Clones that Reduce Fat Content or Alter Fat Deposition Pattern without Reducing Viability

| *C. elegans* Gene | Brief Description | Nile Red Fat Phenotype |
|---|---|---|
| C46H11.2 | flavin binding monooxygenase | moderately reduced |
| M28.6 | serine beta lactamase-like protein | reduced |
| FAT/LIPID interacting (8) | | |
| F37B12.3 | lipid associated protein | much reduced |
| C37H5.3 | esterase/lipase | moderately reduced |
| ZK6.7 | gastric lipase/esterase | reduced |
| R07B7.9 | adult-specific brush border esterase/phospholipase | reduced |
| F31F6.7 | lipase | reduced |
| F13D12.6 | esterase/lipase/Serine carboxypeptidase (S10) | much reduced |
| C15B12.7 | lipocalin and cytosolic fatty-acid binding protein | reduced |
| C44E4.6 | acyl-coA-binding protein | reduced |
| TRANSCRIPTION FACTOR (19) | | |
| Y47D3B.7 | SREBP | distorted |
| C33G8.9 | nuclear hormone receptor/C4-type steroid receptor | distorted |
| K08A2.b | nuclear hormone receptor/hepatocyte nuclear factor 4 | much reduced |
| Y69A2A_7278.1 | nuclear hormone receptor/hepatocyte nuclear factor 4 | reduced, distorted |
| F11C1.6 | steroidogenic factor 1 | reduced |
| B0280.3 | nhr-10 (ribose 5-phosphate ketol-isomerase) | distorted |
| F11A1.3 | similarity to vitamin D (1,25-dihydroxyvitamin D3) receptor | reduced |
| C46E10.9 | zinc finger, C2H2 type | moderately reduced |
| C47C12.3 | zinc finger, C2H2 type/mouse OPR | much reduced |
| T09F3.1 | zinc finger, C2H2 type | reduced |
| T23F11.4 | zinc finger, C2H2 type | moderately reduced |
| ZK686.4 | zinc finger, C2H2 type | reduced |
| Y116A8C.32 | Zn-finger CCHC type transcription factor/ZFM1 | reduced |
| F22A3.4 | homeotic protein PBX2 homology | reduced |
| C09G9.7 | LuxR family/'Paired box' domain | slightly reduced |
| W02C12.3 | microphthalmia transcription factor/Waardenburg syndrome | reduced |
| F22A3.5 | pre-B-cell leukemia transcription factor 1 homology | moderately reduced |
| C01G6.5 | Forkhead-associated (FHA) domain | reduced |
| F39D8.2 | weak similarity to homeobox protein PKNOX | reduced |
| Translational control (5) | | |
| R04A9.4 | translation initiation factor 4E (e1F-4E) | moderately reduced |
| ZK757.3 | translation initiation factor e1F-2C | reduced |
| Y41E3.10 | elongation factor 1 beta/beta'/delta chain | much reduced |
| D2089.2 | RNA-binding region RNP-1 | much reduced |
| F11A10.3 | zinc finger C-x8-C-x5-C-x3-H type | reduced |
| SIGNAL TRANDUCTION (30) | | |
| B0218.5 | serine/threonine protein kinase | moderately reduced |
| T05C12.1 | serine/threonine protein kinase | moderately reduced |
| Y53C12A.1 | serine/threonine protein kinase/membrane associated | reduced |
| C16A11.3 | serine/threonine protein kinase | moderately reduced |
| F45H7.4 | pim1 serine/threonine-protein kinase | reduced |
| ZK930.1 | G-protein beta WD-40 repeats-ser/thr protein kinase/Pl-3 | reduced |
| ZC504.4 | tyrosine kinase and serine/threonine protein kinase | distorted |
| M01B12.5 | tyrosine kinase catalytic domain | reduced |
| C02F4.2 | serine/threonine protein phosphatase (PP2b) | moderately reduced |
| C06A1.3 | serine/threonine specific protein phosphatase | slightly reduced |
| ZC302.1 | serine/threonine specific protein phosphatase | distorted |
| C03D6.3 | dual specificity protein phosphatase/RNA guanylytransferase | distorted |
| T19D2.2 | dual specificity protein phosphatase family | reduced |
| C47D12.1 | phosphatidylinositol 3- and 4-kinase/EF-hand family | reduced |
| ZK909.3 | guanosine-3',5'-bis(diphosphate)-pyrophosphohydrolase | moderately reduced |
| C06A6.1 | phosphotriesterase | moderately reduced |
| R107.4 | IKK-related kinase epsilon | distorted |
| C33H5.17 | D111/G-patch domain | reduced |
| R07E5.1 | D111/G-patch domain | moderately distorted |
| C41D7.2 | HMGCR/Patched 5TM box | distorted |
| ZK675.1 | HMGCR/Patched 5TM box-patched | reduced |
| F20H11.2 | mop-3/strawberry notch (sno) | reduced |
| T04D3.2 | EF-hand family domain protein/no significant similarity | distorted |
| C44F1.5 | guanylate cyclase | much reduced |
| H08M01.2 | RhoGAP domain/glucocorticoid receptor | reduced |
| F46G11.3 | protein kinase | reduced |
| K10D3.5 | adaptor protein/nuclear receptor binding protein/kinase | moderately reduced |
| F41D9.1 | RabGAP/TBC domain/SH3 domain | reduced |
| F07C3.4 | RCC1 domain | distorted |
| F45E4.6 | EGF-like domain/Crystallin | distorted |

TABLE V-continued

RNAi Clones that Reduce Fat Content or Alter Fat Deposition Pattern without Reducing Viability

| *C. elegans* Gene | Brief Description | Nile Red Fat Phenotype |
|---|---|---|
| RECEPTORS (22) | | |
| T14E8.3 | dopamine receptor D2 | much reduced |
| C07A9.2 | G10 protein/edg-2/LPA receptor | reduced |
| Y4C6A.H | metabotropic glutamate receptor | distorted |
| C38C10.1 | rhodopsin-like GPCR superfamily/neurkinin-3 receptor | reduced |
| C34C6.6 | peroxisomal targeting signal 1 receptor | reduced |
| E02C12.3 | rhodopsin-like GPCR superfamily | moderately reduced |
| H09F14.1 | rhodopsin-like GPCR superfamily/somatostatin like | distorted |
| Y44A6B.2 | rhodopsin-like GPCR superfamily | reduced |
| F58G4.2 | chemoreceptor | distorted |
| Y40H7A.7 | Sra family chemoreceptor | reduced |
| F07C4.1 | 7-Helix G-protein coupled receptor, nematode specific | moderately reduced |
| F10A3.13 | 7-Helix G-protein coupled receptor, nematode specific | much reduced |
| F17A2.7 | 7-Helix G-protein coupled receptor, nematode specific | moderately reduced |
| F47C12.3 | 7-Helix G-protein coupled receptor, nematode specific | moderately reduced |
| F49C5.6 | 7-Helix G-protein coupled receptor, nematode specific | reduced |
| T07C12.1 | 7-Helix G-protein coupled receptor, nematode specific | reduced |
| T07C12.5 | 7-Helix G-protein coupled receptor, nematode specific | distorted |
| Y17G9A.d | 7-Helix G-protein coupled receptor, nematode specific | distorted |
| Y94A7B.3 | 7-Helix G-protein coupled receptor, nematode specific | reduced |
| Y9C9A_53.c | 7-Helix G-protein coupled receptor, nematode specific | reduced |
| T04A11.8 | 7TM receptor | reduced |
| F33G12.2 | G-protein beta WD-40 repeats | Moderately reduced |
| ION CHANNELS/PERMEASES/TRANSPORTERS (12) | | |
| C32C4.1 | voltage-dependent potassium channel | distorted |
| B0310.1 | potassium channel/very weak mammalian similarity | reduced |
| C37A5.1 | homology Best's macular dystrophy (BMD) ion exchanger | slightly reduced |
| K04E7.2 | PepT1 oligopeptide symporters | reduced |
| C34G6.4 | ABC transporter | much reduced |
| K05F1.6 | organic solute carrier family 2/ (OCT1) | moderately reduced |
| ZK682.2 | sugar transporter | distorted |
| C13D9.7 | sodium/calcium exchanger protein | reduced |
| F23F1.6 | high affinity cationic amino acid permease | moderately reduced |
| F15H10.4 | lysosomal amino acid transporter | reduced, distorted |
| F59F5.1 | monocarboxylate transporter/XPCT | reduced |
| C46F11.1 | unc-93 protein/ABC-2 type transporter | moderately reduced |
| NEURONAL (4) | | |
| H27A22.1 | glutaminyl cyclase/biosynthesis of pyroglutamyl peptides | distorted |
| T19B4.6 | DCC/axon guidance/Fibronectin type III domain | reduced |
| T19B4.7 | DCC/axon guidance/Fibronectin type III domain | much reduced |
| T27F7.1 | neuroendocrine differentiation factor | much reduced |
| ENERGY METABOLISM (6) | | |
| C33A12.1 | NADH-ubiquinone oxidoreductase B subunit | reduced |
| F28H6.2 | mitochondrial energy transfer proteins/carrier protein | distorted/reduced |
| F20D1.9 | mitochondrial carrier proteins/similarity to uncoupling protein | moderately reduced |
| F14D12.2 | cytochrome c family heme-binding site | moderately reduced |
| K12B6.8 | cytochrome c family heme-binding site | distorted |
| C15H9.7 | kynureninase | reduced |
| VESICULAR TRANSPORT (11) | | |
| W03C9.3 | RAB7 | moderately reduced |
| F11A5.3 | similarity to RAB2 | moderately reduced |
| R11A5.1 | beta-nap protein like/Adaptin | much reduced |
| F53H8.1 | clathrin adaptor medium chain | reduced |
| T14D7.3 | Synaptobrevin | slightly reduced |
| R01H2.3 | sortilin (LDL receptor) family | reduced |
| T22D1.4 | glycotransferase/ribophorin 1 | reduced |
| F54H5.3 | VAMP-associated protein | reduced |
| CO5E11.2 | vacuolar protein sorting, vps16 like | distorted |
| K09B11.9 | uso/p115 homology | moderately distorted |
| Y38E10A.c | similar to RIM binding protein 1A (rab-3 interacting protein) | moderately distorted |
| PROTEIN DEGRADATION (5) | | |
| C49C3.3 | ubiquitin family | moderately reduced |
| F49E12.4 | ubiquitin-conjugating enzymes | moderately reduced |
| F52C6.2 | ubiquitin domain | reduced |
| Y65B4B_10.a | putative ubiquitin-protein ligase | slightly reduced |
| Y65B4B_10.e | putative, ubiquitin-protein lipase | moderately reduced |

TABLE V-continued

RNAi Clones that Reduce Fat Content or Alter Fat Deposition Pattern without Reducing Viability

| C. elegans Gene | Brief Description | Nile Red Fat Phenotype |
|---|---|---|
| CELL SURFACE/STRUCTURAL (8) | | |
| F40H3.5 | heparan sulfate sulfotransferase | reduced |
| ZK39.7 | chondroitin sulfate proteoglycan | much reduced |
| F49E11.4 | extracellular proteins SCP/Tpx-1/Ag5/PR-1/Sc7 homology | distorted |
| K02D7.3 | collagen triple helix repeat | much reduced |
| M01E10.2 | collagen type XIV | reduced |
| Y77E11A_344i | collagen | reduced |
| F07A5.1 | innexin | moderately reduced |
| F26D11.10 | innexin | reduced |
| CYTOSKELETAL (7) | | |
| Y37D8A.1 | actin related protein 2/3 complex | distorted |
| Y17G7B.15 | centaurin beta5 | reduced |
| R107.6 | CLIP-associating protein 1/microtubule dynamics | distorted |
| C23F12.1 | endothelial actin-binding protein repeats | reduced |
| M106.5 | F-actin capping protein beta subunit | distorted |
| C06G3.2 | kinesin motor domain | reduced |
| T28D6.2 | tubulin family protein | reduced |
| GENERAL CELLULAR MACHINERY (11) | | |
| W09D10.3 | mitochondrial ribosomal protein L1 | reduced |
| W10D9.5 | mitochondrial tranport/Tom2 homology | reduced |
| W09D10.3 | mitochondrial ribosomal protein L1 | reduced |
| F54D5.11 | TFIIE beta subunit core domain | reduced |
| F44B9.7 | replication factor C-subunit | reduced |
| Y71H10B.1 | 5'-nucleotidase (purine), cytosolic type B | reduced |
| F21D5.5 | polynucleotide kinase 3' phosphatase | distorted |
| F20D12.2 | germinal center associated nuclear protein/DNA primase | much reduced |
| Y41D4A_3073.a | nucleoporin 155 | much reduced |
| T22D1.10 | ruvB-like DNA helicase | reduced |
| C24A1.4 | transposase | much reduced |
| Y37A1A.1 | set domain and mariner transposase fusion gene | reduced |
| NO FUNCTION ASSIGNED (140) | | |
| W09G3.4 | thiamine pyrophosphate enzyme/RCC1 and WD-40 repeat | distorted |
| H25K10.1 | similarity to ser/thr protein phosphatase | distorted |
| C30F12.1 | strong similarity to a hypothetical protein KIAA1726 | much reduced |
| W09G3.1 | similar to lAA0329 gene product | distorted |
| Y51H4A.m | hypothetical protein HDCMC04P | moderately reduced |
| Y48C3A.b | may be in transposase Tc1/Tc3 family | much reduced |
| F13E6.1 | similarity to (NM_025741) | reduced |
| T21D12.3 | polyglutamine binding protein 1/scurfy 2 candidate | reduced |
| B0041.5 | TonB-dependent receptor protein/solute carrier protein | slightly reduced |
| B0286.4 | similarity to AF113226 expressed in human heart tissue | reduced |
| D1054.14 | hypothetical protein XP_061203 | much reduced |
| F54C9.9 | similarity to hypothetical protein FLJ12949 | reduced |
| B0513.7 | human homolog AF054989/may be transposase like | much reduced |
| Y41D4A_3192.a | strong similarity to human CAB66614 | slightly reduced |
| ZK686.3 | putative prostate cancer tumor suppressor | moderately reduced |
| B0041.3 | putative peptidoglycan binding domain containing protein | distorted |
| C05E11.1 | similarity to human homolog KIAA1715 protein | reduced |
| F38A5.1 | strong similarity to a hypothetical protein FLJ11200 | moderately reduced |
| C07E3.2 | similar to DKFZP564C186 protein | moderately reduced |
| Y47G6A_245.b | similarity to hypothetical protein DKFZp434G1619.1 | distorted |
| R05F9.8 | similarity to S-crystallin/glutathione S-transferase | moderately reduced |
| W04A4.5 | similar to CG12113 | much reduced |
| Y49F6B.n | Red protein (RER protein/arginine (R) and glutamic acid (E) | distorted |
| F14D2.4 | BTB/POZ/MATH (meprin and TRAF homology) domain | distorted |
| C30G4.5 | D. melanogaster finger protein neuralized | moderately reduced |
| F58H1.6 | EGF-like domain | much reduced |
| F55B11.4 | Zinc finger, C2H2 type domain | slightly distorted |
| C47D12.7 | BTB/POZ domainKelch repeat/human kelch 3 like | reduced |
| ZK355.d | domain of unknown function DUF41 | reduced |
| C16C4.2 | MATH (meprin and TRAF homology) BTB/POZ domain | moderately reduced |
| Y50D7_165.b | may be involved in mitochondria | reduced, thin |
| C54H2.5 | surf4 family | reduced |
| T05F1.6 | BRCT domain | slightly reduced |
| R08F11.2 | Domain of unknown function DUF32 | distorted |
| W01B11.5 | proline-rich region | reduced |
| R05H11.1 | F-box domain | reduced |
| C32D5.11 | RING finger | moderately reduced |
| H32C10.3 | DHHC-type Zn-finger Ankyrin-repeat/huntingtin interacting | much reduced |
| T21C9.2 | Type-1 copper (blue) domain/VPS54 | reduced |

TABLE V-continued

RNAi Clones that Reduce Fat Content or Alter Fat Deposition Pattern without Reducing Viability

| *C. elegans* Gene | Brief Description | Nile Red Fat Phenotype |
|---|---|---|
| Y41E3.11 | SPRY domain Proline rich extensin | reduced |
| T10D4.1 | Domain of unknown function DUF19 | slightly distorted |
| C54G7.1 | weak homology to Vitamin K-dependent/(GLA) domain | some reduction |
| Y57G11C.17 | weak homology to glycerol uptake protein | slightly reduced |
| T04C10.2 | Yeast hypothetical protein L8167.6 like/epsin 2 | moderately reduced |
| W06G6.1 | weak similarity to RanBP7/importin | reduced |
| K12D12.4 | weak similarity to zinc finger domain | distorted |
| C23H3.2 | weak similarity to ATP-binding cassette protein ABCB9 | much reduced |
| C56E10.3 | weak similarity to desmoplakin | moderately reduced |
| T27E4.6 | very weak similarity to FMLP-RELATED RECEPTOR II | moderately distorted |
| Y57A10A.bb | very weak similarity to XM_092364 | reduced |
| C14A6.6 | very weak similarity to transcription factor | reduced |
| Y67D8A_380.d | very weak similarity to AB052150) | slightly reduced |
| F08G2.7 | very weakly similar to RCC domain | moderately reduced |
| F29B9.11 | very weak similarity to alpha 1a-adrenoceptor | reduced |
| T26E4.13 | very weak similarity to XM_089955) | reduced |
| H04M03.4 | very weak similarity to lens fiber cell beaded-filament protein | much reduced |
| K02E7.11 | very weak similarity to hypothetical protein AK057380 | much reduced |
| T10C6.10 | very weak similarity to a cytochrome P450 | moderately reduced |
| Y57E12_242.c | very weak similarity to superkiller viralicidic activity | much reduced |
| T10E9.6 | very weak similarity to mouse (BC020184) | moderately distorted |
| Y111B2C.e | very weak similarity to RIM2-4C | much reduced |
| Y71H2_389.a | very weak similarity to spondyloepiphyseal dysplasia | reduced |
| R160.4 | very weak similarity to TNF | reduced |
| Y50E8.q | very weak similarity to anti-DNA immunoglobulin heavy chain | distorted, dumpy |
| F13B6.1 | very weak similarity to vitamin D receptor | reduced |
| T21C9.11 | very weak similarity to hypothetical protein XP_089285 | distorted |
| T02H6.7 | very weak similarity to arachidonate 5-lipoxygenas | reduced |
| F53A9.4 | very weak similarity to hypothetical protein | reduced |
| C14F5.3 | very weak similarity to troponin T | slightly reduced |
| C29H12.6 | very weak similarity to an unknown protein | reduced, distorted |
| C56E6.4 | very weak similarity to hypothetical protein XP_062076 | reduced |
| F46C8.7 | very weak similarity to an plasma membrane urea transporter | reduced |
| F46F5.10 | very weak similarity to an rotocadherin 18 precursor | moderately reduced |
| C42C1.6 | very weak similarity to hypothetical protein XM_087750 | much reduced |
| F27C1.4 | very weak similarity to hypothetical protein AK057039 | reduced |
| B0554.7 | very weak similarity to mouse NP_573485.1 | moderately reduced |
| C18E9.5 | very weak similarity to TRRAP protein | reduced |
| F28H7.6 | very weak similarity to calcium-independent phospholipase | distorted |
| C08G5.2 | very weak similarity to mouse membrane glycoprotein | distorted, dumpy |
| F54F7.2 | very weak similarity to Complement C3 precursor | slightly reduced |
| M01A8.1 | very weak similarity to Eph receptor | distorted, reduced |
| T01D3.4 | very weak similarity to Rhodopsin-like GPCR superfamily | reduced |
| F59E11.5 | very weak similarity to polyadenylation specificity factor 1 | reduced |
| T19D7.1 | very weak similarity to a serotonin receptor | reduced |
| B0554.6 | very weak similarity to mouse ETL1, | reduced |
| ZC84.5 | very weak similarity to thyroid receptor interacting protein 4 | reduced |
| W05E10.2 | very weak similarity to expressed sequence R74613 | moderately distorted |
| ZK652.2 | very weak similarity to (AJ011007) | moderately reduced |
| D2062.10 | very weak similarity to adaptor-related protein complex AP-4 | distorted |
| C17G10.7 | very weak similarity to novel SH2-containing protein | moderately reduced |
| B0207.9 | very weak similarity to hypothetical protein KIAA0153 | reduced |
| F38E9.4 | very weak similarity to cytoplasmic linker 2 | distorted |
| Y65B4B_13.b | very weak similarity to ubiquitin protein ligase | reduced, hazy |
| Y38E10A.b | very weak similarity to a synaptotagmin 8 | reduced |
| ZK593.3 | very weak similarity to Laminin alpha-1 chain precursor | reduced |
| C14C6.8 | very weak similarity to XP_040205.2 | moderately reduced |
| F21H12.3 | very weak similarity to chaperonin containing TCP1 | slightly reduced |
| T23E1.1 | very weak similarity to BC002298) | reduced |
| T17H7.1 | very weak similarity to Ig heavy chain V | much reduced |
| F10A3.11 | very weak similarity to vascular Rab-GAP/TBC-containing | moderately reduced |
| F41C6.6 | very weak similarity to ABC family (CFTR/MRP) | reduced |
| T07C12.11 | very weak similarity to synuclein alpha interacting protein | distorted |
| T14A8.1 | very weak similarity to novel protein dJ180E22.1 | distorted |
| F58F9.1 | very weak similarity to an apolipoprotein precursor | slightly reduced |
| ZK154.4 | very weak similarity to chromodomain helicase | moderately distorted |
| R03H10.4 | very weak similarity to MAPKKK 10 | reduced |
| F55C12.3 | very weak similarity to activin A type IB receptor precursor | moderately reduced |
| Y119D3_456.a | very weak similarity to guanylate binding protein (mouse) | reduced |
| F08D12.4 | no significant mammalian homology | reduced |
| R11H6.6 | no significant mammalian homology | reduced |
| Y57A10A.1 | no significant mammalian homology | distorted |
| C14A4.12 | no significant mammalian homology | distorted |
| Y7A9C.3 | no significant mammalian homology | much distorted |

TABLE V-continued

RNAi Clones that Reduce Fat Content or Alter Fat Deposition Pattern without Reducing Viability

| *C. elegans* Gene | Brief Description | Nile Red Fat Phenotype |
|---|---|---|
| C01G6.9 | no significant mammalian homology | reduced |
| Y51H7C_255.c | no significant mammalian homology | reduced |
| B0041.5 | no significant mammalian homology | slightly reduced |
| C15C7.5 | no significant mammalian homology | reduced |
| T10C6.4 | no significant mammalian homology | moderately reduced |
| Y37D8A.8 | no significant mammalian homology | reduced |
| C50E10.5 | no significant mammalian homology | reduced |
| ZK1290.1 | no significant mammalian homology | reduced |
| F22E5.1 | no significant mammalian homology | reduced |
| F12A10.8 | no significant mammalian homology | reduced |
| B0034.2 | no significant mammalian homology | reduced |
| F36H12.15 | no significant mammalian homology | reduced |
| F52C6.12 | no significant mammalian homology | much reduced |
| Y24D9A.b | no significant mammalian homology | distorted |
| K06B4.3 | no significant mammalian homology | much reduced |
| T11F9.10 | no significant mammalian homology | reduced |
| T19D2.3 | no significant mammalian homology | reduced |
| T27E4.7 | no significant mammalian homology | moderately distorted |
| Y105E8B.a | no significant mammalian homology | slightly reduced |
| Y69A2A_7278. | no significant mammalian homology | reduced, distorted |
| Y51H7B_5.b | no significant mammalian homology | slightly reduced |
| T13F2.6 | no significant mammalian homology | distorted |
| K09H11.2 | no significant mammalian homology | reduced |
| T26E4.10 | no significant mammalian homology | reduced |
| T06H11.2 | no significant mammalian homology | moderately reduced |
| F59F5.2 | no significant mammalian homology | much reduced |
| ZK131.8 | no significant mammalian homology | much reduced |

RNAi Clones that Reduce Fat and Viability/Growth

An additional 225 RNAi clones were identified that dramatically slowed development, or resulted in embryonic lethality. These genes are listed in Table VI.

Some of these RNAi clones interfered with the expression of previously identified genes with critical roles in fat biosynthesis and metabolism such as nematode acetyl-CoA carboxylase (W09B6.1), fatty acid synthase (F32H2.5), and fatty acid desaturase fat-7. The identification of these *C. elegans* homologs of mammalian genes also provides compelling evidence of the usefulness of *C. elegans* in identifying mammalian fat metabolism regulator genes critical to fat metabolism. The effects of other RNAi clones on development were attributed to the inactivation of genes that function in cellular maintenance (e.g., ATP synthesis, ribosomal biogensis). This list identifies the target genes by *C. elegans* cosmid name and open reading frame number.

TABLE VI

RNAi Clones that Reduce Fat Content and Reduce Viability/Growth

| *C. elegans* Gene | BRIEF DESCRIPTION | Nile Red Phenotype |
|---|---|---|
| F10D2.9 | stearoyl-CoA desaturase | not fully grown, reduced |
| F29DH.1 | low density lipid receptor-related protein | much distorted |
| F32H2.5 | fatty acid synthase | much reduced, not grown |
| W06D12.3 | fatty acid desaturase, type l/stearoyl-CoA desaturase | reduced |
| w09b6.1 | acetylCoA carboxylase alpha | much reduced, not grown |
| C09H10.3 | Respiratory-chain NADH dehydrogenase 51 Kd subunit | much reduced |
| C53B7.4 | ATP synthase | reduced, no progeny |
| F02E8.1 | ATP synthase B chain | reduced |
| F35G12.10 | ATP synthase B chain | much reduced |
| F37E3.1 | cytochrome b6/CAP BINDING PROTEIN | distorted, reduced/no progeny |
| W04A8.7 | taf-1/Cytochrome c family heme-binding site/Bromodomain | very hazy |
| Y110A7A.h | ATP synthase alpha and beta subunit | reduced |
| Y37D8A.14 | cytochrome c oxidase subunit Va | much reduced |
| Y57G11C.12 | NADH-ubiquinone oxidoreductase | reduced/no progeny |
| F28B3.1 | cysteine proteases inhibitor | moderately reduced/not grown |
| F59B2.12 | eukaryotic thiol (cysteine) proteases active sites | slow growth, reduced |
| C23H3.4 | serine palmitoyltransferase | much reduced |
| C42C1.5 | bacterial transferase hexapeptide repeat/ADP-glucose pyrophosphorylase | distorted |

TABLE VI-continued

RNAi Clones that Reduce Fat Content and Reduce Viability/Growth

| *C. elegans* Gene | BRIEF DESCRIPTION | Nile Red Phenotype |
|---|---|---|
| D1014.1 | arylsulfatase E precursor | hazy,, reduced |
| E04A4.7 | cytochrome c, class IA and IB/Cytochrome C, Class I | reduced |
| F01G10.1 | Transketolase | moderately reduced |
| F40H3.5 | heparan sulfate sulfotransferase | small, not grown, reduced |
| F44D12.4 | LUT1 C-terminal binding protein/RGS-GAIP interacting protein GIPC | reduced |
| F46E10.1 | AMP-dependent synthetase and ligase | much reduced |
| F57B9.2 | proline-rich region• Glycosyl hydrolases family 5 | not grown, reduced |
| H14A12.2 | fumarate lyase | reduced |
| H15N14.2 | AAA-protein (ATPases associated with various cellular activities) NSF | reduced, not grown |
| K02F2.2 | S-adenosyl-L-homocysteine hydrolase | much reduced, no progeny |
| K06A4.5 | 3-hydroxyanthranilate 3,4-dioxygenase | distorted |
| T05H4.4 | oxidoreductase FAD/NAD-binding domain | reduced |
| T05H4.5 | oxidoreductase FAD/NAD-binding domain /cytochrome B5 reductase | much reduced |
| Y55F3A__750.e | weak similarity to putative~thioredoxin | much reduced, few progeny |
| B0285.1 | serine/Threonine protein kinase family active site | much reduced/no progeny |
| C16C2.3 | inositol-1,4,5-triphosphate 5-phosphatase | reduced |
| F10E9.7 | RA domain/Proline-rich region/Pleckstrin homology (PH) domain | much reduced |
| W03F8.5 | bacterial chemotaxis sensory transducer/EGF-domain/Laminin N-terminal | slight reduction/no progeny |
| W07E6.2 | beta G-protein (transducin)/G-protein beta WD-40 repeats | reduced |
| ZK1067.1 | let-23/tyrosine-protein kinase (Epidermal growth factor receptor subfamily) | much reduced |
| ZK675.1 | HMGCR/Patched 5TM bo3/PTC-2 | few progeny, much reduced |
| C27B7.5 | zn-finger CCHC type | reduced |
| C33D3.1 | elt-2/zinc finger protein (GATA type) | much reduced |
| C34H3.a | C2H2-type zinc finger protein/odd-skipped-related 2A protein | reduced |
| D1081.2 | MADS-box domain | distorted |
| F10C1.5 | DM DNA binding domain | moderately reduced/distortion |
| F22A3.1 | prostate epithelium-specific Ets transcription factor | distorted |
| F23B12.7 | EF-hand family/CCAAT BINDING FACTOR 1 | much distorted |
| F25H8.3 | neutral zinc metallopeptidases/Thrombospondin type/reprolysin (M12B) | slightly reduced |
| W01D2.2 | ligand-binding domain of nuclear hormone receptor | not fully grown, much reduced |
| Y17G7A.2 | zinc finger, C2H2 type | lethal, not grown, reduced |
| C01F6.8 | swelling-induced chloride conductance regulatory | much reduced |
| C56C10.8 | TonB-dependent receptor protein/Nascent polypeptide Associated Complex | reduced, few progeny |
| C56E6.1 | protein-dependent transport systems inner membrane component | reduced, no progeny |
| W06D12.2 | potassium channel, subfamily K | not grown, reduced |
| W10D9.5 | mitochondrial tranport/Tom2 homology | reduced, distorted |
| Y61A9LA__75.a | ABC transporters family | reduced |
| ZK105.e | sodium/potassium-transporting ATPase alpha-4 chain | reduced |
| C36B1.4 | proteasome A-type subunit/Multispecific proteases of the proteasome | much reduced, no progeny |
| CD4.6 | proteasome A-type subunit/Binding-protein-dependent transport systems | much distorted, reduced |
| F23F12.6 | 26S protease regulatory subunit. | much reduced |
| F39H11.5 | multispecific proteases of the proteasome/YEAST NIP80 LIKE | much reduced, not grown |
| T23F2.1 | glycosyl transferases group 1 | reduced |
| Y38A8.2 | proteasome B-type subunit/Multispecific proteases of the proteasome | not fully grown, much reduced |
| C36E8.5 | beta tubulin | distorted |
| D2024.6 | F-actin capping protein alpha subunit | reduced |
| F10C1.2 | intermediate filament protein | reduced, no progeny |
| F20G4.3 | myosin head (motor domain)/Myosin tail | distorted |
| F44F4.11 | cell division protein FtsZ/tubulin | reduced |
| K07C5.1 | actin-related protein 2; ARP2 | reduced |
| T04C12.5 | actin | much reduced |
| Y19D2B.1 | alpha tubulin/FtsZ family | distorted, no growth |
| ZK593.5 | CAP-Gly domain/dynactin | not fully grown, reduced |
| B0303.9 | sec1 family/VPS33 | reduced, |
| C02C6.1 | dynamin 2 | much reduced |
| C05D11.2 | vps-16 like | not fully grown, much reduced |
| F29G9.3 | clathrin adaptor comple3, small chain | much reduced |
| F41C3.4 | got1 homology/vesicular transport | distorted no progeny |

TABLE VI-continued

RNAi Clones that Reduce Fat Content and Reduce Viability/Growth

| *C. elegans* Gene | BRIEF DESCRIPTION | Nile Red Phenotype |
|---|---|---|
| K02D10.5 | synaptosomal associated protein | not fully grown, reduced |
| T21E12.4 | dynein heavy chain | reduced, not much growth |
| ZK1014.1 | NSF | not grown |
| B0222.6 | nematode cuticle collagen N-terminal domain | moderately reduced |
| F57B9.5 | similar to bystin-like | much reduced, no progeny |
| K01A6.4 | Col IV similarity | reduced |
| K12D12.3 | nematode collagen | much reduced, no progeny |
| W10C4.b | ankyrin-repeat | much reduced |
| B0035.7 | histone H2A | much reduced/no progeny |
| B0035.8 | histone H2B | not fully grown, reduced |
| B0035.9 | histone 4 protein~putative | not fully grown, reduced |
| B0041.4 | ribosomal protein L4/L1e | much reduced, no progeny |
| B0495.6 | unknown/weak similarity to eukaryotic translation initiation factor 3 | reduced, /few progeny |
| C03C10.3 | ribonucleotide reductase | moderately reduced |
| C04H5.6 | ATP-dependent helicase, DEAH-box | much reduced |
| C06A8.2 | SNRNA ACTIVATING PROTEIN COMPLE3 43 KDA SUBUNIT | no progeny, much reduced |
| C08B11.5 | poly(A) RNA binding protein | few progeny, much reduced |
| C09H10.2 | forkhead-associated (FHA) domain/ribosomal protein L36a-like | reduced, not grown |
| C15F1.e | translation initiation factor | some distortion/few progeny |
| C15H11.9 | homolog of yeast ribosome biogenesis regulator | much reduced |
| C16A3.3 | 18S and 5.8S rRNA synthesis | moderately reduced, few progeny |
| C16A3.4 | RNA-binding protein C2H2 Zn-finger domain/Zinc finger, C2H2 type | moderately reduced |
| C16A3.6 | RNA binding protein | moderately reduced |
| C26D10.1 | regulator of chromosome condensation (RCC1)/ran-1 | not much growth, much distorted |
| C26F1.9 | ribosomal protein L39e | much reduced |
| C27F2.4 | putative methyltransferase | reduced |
| C29F5.3 | cytidine and deoxycytidylate deaminase zinc-binding region | reduced |
| C37H5.8 | heat shock protein hsp70 | reduced, not grown |
| C42D4.8 | DNA-directed RNA polymerase III largest subunit | reduced |
| C47D12.6 | serine carboxypeptidase (S10)/Aminoacyl-transfer RNA synthetases | reduced, small droplets |
| C50F4.5 | histone H2B | much reduced |
| C52A11.2 | globin | reduced |
| C52E4.3 | small nuclear ribonucleoprotein (Sm protein) | much reduced |
| D1007.6 | 40S ribosomal protein S10 | reduced, not much growth |
| F09E8.3 | DNA mismatch repair protein MutS family, C-terminal domain | moderately reduced |
| F09F7.3 | RNA polymerases beta subunit | reduced |
| F18A1.5 | replication protein A1 (70 kD) | reduced |
| F20D12.4 | centromere/kinetochor/laminin | no progeny |
| F22B3.1 | histone H4 | reduced |
| F22B5.2 | translation initiation factor e1F3-p44 | much reduced |
| F22B5.9 | phenylalanyl-tRNA synthetase | reduced not grown |
| F22B5.9 | phenylalanyl-tRNA synthetase beta-subunit | much reduced |
| F26F4.10 | arginyl tRNA synthase/ligase | not grown, reduced |
| F26F4.11 | DNA-DIRECTED RNA POLYMERASE | much reduced/no or few progeny |
| F32E10.4 | serine-rich RNA polymerase I suppressor protein (SRP1) | much reduced/few progeny |
| F37C12.11 | ribosomal protein S21e | much reduced |
| F37C12.9 | ribosomal protein S11 | not fully grown, much reduced |
| F45E12.3 | cullin family/CELL CYCLE CONTROL | reduced |
| F45F2.13 | histone H3 | reduced, not grown |
| F54E12.1 | histone H3 | much reduced/no progeny |
| F54E12.5 | histone H2A | not fully grown, reduced |
| F55C5.8 | signal recognition particle 68 KD protein | much reduced, not grown |
| F55F10.1 | no significant mammalian similarity | reduced |
| F55F10.2 | sigma-54 factor interaction protein family | reduced/few progeny |

TABLE VI-continued

RNAi Clones that Reduce Fat Content and Reduce Viability/Growth

| *C. elegans* Gene | BRIEF DESCRIPTION | Nile Red Phenotype |
|---|---|---|
| F55G1.10 | histone | much reduced, no progeny |
| F58A4.4 | DNA primase small subunit | reduced, no progeny |
| H02I12.7 | core histones H2A, H2B, H3 and H4 | much reduced/no progeny |
| H06H21.3 | eukaryotic initiation factor 1A | reduced/larger droplets/few progeny |
| H06I04.i | sbp homolog required for ribosomal biosynthesis | reduced |
| H19M22.1 | cell migration/emb. Devel | Reduced |
| H23L24.c | N-6 Adenine-specific DNA methylase | much reduced/no progeny |
| K03A1.1 | histone H3 | Reduced |
| K05F1.5 | hypothetical protein FLJ20321 | moderately reduced/distortion |
| K12D12.2 | nuclear pore comple3 homology | reduced, not fully grown |
| R05D11.3 | nuclear transport factor 2 (NTF2) domain | much distorted/no progeny |
| R08D7.1 | IDN3 homology/bud13 | much reduced/no progeny |
| R11D1.8 | ribosomal L28e protein family | moderately reduced |
| T01C3.6 | ribosomal protein S9 | not fully grown, reduced |
| T02G5.9 | lysyl-tRNA synthetase | not fully grown |
| T03F7.5 | aminoacyl-transfer RNA synthetases class-II | Distorted |
| T10C6.11 | h• istone H2B | much reduced, no progeny |
| T10C6.12 | histone H2A | much reduced |
| T10C6.13 | histone H3 | much reduced, no progeny |
| T13H5.4 | RNA-binding protein C2H2 Zn-finger domain/PRP9 LIKE | much reduced |
| T23B12.2 | ribosomal protein L4/L1e | Reduced |
| T28F3.2 | heat shock protein hsp70 | not fully grown, reduced |
| VW02B12L.1 | V-type ATPase 116 kDa subunit family | much reduced, dauer like |
| W07E6.1 | NOL1/NOP2/sun family | reduced, droplet/no progeny |
| Y106G6H.3 | ribosomal protein L30e | not grown, much reduced |
| Y41D4A__3073.a | nucleoporin 155 | not fully grown, reduced |
| Y41D4A__3457.a | nup homology | not fully grown, reduced |
| Y41D4A__3457.d | nup homology | not fully grown, reduced |
| Y47D3A.c | DNA-directed DNA polymerase family B | reduced |
| Y62E10A.d | 60S Acidic ribosomal protein | not fully grown, reduced |
| Y71G12A__187.b | snRNA-associated Sm-like protein | reduced |
| Y76B12C__66.c | cleavage and polyadenylation specific factor 1 | reduced |
| ZK550.4 | TFIIE alpha subunit | much reduced |
| ZK637.8 | V-type ATPase 116 kDa subunit family | much reduced, few progeny |
| ZK652.1 | small nuclear ribonucleoprotein (Sm protein) | much reduced/no progeny |
| ZK686.1 | ATP-dependent RNA helicase | much reduced |
| B0454.1 | proline-rich region | reduced |
| B0491.5 | very weak similarity to laminin | reduced |
| C02F12.8 | proline-rich region | not fully grown, much reduced |
| C06A1.1 | er94, VCP modulator of polyglutamine-induced neurodegeneration. | reduced |
| C10A4.4 | unknown, very weak similarity to a hypothetical protein | moderately reduced, not grown |
| C14C10.3 | no significant similarity | moderately reduced |
| C15H9.4 | similarity Hypothetical protein KIAA1145 | reduced |
| C16D9.5 | unknown, very weak similarity to protein transport related protein | reduced |
| C18E9.4 | very weak similarity to NADH-ubiquonone oxidoreductase | distorted/reduced |
| C29H12.6 | no significant similarity | distorted, reduced, no progeny |
| C30B5.6 | weak similarity to primitive neuroectodermal unknown protein/HSPC244 | much reduced, no progeny |
| C30C11.2 | domain in components of the proteasome, COP9-complex and eIF3 (PCI) | not fully grown, much reduced |

TABLE VI-continued

RNAi Clones that Reduce Fat Content and Reduce Viability/Growth

| *C. elegans* Gene | BRIEF DESCRIPTION | Nile Red Phenotype |
|---|---|---|
| C37H5.5 | AD24 protein, UNNAMED PROTEIN PRODUCT | reduced, few progeny |
| C40D2.2 | MATH (meprin and TRAF homology) domain | dumpy, distorted |
| C42C1.3 | very weak similarity to oxysterol binding protein | much reduced |
| C47C12.2 | no significant mammalian similarity | not fully grown, distorted |
| D1054.3 | suppressor of skp-1 | much reduced |
| F08D12.7 | no significant mammalian similarity | not fully grown, much reduced |
| F19F10.9 | hypoxia associated factor | much distorted |
| F26A1.10 | no significant mammalian similarity | slow growth, /much reduced |
| F29C4.2 | no significant mammalian similarity | reduced, not grown |
| F32E10.1 | similar to hypothetical protein FLJ14075 | reduced/few progeny |
| F33A8.1 | KIAA1604 protein | much reduced, not grown |
| F40H3.1 | very weak similarity to an unknown protein | some distortion |
| F45C12.7 | BTB/POZ domain | reduced |
| F45H10.4 | no significant mammalian similarity | much reduced |
| F46C8.1 | no significant mammalian similarity | much reduced |
| F47F6.4 | very weak similarity to Langerhans cell specific c-type lectin | little growth, much reduced |
| F52C6.13 | very weak similarity to steerin/solute carrier | much reduced |
| F54F2.7 | similarity to unknown protein | reduced |
| F55C12.2 | no significant mammalian similarity | reduced |
| F57G9.3 | no significant mammalian similarity | reduced |
| F57G9.4 | no significant mammalian similarity | reduced |
| H06I04.h | no significant mammalian similarity | distorted/reduced progeny |
| K02E7.6 | very weak similarity to creatine kinase | reduced |
| K06A4.6 | no significant mammalian similarity | reduced |
| K06A5.4 | no significant mammalian similarity | distorted, much reduced/no progeny |
| R07E3.2 | no significant mammalian similarity | slightly reduced |
| R12E2.2 | membrane protein from human chromosome 1 | no growth, reduced |
| R144.2 | proline-rich region | distorted |
| T12A2.2 | putative-related to OSTSTT3 | moderately reduced |
| T19B10.2 | no significant mammalian similarity | reduced |
| W01A8.4 | no significant mammalian similarity | moderately reduced/no progeny |
| W01B11.5 | proline-rich region | reduced |
| W02B3.7 | no significant mammalian similarity | not fully grown, reduced |
| W04A4.6 | no significant mammalian similarity | much reduced/no progeny |
| W07B3.2 | no significant mammalian similarity | much reduced/few progeny |
| W10C6.1 | repeat in APC and proteasome component | reduced |
| Y38F2A_5743.i | no significant mammalian similarity | much reduced |
| Y51H4A.m | weak similarity to hypothetical protein | moderately reduced |
| Y53C12B.2 | similarity to gi\|17390336\|gb\|AAH18152.1\|AAH18152 | reduced |
| Y57A10A.v | no significant mammalian similarity | reduced |
| Y75B12B.3 | no significant mammalian similarity | not grown/reduced |
| Y75B8A.27 | very weak similarity to dynactin | not grown/reduced |
| ZK121.c | KIAA1002 protein; clone FLB5224 | moderately reduced |
| ZK546.2 | leucine-rich repeat | some distortion/no progeny |
| ZK795.3 | domain of unknown function DUF96 | reduced |
| C04G2.6 | 2Fe—2S Ferredoxin/Homeobox domain/Ribonuclease II domain | reduced/few progeny |
| F41H10.7 | fatty acid elongase (CIG30/Fen1) | much reduced |
| T10B5.5 | chaperonin subunit | mislocalized, slow growth |

RNAi Clone that Increase Fat Content

RNAi, followed by Nile Red staining, also identified genes whose inactivation caused an increase in fat content, but did not interfere with normal growth or development. Interestingly, increased fat content resulted from RNAi inactivation of the nematode homolog of a hepatocyte nuclear factor, hnf-4α. Mutations in human HNF-4α are associated with maturity onset diabetes of the young (Yamagata, et al., *Nature* 384:458–60, 1996). Increased fat phenotypes were observed when several cytochrome c P450 enzymes were inactivated. These enzymes may metabolize the ligands of nuclear hormone receptors affecting body fat.

Further evidence of common fat regulatory circuits in mammals and *C. elegans* came from the identification of several genes that appear to function similarly in regulating fat metabolism in nematodes and mammals. For instance, increased fat levels resulted from RNAi of C43H6.8, a potential ortholog of the hematopoetic/neurogenic transcription factor Nhlh-2/Nscl-2. Mice bearing a knock-out of this transcription factor display hypogonadism and obesity (Good, et al., *Nat. Genet.* 15:397–401, 1997).

Genes whose inactivation results in increased fat content are listed in Table VII. The increased fat phenotypes were categorized as (i) much increased (i.e., at least 2.5-fold the fat content of wild-type nematodes); (ii) increased (i.e., at least 2-fold the fat content of wild-type nematodes); (iii) slightly increased (i.e., at least 1.5-fold increased). Such genes might be useful targets for drug development. For example, drugs that increase the activity of these genes would be expected to decrease fat storage. Drugs that decrease the activity of these genes would be expected to increase fat levels, which might be useful in treating, for example, cachexia. A condition associated with cancer and chemotherapy. This list identifies the target genes by *C. elegans* cosmid name and open reading frame number.

TABLE VII

RNAi Clones that Increase Fat Content

| *C. elegans* Gene | Brief Description | Nile Red Phenotype |
|---|---|---|
| C33A12.6 | UDP-glucoronosyl and UDP-glucosyl transferase | moderately increased |
| E04F6.3 | MaoC-like dehydrogenase-epimerase-[17 beta HSD] | moderately increased |
| E04F6.6 | Orn/DAP/Arg-type decarboxylases | moderately increased |
| F15B9.5 | serine protease | moderately increased |
| F28F8.2 | long chain fatty acid CoA synthetase/ligase | moderately increased |
| F47B8.3 | glutaredoxin 3/thioredoxin | moderately increased |
| VF13D12L.1 | myo-inositol-1-phosphate synthase | increased, dumpy |
| C37F5.1 | elk-1 | slightly increased |
| C43H6.8 | nhlh2/nscl-2 | moderately increased |
| C56C10.10 | aryl hydrocarbon receptor (Leber congenital amaurosis) | increased |
| C56E10.4 | C4-type steroid receptor zinc finger | enlarged droplet |
| F16B4.9 | C4-type steroid receptor zinc finger | moderately increased |
| F33D4.1 | nuclear hormone receptor/estrogen-type | slightly increased |
| H12C20.3 | C4-type steroid receptor zinc finger | moderately increased |
| K10C3.6 | hepatocyte nuclear factor 4 receptor | moderately increased |
| R11H6.5 | interleukin enhancer binding factor 2 | increased |
| C04G2.2 | serine/threonine protein kinase/tau tubulin kinase | slightly increased |
| C09G5.8 | Protein interactiung with retinitis pigmentosa GTPase | increased |
| C18H9.7 | RAPSN (associated with nicotinic acetylcholine receptor) | increased |
| C24F3.2 | glucokinase-associated dual specificity phosphatase | slightly increased |
| F39B1.1 | phosphoinositide 3-kinase | moderately increased |
| F46C5.6 | Protein phosphatase PP2A subunit A | moderately increased |
| F56D5.9 | BRCT/ankyrin-repeat/protein phosphatase domains | moderately increased |
| F56H11.6 | casein kinase/tau-tubulin kinase | moderately increased |
| K08F8.1 | ribosomal S6 kinase | increased |
| R10D12.10 | casein kinase/tau-tubulin kinase | increased |
| T04B2.2 | fms/fps protein kinase | slightly increased |
| T04C9.1 | oligophrenin-1 (focal adhesion GTPase) | moderately increased |
| W03A5.4 | guanylate kinase associated protein | increased |
| W08D2.1 | wnt-1 family kinase | moderately increased |
| Y11D7A.9 | FGF receptor activating protein | much distortion, some increase |
| ZC513.1 | permeability increasing/phospholipid transfer protein | increased when starved |
| C43H6.9 | glutamate receptor | moderately increased |
| F08H9.5 | cubilin/endocytic receptor | moderately increased |
| F56B6.5 | major hippocampal somatostatin receptor | increased |
| T19D12.8 | nematode specific 7-TM receptor | increased |
| Y27F2A.g | chemoreceptor | increased |
| Y40H7A.1 | nematode specific G-coupled protein receptor | moderately increased |
| Y46H3C_11.b | rhodopsin-like GPCR superfamily | enlarged droplet |
| F32B6.9 | vitelliform macular dystrophy protein/bestrophin | slightly increased |
| ZC410.4 | potassium channel | slightly increased |
| C18H9.5 | sugar transporter | increased |
| F14E5.1 | glucose transporter-3 | enlarged droplet |
| F52H2.2 | amino acid permease | moderately increased |
| C04G2.4 | vesicle associated protein | moderately increased |
| F32B6.6 | Vamp-associated protein | moderately increased |
| C15A11.3 | procollagen proteinase enhancer | moderately increased |
| C34F6.3 | collagen triple helix repeat | moderately increased |
| C53B4.5 | collagen triple helix repeat | slightly increased, distorted |
| EGAP7.1 | collagen triple helix repeat | increased |
| F46C8.6 | cuticle collagen | moderately increased |
| T14B4.7 | collagen triple helix repeat | increased, dumpy |
| T28C6.6 | collagen triple helix repeat | moderately increased |
| Y38F1A.9 | contactin 6/myopalladin | moderately increased |
| Y41E3.2 | collagen triple helix repeat | increased, dumpy |
| K02D7.5 | recombination activating gene | moderately increased |
| C04G2.5 | very weakly similar to AK027463 | slightly increased |
| C09G12.5 | very weakly similar to CREB-binding protein | slightly increased |
| C14A4.1 | strongly similar to CG2245 gene product [*Mus musculus*] | moderately increased |
| C24F3.1 | no significant mammalian homology | slightly increased |
| C33A12.14 | very weakly similar to fibronectin 2 | moderately increased |
| C36A4.5 | claustrine like/very weak similarity to bile acid activated lipase | moderately increased |

TABLE VII-continued

RNAi Clones that Increase Fat Content

| *C. elegans* Gene | Brief Description | Nile Red Phenotype |
|---|---|---|
| C44E4.5 | similarity to chronic myelogenous leukemia tumor antigen 66 | moderately increased |
| C50C10.4 | no significant mammalian homology | increased |
| C50D2.1 | no significant mammalian homology | moderately increased |
| D1007.5 | similar to hypothetical protein XM_147195 | moderately increased |
| F12E12.h | very weakly similar to AB028991 | increased |
| F25G6.9 | very weakly similar to AK056522 | moderately increased |
| F25H8.1 | strong similarity to unknown protein AK056522 | slightly increased |
| F25H8.2 | very weakly similar to NM_138386 | slightly increased |
| F25H8.5 | proline-rich region | distorted |
| F26H9.4 | strong similarity to unknown protein XM_135042 | increased |
| F31F6.2 | very weakly similar to XM_067663) | increase |
| F42G8.5 | very weakly similar to BC030641 | slightly increased |
| F44D12.7 | Major sperm protein (MSP) domain | moderately increased |
| F49C12.15 | no significant mammalian homology | moderately increased |
| F49F1.4 | no significant mammalian homology | increased |
| F52C12.2 | no significant mammalian homology | enlarged droplet |
| F56B3.2 | no significant mammalian homology | moderately increased |
| F56F3.4 | AN1-like Zinc finger/Ubiquitin domain | moderately increased |
| H05L03.3 | no significant mammalian homology | increased |
| H05L14.2 | very weakly similar to zinc finger protein NY-REN-4 | moderately increased |
| K01G5.8a | very weakly similar to AB041658 | increased |
| K02E10.3 | no significant mammalian homology | increased |
| K02E10.5 | very weakly similar to AE006464 | moderately increased |
| K07A1.13 | very weakly similar to cytochrome P450, | moderately increased |
| K07E8.3 | very weak similarity to activin interactin protein | slightly increased |
| K09C4.5 | very weak similarity to AraC H1H/Sugar transporter domain | increased |
| LLC1.2 | very weakly similar to hypothetical protein XP_095577 | slightly increased |
| M70.1 | Domain of unknown function (WSN) | slightly increased |
| M70.3 | no significant mammalian homology | increased |
| R07A4.2 | very weakly similar to nectin-like protein 1 | increased |
| R105.1 | very weakly similar to KIAA1048 protein | some increase |
| T01C1.2 | very weakly similar to NM_053797) crooked neck protein | slightly increased |
| T02C5.3 | very weakly similar to neural cell adhesion molecule | moderately increased |
| T04C9.2 | no significant mammalian homology | moderately increased |
| T05E8.2 | very weakly similar to germ cell-specific gene 2 | increased |
| T07F8.1 | very weakly similar to neurofilament, medium polypeptide | slightly increased |
| T12A2.5 | no significant mammalian homology | moderately increased |
| T12B5.8 | F-box domain/Domain of unknown function DUF38 | slightly increased |
| T14B1.1 | very weakly similar to plexin 3 | increase |
| T14B4.8 | no significant mammalian homology | moderately increased |
| T14F9.4 | very weakly similar to BC001973 | moderately increased |
| T19D12.3 | very weakly similar to polyadenylation specificity factor 3 | slightly increased |
| T27A8.4 | very weakly similar to NA repair protein XRCC1 | moderately increased |
| W06H12.1 | similar to hypothetical protein MGC4054 | increased |
| Y11D7A.8 | very weakly similar to XM_163806 | moderately increased |
| Y47D9A.e | no significant mammalian homology | Increased |
| Y57A10B.1 | similar to hypothetical protein AK005032 | slightly increased |
| Y5H2B.e | very weak similarity to G protein-coupled receptor GPR26 | moderately increased |
| Y67A6A.1 | no significant mammalian homology | increased |
| Y73C8C.4 | very weakly similar to AB055252 | moderately increased |
| ZC64.2 | transthyretin-like family | slightly increased |
| ZK1320.10 | very weakly similar to XM_164500 | moderately increased |
| ZK1321.1 | very weakly similar to slit homolog | slightly increased |
| ZK666.10 | very weakly similar to XM_088171 | moderately increased |

Epistasis Analysis Orders Genes in Fat Metabolism Regulatory Pathway

RNAi was also used to inactivate genes in mutant genetic backgrounds. For this epistasis analysis, mutant nematodes with increased fat phenotypes including lpo-1, daf-2(e1370), tub-1(nr2004), and tph-1(mg280) were grown on RNAi bacteria, which had been shown to cause a reduced fat phenotype in wild-type nematodes, stained with Nile Red, and examined. In most cases, the RNAi clone caused a reduced fat phenotype in the increased fat mutant background. This indicated that the reduced fat RNAi gene was epistatic to the increased fat mutant gene. In some cases, however, the fat content of the increased fat mutant nematodes was unaffected by a reduced fat RNAi clone. Analysing such epistatic relationships among fat metabolism regulator genes allows the genes to be ordered in a pathway. The results of this epistasis analysis are shown in Tables VIIIA and VIIIB. Those RNAi clones that failed to produce a change in fat content are denoted by an F. Those RNAi clones that reduced fat content or altered fat droplet morphology are denoted with an O. Those RNAi clones that were not tested in a particular genetic background are denoted with an ND (Not Done).

TABLE VIIIA

Epistasis Analysis on RNAi Targets that Reduce Fat without Reducing Viability

| Wild-type | tph-1 (mg280) | tub-1 (nr2004) | daf-2 (e1370) | lpo-1 | lpo-6 | |
|---|---|---|---|---|---|---|
| O | O | O | O | O | O | C34G6.4 |
| O | O | O | O | O | O | ZK675.1 |
| O | O | O | O | O | O | F11E6.5 |
| O | O | O | O | O | O | K07C6.5 |
| O | O | O | O | O | O | F59F5.2 |
| O | O | O | O | O | O | F13D11.1 |
| O | O | O | O | O | O | T14E8.3 |
| O | O | O | O | O | O | Y47D3B.7 |
| O | O | O | O | O | O | C30F12.1 |
| O | O | O | O | O | O | F52C6.12 |
| O | O | O | O | O | O | Y119D3_456.a |
| O | O | O | O | O | O | ZK131.8 |
| O | O | O | O | O | F | K09D9.2 |
| O | O | O | O | O | O | W10D9.5 |
| O | O | O | O | O | O | F53H8.1 |
| O | O | O | O | O | O | C49C3.3 |
| O | O | O | O | O | O | Y41D4A_3073.a |
| O | O | O | O | O | O | Y71H10B.1 |
| O | O | O | O | O | O | C15C7.5 |
| O | O | O | O | O | F | K04E7.2 |
| O | O | O | O | O | O | F54D5.11 |
| O | O | F | O | O | O | F46G11.3 |
| O | O | O | O | O | O | F15H10.4 |
| O | F | F | O | O | F | Y57A10A.bb |
| O | F | F | F | O | F | F41H10.7 |
| O | O | O | O | O | F | F13D12.6 |
| O | O | O | F | O | O | F20H11.2 |
| O | F | O | O | O | O | T01D3.4 |
| O | O | O | F | O | O | F52C6.2 |
| O | O | O | F | O | O | Y37D8A.1 |
| O | F | F | F | F | O | Y50E8.q |
| O | O | O | O | O | O | C06E7.3 |
| O | O | O | O | O | O | K10B3.7 |
| O | O | O | F | O | O | F49E11.4 |
| O | O | F | O | O | O | F11A10.3 |
| O | O | O | O | O | O | F38E9.4 |
| O | O | O | O | F | O | K09H11.2 |
| O | O | O | O | F | O | T04C10.2 |
| O | F | O | O | O | O | Y51H4A.m |
| F | O | O | O | O | F | M01B12.5 |
| O | O | O | F | O | O | F47C12.3 |
| O | F | O | O | O | O | F22A3.5 |
| O | O | F | F | O | O | R11A5.1 |
| O | O | F | O | O | O | F49E12.4 |
| O | O | F | O | O | F | C06G3.2 |
| O | O | O | F | O | O | T28D6.2 |
| O | O | O | F | O | O | D2089.2 |
| O | O | O | F | O | O | C32D5.11 |
| O | F | F | O | O | O | H04M03.4 |
| O | F | O | F | O | O | Y57E12_242.c |
| O | O | O | F | O | F | F37B12.3 |
| O | F | O | O | O | O | C33A12.1 |
| O | F | O | O | O | O | C13D9.7 |
| O | O | O | O | O | F | K02D7.3 |
| O | O | F | O | O | O | R04A9.4 |
| O | O | O | F | O | F | F20D12.2 |
| O | F | F | O | O | O | W09G3.1 |
| O | O | O | F | O | O | Y111B2C.e |
| O | O | F | O | O | F | T19D2.2 |
| O | O | O | O | F | F | F07C4.1 |
| O | O | O | O | F | F | T07C12.5 |
| O | F | F | O | O | F | K08A2.b |
| O | O | F | F | F | O | Y65B4B_10.e |
| O | O | O | F | O | F | M106.5 |
| O | O | O | F | F | O | W09D10.3 |
| O | F | F | F | O | F | Y48C3A.b |
| O | O | F | O | O | F | B0554.6 |
| O | F | O | F | O | O | C07E3.2 |
| O | O | F | O | O | F | C47D12.7 |
| O | F | F | O | O | O | F10A3.11 |
| O | F | F | O | O | O | F29B9.11 |
| O | O | O | O | O | F | T19D2.3 |
| O | O | O | O | O | O | ZC84.5 |
| O | O | F | O | O | O | R07B7.9 |

TABLE VIIIA-continued

Epistasis Analysis on RNAi Targets that Reduce Fat without Reducing Viability

| Wild-type | tph-1 (mg280) | tub-1 (nr2004) | daf-2 (e1370) | lpo-1 | lpo-6 | |
|---|---|---|---|---|---|---|
| O | F | F | O | O | O | F52B11.2 |
| O | F | O | F | O | F | F28H6.2 |
| O | F | F | O | O | O | F10A3.13 |
| O | F | F | O | O | O | Y77E11A_3443.i |
| O | O | O | F | O | F | F44B9.7 |
| O | O | F | F | O | O | T22D1.10 |
| O | O | F | O | O | F | F38A5.1 |
| O | F | F | O | O | O | T21D12.3 |
| O | F | O | O | O | F | W05E10.2 |
| O | O | F | F | O | F | Y54G9A.2 |
| O | O | O | O | F | F | ZK593.3 |
| O | F | F | F | O | O | C34C6.6 |
| O | O | O | ND | O | F | B0218.5 |
| O | O | F | F | O | O | C07A9.2 |
| O | O | O | F | O | F | E02C12.3 |
| O | F | F | F | O | F | H09F14.1 |
| O | O | F | F | F | O | T07C12.1 |
| O | F | F | O | O | F | B0280.3 |
| O | F | F | F | O | O | C01G6.5 |
| O | F | F | F | O | O | Y116A8C.32 |
| O | F | F | O | O | F | ZK686.4 |
| O | F | O | F | O | F | T19B4.7 |
| O | F | F | F | O | O | T27F7.1 |
| O | O | F | F | O | F | F26D11.10 |
| O | F | O | O | O | F | C18E9.5 |
| O | F | F | F | O | O | D1054.14 |
| O | O | F | O | O | F | F28H7.6 |
| O | O | O | F | F | F | K06B4.3 |
| O | F | F | O | O | | W04A4.5 |
| O | F | F | F | O | O | Y7A9C.3 |
| O | O | O | F | O | F | ZK652.2 |
| O | O | F | F | O | F | AH10.1 |
| O | O | O | F | F | F | F11C1.6 |
| O | O | F | O | O | F | Y49A3A.1 |
| O | O | F | F | O | F | C24A11.9 |
| O | O | F | F | O | F | F43H9.2 |
| O | F | F | O | O | O | Y55F3C.c |
| F | O | F | F | O | F | K12B6.8 |
| O | O | F | F | O | O | C47D12.1 |
| O | F | O | O | O | F | F41D9.1 |
| F | F | F | O | O | O | T04D3.2 |
| O | F | F | F | O | O | Y44A6B.2 |
| O | F | F | F | O | O | Y9C9A_53.c |
| O | F | O | O | F | F | C32C4.1 |
| O | F | F | O | O | F | F11A1.3 |
| O | F | F | O | O | F | T09F3.1 |
| O | F | F | O | F | F | H27A22.1 |
| O | F | F | F | O | O | C05E11.1 |
| O | F | F | O | O | F | C14A6.6 |
| O | F | F | F | O | O | C42C1.6 |
| O | O | O | F | O | F | F13B6.1 |
| O | F | F | F | O | O | H32C10.3 |
| O | F | F | O | F | F | K12D12.4 |
| O | F | F | O | O | F | R08F11.2 |
| O | O | O | F | F | F | R11H6.6 |
| O | F | F | F | O | O | Y37D8A.8 |
| O | O | O | O | O | O | Y40H7A.7 |
| O | F | O | F | O | O | Y41D4A_3192.a |
| O | O | F | O | O | O | Y65B4B_13.b |
| O | F | F | F | O | O | C37H5.3 |
| O | F | O | F | F | F | C54G7.1 |
| O | F | F | O | O | O | C33H5.17 |
| O | F | F | F | O | O | F45H7.4 |
| O | O | F | F | O | O | W03C9.3 |
| O | O | F | F | F | F | Y53C12A.1 |
| O | F | F | O | O | F | ZC302.1 |
| O | O | F | F | O | O | F33G12.2 |
| O | O | F | O | F | F | K05F1.6 |
| O | O | F | F | O | F | F22A3.4 |
| O | F | F | F | O | F | W02C12.3 |
| O | F | F | F | O | F | ZK39.7 |
| O | F | F | F | O | O | ZK757.3 |
| O | F | F | O | O | F | B0034.2 |
| O | F | F | O | O | F | B0041.3 |

TABLE VIIIA-continued

Epistasis Analysis on RNAi Targets that Reduce Fat without Reducing Viability

| Wild-type | tph-1 (mg280) | tub-1 (nr2004) | daf-2 (e1370) | lpo-1 | lpo-6 | |
|---|---|---|---|---|---|---|
| O | O | F | F | O | F | B0286.4 |
| O | F | F | O | O | F | B0554.7 |
| O | F | F | O | O | F | C30G4.5 |
| O | O | F | F | O | F | C56E6.4 |
| O | O | O | F | F | F | F41C6.6 |
| O | F | F | F | O | F | K02E7.11 |
| O | F | O | F | O | F | R05H11.1 |
| O | F | F | O | O | F | T10D4.1 |
| O | F | F | O | F | O | T26E4.13 |
| O | F | F | F | O | F | Y105E8B.a |
| O | F | F | O | O | F | Y24D9A.b |
| O | F | F | F | F | O | Y41E3.10 |
| O | F | F | F | O | F | T12A2.1 |
| F | O | ND | F | F | F | C02F4.2 |
| O | O | F | F | O | F | C16A11.3 |
| O | F | F | F | F | O | Y69A2A_7278.l |
| O | O | F | F | O | F | C06G3.10 |
| O | F | F | O | O | F | F11A5.3 |
| O | F | F | F | O | F | T22D1.4 |
| O | F | F | F | O | F | R107.6 |
| O | F | F | F | O | F | Y17G7B.15 |
| O | F | F | F | O | F | C23H3.2 |
| O | F | F | F | O | F | F12A10.8 |
| O | F | F | F | O | F | F14D2.4 |
| F | F | F | O | O | F | F46F5.10 |
| O | F | F | F | F | O | F58H1.6 |
| O | F | F | O | F | F | T17H7.1 |
| O | F | O | O | O | O | Y51H7B_5.b |
| F | O | F | O | F | F | R13H8.1 |
| F | O | F | O | F | F | T07A9.6 |
| O | F | F | F | O | F | F14H8.1 |
| O | F | F | F | O | F | F15A8.6 |
| O | F | F | F | O | F | E01A2.i |
| O | F | F | F | O | F | H04M03.1 |
| O | ND | ND | F | ND | F | C15H9.7 |
| O | F | F | F | O | O | C06A1.3 |
| F | F | F | F | O | F | C41D7.2 |
| O | F | F | F | O | F | H25K10.1 |
| O | ND | F | F | O | F | R107.4 |
| O | F | F | O | F | F | ZC504.4 |
| O | F | F | F | O | F | F58G4.2 |
| O | F | F | F | O | F | T04A11.8 |
| O | F | F | F | O | F | F59F5.1 |
| O | F | F | O | F | F | ZK682.2 |
| O | F | O | F | F | F | C33G8.9 |
| O | F | F | F | F | O | F55B11.4 |
| O | F | F | F | O | F | Y4C6A.h |
| O | F | F | F | O | F | F40H3.5 |
| O | F | F | F | O | F | CO5E11.2 |
| O | F | F | F | O | F | M01E10.2 |
| O | F | F | F | O | F | C23F12.1 |
| O | ND | ND | ND | O | ND | B0207.9 |
| O | F | F | F | O | F | B0513.7 |
| O | O | F | F | F | F | C01G6.9 |
| O | F | F | F | F | O | C08G5.2 |
| O | ND | ND | ND | O | ND | C29H12.6 |
| O | F | F | F | F | O | C50E10.5 |
| O | F | F | F | O | O | F21H12.3 |
| O | F | F | F | O | F | F27C1.4 |
| F | F | F | F | O | F | F36H12.15 |
| O | F | F | F | O | F | F39D8.2 |
| O | ND | ND | ND | O | ND | F54C9.9 |
| O | O | F | F | F | F | R03H10.4 |
| O | F | F | F | O | F | T02H6.7 |
| O | F | F | F | O | F | T07C12.11 |
| F | F | F | O | O | F | T14A8.1 |
| O | F | F | O | F | F | T21C9.11 |
| O | F | F | O | O | F | T21C9.2 |
| O | F | F | F | F | O | T23E1.1 |
| O | F | F | F | F | O | W06G6.1 |
| O | F | F | F | O | F | Y38E10A.b |
| O | O | O | O | O | O | Y47G6A_245.b |
| O | F | O | F | O | F | Y51H7C_255.c |
| O | F | F | F | O | F | Y69A2A_7278.m |

TABLE VIIIA-continued

Epistasis Analysis on RNAi Targets that Reduce Fat without Reducing Viability

| Wild-type | tph-1 (mg280) | tub-1 (nr2004) | daf-2 (e1370) | lpo-1 | lpo-6 | |
|---|---|---|---|---|---|---|
| O | F | F | F | F | O | Y71H2_389.a |
| O | O | F | F | F | F | ZK1290.1 |
| O | F | F | F | O | F | ZK355.d |
| O | F | F | F | O | F | C17C3.1 |
| O | F | F | F | O | F | ZK6.7 |
| O | F | F | F | F | F | F28H6.3 |
| O | F | F | O | O | F | Y6B3B.10 |
| O | F | F | F | O | F | T04A8.16 |
| O | F | O | O | O | O | F14D12.2 |
| O | F | F | F | O | F | F07C3.4 |
| O | F | F | F | O | F | T05C12.1 |
| O | F | F | O | F | F | C38C10.1 |
| O | F | F | O | F | F | F17A2.7 |
| O | F | O | O | O | F | C37A5.1 |
| O | F | F | F | O | F | F54H5.3 |
| O | F | F | F | O | F | K09B11.9 |
| O | F | F | ND | O | F | Y65B4B_10.a |
| O | F | F | F | O | F | F07A5.1 |
| O | F | F | F | O | F | Y37A1A.1 |
| O | F | F | F | O | F | C14F5.3 |
| O | F | F | F | O | F | F13E6.1 |
| O | F | F | F | O | F | F46C8.7 |
| O | F | F | F | O | F | F55C12.3 |
| O | F | F | F | F | O | F59E11.5 |
| O | F | F | F | O | F | M01A8.1 |
| O | F | F | F | O | F | R160.4 |
| O | F | F | O | O | F | T10E9.6 |
| O | F | F | O | O | F | T19D7.1 |
| O | F | F | F | O | F | T27E4.7 |
| O | F | F | F | O | F | Y41E3.11 |
| O | F | F | F | O | F | Y49F6B.n |
| O | F | F | F | O | F | C01C10.3 |
| O | F | F | F | O | F | F23H11.9 |
| O | O | F | F | O | O | Y57G11C.17 |
| O | F | F | F | O | F | K07C6.4 |
| O | F | F | F | F | F | T08B2.7 |
| O | F | F | O | F | F | F20D1.9 |
| O | F | F | F | F | F | C44F1.5 |
| F | F | F | F | O | F | K10D3.5 |
| O | F | F | F | O | F | R07E5.1 |
| F | F | F | F | O | F | ZK909.3 |
| O | F | F | F | ND | F | B0041.5 |
| O | F | O | F | F | F | B0310.1 |
| O | F | F | F | O | F | C46F11.1 |
| O | F | F | F | O | F | F23F1.6 |
| O | F | F | F | F | F | C47C12.3 |
| O | F | F | F | O | F | T23F11.4 |
| O | F | F | F | O | F | T14D7.3 |
| O | F | F | F | F | F | C24A1.4 |
| O | F | F | F | O | F | C14C6.8 |
| O | O | O | O | O | F | C56E10.3 |
| O | ND | ND | ND | O | ND | F08D12.4 |
| O | ND | ND | ND | O | ND | F08G2.7 |
| O | O | F | F | F | F | F54F7.2 |
| O | F | F | F | F | O | T10C6.4 |
| O | O | F | F | O | F | T27E4.6 |
| O | F | F | F | O | F | Y50D7_165.b |
| O | F | F | F | O | O | Y67D8A_380.d |
| O | F | F | F | O | F | ZK686.3 |
| F | O | F | F | F | F | F25E2.5 |
| O | F | F | F | F | F | B0285.8 |
| O | F | F | F | F | F | C15B12.7 |
| O | F | F | F | F | F | C44E4.6 |
| O | F | F | F | F | F | F31F6.7 |
| O | F | F | F | F | F | K02D3.2 |
| O | F | F | F | F | F | M05B5.4 |
| O | F | F | F | O | F | W01C9.4 |
| O | F | F | F | F | F | M28.6 |
| O | F | F | F | F | F | T09B4.8 |
| O | F | F | F | F | F | K03B8.3 |
| O | F | F | F | F | F | C03D6.3 |
| O | F | F | F | O | F | C06A6.1 |
| O | F | F | F | F | F | F45E4.6 |
| O | F | F | F | F | F | H08M01.2 |

TABLE VIIIA-continued

Epistasis Analysis on RNAi Targets that Reduce Fat without Reducing Viability

| Wild-type | tph-1 (mg280) | tub-1 (nr2004) | daf-2 (e1370) | lpo-1 | lpo-6 | |
|---|---|---|---|---|---|---|
| O | F | F | F | F | F | W09G3.4 |
| O | F | F | F | F | F | ZK930.1 |
| O | F | F | F | F | F | F49C5.6 |
| O | F | F | F | O | F | Y17G9A.d |
| O | F | F | F | F | F | Y94A7B.3 |
| O | F | F | F | O | F | C09G9.7 |
| O | F | F | O | F | F | T19B4.6 |
| O | F | F | F | F | F | F21D5.5 |
| O | F | F | F | F | F | C14A4.12 |
| O | ND | ND | ND | F | ND | C54H2.5 |
| O | F | F | F | F | F | D2062.10 |
| O | F | F | F | F | F | F22E5.1 |
| O | ND | ND | ND | F | ND | F53A9.4 |
| O | F | F | F | O | F | F58F9.1 |
| O | F | F | F | F | F | T10C6.10 |
| O | F | F | F | F | F | T11F9.10 |
| O | F | F | F | F | F | T26E4.10 |
| O | ND | ND | ND | ND | ND | W01B11.5 |
| O | O | O | O | O | O | Y57A10A.1 |
| O | F | O | F | F | F | ZK154.4 |
| O | F | F | F | F | F | C46H11.2 |
| O | F | F | F | F | F | R05F9.8 |
| O | F | F | F | F | F | C31H2.3 |
| O | F | F | F | F | F | C46E10.9 |
| O | F | F | F | F | F | C16C4.2 |
| O | F | F | O | O | F | T05F1.6 |
| O | F | F | F | F | F | T06H11.2 |
| O | F | F | F | F | F | Y38E10A.c |
| F | F | F | F | F | F | L4440 |

TABLE VIIIB

Epistasis Analysis on Genes that Reduce Fat and Growth/Viability

| Wild type | tph-1 (mg280) | tub-1 (nr2004) | daf-2 (e1370) | lpo-1 | lpo-6 | |
|---|---|---|---|---|---|---|
| O | o | o | o | o | o | F10D2.9 |
| O | o | o | o | o | o | F29D11.1 |
| O | o | o | o | o | o | F32H2.5 |
| O | o | F | ND | F | o | W06D12.3 |
| O | o | o | o | o | o | w09b6.1 |
| O | o | o | o | o | F | C09H10.3 |
| ND | ND | ND | ND | ND | ND | C53B7.4 |
| O | o | o | o | o | F | F02E8.1 |
| O | o | o | o | o | o | F35G12.10 |
| O | o | o | o | o | o | F37E3.1 |
| O | o | o | o | o | F | W04A8.7 |
| O | o | o | o | o | F | Y110A7A.h |
| O | o | o | o | o | o | Y37D8A.14 |
| O | o | o | o | o | o | Y57G11C.12 |
| O | F | F | F | F | F | F28B3.1 |
| O | F | F | o | o | o | F59B2.12 |
| O | o | o | o | o | o | C23H3.4 |
| O | F | o | F | o | o | C42C1.5 |
| O | o | o | o | o | o | D1014.1 |
| O | o | o | o | o | o | E04A4.7 |
| O | o | o | o | o | o | F01G10.1 |
| O | o | o | F | o | o | F40H3.5 |
| O | o | o | o | o | o | F44D12.4 |
| O | o | o | o | o | o | F46E10.1 |
| O | o | o | o | o | F | F57B9.2 |
| O | o | F | o | o | F | H14A12.2 |
| O | o | o | o | o | o | H15N14.2 |
| o | o | o | o | o | o | K02F2.2 |
| o | o | o | o | o | o | K06A4.5 |
| o | o | F | o | o | F | T05H4.4 |
| o | o | o | o | o | F | T05H4.5 |
| o | o | o | o | o | o | Y55F3A__750.e |
| o | F | F | F | o | F | B0285.1 |
| o | o | o | F | o | o | C16C2.3 |
| o | o | o | o | o | o | F10E9.7 |
| F | o | o | o | o | F | W03F8.5 |
| o | F | F | o | o | F | W07E6.2 |
| o | ND | ND | ND | ND | ND | ZK1067.1 |
| o | o | o | o | o | o | ZK675.1 |
| o | F | F | F | o | F | C27B7.5 |
| o | F | o | o | o | ND | C33D3.1 |
| o | o | o | o | o | o | C34H3.a |
| o | F | o | o | o | F | D1081.2 |
| o | o | o | o | o | F | F10C1.5 |
| o | o | o | o | o | o | F22A3.1 |
| o | o | F | F | F | F | F23B12.7 |
| F | o | o | o | o | F | F25H8.3 |
| o | o | o | o | o | o | W01D2.2 |
| o | o | o | o | o | o | Y17G7A.2 |
| o | o | F | o | o | o | C01F6.8 |
| o | o | o | F | o | F | C56C10.8 |
| o | o | o | o | o | F | C56E6.1 |
| o | F | F | F | F | o | W06D12.2 |
| o | ND | ND | ND | o | ND | W10D9.5 |
| o | o | o | o | o | F | Y61A9LA__75.a |
| o | o | o | o | o | F | ZK105.e |
| o | o | o | o | o | o | C36B1.4 |
| o | o | o | o | o | o | CD4.6 |
| o | o | o | o | F | o | F23F12.6 |
| o | o | o | o | o | | F39H11.5 |
| | o | o | o | ND | o | T23F2.1 |
| o | o | o | o | o | o | Y38A8.2 |
| o | o | o | o | o | o | C36E8.5 |
| o | F | F | F | o | F | D2024.6 |
| ND | ND | ND | ND | ND | ND | F10C1.2 |
| o | F | F | F | o | F | F20G4.3 |

TABLE VIIIB-continued

Epistasis Analysis on Genes that Reduce Fat and Growth/Viability

| Wild type | tph-1 (mg280) | tub-1 (nr2004) | daf-2 (e1370) | lpo-1 | lpo-6 | |
|---|---|---|---|---|---|---|
| o | o | o | o | o | o | F44F4.11 |
| o | o | o | o | o | o | K07C5.1 |
| | o | o | o | F | o | T04C12.5 |
| o | o | F | o | o | o | Y19D2B.1 |
| o | F | o | F | o | F | ZK593.5 |
| o | o | o | o | o | o | B0303.9 |
| | o | o | o | v | o | C02C6.1 |
| o | o | F | o | o | o | C05D11.2 |
| o | o | o | o | o | o | F29G9.3 |
| | | | | | | F41C3.4 |
| o | o | o | o | o | o | K02D10.5 |
| o | o | o | o | o | F | T21E12.4 |
| o | o | o | o | ND | o | ZK1014.1 |
| o | F | F | o | F | o | B0222.6 |
| o | o | o | F | o | o | F57B9.5 |
| o | o | o | o | o | F | K01A6.4 |
| o | F | o | o | o | o | K12D12.3 |
| o | o | o | o | o | o | W10C4.b |
| o | o | o, | o | o | o | B0035.7 |
| o | o | o | o | o | o | B0035.8 |
| o | o | o | o | o | o | B0035.9 |
| o | o | F | F | o | o | B0041.4 |
| o | o | o | o | o | o | B0495.6 |
| o | o | o | F | o | o | C03C10.3 |
| o | o | o | o | o | o | C04H5.6 |
| o | o | o | o | o | o | C06A8.2 |
| o | o | o | o | o | o | C08B11.5 |
| o | o | o | o | o | o | C09H10.2 |
| o | o | F | o | o | F | C15F1.e |
| o | o | o | o | o | o | C15H11.9 |
| o | o | o | F | o | o | C16A3.3 |
| o | o | o | o | o | F | C16A3.4 |
| o | F | o | o | F | F | C16A3.6 |
| o | o | F | o | o | F | C26D10.1 |
| o | o | o | o | o | o | C26F1.9 |
| o | F | o | o | o | o | C27F2.4 |
| o | F | o | F | o | F | C29F5.3 |
| o | o | o | F | o | o | C37H5.8 |
| o | o | o | o | o | o | C42D4.8 |
| o | o | o | o | o | F | C47D12.6 |
| o | o | o | o | o | o | C50F4.5 |
| o | F | F | o | o | F | C52A11.2 |
| o | ND | o | o | o | o | C52E4.3 |
| o | o | o | o | o | o | D1007.6 |
| o | o | F | o | F | F | F09E8.3 |
| o | o | F | o | o | F | F09F7.3 |
| ND | o | ND | o | o | F | F18A1.5 |
| o | F | F | F | o | o | F20D12.4 |
| o | o | o | F | o | o | F22B3.1 |
| o | o | o | o | o | o | F22B5.2 |
| o | o | o | o | o | F | F22B5.9 |
| o | o | F | F | o | o | F26F4.10 |
| o | o | o | o | o | o | F26F4.11 |
| o | o | o | F | o | o | F32E10.4 |
| o | o | o | o | o | o | F37C12.11 |
| o | o | o | o | o | o | F37C12.9 |
| o | F | o | F | o | o | F45E12.3 |
| o | o | o | o | o | o | F45F2.13 |
| o | o | o | o | o | o | F54E12.1 |
| o | o | o | o | o | o | F54E12.5 |
| o | ND | o | o | o | o | F55C5.8 |
| o | o | o | o | o | F | F55F10.1 |
| o | o | o | o | o | F | F55F10.2 |
| o | o | o | o | o | o | F55G1.10 |
| o | o | o | F | o | o | F58A4.4 |
| o | o | o | o | o | o | H02I12.7 |
| o | F | o | o | o | F | H06H21.3 |
| F | o | o | o | o | o | H06I04.i |
| o | o | o | o | o | F | H19M22.1 |
| o | o | o | o | o | o | H23L24.c |
| o | o | o | o | o | o | K03A1.1 |
| o | o | o | F | o | F | K05F1.5 |
| o | o | o | o | o | F | K12D12.2 |
| o | o | o | o | o | o | R05D11.3 |
| o | o | F | F | o | F | R08D7.1 |
| o | ND | o | o | o | F | R11D1.8 |
| o | o | o | o | o | o | T01C3.6 |
| o | o | o | o | o | F | T02G5.9 |
| o | ND | F | F | F | F | T03F7.5 |
| o | o | o | o | o | o | T10C6.11 |
| o | o | o | F | o | o | T10C6.12 |
| o | o | o | o | o | o | T10C6.13 |
| o | o | o | o | o | o | T13H5.4 |
| o | o | o | o | F | F | T23B12.2 |
| o | o | o | o | o | o | T28F3.2 |
| o | o | o | o | o | o | VW02B12L.1 |
| o | F | F | o | o | F | W07E6.1 |
| o | o | o | o | o | o | Y106G6H.3 |
| o | o | o | o | o | o | Y41D4A_3073.a |
| o | o | o | o | o | o | Y41D4A_3457.a |
| o | o | o | o | o | o | Y41D4A_3457.d |
| o | o | o | o | o | F | Y47D3A.c |
| o | o | o | o | o | o | Y62E10A.d |
| o | o | o | o | o | o | Y71G12A_187.b |
| o | o | o | o | o | o | Y76B12C_66.c |
| o | F | o | F | o | o | ZK550.4 |
| o | o | o | F | o | o | ZK637.8 |
| o | o | o | o | o | o | ZK652.1 |
| o | o | o | F | o | F | ZK686.1 |
| o | F | F | F | F | F | B0454.1 |
| o | o | o | o | o | F | B0491.5 |
| o | o | F | o | o | o | C02F12.8 |
| o | o | o | o | o | o | C06A1.1 |
| o | F | F | F | F | F | C10A4.4 |
| o | | o | o | o | o | C14C10.3 |
| o | o | o | o | o | F | C15H9.4 |
| o | o | o | o | F | o | C16D9.5 |
| o | o | o | F | o | F | C18E9.4 |
| o | o | o | F | o | F | C29H12.6 |
| o | o | o | o | o | o | C30B5.6 |
| o | o | o | F | o | F | C30C11.2 |
| o | o | F | o | o | F | C37H5.5 |
| o | F | F | F | F | F | C40D2.2 |
| o | o | o | o | o | o | C42C1.3 |
| o | F | F | F | F | F | C47C12.2 |
| | F | F | F | | F | D1054.3 |
| o | F | F | F | o | F | F08D12.7 |
| o | o | o | o | o | F | F19F10.9 |
| o | o | o | o | o | o | F26A1.10 |
| o | o | o | o | o | o | F29C4.2 |
| o | F | F | F | o | o | F32E10.1 |
| o | o | o | o | o | o | F33A8.1 |
| o | F | F | F | F | F | F40H3.1 |
| o | F | F | F | o | F | F45C12.7 |
| o | F | o | o | o | o | F45H10.4 |
| o | F | F | o | o | F | F46C8.1 |
| o | F | F | F | o | F | F47F6.4 |
| o | o | o | o | o | o | F52C6.13 |
| o | F | F | F | o | F | F54F2.7 |
| o | F | F | F | F | o | F55C12.2 |
| ND | ND | o | ND | o | ND | F57G9.3 |
| ND | ND | F | ND | F | ND | F57G9.4 |
| o | o | o | F | F | o | H06I04.h |
| o | o | o | o | o | o | K02E7.6 |
| | o | o | o | o | o | K06A4.6 |
| o | o | o | o | o | F | K06A5.4 |
| o | F | F | o | o | F | R07E3.2 |
| o | o | o | o | o | o | R12E2.2 |
| o | o | o | o | o | o | R144.2 |
| o | o | o | o | o | F | T12A2.2 |
| ND | o | F | F | o | F | T19B10.2 |
| o | o | o | o | o | F | W01A8.4 |
| o | F | F | F | o | F | W01B11.5 |
| o | F | F | F | o | o | W02B3.7 |
| o | o | o | o | o | o | W04A4.6 |
| o | o | o | o | o | o | W07B3.2 |
| o | o | o | o | o | o | W10C6.1 |
| o | o | o | o | o | o | Y38F2A_5743.i |

TABLE VIIIB-continued

Epistasis Analysis on Genes that Reduce Fat and Growth/Viability

| Wild type | tph-1 (mg280) | tub-1 (nr2004) | daf-2 (e1370) | lpo-1 | lpo-6 | |
|---|---|---|---|---|---|---|
| o | F | F | o | o | F | Y51H4A.m |
| o | o | o | o | o | F | Y53C12B.2 |
| o | F | o | F | o | o | Y57A10A.v |
| o | o | o | o | o | o | Y75B12B.3 |
| o | o | o | o | o | o | Y75B8A.27 |
| o | o | o | F | o | o | ZK121.c |
| o | o | F | F | F | o | ZK546.2 |
| o | F | o | F | o | F | ZK795.3 |
| o | o | o | o | o | o | C04G2.6 |
| o | o | o | o | o | o | F41H10.7 |
| ND | ND | ND | ND | ND | ND | T10B5.5 |

As indicated above, the epistasis analysis may be used to order *C. elegans* genes in a genetic pathway. Mammalian orthologs of *C. elegans* genes are expected to occupy similar positions in the mammalian fat metabolism regulatory pathway. For example, this analysis places *C. elegans* lpo-3 gene downstream of daf-2, tub-1, tph-1, lpo-1 and lpo-6. Based on this result, it is expected that inactivation of the human lpo-3 ortholog would cause a reduction in fat content in normal individuals, as well as in obese individuals who have a mutation in a fat storage gene upstream of lpo-3.

Understanding the position of mammalian genes in a fat metabolism pathway facilitates the development of therapeutics for the treatment of obesity and obesity-related disease. Drugs that target downstream fat metabolism regulator gene will likely be effective for the treatment of any fat metabolism regulation disorder, obesity, or obesity-related disease that results from a defect in an upstream gene. The downstream genes identified in *C. elegans* are promising drug targets for the treatment of obesity and obesity-related diseases, such as atherosclerosis and diabetes, or even hyperphagia-related syndromes.

RNAi Screens in Sensitized Genetic Backgrounds

In mammals, activation of the sterol responsive transcription factor, SREBP, depends on its cleavage by two proteases that liberate the transcription factor from the lipid membrane. In *C. elegans*, RNAi of SREBP resulted in a reduced fat phenotype. RNAi of *C. elegans* site 1 and site 2 proteases, however, failed to affect the fat content of wild-type nematodes. Interestingly, when RNAi of these proteases was carried out in lpo-1 (VLDL-R) mutant nematodes, a reduction in the fat content of the mutant nematodes was identified. Similarly, RNAi of the nematode long chain fatty acid transporter (D1009.1), sterol carrier proteins, SCP1 and SCP2 (D2013.8 & ZK892.2), and ERG-3 like sterol desaturase (F49E12.10) decreased lpo-1 mutant nematode fat content, but had no effect on wild-type nematodes. Thus, the high fat content of lpo-1 provides a sensitized background for the identification of fat metabolism regulator genes that cannot be detected in a wild-type background. Systematic RNAi of the *C. elegans* genome could be carried out in any sensitized background (e.g., lpo-1, lpo-2, lpo-3, lpo-4, lpo-5, or lpo-6) to identify new fat metabolism regulator genes.

Mammalian Orthologs

The results detailed above indicated that key mechanisms of body fat and sterol regulation were conserved between mammals and *C. elegans*. Thus the powerful genetics and genomics of *C. elegans* can be exploited for the systematic identification of mammalian fat metabolism regulator genes, their interactions, responses to environmental perturbations, and changes over the lifespan of the animal. Importantly, analysis in *C. elegans* provides insights into the dysregulation of energy balance that underlies human obesity-associated diseases. Moreover, the comprehensive RNAi system described herein allows for the rapid identification and classification of new fat metabolism regulator genes in *C. elegans*. Many of these genes have mammalian orthologs not previously associated with fat metabolism. These mammalian genes may be unidentified components of known fat pathways, or present new paradigms for fat balance. Given the regulatory interactions that exist between fat cells and the CNS, the study of fat regulation in a physiologically intact animal, such as *C. elegans*, can provide insights unattainable in other model systems, such as cultured mammalian adipocytes.

Most of the genetic loci identified herein cause a decrease in fat storage when inactivated. Activating mutations in such genes could cause obesity in humans. The mammalian orthologs of these *C. elegans* genes represent candidates for pedigree analysis in obesity and lipodystrophy syndromes. The mammalian orthologs of identified *C. elegans* fat metabolism regulator genes that decrease *C. elegans* fat content are shown in Tables IX and X. These genes were identified as follows.

Protein sequences corresponding to genes of interest were retrieved from the repositories of *C. elegans* sequence information at the wormbase website and matched against the *C. elegans* orfeome database from the Vidal laboratory (worfdb) hosted by Harvard to ensure the accuracy of known or predicted protein sequences. The protein sequence was then used for standard [BLASTP] searching using the National Center for Biotechnology Information, National Library of Medicine, National Institutes of Health BLAST website. The search was limited to "non-redundant mammalian database." Translated database [tblastn] searches were performed in the same way except that the [tblastn] search site was used instead of BLASTp. The protein sequence corresponding to the top mammalian candidate produced by tblastn was retrieved from Genbank at the National Center for Biotechnology Information, National Library of Medicine, National Institutes of Health website and used for BLASTp search of *C. elegans* proteins using the wormbase site.

These methods allowed us to identify mammalian orthologs of the worm genes revealed by our genetic or RNAi analysis. An ortholog is a protein that is highly related to a reference sequence.

Mammalian Orthologs of *C. elegans* RNAi Clones that Reduce Fat Content without Reducing Viability/Growth Mammalian orthologs of *C. elegans* RNAi clones that reduce fat levels without altering growth or viability are shown in Table IX. Such genes are particularly promising therapeutic targets for the treatment of obesity or obesity-related disease, since drugs that inactivate them are unlikely to cause adverse side-effects. This list identifies the *C. elegans* genes by *C. elegans* cosmid name and open reading frame number. The mammalian orthologs are listed by the Genbank protein accession number.

TABLE IX

Mammalian Orthologs of RNAi Clones that Reduce Fat Content without Reducing Viability/Growth

| GENE NAME | MAMMALIAN ACCESSION NUMBERS | | | | |
|---|---|---|---|---|---|
| C36A4.9 | 8923896 | 15082523 | 20861072 | 9790021 | 21269872 |
| AH10.1 | 13376741 | 15559516 | 17390865 | 16418449 | 18034773 |
| C17C3.1 | 14548007 | 18543371 | 18875408 | 14285685 | 4885565 |
| K05F1.3 | 17440754 | 4557231 | 7542837 | 8392833 | 2392312 |
| T08B2.7 | 595267 | 14328041 | 4504325 | 7387634 | 18677763 |
| W01C9.4 | 4503301 | 18571478 | 1575000 | 111287 | 17105350 |
| T02G5.4 | 4557237 | 86728 | 499158 | 135757 | 21450129 |
| F14H8.1 | 19718741 | 17529999 | 17529997 | 19718746 | 7662298 |
| F11E6.5 | 18496985 | 17454617 | 10444345 | 13129088r | 16151801 |
| B0285.8 | 4557455 | 18603990 | 6671748 | 6978649 | 8393104 |
| Y49A3A.1 | 19527084 | 5174415 | 18580821 | 9910384 | 12841853 |
| F23H11.9 | 10092647 | 12832369 | 12835319 | 12854793 | 18560903 |
| C01C10.3 | 15489111 | 7661996 | 19353717 | 12834446 | 11427110 |
| F08F8.2 | 90238 | 123344sp | 2495262 | 123341 | 4557643 |
| F15A8.6 | 4388919 | 108929 | 3219994 | 3212451 | 3401962 |
| K02D3.2 | 11992399 | 19525698 | 19525702 | 11992401 | 19526998 |
| M05B5.4 | 6912484 | 18265286 | 19527008 | 6678672 | 12836459 |
| K10B3.7 | 8393418 | 6679937 | 2506441 | 120707 | 6983849 |
| H04M03.1 | 130757 | 13653992 | 539657 | 1709731 | 4505639 |
| F43H9.2 | 6685594 | 6755656 | 4758668 | 2137762 | 6691980 |
| Y6B3B.10 | 137047 | 11641421 | 18490663 | 3264848 | 13385556 |
| K09D9.2 | 117254 | 6166042 | 117218 | 10835506 | 19071838 |
| K07C6.4 | 117219 | 2144294 | 117197 | 15147326 | 65684 |
| K07C6.5 | 2134974 | 18088282 | 117225 | 1168128 | 117235 |
| T04A8.16 | 6753258 | 7656959 | 4495099 | 2970661 | 2584822 |
| F28H6.3 | 4757928 | 6318318 | 2143819 | 1083706 | 2144056 |
| C06E7.3 | 13097429 | 5174529 | 19705457 | 284301 | 4557737 |
| F13D11.1 | 8392842 | 19484058 | 130728 | 13111975 | 4557010 |
| F52B11.2 | 4557839 | 12833938 | 14776420 | 8393988 | 18594118 |
| K03B8.3 | 6678862 | 285323 | 6981198 | 1083414 | 91080 |
| C24A11.9 | 18575685 | 7657653 | 9507201 | 12848965 | 9966853 |
| T09B4.8 | 13994255 | 13929196 | 2492864 | 1096025 | 12836724 |
| Y55F3C.c | 14548281 | 2331277 | 2136328 | 6755885 | 2052504 |
| T12A2.1 | 18579028 | 12836736 | 18490737 | 17511765 | 7705596 |
| C31H2.3 | 12659007 | 14758806 | 7406615 | 4468339 | 18553930 |
| E01A2.i | 8393446 | 6680019 | 4504011 | 9588455 | 556518 |
| C46H11.2 | 18252634 | 3171877 | 4503759 | 19421731 | 2494584 |
| M28.6 | 13507666 | 14249588 | 17380287 | | |
| F37B12.3 | 16173159 | 16171486 | 13384840 | 18594817 | 5835803 |
| C37H5.3 | 19527302 | 19353227 | 11545767 | 13649744 | 13385690 |
| ZK6.7 | 758064 | 4758676 | 7546565 | 6647602 | 7434997 |
| R07B7.9 | 3172337 | 464376 | 2696236 | 18599609 | 12854561 |
| F31F6.7 | 15277824 | 18916767 | 18572895 | 7513594 | 17512305 |
| F13D12.6 | 2098347 | 4505989 | 13929457 | 12653639 | 3191969 |
| C15B12.7 | 14141726 | 12408302 | 6678017 | 8922155 | 20834606 |
| C44E4.6 | 118276 | 10140853 | 118275 | 493800 | 13937379 |
| Y47D3B.7 | 3318712 | 12249193 | 12249195 | 17380503 | 13543808 |
| C33G8.9 | 643611 | 543297 | 14149746 | 18158445 | 6753104 |
| K08A2.b | 7446194 | 1082439 | 2135340 | 4504443 | 9714201 |
| Y69A2A_7278.m | No significant similarity found. | | | | |
| F11C1.6 | 15290639 | 11493781 | 3121738 | 416584 | 10945629 |
| B0280.3 | 6677767 | 15930194 | 1350838 | 18550866 | 17456433 |
| F11A1.3 | 8394529 | 2500921 | 4507883 | 13879475 | 6678561 |
| C46E10.9 | 18561872 | 18595962 | 4505855 | 9910494 | 14250235 |
| C47C12.3 | 11463867 | 14916471 | 6677645 | 6677643 | 6677647 |
| T09F3.1 | 16551981 | 18590023 | 18546120 | 14349043 | 17482343 |
| T23F11.4 | 9055310 | 14245734 | 1663696 | 14747600 | 6031194 |
| ZK686.4 | 13385046 | 17391140 | 13507650 | 18572630 | 10436199 |
| Y116A8C.32 | 7513392 | 1620405 | 14318588 | 14165553 | 7513389 |
| F22A3.4 | No significant similarity found. | | | | |
| C09G9.7 | 4557827 | 4557823 | 110788 | 417447 | 280984 |
| W02C12.3 | 15282044 | 4557755 | 1092105 | 6678884 | 13124344 |
| F22A3.5 | 339895 | 18149007 | 107390 | 8567384 | 14782520 |
| C01G6.5 | 6624734 | 631765 | 13435494 | 14782132 | 5420465 |
| F39D8.2 | 14780600 | 14043520 | 4758930 | 2190414 | 7710080 |
| R04A9.4 | 124222 | 7546552 | 110568 | 4503535 | 6681293 |
| ZK757.3 | 11386878 | 11024680 | 18570004 | 6912352 | 13376275 |
| Y41E3.10 | 12653785 | 12856949 | 12845656 | 12845723 | 4503477 |
| D2089.2 | 12836671 | 19263985 | 16358983 | 12805349 | 7706043 |
| F11A10.3 | 2327052 | 13111867 | 5729939 | 2687591 | 5931741 |
| B0218.5 | 18201865 | 14781533 | 13122442 | 13435470 | 13097702 |

TABLE IX-continued

Mammalian Orthologs of RNAi Clones that Reduce Fat Content without Reducing Viability/Growth

| GENE NAME | MAMMALIAN ACCESSION NUMBERS | | | | |
|---|---|---|---|---|---|
| T05C12.1 | 20900385 | 18201865 | 20555151 | 6526520 | 13122442 |
| Y53C12A.1 | 19264036 | 12746438 | 2914671 | 4758928 | 2460023 |
| C16A11.3 | 110864 | 125290 | 4502885 | 4758008 | 13623342 |
| F45H7.4 | 9506973 | 8393959 | 16580805 | 3800869 | 4505811 |
| ZK930.1 | 14728229 | 17028437 | 12836135 | 14150114 | 4507281 |
| ZC504.4 | 3721838 | 18553056 | 3327188 | 6679060 | 18555837 |
| M01B12.5 | 16549132 | 13899340 | 12856491 | 16163884 | 18152791 |
| C02F4.2 | 4584820 | 19343933 | 8394030 | 14209665 | 6715568 |
| C06A1.3 | 130706 | 13994195 | 542987 | 4506003 | 1535 |
| ZC302.1 | 5031921 | 11560107 | 5031923 | 9055282 | 1401337 |
| C03D6.3 | 6755342 | 18042848 | 14750499 | 4506563 | 12833263 |
| T19D2.2 | 4506283 | 17528929 | 4506285 | 1246236 | 17865337 |
| C47D12.1 | 4507691 | 4151929 | 14748864 | 3694663 | 7512506 |
| ZK909.3 | 12835118 | 18584663 | | | |
| C06A6.1 | No significant similarity found. | | | | |
| R107.4 | 7661946 | 9789983 | 7019547 | 12835969 | 9790253 |
| C33H5.17 | 17939660 | 14017911 | 14249740 | 14042873 | 18204508 |
| R07E5.1 | 14763089 | 13543933 | 13385692 | 8922283 | 12852170 |
| C41D7.2 | 12853786 | 4557803 | 8134591 | 10945625 | 8099648 |
| ZK675.1 | 4506247 | 6679519 | 1335864 | 6679517 | 4325111 |
| F20H11.2 | 11990420 | 7023114 | 18255692 | 7662410 | 16163366 |
| T04D3.2 | No significant similarity found. | | | | |
| C44F1.5 | 12018268 | 729241 | 8176552 | 284522 | 423625 |
| H08M01.2 | 17482677 | 12697989 | 8886143 | 285370 | 13649298 |
| F46G11.3 | 12730586 | 4885251 | 17375734 | 13591947 | 12803719 |
| K10D3.5 | 14042287 | 7019333 | 13435804 | 15079264 | 11360161 |
| F41D9.1 | 14165549 | 19527318 | 11034851 | 7209313 | 5689447 |
| F07C3.4 | 7657152 | 627469 | 12856817 | 7305093 | 7705931 |
| F45E4.6 | 3108187 | 4557799 | 13633370 | 8705244 | 9506547 |
| T14E8.3 | 7381416 | 17986270 | 3820492 | 4503385 | 11344838 |
| C07A9.2 | 17449930 | 16758328 | 4503837 | 18570787 | 17473912 |
| Y4C6A.h | 18490394 | 400254 | 4504139 | 6288800 | 11279202 |
| C38C10.1 | 107184 | 7669548 | 6678213 | 107185 | 8394408 |
| C34C6.6 | 6679581 | 12084650 | 9663119 | 3005920 | 16197740 |
| E02C12.3 | 17559196 | 17559194 | 17566398 | 17562326 | 17564240 |
| H09F14.1 | 11225272 | 4557859 | 464813 | 464812 | 7229404 |
| Y44A6B.2 | No significant similarity found. | | | | |
| F58G4.2 | 17464941 | 6981586 | 13358632 | 14388397 | |
| Y40H7A.7 | 18567340 | | | | |
| F07C4.1 | No significant similarity found. | | | | |
| F10A3.13 | No significant similarity found. | | | | |
| F17A2.7 | No significant similarity found. | | | | |
| F47C12.3 | 4505807 | 1944499 | 7547268 | 17105400 | 2136690 |
| F49C5.6 | No significant similarity found. | | | | |
| T07C12.1 | 18556170 | 5834956 | | | |
| T07C12.5 | 11023094 | 6755913 | 66358 | 2117664 | 136595 |
| Y17G9A.d | No significant similarity found. | | | | |
| Y94A7B.3 | No significant similarity found. | | | | |
| Y9C9A_53.c | No significant similarity found. | | | | |
| T04A11.8 | 4115532 | 4959453 | 7159263 | 7159275 | 7159273 |
| F33G12.2 | 14150114 | 18044039 | 12838548 | 13385884 | 13542766 |
| C32C4.1 | 16758912 | 4758622 | 13242172 | 15418950 | 5921784 |
| B0310.1 | 4504851 | 4504849 | 14149764 | 11496265 | 13124041 |
| C37A5.1 | 4759310 | 18044531 | 8923137 | 3335161 | 18476496 |
| K04E7.2 | 2143888 | 2832268 | 1136776 | 4827008 | 15301458 |

TABLE IX-continued

Mammalian Orthologs of RNAi Clones that Reduce Fat Content without Reducing Viability/Growth

| GENE NAME | MAMMALIAN ACCESSION NUMBERS | | | | |
|---|---|---|---|---|---|
| C34G6.4 | 6755046 | 6755048 | 266517 | 2506118 | 307180 |
| K05F1.6 | 4506999 | 8918937 | 2511670 | 4507005 | 15147378 |
| ZK682.2 | 9719374 | 6912666 | 9719376 | 4885441 | 15487160 |
| C13D9.7 | 18875376 | 13376449 | 17865509 | 17865499 | 12597441 |
| F23F1.6 | 6671596 | 18181964 | 6981556 | 539952 | 1706187 |
| F15H10.4 | 17505223 | 18426842 | 17473038 | 12005633 | 14767497 |
| F59F5.1 | 7513431 | 5730045 | 6677997 | 4759116 | 4759112 |
| C46F11.1 | 3355534 | 10092641 | 18564398 | 17390915 | 13569893 |
| H27A22.1 | 12856921 | 18043218 | 6912618 | 2498823 | 12841414 |
| T19B4.6 | 18203852 | | | | |
| T19B4.7 | 4885175 | 6681139 | 6978755 | 4505375 | 2078518 |
| T27F7.1 | 6716764 | 7706353 | 12852884 | 12844196 | 12858406 |
| C33A12.1 | 400650 | 4826848 | 14777313 | 12844560 | 6981260 |
| F28H6.2 | 3336980 | 12839964 | 1083460 | 6753746 | 3024410 |
| F20D1.9 | 12845461 | 13375983 | 13899342 | 12837673 | 18848167 |
| F14D12.2 | 17462167 | 10433878 | 18860509 | 13542844 | 14789889 |
| K12B6.8 | 7662244 | 17068424 | 18590847 | 14149702 | 14789737 |
| C15H9.7 | 16758776 | 2143818 | 12852371 | 4504937 | 12654129 |
| W03C9.3 | 13027392 | 14746535 | 131797 | 13794267 | 6679599 |
| F11A5.3 | 18088786 | 12837642 | 10946940 | 13929006 | 108107 |
| R11A5.1 | 4501975 | 18201935 | 15929245 | 20909238 | 6753076 |
| F53H8.1 | 9055268 | 6912240 | 19424296 | 12836141 | 10439979 |
| T14D7.3 | 12851438 | 7949160 | 14736500 | 4507863 | 4200247 |
| R01H2.3 | 4507157 | 8928391 | 8928392 | 7513715 | 7513686 |
| T22D1.4 | 4506675 | 19527152 | 9857227 | 14124942 | 6981486 |
| F54H5.3 | 8099350 | 12842294 | 14759532 | 4507867 | 7305623 |
| C05E11.2 | No significant similarity found. | | | | |
| K09B11.9 | 16359203 | 13431959 | 1171952 | 9507177 | 1171950 |
| Y38E10A.c | 8925888 | 8925890 | 7513043 | 4758956 | 14769776 |
| C49C3.3 | No significant similarity found. | | | | |
| F49E12.4 | 4507789 | 10444495 | 8134778 | 4759282 | 18582039 |
| F52C6.2 | No significant similarity found. | | | | |
| Y65B4B_10.a | No significant similarity found. | | | | |
| Y65B4B_10.e | 6680476 | 13654239 | 15079474 | 14010859 | 18554931 |
| F40H3.5 | 14336772 | 4826764 | 14494990 | 20899626 | 9957244 |
| ZK39.7 | 12742008 | 4758084 | 6681063 | 13928904 | 3288885 |
| F49E11.4 | 13899332 | 18490353 | 6678423 | 14042040 | 15779065 |
| K02D7.3 | No significant similarity found. | | | | |
| M01E10.2 | 2065167 | 18201921 | 3182940 | 18201923 | 14757167 |
| Y77E11A_3443.i | 19343543 | | | | |
| F07A5.1 | No significant similarity found. | | | | |
| F26D11.10 | 16418341 | 6572227 | 16418453 | 8393886 | |
| Y37D8A.1 | 9790141 | 5031597 | 2209347 | 18104938 | 13639437 |
| Y17G7B.15 | 17434817 | 16945966 | 12697977 | 7661880 | 18551362 |
| R107.6 | 7513102 | 14726914 | 7513045 | 16758540 | 12839687 |
| C23F12.1 | 7677526 | 14744078 | 4557597 | 5419655 | 8885790 |
| M106.5 | 11131728 | 13124696 | 1345668 | 4826659 | 19352984 |
| C06G3.2 | 9910266 | 14424665 | 13194197 | 3891936 | 9910292 |
| T28D6.2 | 135395 | 223556 | 135412 | 18601895 | 6755901 |
| W09D10.3 | 4506673 | 11177148 | 12837801 | 17865556 | 12832973 |
| W10D9.5 | 12842129 | 20902823 | 9910382 | 20841046 | 17475714 |
| F54D5.11 | 4504195 | 13386074 | 18043581 | 228300 | 11611843 |
| F44B9.7 | 12847646 | 6677723 | 4506491 | 283966 | 13097123 |
| Y71H10B.1 | 6912598 | 2668557 | 12841987 | 18544261 | 7706749 |
| F21D5.5 | 14211141 | 6005836 | 5757919 | 12803393 | 14786918 |
| F20D12.2 | 11225270 | 19923191 | 7513026 | 13938593 | 14780851 |
| Y41D4A_3073.a | 4758844 | 6093462 | 18875386 | 16758834 | 7512639 |
| T22D1.10 | 5730023 | 6755382 | 4929561 | 9790083 | 4506753 |
| C24A1.4 | 1263081 | 1585320 | 14286268 | 3005702 | 5730039 |
| Y37A1A.1 | 3005702 | 5730039 | 1263081 | 14286268 | 1585320 |
| W09G3.4 | 11056006 | 18546470 | 14744278 | 14602983 | 12846468 |
| H25K10.1 | 164720 | 130722 | 178006 | 13016699 | 7767180 |
| C30F12.1 | 18604558 | 13376632 | 14750657 | 2224587 | 16041792 |

TABLE IX-continued

Mammalian Orthologs of RNAi Clones that Reduce Fat Content without Reducing Viability/Growth

| GENE NAME | MAMMALIAN ACCESSION NUMBERS | | | | |
|---|---|---|---|---|---|
| W09G3.1 | 18582801 | 7662058 | 18578718 | 6005796 | 14388374 |
| Y51H4A.m | 19483873 | 20985890 | 14760337 | | |
| Y48C3A.b | 13507702 | 18558641 | 13507706 | | |
| F13E6.1 | 13385202 | 4507643 | 11125673 | 15723372 | 17450493 |
| T21D12.3 | 9506989 | 16307140 | 5031957 | 11125356 | 10801584 |
| B0041.5 | 17391272 | 12836420 | 10437002 | 13376774 | 4758846 |
| B0286.4 | 11640600 | 7657385 | 12847218 | 7020899 | 6841484 |
| D1054.14 | 20841107 | 20472100 | 20881439 | 14249602 | 14149989 |
| F54C9.9 | 14602715 | 12804075 | 10438567 | 12711672 | 13649858 |
| B0513.7 | 3005702 | 5730039 | 1263081 | 14286268 | 1585320 |
| Y41D4A__3192.a | 12052882 | 8922808 | 12849037 | 18548855 | 16550576 |
| ZK686.3 | 14714487 | 6166601 | 1353701 | 6996934 | 14149775 |
| B0041.3 | 12843216 | 14585867 | 9651081 | 12847693 | 13385022 |
| C05E11.1 | 14725463 | 12697975 | 16551959 | 15777193 | 15843561 |
| F38A5.1 | 18559316 | 14714703 | 8922938 | 13529584 | 13899211 |
| C07E3.2 | 18550740 | 10434347 | 18598995 | 8480755 | 7512721 |
| Y47G6A__245.b | 11360017 | 5689555 | 14725071 | 11360104 | 18544047 |
| R05F9.8 | 8099350 | 14759532 | 4507867 | 12842294 | 13928870 |
| W04A4.5 | 14124974 | 16553697 | 18566093 | 15809018 | 14602672 |
| Y49F6B.n | 6919955 | 15278160 | 15928532 | 14767139 | 5901878 |
| F14D2.4 | 18556673 | 13528918 | 12314036 | 13627447 | 7656845 |
| C30G4.5 | No significant similarity found. | | | | |
| F58H1.6 | 6912322 | 18875406 | 18175295 | 17464187 | 18175284 |
| F55B11.4 | 18602286 | 20557594 | 20825014 | 5419655 | 14744078 |
| C47D12.7 | 13431657 | 6329805 | 8393672 | 6644293 | 18490684 |
| ZK355.d | 18490618 | 458124 | 1352359 | 1071851 | 10880776 |
| C16C4.2 | no similarity | | | | |
| Y50D7__165.b | No significant similarity found. | | | | |
| C54H2.5 | 6755698 | 19557691 | 2414516 | 5531849 | 18571517 |
| T05F1.6 | 20151156 | 2135874 | 5032189 | 16754836 | 20911529 |
| R08F11.2 | 8567364 | | | | |
| W01B11.5 | No significant similarity found. | | | | |
| R05H11.1 | 2498010 | 8659574 | 1524099 | 107912 | 6470339 |
| C32D5.11 | 4504867 | 13645747 | 18255721 | 13905224 | 12585549 |
| H32C10.3 | 9506623 | 4589536 | 14755049 | 6841238 | 3329427 |
| T21C9.2 | 7023936 | 15297473 | 16518394 | 8980452 | 7705397 |
| Y41E3.11 | 12803479 | 14786840 | 5901942 | 18204832 | 16041796 |
| T10D4.1 | 28880 | 402621 | 556809 | 7435163 | 114258 |
| C54G7.1 | 18581301 | 13872241 | | | |
| Y57G11C.17 | 14198202 | 8922621 | 4826524 | 14149736 | 18490309 |
| T04C10.2 | 7019369 | 3894395 | 11177890 | 10433856 | 16923990 |
| W06G6.1 | 18588797 | 11342591 | 5453998 | 11544639 | |
| K12D12.4 | 12849906 | 15277327 | 15777917 | | |
| C23H3.2 | 9955966 | 16878304 | 9845230 | 11560034 | 9588087 |
| C56E10.3 | 4758200 | 3702136 | 2134996 | 14781619 | 181608 |
| T27E4.6 | 18588797 | 3023767 | | | |
| Y57A10A.bb | 18599579 | 13874598 | 1235902 | 4502325 | |
| C14A6.6 | 13654761 | 4502265 | 14779030 | | |
| Y67D8A__380.d | 11611581 | 7022736 | | | |
| F08G2.7 | No significant similarity found. | | | | |
| F29B9.11 | 8843925 | 3023219 | 8843927 | 409029 | |
| T26E4.13 | 18604070 | | | | |
| H04M03.4 | 92459 | 13236528 | 226416 | 87490 | 6680904 |
| K02E7.11 | 16553058 | 18590066 | 17026040 | 14210297 | 2344954 |
| T10C6.10 | 16758598 | 2623539 | 7661820 | | |
| Y57E12__242.c | 16041755 | 1754827 | 13787219 | 7671650 | 1403336 |
| T10E9.6 | 18043543 | 13623239 | 182403 | 18560910 | 17443348 |
| Y111B2C.e | 8925872 | 6753636 | | | |
| Y71H2__389.a | 17433405 | | | | |
| R160.4 | 4507575 | 339760 | 8923171 | | |
| Y50E8.q | 1872417 | 6907077 | 951291 | 2291076 | 2291068 |
| F13B6.1 | 6678561 | 13879475 | 8394529 | 4557543 | |
| T21C9.11 | 18548863 | 18557544 | | | |
| T02H6.7 | 6978493 | 1346465 | 729945 | 17505210 | 16716337 |
| F53A9.4 | 18552947 | 18028934 | 18028932 | 11934691 | 11641259 |
| C14F5.3 | 2148107 | 4507627 | 2144843 | 15072321 | 1717775 |
| C29H12.6 | 20341671 | 3661610 | 7023218 | 20149742 | 19745190 |

TABLE IX-continued

Mammalian Orthologs of RNAi Clones that Reduce Fat Content without Reducing Viability/Growth

| GENE NAME | MAMMALIAN ACCESSION NUMBERS | | | | |
|---|---|---|---|---|---|
| C56E6.4 | 17459650 | 15072441 | 16933555 | 14581464 | 18583597 |
| F46C8.7 | 2499095 | 9507113 | 2499094 | 18543351 | |
| F46F5.10 | 14589929 | 10047189 | 18485486 | 14773966 | 11360033 |
| C42C1.6 | 18561804 | 18702327 | 19684085 | 17469647 | |
| F27C1.4 | 13386030 | 12856989 | 6981448 | 7706123 | 16758970 |
| B0554.7 | 13236549 | 2708503 | 2708511 | 2708501 | |
| C18E9.5 | 4507691 | 7512506 | 4151929 | | |
| F28H7.6 | 6685708 | 8101764 | 8393978 | | |
| C08G5.2 | gbAAL29692.1 | gbAAC32740.1 | gbAAA36456.1 | dbjBAA83105.1 | NP__033853.1 |
| F54F7.2 | 4557385 | 1082640 | 5453774 | 506818 | 14720600 |
| M01A8.1 | 6753760 | 17225492 | 7650140 | 13492036 | 1708335 |
| T01D3.4 | 13027456 | 14041800 | 14765556 | 16716571 | 14211847 |
| F59E11.5 | 16751835 | | | | |
| T19D7.1 | 18640740 | 9938026 | 11120504 | 11559956 | 5174469 |
| B0554.6 | 18875378 | 16877798 | | | |
| ZC84.5 | 7706431 | 9790043 | 17457573 | 2499057 | 18157547 |
| W05E10.2 | 18552761 | 19527020 | 20072462 | 14784755 | 8923510 |
| ZK652.2 | 4468341 | 9506859 | 12834792 | 13643685 | |
| D2062.10 | 10946736 | 5442366 | 13431270 | 14917111 | |
| C17G10.7 | 4885525 | 13623360 | | | |
| B0207.9 | 6686100 | 11056036 | | | |
| F38E9.4 | 7427513 | 18555663 | 9506701 | 18561409 | |
| Y65B4B__13.b | 6643819 | 17441938 | 185364 | 6643719 | 5454100 |
| Y38E10A.b | 16758026 | 14210276 | 17448743 | 6331226 | 14758637 |
| ZK593.3 | 126363 | 34226 | | | |
| C14C6.8 | 15307762 | 13899227 | 9055260 | | |
| F21H12.3 | 5453607 | 2947308 | 6679517 | 4325111 | 4588015 |
| T23E1.1 | 12805635 | 6981448 | 4505111 | 180654 | 18588157 |
| T17H7.1 | 110087 | 18581352 | | | |
| F10A3.11 | 5902154 | 4586880 | 6552408 | 6552404 | |
| F41C6.6 | 16758936 | 4587083 | 18599218 | 5006891 | 5032101 |
| T07C12.11 | 4885603 | 10443498 | 17368511 | 18572506 | 10880987 |
| T14A8.1 | 6850974 | 18044375 | 12731793 | 8922436 | |
| F58F9.1 | 1703342 | 6680706 | 18548973 | | |
| ZK154.4 | 19421557 | 11345539 | 14133197 | 7657697 | |
| R03H10.4 | 14763809 | 6686295 | 4505263 | 5032003 | 6755246 |
| F55C12.3 | 4757720 | 10862692 | | | |
| Y119D3__456.a | 6678922 | 5533377 | 7243011 | 7514128 | 6760665 |
| F08D12.4 | No significant similarity found. | | | | |
| R11H6.6 | No significant similarity found. | | | | |
| Y57A10A.I | No significant similarity found | | | | |
| C14A4.12 | No significant similarity found. | | | | |
| Y7A9C.3 | No significant similarity found. | | | | |
| C01G6.9 | No significant similarity found. | | | | |
| Y51H7C__255.c | No significant similarity found. | | | | |
| C15C7.5 | No significant similarity found. | | | | |
| T10C6.4 | No significant similarity found. | | | | |
| Y37D8A.8 | No significant similarity found. | | | | |
| C50E10.5 | No significant similarity found. | | | | |
| ZK1290.1 | No significant similarity found. | | | | |
| F22E5.1 | 16552612 | 17976800 | 13994213 | 17976802 | |

TABLE IX-continued

Mammalian Orthologs of RNAi Clones that Reduce Fat Content without Reducing Viability/Growth

| GENE NAME | MAMMALIAN ACCESSION NUMBERS | | | | |
|---|---|---|---|---|---|
| F12A10.8 | No significant similarity found. | | | | |
| B0034.2 | No significant similarity found. | | | | |
| F36H12.15 | No significant similarity found. | | | | |
| F52C6.12 | 20841107 | 20472100l | 20881439 | 14249602 | 14149989 |
| Y24D9A.b | No significant similarity found. | | | | |
| K06B4.3 | No significant similarity found. | | | | |
| T11F9.10 | No significant similarity found. | | | | |
| T19D2.3 | No significant similarity found. | | | | |
| T27E4.7 | No significant similarity found. | | | | |
| Y105E8B.3 | No significant similarity found. | | | | |
| Y69A2A_7278.l | 1843522 | 7446193 | 2135340 | 9714201 | 6166208 |
| Y51H7B_5.b | No significant similarity found. | | | | |
| T13F2.6 | No significant similarity found. | | | | |
| K09H11.2 | No significant similarity found. | | | | |
| T26E4.10 | No significant similarity found. | | | | |
| T06H11.2 | No significant similarity found. | | | | |
| F59F5.2 | No significant similarity found. | | | | |
| ZK131.8 | 12854993 | 12847763 | 4504301 | 70762 | 223582 |

Mammalian Orthologs of *C. elegans* RNAi Clones that Reduce Fat and Reduce Viability/Growth Mammalian orthologs of *C. elegans* RNAi clones that reduce fat content but adversely affect nematode growth or viability are shown in Table X. This list identifies the *C. elegans* genes by *C. elegans* cosmid name and open reading frame number. The mammalian orthologs are listed by the Genbank protein accession number.

TABLE X

Mammalian Orthologs of *C. elagans* RNAi Clones that Reduce Fat and Reduce Viability/Growth

| *C. elegans* Gene | Mammalian Accession Numbers | | | | |
|---|---|---|---|---|---|
| F10D2.9 | 13929208 | 91311 | 13938635 | 6677861 | 13277368 |
| F29D11.1 | 13562118 | 6806919 | 15825096 | 4758686 | 15825005 |
| F32H2.5 | 2506136 | 8394158 | 204099 | 9937097 | 7433799 |
| W06D12.3 | 12698736 | 13431283 | 13431274 | 14388941 | 11360339 |
| w09b6.1 | 542750 | 20559521 | 13626188 | 3023534 | 16758804 |
| C09H10.3 | 19526814 | 163412 | 17472883 | 14198176 | 548387 |
| C53B7.4 | 15929392 | 5453561 | 7513261 | 2493093 | 12841973 |
| F02E8.1 | 19705465 | 114617 | 12833323 | 13637998 | 4502299 |
| F35G12.10 | 19705465 | 114617 | 12833323 | 13637998 | 4502299 |

TABLE X-continued

Mammalian Orthologs of *C. elagans* RNAi Clones that Reduce Fat and Reduce Viability/Growth

| *C. elegans* Gene | Mammalian Accession Numbers | | | | |
|---|---|---|---|---|---|
| F37E3.1 | 4505343 | 627397 | 15988381 | 5441937 | 12851646 |
| W04A8.7 | 29733 | 2137085 | 2136308 | 4759206 | 6680936 |
| Y110A7A.h | 162703 | 4502311 | 549205 | 12643271 | 17105370 |
| Y37D8A.14 | 6680986 | 12858580 | 117100 | 18999392 | 4758038 |
| Y57G11C.12 | 4505359 | 400384 | 13385492 | | |
| F28B3.1 | 17471893 | 6686133 | 14043353 | 17457389 | 6686101 |
| C23H3.4 | 6678125 | 2853289 | 6685595 | 5454084 | 2136140 |
| C42C1.5 | | | | | |
| D1014.1 | 4502241 | 1399961 | 15559708 | 6005990 | 14766617 |
| E01A2.i | 8393446 | 6680019 | 4504011 | 9588455 | 556518 |
| E04A4.7 | 229351 | 118007 | 118014 | 117994 | 117966 |
| F01G10.1 | 12855432 | 388891 | 12018252 | 4507521 | 1729977 |
| F40H3.5 | 14336772 | 4826764 | 14494990 | 9957244 | 6754246 |
| F44D12.4 | 18203658 | 16758060 | 5031715 | 9055336 | 18656362 |
| F46E10.1 | 17390865 | 13376741 | 15559516 | 16553412 | 4164168 |
| F57B9.2 | 4589658 | 12653967 | 18598275 | 19354215 | 7706214 |
| H14A12.2 | 8393358 | 227665 | 68293 | 13543801 | 12832319 |
| H15N14.2 | 20913355 | 13489067 | 6679140 | 134267 | 90219 |
| K02F2..2 | 20892597 | 9951915 | 7709980 | 178277 | 13096485 |
| K06A4.5 | 17921976 | 6912406 | 9910256 | 13637831 | 4433351 |
| T05H4.4 | 1709233 | 1070443 | 4503327 | 19421846 | 553600 |
| T05H4.5 | 127847 | 1070444 | 17943396 | 1709233 | 19745150 |
| Y55F3A__750.e | 12841560 | 6755911 | 16758644 | 4759274 | 7949156 |
| B0285.1 | 14110390 | 14110387 | 7706549 | 4240297 | 14748750 |
| C16C2.3 | 1352493 | 9966773 | 12836107 | 13249985 | 346209 |
| F10E9.7 | 11137114 | 6978573 | 18588573 | 186083 | 1699382 |
| WQ3F8.5 | 4504951 | 293690 | 126367 | 226290 | 6981142 |
| W07E6.2 | 8922428 | 12804063 | 17390943 | 3043443 | 7305363 |
| ZK1067.1 | 4503597 | 280818 | 119534 | 17432904 | 10880776 |
| ZK675.1 | 4506247 | 6679519 | 1335864 | 6679517 | 4325111 |
| C33D3.1 | 8648977 | 3123218 | 477102 | 15593990 | 5882288 |
| C34H3.a | 16506291 | 17298684 | 16877372 | 6754928 | 19344028 |
| D1081.2 | 14719546 | 18655799 | 10048414 | 4507205 | 7546482 |
| F10C1.5 | 13940223 | 18572015 | 11230443 | 12229781 | 11386173 |
| F22A3.1 | 6912580 | 7305415 | 18204910 | 15214598 | 4557551 |
| F23B12.7 | 1705659 | 5031625 | 6753402 | 10439934 | 10434534 |
| F25H8.3 | 13626125 | 7242979 | 9910122 | 7243073 | 6685072 |
| W01D2.2 | 9453875 | 1843522 | 2135340 | 4504443 | 2135341 |
| Y17G7A.2 | 18027804 | 11870006 | 18602376 | 6729087 | 19173808 |
| C01F6.8 | 12848135 | 2197127 | 1095482 | 7513563 | 1060971 |
| C56C10.8 | 17441804 | 2851417 | 115143 | 107909 | 29507 |
| C56E6.1 | 11967969 | 16758590 | 14141178 | 16158955 | 15146444 |
| W06D12.2 | 16306555 | 11560129 | 11177516 | 19483870 | 13124041 |
| W10D9.5 | 12842129 | 12844929 | 9910382 | 17475714 | 16930809 |
| Y61A9LA__75.a | 7661980 | 18575034 | 14737076 | 18576250 | 7243183 |
| ZK105.e | 12408294 | 205634 | 17149816 | 18203577 | 18202498 |
| C36B1.4 | 4506189 | 7106389 | 4092058 | 18577124 | 1346784 |
| CD4.6 | 9910833 | 8394060 | 4506179 | 14768212 | 13543551 |
| F23F12.6 | 2492517 | 5729991 | 1172637 | 3450955 | 7110701 |
| F39H11.5 | 3914439 | 14198355 | 3915806 | 16165126 | 13928866 |
| T23F2.1 | 12846285 | 14861836 | 9910440 | 12836608 | 18572937 |
| Y38A8.2 | 4506197 | 11424309 | 6755202 | 8394082 | 17447021 |
| C36E8.5 | 7106439 | 135490 | 5174735 | 14758306 | 12846758 |
| D2024.6 | 12841166 | 5453597 | 16740716 | 1345694 | 6671672 |
| F10C1.2 | 34228 | 125962 | 5031875 | 1072002 | 383110 |
| F20G4.3 | 13928704 | 1346640 | 13431706 | 17978023 | 12667788 |
| F44F4.11 | 6678469 | 14389309 | 135395 | 90217 | 135412 |
| K07C5.1 | 5031571 | 15778930 | 14769120 | 12852068 | 1351867 |
| T04C12.5 | 71621 | 4501885 | 16304154 | 1351867 | 16359158 |
| Y19D2B.1 | 6678469 | 12850141 | 12839396 | 90217 | 2843123 |
| ZK593.5 | 13259510 | 4139121 | 1419567 | 13259508 | 6681147 |
| B0303.9 | 18105056 | 12621146 | 12859683 | 7514114 | 10439792 |
| C02C6.1 | 6681207 | 729381 | 1083647 | 18093102 | 539580 |
| C05D11.2 | 19343731 | 15553046 | 17978479 | 11345382 | 13385360 |
| F29G9.3 | 12005732 | 4506957 | 12837633 | 4557471 | 5630084 |
| F41C3.4 | 7634779 | 7705636 | 13385354 | 20340619 | 17488855 |
| K02D10.5 | 16758654 | 6685966 | 12836691 | 12963651 | 4759154 |
| T21E12.4 | 9506549 | 13384736 | 729378 | 18582791 | 2224591 |
| B0222.6 | NF | | | | |
| F57B9.5 | 17028426 | 13938404 | 15011984 | 15208645 | 3929339 |
| K01A6.4 | NF | | | | |
| K12D12.3 | 18780273 | 12052774 | 17974510 | 18563487 | 5102636 |
| W10C4.b | 12857852 | 4506217 | 20532221 | 20985633 | 8394085 |

TABLE X-continued

Mammalian Orthologs of *C. elagans* RNAi Clones that Reduce Fat and Reduce Viability/Growth

| *C. elegans* Gene | Mammalian Accession Numbers | | | | |
|---|---|---|---|---|---|
| B0035.7 | 631691 | 17455198 | 18545931r | 1458139 | 18580602 |
| B0035.8 | 223096 | 280961 | 18564726 | 4504263 | 15030326 |
| B0035.9 | 12854993 | 12847763 | 4504301 | 70762 | 223582 |
| B0041.4 | 2500343 | 11968086 | 16579885 | 12846949 | 1363989 |
| B0495.6 | 18585599 | 1931584 | 4503525 | 19263839 | 19354442 |
| C03C10.3 | 4557845 | 7106399 | 2500209 | 11256408 | 14743689 |
| C04H5.6 | 14318701 | 14250712 | 14752410 | 4503293 | 7770157 |
| C06A8.2 | 4507101 | 7243201 | | | |
| C08B11.5 | 5032069 | 18582960 | 18582878 | 4504715 | 17489281 |
| C09H10.2 | 4506651 | 14750580 | 13645150 | 9845295 | 17472837 |
| C15F1.e | 19424322 | 17511746 | 10436247 | 9966779 | 10433787 |
| C15H11.9 | 3183219 | 14719402 | 10946930 | 12857046 | 12845436 |
| C16A3.3 | 12834845 | 2498864 | 17454886 | 4454542 | 13385288 |
| C16A3.4 | 15529978 | 8922413 | 10435029 | 18583383 | 12698069 |
| C16A3.6 | 14042167 | 14210516 | 14747081 | 15341814 | 12853682 |
| C26D10.1 | 4502801 | 14278207 | 4389390 | 87057 | 132171 |
| C26F1.9 | 18592185 | 18590969 | 4506647 | 14738021 | 17449824 |
| C27F2.4 | 12846835 | 16226067 | 13384748 | 12843473 | 12652833 |
| C29F5.3 | 7662204 | 4521188 | 14750657 | 2224587 | 16041792 |
| C37H5.8 | 16158324 | 12653415 | 6754256 | 1072476 | 4758570 |
| C42D4.8 | 5902062 | 133327 | 2145091 | 7434727 | 4505939 |
| C47D12.6 | 14861852 | 12653491 | 14714853 | 12845562 | 4507367 |
| C50F4.5 | 223096 | 280961 | 18564726 | 15030326 | 16306566 |
| C52A11.2 | 338669 | | | | |
| C52E4.3 | 4759158 | 17471847 | 2833357 | 12862083 | 7657315 |
| D1007.6 | 14195014 | 14782930 | 13540714 | 13639605 | 14195007 |
| F09E8.3 | 4505253 | 3108220 | 5725250 | 12655021 | 3986757 |
| F09F7.3 | 4505941 | 7022241 | 8922399 | 6677789 | 3005758 |
| F18A1.5 | 4506583 | 18390321 | 12860240 | 2624702 | 13096131 |
| F20D12.4 | 15214617 | 4759344 | 11387254 | 18546147 | 126369 |
| F22B3.1 | 12854993 | 12847763 | 4504301 | 70762 | 223582 |
| F22B5.2 | 8393308 | 6492222 | 2460200 | 4503517 | 14280325 |
| F22B5.9 | 15296128 | 5032011 | 6841566 | 12845588 | 12644592 |
| F26F4.10 | 586063 | 18043638 | 15149476 | 12847471 | 1711647 |
| F26F4.11 | 14589953 | 1710659 | 4406232 | 476961 | 6680928 |
| F32E10.4 | 6680598 | 4504901 | 6680596 | 14758897 | 2654139 |
| F37C12.11 | 4506699 | 17390310 | 12841661 | 13592073 | 12964241 |
| F37C12.9 | 5032051 | 12083607 | 10181112 | 7440317 | 16158168 |
| F45E12.3 | 11140811 | 13270467 | 13259127 | 16307345 | 13386300 |
| F45F2.13 | 4504281 | 4504299 | 386772 | 18595043 | 70749 |
| F54E12.1 | 4504281 | 4504299 | 386772 | 18595043 | 70749 |
| F54E12.5 | 631691 | 17455198 | 121983 | 8922758 | 18545931 |
| F55C5.8 | 7657617 | 134889 | 7513444 | 18044248 | 14041927 |
| F55F10.1 | 7305641 | 14250229 | 17459629 | 6981606 | 1655681 |
| F55F10.2 | 7529573 | 17512348 | 4678973 | 15029526 | 18604727 |
| F55G1.10 | 631691 | 17455198 | 18545931 | 1458139 | 18580602 |
| F58A4.4 | 6679459 | 110830 | 3676248 | 4506051 | 12847590 |
| H02I12.7 | 631691 | 17455198 | 18545931 | 1458139 | 18580602 |
| H06H21.3 | 4758254 | 12859663 | 11418342 | 4503499 | 3746340 |
| H06I04.i | 18028291 | 17017991 | 13384672 | 15126717 | 7019917 |
| H19M22.1 | 18676514 | 18702313 | 7959295 | 9507013 | 18860896 |
| H23L24.c | 11024694 | 17480509 | 18587523 | 18572403 | 12853018 |
| K03A1.1 | 7305139 | 70743 | 70749 | 4504281 | 2119013 |
| K05F1.5 | 8923303 | 18070860 | 18545138 | 18070859 | 14762794 |
| K12D12.2 | 18566874 | 1504030 | 12852259 | 17646641 | |
| R05D11.3 | 5031985 | 2914436 | 2780953 | 7246005 | 17451119 |
| R08D7.1 | 14249338 | 3337385 | 19344062 | 17446135r | 18565781 |
| R11D1.8 | 13904866 | 14603467 | 1173012 | 12083655 | 6677779 |
| T01C3.6 | 4506691 | 18549572 | 18591367 | 7305445 | 70920 |
| T02G5.9 | 16716381 | 586059 | 11095909 | 505108 | 2501023 |
| T03F7.5 | 4104236gb | | | | |
| T10C6.11 | 223096 | 280961 | 18564726 | 87672 | 4504263 |
| T10C6.12 | 631691 | 17455198 | 121983 | 8922758 | 18545931 |
| T10C6.13 | 4504281 | 4504299 | 386772 | 18595043 | 70749 |
| T13H5.4 | 1082801 | 18202846 | 5803167 | 12854243 | 18578493 |
| T23B12.2 | 14756630 | 12832465 | 12653925 | 7705722 | 9956063 |
| T28F3.2 | 18565400 | 13242237 | 5729877 | 1708309 | 347019 |
| VW02B12L.1 | 12643966 | 12025532 | 7329154 | 13928826 | 3915315 |
| W07E6.1 | 189422 | 5453792 | 14784289 | 477430 | 12653741 |
| Y106G6H.3 | 4506631 | 17463853 | 17435581 | 18561308 | 18087841 |
| Y41D4A_3073.a | 14603084 | 18875386 | 16758834 | 6093462 | 6678764 |
| Y41D4A_3457.a | 15011027 | 14249612 | 9280134 | 15299647 | |
| Y41D4A_3457.d | 4758844 | 6093462 | 18875386 | 16758834 | 18559983 |

TABLE X-continued

Mammalian Orthologs of *C. elagans* RNAi Clones that Reduce Fat and Reduce Viability/Growth

| *C. elegans* Gene | Mammalian Accession Numbers | | | | |
|---|---|---|---|---|---|
| Y47D3A.c | 6679409 | 6015013 | 15858951 | 118838 | 479803 |
| Y62E10A.d | 18561782 | 133063 | 12849327 | 1173072 | 4506671 |
| Y71G12A_187.b | 5901998 | 4507131 | 14755615 | 4507133 | 13644938 |
| Y76B12C_66.c | 18570089 | 1706101 | 16878041 | 16751835 | 9558725 |
| ZK550.4 | 11432489 | 5031727 | 12847734 | | |
| ZK637.8 | 12643966 | 3955096 | 12644129 | 6755799 | 8392941 |
| ZK652.1 | 14755615 | 4507131 | 5901998 | 4507133 | 11138539 |
| ZK686.1 | 4506631 | 7661954 | 10048468 | 10442822 | 6331420 |
| B0454.1 | 13385706 | 9506389 | 5729742 | 18543825 | 12643413 |
| B0491.5 | 14249736 | 15620873 | 17865712 | 18581996 | 18916890 |
| C02F12.8 | 14743070 | 6754316 | 14579296 | 15620831 | |
| C06A1.1 | 2144498 | 17865351 | 6005942 | 6678559 | 1174636 |
| C10A4.4 | 18571651 | 17474970 | 15546041 | | |
| C14C10.3 | 4826688 | | | | |
| C15H9.4 | 14916851 | 14753980 | 14916847 | 14724805 | 13874437 |
| C16D9.5 | 2498884 | | | | |
| C18E9.4 | 400383 | | | | |
| C29H12.6 | 7023218 | 17438790 | 18043079 | 18568537 | 14211703 |
| C30B5.6 | 12834595 | 14250466 | 18605027 | 7706047 | 12856705 |
| C30C11.2 | 15310156 | 16550621 | 4506229 | 12652653 | 15126760 |
| C37H5.5 | 18482381 | 18389431 | 10434534 | 7208452 | 10439934 |
| C40D2.2 | 3115347 | 1770454 | 3115346 | 12230855 | 17465991 |
| C42C1.3 | 4505531 | 129309 | 17459136 | 2055435 | |
| C47C12.2 | No significant similarity found. | | | | |
| D1054.3 | 12846547 | 12841721 | 12861014 | 5730041 | 18567662 |
| F08D12.7 | 19527308 | 4557445 | | | |
| F19F10.9 | 2342526 | 8394236 | 10863889 | 4427065 | 13928810 |
| F26A1.10 | No similarity | | | | |
| F29C4.2 | No similarity | | | | |
| F32E10.1 | 13477303 | 13430872 | 17437341 | 10436236 | 14010904 |
| F33A8.1 | 10047283 | 10438214 | 13385386 | 10439972 | 14727768 |
| F40H3.1 | 13276695 | 16551785 | 12848994 | 9055326 | 6624092 |
| F45C12.7 | 4557445 | 19527308 | 13699242 | 8922617 | 5174665 |
| F45H10.4 | No similarity | | | | |
| F46C8.1 | No similarity | | | | |
| F47F6.4 | 7657291 | 6678762 | 14043211 | 18598633 | 281042 |
| F52C6.13 | 18548934 | 6706620 | 16306483 | 18643950 | 18643952 |
| F54F2.7 | 8923431 | 17470330 | 7513001 | 13446227 | 14010849 |
| F55C12.2 | No similarity | | | | |
| F57G9.3 | 1168245 | 547221 | 4501959 | 631067 | 345733 |
| F57G9.4 | 19071455 | 19071447 | 20836029 | 18700000 | 15488938 |
| H06I04.H | No similarity | | | | |
| K02E7.6 | 4502853 | 15823648 | 13938619 | 14763181 | 18157651 |
| K06A4.6 | No similarity | | | | |
| K06A5.4 | 15620865 | 18597077 | | | |
| R07E3.2 | No similarity found | | | | |
| R12E2.2 | 7705322 | 13638924 | 7656940 | 11359862 | |
| R144.2 | 13431763 | 4240137 | 7706224 | 13435542 | 14603356 |
| T12A2.2 | 12858636 | 13639549 | 7513277 | 6680498 | 4504787 |
| T19B10.2 | 4506521 | 9957313 | 14774724 | 6755320 | 14915764 |
| W01A8.4 | No similarity | | | | |
| W01B11.5 | 6679661 | | | | |
| W02B3.7 | 10946676 | 12858334 | 18553555 | 5921784 | 18490468 |
| W04A4.6 | 2134794 | 7657510 | 18308012 | 10047205 | |
| W10C6.1 | 12056971 | 10435855 | 6678834 | 18550879 | 7804450 |
| Y38F2A_5743.i | No similarity | | | | |
| Y51H4A.m | 8923726 | 4153862 | 18568744 | 7021918 | 12841382 |
| Y53C12B.2 | 17390336 | 10047140 | 13384846 | 12844974 | |
| Y57A10A.v | 9087217 | 14719825 | 7671639 | 539698 | 7106435 |
| Y75B12B.3 | 13569852 | 18676446 | 12382773 | 16507952 | |
| Y75B8A.27 | 6681147 | 1419567 | 13259510 | 4139121 | 13259508 |
| ZK121.C | 7662442 | 7661874 | 15149484 | 18599919 | 11360196 |
| ZK546.2 | 12834355 | 18597991 | 12833443 | 12859847 | 12849514 |
| ZK795.3 | 12835200 | 12850634 | 18478512 | 15529982 | 12845999 |
| C04G2.6 | 18582324 | 19923416 | 7451876 | 7674415 | 7512650 |
| F41H10.7 | 17454617 | 20137972 | 18496985 | 12836437 | 16151801 |
| T10B5.5 | 6671704 | 5453607 | 12848801 | 1800303 | 13540473 |

Mammalian orthologs of *C. elegans* RNAi Clones that Increase Fat Content

Mammalian orthologs of *C. elegans* RNAi clones that increase *C. elegans* fat content are shown in Table XI. This list identifies the *C. elegans* genes by *C. elegans* cosmid name and open reading frame number. The mammalian orthologs are listed by the Genbank protein accession number.

TABLE XI

Mammalian Orthologs of *C. elegans* Increased Fat Content Genes

| *C. elegans* Gene | Mammalian Accession Numbers | | | | |
|---|---|---|---|---|---|
| C33A12.6 | 549160 | 6537138 | 19527110 | 5803213 | 18308170 |
| E04F6.3 | 4504505 | 499340 | 20878362 | 6680287 | 13242303 |
| E04F6.6 | 20896611 | 12857271 | 4505257 | 18602081 | |
| F15B9.5 | 15529992 | 7435611 | 15029967 | 12840914 | 17487950 |
| F28F8.2 | 17390865 | 13376741 | 15559516 | 5019275 | 13517077 |
| F47B8.3 | 6840947 | 5730104 | 14738770 | 15680089 | 17447529 |
| VF13D12L.1 | 7022512 | 7705558 | 11493904 | 12963757 | 11281329 |
| C37F5.1 | 7767065 | 4100456 | 535923 | 14758312 | 4885201 |
| C43H6.8 | 2498013 | 5031945 | 6754852 | 5031943 | 16758982 |
| C56C10.10 | 4502009 | 1765936 | 7709982 | 6225016 | 8248030 |
| C56E10.4 | 5902068 | 6677829 | 285012 | 2780196 | 386369 |
| F16B4.9 | 6681852 | 12803755 | 5453940 | 346286 | 1144348 |
| F33D4.1 | 15418805 | 12230055 | 12230056 | 5821726 | 2500908 |
| H12C20.3 | 12230056 | 2134678 | 2500908 | 4503603 | 15301634 |
| K10C3.6 | 7657395 | 6681852 | 6680239 | 11559939 | 227511 |
| R11H6.5 | 20534593 | 4758602 | 13385872 | 6855637 | 13278459 |
| C04G2.2 | 20900385 | 20555151 | 18201865 | 7949025 | 20149530 |
| C09G5.8 | 4589654 | 20888031 | 9965252 | 9966409 | 9965248 |
| C18H9.7 | 20839618 | 6677669 | 15619013 | 20178328 | 631056 |
| C24F3.2 | 6005956 | 11560052 | 12963553 | 12835696 | 13435759 |
| F39B1.1 | 11259849 | 20843206 | 20561002 | 4505799 | 6755058 |
| F46C5.6 | 10047321 | 17402886 | 12858102 | 1702997 | 11386167 |
| F56D5.9 | 1695739 | 2642034 | 2143944 | 7513459 | 13647589 |
| F56H11.6 | 18201865 | 14781533 | 5579454 | 547767 | 11545751 |
| K08F8.1 | 10863901 | 4758700 | 14589904 | 1346538 | 1346539 |
| R10D12.10 | 18201865 | 14781533 | 1311054 | 1346368 | 20149530 |
| T04B2.2 | 6679773 | 1673620 | 6003683 | 4885231 | 4503687 |
| T04C9.1 | 7662208 | 6433901 | 14587851 | 13386454 | 20340540 |
| W03A5.4 | 19923689 | 19923274 | 7514059 | 1857137 | 1857139 |
| W08D2.1 | 17402916 | 5020354 | 16716413 | 17402914 | 13518017 |
| Y11D7A.9 | 7657102 | 6606290 | 7512548 | 14602865 | 16758956 |
| ZC513.1 | 14583090 | 18377358 | 2497615 | 13929458 | 5453914 |
| C43H6.9 | 3935134 | 2598978 | 1169965 | 4504119 | 3287976 |
| F08H9.5 | 20903753 | 6492289 | 4557503 | 20473663 | 14388673 |
| F56B6.5 | 6981586 | 6678043 | 5912550 | 2136182 | 4557865 |
| T19D12.8 | 13938199 | 13375695 | 12862152 | 12845041 | 12805161 |
| Y27F2A.g | 20070376 | 17457778 | | | |
| Y40H7A.1 | NF | | | | |
| Y46H3C_11.b | NF | | | | |
| F32B6.9 | 4759310 | 8923137 | 18044531 | 3335161 | 18476496 |
| ZC410.4 | 9988112 | 14149764 | 18652258 | 11496265 | 4504851 |
| C18H9.5 | 9719374 | 6912666 | 9719376 | 18252796 | 16758166 |
| F14E5.1 | 687622 | 8394301 | 121750 | 20301952 | 6755550 |
| F52H2.2 | 4507053 | 6103627 | 3970791 | 7106415 | 6319236 |
| C04G2.4 | 13928870 | 7305623 | 6671046 | 8099350 | 20070156 |
| F32B6.6 | 8099350 | 14759532 | 3320446 | 12842294 | 13928870 |
| C15A11.3 | 19070657 | 11907926 | 11934950 | 11907928 | 11934951 |
| C34F6.3 | 3236370 | 420194 | 18204626 | 17149807 | 18568576 |
| C53B4.5 | 5730019 | | | | |
| EGAP7.1 | NF | | | | |
| F46C8.6 | 14209684 | 20875879 | 12849231 | 177924 | 2493785 |
| T14B4.7 | NF | | | | |
| T28C6.6 | NF | | | | |
| Y38F1A.9 | 14211895 | 14748249 | 3928489 | 7513113 | 7657361 |
| Y41E3.2 | NF | | | | |
| K02D7.5 | 6677733 | 12852065 | 20872938 | 13543580 | 10047124 |
| C04G2.5 | 14042155 | 17017991 | 15126717 | 13384672 | |
| C09G12.5 | 631119 | 4758056 | 2996629 | 4321116 | 19547885 |
| C14A4.1 | 19527182 | 13775228 | 20862789 | 3482908 | 16306483 |
| C24F3.1a | 401208 | 7657655 | 13774095 | 18875432 | 18202920 |
| C33A12.14 | 204157 | 204158 | 204156 | 20849315 | |
| C36A4.5 | 8176554 | 231629 | 4502771 | 19527136 | 7512404 |
| C44E4.5 | 14042905 | 12654293 | 14718862 | 14745963 | 20902053 |
| C50C10.4 | NF | | | | |
| C50D2.1 | NF | | | | |
| D1007.5 | 20892497 | 8922756 | 20845045 | 10435222 | 13385900 |
| F12E12.h | 5689473 | 7662364 | 8574032 | 17472155 | 8217421 |
| F25G6.9 | 16551945 | 6330933 | 14250922 | 13644653 | 15823631 |

TABLE XI-continued

Mammalian Orthologs of *C. elegans* Increased Fat Content Genes

| *C. elegans* Gene | Mammalian Accession Numbers | | | | |
|---|---|---|---|---|---|
| F25H8.1 | 18381001 | 14724179 | 4454968 | 18572769 | 18043204 |
| F25H8.2 | 19923911 | 14734590 | 2506778 | | |
| F25H8.5 | NF | | | | |
| F26H9.4 | 20893587 | 20536806 | 14029540 | 3413920 | 12620200 |
| F31F6.2 | 17445681 | 9651075 | | | |
| F42G8.5 | NF | | | | |
| F44D12.7 | 21040405 | 12845958 | 20986214 | 20071715 | 20878200 |
| F49C12.15 | NF | | | | |
| F49F1.4 | NF | | | | |
| F52C12.2b | 20899132 | 21489947 | 18598168 | 11359878 | 12834488 |
| F56B3.2 | NF | | | | |
| F56F3.4 | 14741660 | 11275984 | 20831147 | 6677605 | 5174755 |
| H05L03.3 | NF | | | | |
| H05L14.2 | 7705835 | 10944884 | 13124522 | 7022528 | 15426504 |
| K01G5.8a | 21165518 | 13385950 | 7512937 | 7661696 | 2499753 |
| K02E10.3 | NF | | | | |
| K02E10.5 | 14336702 | 18585356 | | | |
| K07A1.13 | 14789674 | 6681103 | | | |
| K07E8.3 | 6912462 | 16758422 | 13811697 | 18583767 | 18546498 |
| K09C4.5 | 19526426 | 19526424 | 9910554 | 5902090 | 17511906 |
| LLC1.2 | 18570489 | 13376713 | | | |
| M70.1 | 5757675 | | | | |
| M70.3 | NF | | | | |
| R07A4.2 | 11056046 | 15636798 | 1483238 | 16716503 | 6981128 |
| R105.1 | 12728973 | 12803719 | 7662462 | | |
| T01C1.2 | 13385288 | 17462966 | 12643822 | 13876382 | 9716884 |
| T02C5.3 | 13928706 | 72067 | 20825059 | 14575679 | 14767192 |
| T04C9.2 | NF | | | | |
| T05E8.2 | 7106329 | 9229937 | 13561418 | 13994374 | 16923261 |
| T07F8.1 | 6679048 | 11424724 | 4885513 | 13629976 | 13592049 |
| T12A2.5 | NF | | | | |
| T12B5.8 | 6093441 | 105949 | 19923219 | 107355 | 11385307 |
| T14B1.1 | 6679391 | 8923793 | 18582525 | 16758990 | 12841832 |
| T14B4.8 | 9837158 | | | | |
| T14F9.4 | 12805039 | 17511715 | 10047169 | | |
| T19D12.3 | 9055194 | | | | |
| T27A8.4 | 2906008 | 7662466 | | | |
| W06H12.1 | 13236593 | 20454983 | 20521730 | 16307459 | 20864376 |
| Y11D7A.8 | 20860387 | 20070702 | 20824271 | 2497573 | 556789 |
| Y47D9A.e | NF | | | | |
| Y57A10B.1 | 12836671 | 19584503 | 8923613 | 7513036 | 19263985 |
| Y5H2B.e | 17472322 | 6644328 | | | |
| Y67A6A.1 | NF | | | | |
| Y73C8C.4 | 12698099 | 9966809 | 14042659 | | |
| ZC64.2 | NF | | | | |
| ZK1320.10 | 20886891 | 20561771 | 19743877 | 132518 | |
| ZK1321.1 | 4585572 | 4759146 | 4151205 | 20073051 | 6680427 |
| ZK666.10 | 18567302 | | | | |

Novel Genes Not Previously Associated with Fat Content Reduction

Tables XII and XIII show *C. elegans* genes, and their mammalian orthologs, not previously shown to reduce fat content when inactivated. This list identifies the *C. elegans* genes by *C. elegans* cosmid name and open reading frame number. The mammalian orthologs are listed by the Genbank protein accession number.

TABLE XII

Novel Genes that Reduce Fat Content when Inactivated without Affecting Viability

| *C. elegans* Gene | Mammalian Accession Numbers | | | | |
|---|---|---|---|---|---|
| AH10.1 | 13376741 | 15559516 | 17390865 | | |
| C17C3.1 | 14548007 | 18543371 | 18875408 | 14285685 | 4885565 |
| W01C9.4 | 4503301 | 18571478 | 1575000 | 111287 | 17105350 |
| F11E6.5 | 18496985 | 17454617 | 10444345 | 13129088r | 16151801 |
| B0285.8 | 4557455 | 18603990 | 6671748 | 6978649 | |
| Y49A3A.1 | 19527084 | 5174415 | 18580821 | 9910384 | 12841853 |
| F23H11.9 | 10092647 | 12832369 | 12835319 | 12854793 | |
| C01C10.3 | 15489111 | 7661996 | 19353717 | 12834446 | 11427110 |

TABLE XII-continued

Novel Genes that Reduce Fat Content when Inactivated without Affecting Viability

| *C. elegans* Gene | Mammalian Accession Numbers | | | | |
|---|---|---|---|---|---|
| F43H9.2 | 6685594 | 6755656 | 4758668 | 2137762 | 6691980 |
| Y6B3B.10 | 137047 | 11641421 | 18490663 | 3264848 | 13385556 |
| K09D9.2 | 117254 | 6166042 | 117218 | 10835506 | 19071838 |
| K07C6.4 | 117219 | 2144294 | 117197 | 15147326 | 65684 |
| K07C6.5 | 2134974 | 18088282 | 117225 | 1168128 | 117235 |
| T04A8.16 | 6753258 | 7656959 | 4495099 | 2970661 | 2584822 |
| F28H6.3 | 4757928 | 6318318 | 2143819 | 1083706 | 2144056 |
| C06E7.3 | 13097429 | 5174529 | 19705457 | 284301 | 4557737 |
| F13D12.6 | 2098347 | 4505989 | 13929457 | 12653639 | 3191969 |
| F52B11.2 | 4557839 | 12833938 | 14776420 | 8393988 | 18594118 |
| K03B8.3 | 6678862 | 285323 | 6981198 | 1083414 | 91080 |
| C24A11.9 | 18575685 | 7657653 | 9507201 | 12848965 | 9966853 |
| T09B4.8 | 13994255 | 13929196 | 2492864 | 1096025 | 12836724 |
| T12A2.1 | 18579028 | 12836736 | 18490737 | 17511765 | 7705596 |
| E01A2.i | 8393446 | 6680019 | 4504011 | 9588455 | 556518 |
| C46H11.2 | 18252634 | 3171877 | 4503759 | 19421731 | 2494584 |
| M28.6 | 13507666 | 14249588 | | | |
| C37H5.3 | 19527302 | 19353227 | 11545767 | 13649744 | 13385690 |
| C15H9.7 | 16758776 | 2143818 | 12852371 | 4504937 | 12654129 |
| K08A2.b | 7446194 | | | | |
| B0280.3 | 6677767 | 15930194 | 1350838 | 18550866 | 17456433 |
| C46E10.9 | 18561872 | 18595962 | 4505855 | 9910494 | 14250235 |
| C47C12.3 | 11463867 | 14916471 | 6677645 | 6677643 | 6677647 |
| T09F3.1 | 16551981 | 18590023 | | | |
| ZK686.4 | 13385046 | | | | |
| Y116A8C.32 | 7513392 | 1620405 | 14318588 | 14165553 | 7513389 |
| C09G9.7 | 4557827 | 4557823 | 110788 | 417447 | 280984 |
| W02C12.3 | 15282044 | 4557755 | 1092105 | 6678884 | 13124344 |
| F22A3.5 | 339895 | 18149007 | 107390 | 8567384 | 14782520 |
| C02F4.2 | 4584820 | 19343933 | 8394030 | 14209665 | 6715568 |
| F39D8.2 | 14780600 | 14043520 | 4758930 | 2190414 | 7710080 |
| ZK757.3 | 11386878 | 11024680 | 18570004 | 6912352 | 13376275 |
| D2089.2 | 12836671 | 19263985 | 16358983 | 12805349 | 7706043 |
| F11A10.3 | 2327052 | 13111867 | 5729939 | 2687591 | 5931741 |
| B0218.5 | 18201865 | 14781533 | 13122442 | 13435470 | 13097702 |
| T05C12.1 | 20900385 | 18201865 | 20555151 | 6526520 | 13122442 |
| Y53C12A.1 | 19264036 | 12746438 | 2914671 | 4758928 | 2460023 |
| C16A11.3 | 110864 | 125290 | 4502885 | 4758008 | 13623342 |
| ZK930.1 | 14728229 | 17028437 | 12836135 | 14150114 | 4507281 |
| ZC504.4 | 3721838 | 18553056 | 3327188 | 6679060 | 18555837 |
| M01B12.5 | 16549132 | 13899340 | 12856491 | 16163884 | 18152791 |
| C06A1.3 | 130706 | 13994195 | 542987 | 4506003 | 1535 |
| ZC302.1 | 5031921 | 11560107 | 5031923 | 9055282 | 1401337 |
| C03D6.3 | 6755342 | 18042848 | 14750499 | 4506563 | 12833263 |
| T19D2.2 | 4506283 | 17528929 | 4506285 | 1246236 | 17865337 |
| C47D12.1 | 4507691 | 4151929 | 14748864 | 3694663 | 7512506 |
| ZK909.3 | 12835118 | 18584663 | | | |
| R107.4 | 7661946 | 9789983 | 7019547 | 12835969 | 9790253 |
| C33H5.17 | 17939660 | 14017911 | 14249740 | 14042873 | 18204508 |
| R07E5.1 | 14763089 | 13543933 | 13385692 | 8922283 | 12852170 |
| C41D7.2 | 12853786 | 4557803 | 8134591 | 10945625 | 8099648 |
| ZK675.1 | 4506247 | 6679519 | 1335864 | 6679517 | 4325111 |
| F20H11.2 | 11990420 | 7023114 | 18255692 | 7662410 | 16163366 |
| C44F1.5 | 12018268 | 729241 | 8176552 | 284522 | 423625 |
| F46G11.3 | 12730586 | 4885251 | 17375734 | 13591947 | 12803719 |
| K10D3.5 | 14042287 | 7019333 | 13435804 | 15079264 | 11360161 |
| F41D9.1 | 14165549 | 19527318 | 11034851 | 7209313 | 5689447 |
| F07C3.4 | 7657152 | | 12856817 | 7305093 | 7705931 |
| F45H7.4 | 9506973 | 8393959 | 16580805 | 3800869 | 4505811 |
| C07E3.2 | 18550740 | 10434347 | 18598995 | 8480755 | 7512721 |
| C38C10.1 | 107184 | 7669548 | 6678213 | 107185 | 8394408 |
| C34C6.6 | 6679581 | 12084650 | 9663119 | 3005920 | 16197740 |
| E02C12.3 | 17559196 | 17559194 | 17566398 | 17562326 | 17564240 |
| F33G12.2 | 14150114 | 18044039 | 12838548 | 13385884 | 13542766 |
| C32C4.1 | 16758912 | 4758622 | 13242172 | 15418950 | 5921784 |
| C37A5.1 | 4759310 | 18044531 | 8923137 | 3335161 | 18476496 |
| K04E7.2 | 2143888 | 2832268 | 1136776 | 4827008 | 15301458 |
| C34G6.4 | 6755046 | 6755048 | 266517 | 2506118 | 307180 |
| K05F1.6 | 4506999 | 8918937 | 2511670 | 4507005 | 15147378 |
| ZK682.2 | 9719374 | 6912666 | 9719376 | 4885441 | 15487160 |
| C13D9.7 | 18875376 | 13376449 | 17865509 | 17865499 | 12597441 |
| F23F1.6 | 6671596 | 18181964 | 6981556 | 539952 | 1706187 |
| F15H10.4 | 17505223 | 18426842 | 17473038 | 12005633 | 14767497 |

TABLE XII-continued

Novel Genes that Reduce Fat Content when Inactivated without Affecting Viability

| *C. elegans* Gene | Mammalian Accession Numbers | | | | |
|---|---|---|---|---|---|
| F59F5.1 | 7513431 | 5730045 | 6677997 | 4759116 | 4759112 |
| C46F11.1 | 3355534 | 10092641 | 18564398 | 17390915 | 13569893 |
| H27A22.1 | 12856921 | 18043218 | 6912618 | 2498823 | 12841414 |
| T19B4.7 | 4885175 | 6681139 | 6978755 | 4505375 | 2078518 |
| T27F7.1 | 6716764 | 7706353 | 12852884 | 12844196 | 12858406 |
| C33A12.1 | 400650 | 4826848 | 14777313 | 12844560 | 6981260 |
| F20D1.9 | 12845461 | 13375983 | 13899342 | 12837673 | 18848167 |
| F14D12.2 | 17462167 | 10433878 | 18860509 | 13542844 | 14789889 |
| W03C9.3 | 13027392 | 14746535 | 131797 | 13794267 | 6679599 |
| F11A5.3 | 18088786 | 12837642 | 10946940 | 13929006 | 108107 |
| R11A5.1 | 4501975 | 18201935 | 15929245 | 20909238 | 6753076 |
| F53H8.1 | 9055268 | 6912240 | 19424296 | 12836141 | 10439979 |
| T14D7.3 | 12851438 | 7949160 | 14736500 | 4507863 | 4200247 |
| R01H2.3 | 4507157 | 8928391 | 8928392 | 7513715 | 7513686 |
| T22D1.4 | 4506675 | 19527152 | 9857227 | 14124942 | 6981486 |
| F54H5.3 | 8099350 | 12842294 | 14759532 | 4507867 | 7305623 |
| K09B11.9 | 16359203 | 13431959 | 1171952 | 9507177 | 1171950 |
| Y38E10A.c | 8925888 | 8925890 | | | |
| F49E12.4 | 4507789 | 10444495 | 8134778 | 4759282 | 18582039 |
| F40H3.5 | 14336772 | 4826764 | 14494990 | 20899626 | 9957244 |
| F49E11.4 | 13899332 | 18490353 | 6678423 | 14042040 | 15779065 |
| M01E10.2 | 2065167 | 18201921 | 3182940 | 18201923 | 14757167 |
| F26D11.10 | 16418341 | 6572227 | | | |
| Y37D8A.1 | 9790141 | 5031597 | 2209347 | 18104938 | 13639437 |
| Y17G7B.15 | 17434817 | 16945966 | 12697977 | 7661880 | 18551362 |
| R107.6 | | 14726914 | 7513045 | 16758540 | 12839687 |
| C23F12.1 | 7677526 | 14744078 | 4557597 | 5419655 | 8885790 |
| M106.5 | 11131728 | 13124696 | 1345668 | 4826659 | 19352984 |
| C06G3.2 | 9910266 | 14424665 | 13194197 | 3891936 | 9910292 |
| T28D6.2 | 135395 | 223556 | 135412 | 18601895 | 6755901 |
| W09D10.3 | 4506673 | 11177148 | 12837801 | 17865556 | 12832973 |
| W10D9.5 | 12842129 | 20902823 | | | |
| F54D5.11 | 4504195 | 13386074 | 18043581 | 228300 | 11611843 |
| F44B9.7 | 12847646 | 6677723 | 4506491 | 283966 | 13097123 |
| Y71H10B.1 | 6912598 | 2668557 | 12841987 | 18544261 | 7706749 |
| F21D5.5 | 14211141 | 6005836 | 5757919 | 12803393 | 14786918 |
| F20D12.2 | 11225270 | 19923191 | 7513026 | 13938593 | 14780851 |
| T22D1.10 | 5730023 | 6755382 | 4929561 | 9790083 | 4506753 |
| C24A1.4 | 1263081 | 1585320 | 14286268 | 3005702 | 5730039 |
| Y37A1A.1 | 3005702 | 5730039 | 1263081 | 14286268 | 1585320 |
| C30F12.1 | 18604558 | 13376632 | 14750657 | 2224587 | 16041792 |
| W09G3.1 | 18582801 | 7662058 | 18578718 | 6005796 | 14388374 |
| F13E6.1 | 13385202 | 4507643 | 11125673 | 15723372 | 17450493 |
| T21D12.3 | 9506989 | 16307140 | 5031957 | 11125356 | 10801584 |
| B0041.5 | 17391272 | 12836420 | 10437002 | 13376774 | 4758846 |
| B0286.4 | 11640600 | 7657385 | 12847218 | 7020899 | 6841484 |
| D1054.14 | 20841107 | 20472100 | 20881439 | 14249602 | 14149989 |
| F54C9.9 | 14602715 | 12804075 | 10438567 | 12711672 | 13649858 |
| B0513.7 | 3005702 | 5730039 | 1263081 | 14286268 | 1585320 |
| Y41D4A__3192.a | 12052882 | 8922808 | 12849037 | 18548855 | 16550576 |
| ZK686.3 | 14714487 | 6166601 | 1353701 | 6996934 | 14149775 |
| B0041.3 | 12843216 | 14585867 | | | |
| C05E11.1 | 14725463 | 12697975 | 16551959 | 15777193 | 15843561 |
| F38A5.1 | 18559316 | 14714703 | 8922938 | 13529584 | 13899211 |
| Y47G6A__245.b | 11360017 | 5689555 | 14725071 | 11360104 | 18544047 |
| R05F9.8 | 8099350 | 14759532 | 4507867 | 12842294 | 13928870 |
| W04A4.5 | 14124974 | 16553697 | 18566093 | 15809018 | 14602672 |
| Y49F6B.n | 6919955 | 15278160 | 15928532 | 14767139 | 5901878 |
| C47D12.7 | 13431657 | 6329805 | 8393672 | 6644293 | 18490684 |
| C32D5.11 | 4504867 | 13645747 | 18255721 | 13905224 | 12585549 |
| H32C10.3 | 9506623 | 4589536 | 14755049 | 6841238 | 3329427 |
| T21C9.2 | 7023936 | 15297473 | 16518394 | 8980452 | 7705397 |
| Y41E3.11 | 12803479 | 14786840 | 5901942 | 18204832 | 16041796 |
| Y57G11C.17 | 14198202 | 8922621 | 4826524 | 14149736 | 18490309 |
| T04C10.2 | 7019369 | 3894395 | 11177890 | 10433856 | 16923990 |
| F13D11.1 | 8392842 | 19484058 | 130728 | 13111975 | 4557010 |
| R04A9.4 | 124222 | 7546552 | 110568 | 4503535 | 6681293 |
| C54H2.5 | 6755698 | 19557691 | 2414516 | 5531849 | 18571517 |

TABLE XIII

| Novel Genes that Reduce Fat Content And Viability/Growth | | | | | |
|---|---|---|---|---|---|
| F37E3.1 | 4505343 | 627397 | 15988381 | 5441937 | 12851646 |
| Y37D8A.14 | 6680986 | 12858580 | 117100 | 18999392 | 4758038 |
| Y57G11C.12 | 4505359 | 400384 | 13385492 | | |
| F28B3.1 | 17471893 | 6686133 | 14043353 | 17457389 | 6686101 |
| C23H3.4 | 6678125 | 2853289 | 6685595 | 5454084 | 2136140 |
| E04A4.7 | 229351 | 118007 | 118014 | 117994 | 117966 |
| F01G10.1 | 12855432 | 388891 | 12018252 | 4507521 | 1729977 |
| F44D12.4 | 18203658 | 16758060 | 5031715 | 9055336 | 18656362 |
| F46E10.1 | 17390865 | 13376741 | 15559516 | 16553412 | 4164168 |
| F57B9.2 | 4589658 | 12653967 | 18598275 | 19354215 | 7706214 |
| H14A12.2 | 8393358 | 227665 | 68293 | 13543801 | 12832319 |
| H15N14.2 | 20913355 | 13489067 | 6679140 | 134267 | 90219 |
| K02F2..2 | 20892597 | 9951915 | 7709980 | 178277 | 13096485 |
| K06A4.5 | 17921976 | 6912406 | 9910256 | 13637831 | 4433351 |
| T05H4.4 | 1709233 | 1070443 | 4503327 | 19421846 | 553600 |
| T05H4.5 | 127847 | 1070444 | 17943396 | 1709233 | 19745150 |
| Y55F3A__750.e | 12841560 | 6755911 | 16758644 | 4759274 | 7949156 |
| B0285.1 | 14110390 | 14110387 | 7706549 | 4240297 | 14748750 |
| C16C2.3 | 1352493 | 9966773 | 12836107 | 13249985 | 346209 |
| W03F8.5 | 4504951 | 293690 | 126367 | 226290 | 6981142 |
| W07E6.2 | 8922428 | 12804063 | 17390943 | 3043443 | 7305363 |
| ZK1067.1 | 4503597 | 280818 | 119534 | 17432904 | 10880776 |
| ZK675.1 | 4506247 | 6679519 | 1335864 | 6679517 | 4325111 |
| C33D3.1 | 8648977 | 3123218 | 477102 | 15593990 | 5882288 |
| C34H3.a | 16506291 | 17298684 | 16877372 | 6754928 | 19344028 |
| D1081.2 | 14719546 | 18655799 | 10048414 | 4507205 | 7546482 |
| F10C1.5 | 13940223 | 18572015 | 11230443 | 12229781 | 11386173 |
| F22A3.1 | 6912580 | 7305415 | 18204910 | 15214598 | 4557551 |
| F23B12.7 | 1705659 | 5031625 | 6753402 | 10439934 | 10434534 |
| F25H8.3 | 13626125 | 7242979 | 9910122 | 7243073 | 6685072 |
| Y17G7A.2 | 18027804 | 11870006 | 18602376 | 6729087 | 19173808 |
| C01F6.8 | 12848135 | 2197127 | 1095482 | 7513563 | 1060971 |
| C56C10.8 | 17441804 | 2851417 | 115143 | 107909 | 29507 |
| C56E6.1 | 11967969 | 16758590 | 14141178 | 16158955 | 15146444 |
| W06D12.2 | 16306555 | 11560129 | 11177516 | 19483870 | 13124041 |
| W10D9.5 | 12842129 | 12844929 | 9910382 | 17475714 | 16930809 |
| Y61A9LA__75.a | 7661980 | 18575034 | 14737076 | 18576250 | 7243183 |
| C36B1.4 | 4506189 | 7106389 | 4092058 | 18577124 | 1346784 |
| CD4.6 | 9910833 | 8394060 | 4506179 | 14768212 | 13543551 |
| F23F12.6 | 2492517 | 5729991 | 1172637 | 3450955 | 7110701 |
| F39H11.5 | 3914439 | 14198355 | 3915806 | 16165126 | 13928866 |
| T23F2.1 | 12846285 | 14861836 | 9910440 | 12836608 | 18572937 |
| Y38A8.2 | 4506197 | 11424309 | 6755202 | 8394082 | 17447021 |
| C36E8.5 | 7106439 | 135490 | 5174735 | 14758306 | 12846758 |
| D2024.6 | 12841166 | 5453597 | 16740716 | 1345694 | 6671672 |
| F10C1.2 | 34228 | 125962 | 5031875 | 1072002 | 383110 |
| F20G4.3 | 13928704 | 1346640 | 13431706 | 17978023 | 12667788 |
| K07C5.1 | 5031571 | 15778930 | 14769120 | 12852068 | 1351867 |
| T04C12.5 | 71621 | 4501885 | 16304154 | 1351867 | 16359158 |
| Y19D2B.1 | 6678469 | 12850141 | 12839396 | 90217 | 2843123 |
| ZK593.5 | 13259510 | 4139121 | 1419567 | 13259508 | 6681147 |
| B0303.9 | 18105056 | 12621146 | 12859683 | 7514114 | 10439792 |
| C02C6.1 | 6681207 | 729381 | 1083647 | 18093102 | 539580 |
| C05D11.2 | 19343731 | 15553046 | 17978479 | 11345382 | 13385360 |
| F29G9.3 | 12005732 | 4506957 | 12837633 | 4557471 | 5630084 |
| F41C3.4 | 7634779 | 7705636 | 13385354 | 20340619 | 17488855 |
| K02D10.5 | 16758654 | 6685966 | 12836691 | 12963651 | 4759154 |
| T21E12.4 | 9506549 | 13384736 | 729378 | 18582791 | 2224591 |
| B0035.7 | 631691 | 17455198 | 18545931r | 1458139 | 18580602 |
| B0035.8 | 223096 | 280961 | 18564726 | 4504263 | 15030326 |
| B0035.9 | 12854993 | 12847763 | 4504301 | 70762 | 223582 |
| B0041.4 | 2500343 | 11968086 | 16579885 | 12846949 | 1363989 |
| C03C10.3 | 4557845 | 7106399 | 2500209 | 11256408 | 14743689 |
| C04H5.6 | 14318701 | 14250712 | 14752410 | 4503293 | 7770157 |
| C06A8.2 | 4507101 | 7243201 | | | |
| C08B11.5 | 5032069 | 18582960 | 18582878 | 4504715 | 17489281 |
| C09H10.2 | 4506651 | 14750580 | 13645150 | 9845295 | 17472837 |
| C15F1.e | 19424322 | 17511746 | 10436247 | 9966779 | 10433787 |
| C15H11.9 | 3183219 | 14719402 | 10946930 | 12857046 | 12845436 |
| C16A3.3 | 12834845 | 2498864 | 17454886 | 4454542 | 13385288 |
| C16A3.4 | 15529978 | 8922413 | 10435029 | 18583383 | 12698069 |
| C16A3.6 | 14042167 | 14210516 | 14747081 | 15341814 | 12853682 |
| C26D10.1 | 4502801 | 14278207 | 4389390 | 87057 | 132171 |
| C26F1.9 | 18592185 | 18590969 | 4506647 | 14738021 | 17449824 |
| C27F2.4 | 12846835 | 16226067 | 13384748 | 12843473 | 12652833 |
| C29F5.3 | 7662204 | 4521188 | 14750657 | 2224587 | 16041792 |
| C37H5.8 | 16158324 | 12653415 | 6754256 | 1072476 | 4758570 |

TABLE XIII-continued

Novel Genes that Reduce Fat Content And Viability/Growth

| | | | | | |
|---|---|---|---|---|---|
| C42D4.8 | 5902062 | 133327 | 2145091 | 7434727 | 4505939 |
| C47D12.6 | 14861852 | 12653491 | 14714853 | 12845562 | 4507367 |
| C50F4.5 | 223096 | 280961 | 18564726 | 15030326 | 16306566 |
| C52E4.3 | 4759158 | 17471847 | 2833357 | 12862083 | 7657315 |
| D1007.6 | 14195014 | 14782930 | 13540714 | 13639605 | 14195007 |
| F09E8.3 | 4505253 | 3108220 | 5725250 | 12655021 | 3986757 |
| F09F7.3 | 4505941 | 7022241 | 8922399 | 6677789 | 3005758 |
| F18A1.5 | 4506583 | 18390321 | 12860240 | 2624702 | 13096131 |
| F20D12.4 | 15214617 | 4759344 | 11387254 | 18546147 | 126369 |
| F22B3.1 | 12854993 | 12847763 | 4504301 | 70762 | 223582 |
| F22B5.2 | 8393308 | 6492222 | 2460200 | 4503517 | 14280325 |
| F22B5.9 | 15296128 | 5032011 | 6841566 | 12845588 | 12644592 |
| F26F4.10 | 586063 | 18043638 | 15149476 | 12847471 | 1711647 |
| F26F4.11 | 14589953 | 1710659 | 4406232 | 476961 | 6680928 |
| F32E10.4 | 6680598 | 4504901 | 6680596 | 14758897 | 2654139 |
| F37C12.11 | 4506699 | 17390310 | 12841661 | 13592073 | 12964241 |
| F37C12.9 | 5032051 | 12083607 | 10181112 | 7440317 | 16158168 |
| F45E12.3 | 11140811 | 13270467 | 13259127 | 16307345 | 13386300 |
| F45F2.13 | 4504281 | 4504299 | 386772 | 18595043 | 70749 |
| F54E12.1 | 4504281 | 4504299 | 386772 | 18595043 | 70749 |
| F54E12.5 | 631691 | 17455198 | 121983 | 8922758 | 18545931 |
| F55C5.8 | 7657617 | 134889 | 7513444 | 18044248 | 14041927 |
| F55F10.2 | 7529573 | 17512348 | 4678973 | 15029526 | 18604727 |
| F55G1.10 | 631691 | 17455198 | 18545931 | 1458139 | 18580602 |
| F58A4.4 | 6679459 | 110830 | 3676248 | 4506051 | 12847590 |
| H02I12.7 | 631691 | 17455198 | 18545931 | 1458139 | 18580602 |
| H06H21.3 | 4758254 | 12859663 | 11418342 | 4503499 | 3746340 |
| H06I04.i | 18028291 | 17017991 | 13384672 | 15126717 | 7019917 |
| H19M22.1 | 18676514 | 18702313 | 7959295 | 9507013 | 18860896 |
| H23L24.c | 11024694 | 17480509 | 18587523 | 18572403 | 12853018 |
| K03A1.1 | 7305139 | 70743 | 70749 | 4504281 | 2119013 |
| K12D12.2 | 18566874 | 1504030 | 12852259 | 17646641 | |
| R05D11.3 | 5031985 | 2914436 | 2780953 | 7246005 | 17451119 |
| T01C3.6 | 4506691 | 18549572 | 18591367 | 7305445 | 70920 |
| T02G5.9 | 16716381 | 586059 | 11095909 | 505108 | 2501023 |
| T10C6.11 | 223096 | 280961 | 18564726 | 87672 | 4504263 |
| T10C6.12 | 631691 | 17455198 | 121983 | 8922758 | 18545931 |
| T10C6.13 | 4504281 | 4504299 | 386772 | 18595043 | 70749 |
| T13H5.4 | 1082801 | 18202846 | 5803167 | 12854243 | 18578493 |
| T23B12.2 | 14756630 | 12832465 | 12653925 | 7705722 | 9956063 |
| T28F3.2 | 18565400 | 13242237 | 5729877 | 1708309 | 347019 |
| VW02B12L.1 | 12643966 | 12025532 | 7329154 | 13928826 | 3915315 |
| W07E6.1 | 189422 | 5453792 | 14784289 | 477430 | 12653741 |
| Y106G6H.3 | 4506631 | 17463853 | 17435581 | 18561308 | 18087841 |
| Y41D4A__3457.d | 4758844 | 6093462 | 18875386 | 16758834 | 18559983 |
| Y47D3A.c | 6679409 | 6015013 | 15858951 | 118838 | 479803 |
| Y62E10A.d | 18561782 | 133063 | 12849327 | 1173072 | 4506671 |
| Y71G12A__187.b | 5901998 | 4507131 | 14755615 | 4507133 | 13644938 |
| Y76B12C__66.c | 18570089 | 1706101 | 16878041 | 16751835 | 9558725 |
| ZK550.4 | 11432489 | 5031727 | 12847734 | | |
| ZK652.1 | 14755615 | 4507131 | 5901998 | 4507133 | 11138539 |
| C06A1.1 | 2144498 | 17865351 | 6005942 | 6678559 | 1174636 |
| C15H9.4 | 14916851 | 14753980 | 14916847 | 14724805 | 13874437 |
| C30B5.6 | 12834595 | 14250466 | 18605027 | 7706047 | 12856705 |
| C30C11.2 | 15310156 | 16550621 | 4506229 | 12652653 | 15126760 |
| C37H5.5 | 18482381 | 18389431 | 10434534 | 7208452 | 10439934 |
| D1054.3 | 12846547 | 12841721 | 12861014 | 5730041 | 18567662 |
| F19F10.9 | 2342526 | 8394236 | 10863889 | 4427065 | 13928810 |
| F32E10.1 | 13477303 | 13430872 | 17437341 | 10436236 | 14010904 |
| F33A8.1 | 10047283 | 10438214 | 13385386 | 10439972 | 14727768 |
| F54F2.7 | 8923431 | 17470330 | 7513001 | 13446227 | 14010849 |
| R12E2.2 | 7705322 | | | | |
| R144.2 | 13431763 | 4240137 | 7706224 | 13435542 | 14603356 |
| Y51H4A.m | 8923726 | 4153862 | 18568744 | 7021918 | |
| Y53C12B.2 | 17390336 | 10047140 | 13384846 | 12844974 | |
| ZK121.c | 7662442 | 7661874 | 15149484 | 18599919 | 11360196 |
| ZK546.2 | 12834355 | 18597991 | 12833443 | 12859847 | 12849514 |
| ZK795.3 | 12835200 | 12850634 | 18478512 | 15529982 | 12845999 |
| C04G2.6 | 18582324 | 19923416 | 7451876 | 7674415 | 7512650 |
| F41H10.7 | 17454617 | 20137972 | 18496985 | 12836437 | 16151801 |
| T10B5.5 | 6671704 | 5453607 | 12848801 | 1800303 | 13540473 |

Novel Genes that Increase Fat Content

Table XIV shows *C. elegans* genes and their mammalian orthologs that have not previously been shown to increase fat content when inactivated. This list identifies the *C. elegans* genes by *C. elegans* cosmid name and open reading frame number. The mammalian orthologs are listed by the Genbank protein accession number.

TABLE XIV

| Novel Genes that Increase Fat Content | | | | | |
|---|---|---|---|---|---|
| C33A12.6 | 549160 | 6537138 | 19527110 | 5803213 | 18308170 |
| VF13D12L.1 | 7022512 | 7705558 | 11493904 | 12963757 | 11281329 |
| C37F5.1 | 7767065 | 4100456 | 535923 | 14758312 | 4885201 |
| C56C10.10 | 4502009 | 1765936 | 7709982 | 6225016 | 8248030 |
| F16B4.9 | 6681852 | 12803755 | 5453940 | 346286 | 1144348 |
| K10C3.6 | 7657395 | 6681852 | 6680239 | 11559939 | 227511 |
| R11H6.5 | 20534593 | 4758602 | 13385872 | 6855637 | 13278459 |
| C04G2.2 | 20900385 | 20555151 | 18201865 | 7949025 | 20149530 |
| C09G5.8 | 4589654 | 20888031 | 9965252 | 9966409 | 9965248 |
| C18H9.7 | 20839618 | 6677669 | 15619013 | 20178328 | 631056 |
| C24F3.2 | 6005956 | 11560052 | 12963553 | 12835696 | 13435759 |
| F39B1.1 | 11259849 | 20843206 | 20561002 | 4505799 | 6755058 |
| F46C5.6 | 10047321 | 17402886 | 12858102 | 1702997 | 11386167 |
| F56D5.9 | 1695739 | 2642034 | 2143944 | 7513459 | 13647589 |
| F56H11.6 | 18201865 | 14781533 | 5579454 | 547767 | 11545751 |
| R10D12.10 | 18201865 | 14781533 | 1311054 | 1346368 | 20149530 |
| T04B2.2 | 6679773 | 1673620 | 6003683 | 4885231 | 4503687 |
| T04C9.1 | 7662208 | 6433901 | 14587851 | 13386454 | 20340540 |
| W03A5.4 | 19923689 | 19923274 | 7514059 | 1857137 | 1857139 |
| W08D2.1 | 17402916 | 5020354 | 16716413 | 17402914 | 13518017 |
| Y11D7A.9 | 7657102 | 6606290 | 7512548 | 14602865 | 16758956 |
| ZC513.1 | 14583090 | 18377358 | 2497615 | 13929458 | 5453914 |
| C43H6.9 | 3935134 | 2598978 | 1169965 | 4504119 | 3287976 |
| F08H9.5 | 20903753 | 6492289 | 4557503 | 20473663 | 14388673 |
| F32B6.9 | 4759310 | 8923137 | 18044531 | 3335161 | 18476496 |
| ZC410.4 | 9988112 | 14149764 | 18652258 | 11496265 | 4504851 |
| C18H9.5 | 9719374 | 6912666 | 9719376 | 18252796 | 16758166 |
| F14E5.1 | 687622 | 8394301 | 121750 | 20301952 | 6755550 |
| F52H2.2 | 4507053 | 6103627 | 3970791 | 7106415 | 6319236 |
| C04G2.4 | 13928870 | 7305623 | 6671046 | 8099350 | 20070156 |
| F32B6.6 | 8099350 | 14759532 | 3320446 | 12842294 | 13928870 |
| C15A11.3 | 19070657 | 11907926 | 11934950 | 11907928 | 11934951 |
| Y38F1A.9 | 14211895 | 14748249 | 3928489 | 7513113 | 7657361 |
| K02D7.5 | 6677733 | 12852065 | 20872938 | 13543580 | 10047124 |
| C14A4.1 | 19527182 | 13775228 | 20862789 | 3482908 | 16306483 |
| C44E4.5 | 14042905 | 12654293 | 14718862 | 14745963 | 20902053 |
| D1007.5 | 20892497 | 8922756 | 20845045 | 10435222 | 13385900 |
| F25H8.1 | 18381001 | 14724179 | 4454968 | 18572769 | 18043204 |
| F26H9.4 | 20893587 | 20536806 | 14029540 | 3413920 | 12620200 |
| W06H12.1 | 13236593 | 20454983 | 20521730 | 16307459 | 20864376 |
| Y57A10B.1 | 12836671 | 19584503 | 8923613 | 7513036 | 19263985 |

Novel Genes with No Previously Identified Function

Below are shown lists of *C. elegans* genes and mammalian polypeptides for which no known function has been previously identified. This list identifies the *C. elegans* genes by *C. elegans* cosmid name and open reading frame number. The mammalian orthologs are listed by the Genbank protein accession number. It has been demonstrated herein that the genes and polypeptides identified in Tables XV, XVI, and XVII are involved in fat metabolism.

TABLE XV

| Reduced Fat: No Previous Function Identified | | | | |
|---|---|---|---|---|
| *C. elegans* Gene | Mammalian Accession Numbers | | | |
| AH10.1 | 13376741 | 15559516 | 17390865 | |
| C06E7.3 | 13097429 | | | |
| F23H11.9 | 10092647 | | | |
| T12A2.1 | 18579028 | 18490737 | | |
| Y41E3.10 | 12653785 | | | |
| C46E10.9 | 18561872 | 18595962 | | |
| T09F3.1 | 16551981 | 18590023 | 18546120 | |
| C33H5.17 | 17939660 | 14249740 | 14042873 | 18204508 |
| F41D9.1 | 14165549 | 11034851 | | |
| K10D3.5 | 14042287 | 15079264 | 11360161 | |
| M01B12.5 | 16549132 | 13899340 | | |
| R07E5.1 | 14763089 | 8922283 | | |
| ZK909.3 | 18584663 | | | |
| F33G12.2 | 14150114 | | | |
| F14D12.2 | 17462167 | 10433878 | 14789889 | |
| F20D1.9 | 13375983 | 18848167 | | |
| F49E11.4 | 13899332 | 18490353 | 14042040 | |
| B0286.4 | 7020899 | 6841484 | | |
| B0513.7 | 3005702 | | | |
| C05E11.1 | 16551959 | | | |
| C30F12.1 | 13376632 | 16041792 | | |
| F38A5.1 | 18559316 | 14714703 | 8922938 | 13529584 |
| F54C9.9 | 14602715 | 12804075 | 10438567 | 12711672 |
| Y41D4A_3192.a | 12052882 | 8922808 | 18548855 | 16550576 |
| H32C10.3 | 9506623 | | | |
| T21C9.2 | 7023936 | | | |

TABLE XVI

| Reduced Fat and Reduced Growth/Viability: No Previous Function Identified | | | | | |
|---|---|---|---|---|---|
| *C. elegans* Gene | Mammalian Accession Numbers | | | | |
| F46E10.1 | 17390865 | 13376741 | 15559516 | 16553412 | 4164168 |
| Y53C12B.2 | 17390336 | 10047140 | 13384846 | 12844974 | |
| F32E10.1 | 13477303 | 13430872 | 17437341r | 10436236d | 14010904 |
| F08D12.7 | 19527308 | 4557445 | | | |
| C53B7.4 | 15929392 | | | | |
| W07E6.2 | 8922428 | 12804063 | 17390943 | 3043443 | |
| Y17G7A.2 | 18027804 | | | | |
| C15H11.9 | 3183219 | | | | |
| C16A3.4 | 15529978 | 8922413 | 10435029 | | |
| C16A3.6 | 14042167 | | | | |
| C26F1.9 | 18592185 | 18590969 | | | |
| C47D12.6 | 14861852 | 14714853 | | | |

TABLE XVI-continued

| Reduced Fat and Reduced Growth/Viability: No Previous Function Identified | | | |
|---|---|---|---|
| *C. elegans* Gene | Mammalian Accession Numbers | | |
| H06104.i | 18028291 | 7019917 | |
| Y62E10A.d | 18561782 | | |
| C15H9.4 | 14916851 | 14916847 | |
| F54F2.7 | 8923431 | | |
| Y51H4A.m | 8923726 | 18568744 | 7021918 |

TABLE XVII

| Increased Fat Genes: No Previous Function Identified | | | | |
|---|---|---|---|---|
| *C. elegans* Genes | Mammalian Accession Numbers | | | |
| VF13D12L.1 | 7022512 | 11281329 | | |
| C44E4.5 | 14042905 | 12654293 | 14745963 | |
| F25H8.1 | 18381001 | 14724179 | 4454968 | 18572769 |
| W06H12.1 | 13236593 | | | |

Working Examples of Mammalian Orthologs

LPO-3 Mammalian Ortholog

The ABC transporter, lpo-3, encodes the Wormpep database protein C34G6.4 (Wormpep is the database of translated and assembled open reading frames derived from the *C. elegans* genome sequence). RNAi analysis of lpo-3 indicated that its inactivation dramatically reduces fat levels in wild-type nematodes, and in high fat nematode mutants (e.g., tub-1, tph-1, daf-2, lpo-1, and lpo-6). The inactivation of C34G6.4 reverses a *C. elegans* high fat phenotype, regardless of whether the increase in fat level results from a neural defect, such as a defect in tub-1, which is expressed in sensory neurons, or a defect in tph-1, which is expressed in serotonergic neurons; or from a neuroendocrine defect, such as a defect in the daf-2 insulin receptor gene, which may be expressed in neurons (Wolkow et al., *Science* 290:147–50, 2000).

Blast analysis of C34G6.4 was carried out versus the Genbank protein database, that contains the complete genome sequences of humans, *Drosophila,* and *C. elegans* (as well as yeast and other microbes). This analysis identified C34G6.4 highly related proteins. These results are shown below.

```
gi|17508505|ref|NP_491707.1|  (NM_059306) ABC transporter [C. 2131 0.0 .... (C34G6.4)
gi|7511698|pir||T31073  multidrug resistance p-glycoprotein ... 1539 0.0 ... .(mouse)
gi|6755046|ref|NP_035205.1|  (NM_011075) ATP-binding cassett...  969 0.0
gi|2506118|sp|P08183|MDR1_HUMAN  Multidrug resistance protein. 964 0.0 (human shown below)
gi|2506118|sp|P08183|MDR1_HUMAN  Multidrug resistance protein 1 (P-glycoprotein 1)
gi|1070659|pir||DVHU1  multidrug resistance protein 1 - human
gi|386862|gb|AAA59576.1|  (M29447) P glycoprotein [Homo sapiens]          Length = 1280

Score = 964 bits (3277), Expect = 0.0
Identities = 573/1256 (45%), Positives = 828/1256 (65%), Gaps = 18/1256 (1%)

Query: 13   KPLLKRSHSSDSSIDESTVKLTNYGIFYYTQGVDLLLLITGTVAAVIHGAGFPLLAIVLG  72
             K   K ++ S+    E    ++ + +F Y+  +D L ++ GT+AA+IHGAG PL+ +V G
Sbjct: 14   KNFFKLNNKSEKDKKEKKPTVSVFSMFRYSNWLDKLYMVVGTLAAIIHGAGLPLMMLVFG  73

Query: 73   GMTTVFLRAQN-SDFVVGVDNVNPEGLVPISLDEFNSEVVKYCIYYLVLGVLMFFTSYVQ  131
              MT +F  A N  D +  + N +        ++     ++ +Y  ++  +G  +    +Y+Q
Sbjct: 74   EMTDIFANAGNLEDLMSNITNRSDINDTGFFMN-LEEDMTRYAYYYSGIGAGVLVAAYIQ  132

Query: 132  IACFESYAERLVHKLRQNYLKAILRQQIQWFDKQQTGNLTARLTDDLERVREGLGDKFAL  191
             ++ +    A R +HK+R+ +  AI+RQ+I WFD    G L  RLTDD+ ++ EG+GDK  +
Sbjct: 133  VSFWCLAAGRQIHKIRKQFFHAIMRQEIGWFDVHDVGELNTRLTDDVSKINEGIGDKIGM  192

Query: 192  LVQMFAAFLAGYGVGFFYSWSMTLVMMGFAPLIVLSGAKMSKSMATRTRVEQETYAVAGA  251
              Q  A F  G+ VGF   W +TLV++  +P++ LS A  +K +++ T  E   YA AGA
Sbjct: 193  FFQSMATFFTGFIVGFTRGWKLTLVILAISPVLGLSAAVWAKILSSFTDKELLAYAKAGA  252

Query: 252  IAEETFSSIRTVHSLNGHKRELDRFYNALEVGRQTGIVKYCYMGIGVGFSNLCMYSSYAL  311
             +AEE  ++IRTV +  G K+EL+R+  LE  ++ GI K     I +G + L +Y+SYAL
Sbjct: 253  VAEEVLAAIRTVIAFGGQKKELERYNKNLEEAKRIGIKKAITANISIGAAFLLIYASYAL  312

Query: 312  AFWYGSTLIINDPTFDRGLIFTVFFAVLSGSTSLGGALPHLASFGTARGAASTVLRVINS  371
             AFWYG+TL+++   +  G + TVFF+VL G+ S+G A P + +F  ARGAA  + ++I++
Sbjct: 313  AFWYGTTLVLSGE-YSIGQVLTVFFSVLIGAFSVGQASPSIEAFANARGAAYEIFKIIDN  371

Query: 372  HPKIDRYSLEGILVDNMKGDISFKDVHFRYPSRKDIHVLKGISLELKAGDKIALVGSSGC  431
              P ID YS  G   DN+KG++ F++VHF YPSRK++ +LKG++L+++++G  +ALVG+SGC
Sbjct: 372  KPSIDSYSKSGHKPDNIKGNLEFRNVHFSYPSRKEVKILKGLNLKVQSGQTVALVGNSGC  431

Query: 432  GKSTIVNLLQRFYDPTKGRVLIDGVDLREVNVHSLREQIGIVSQEPVLFDGTIYENIKMG  491
             GKST V L+QR YDPT+G V +DG D+R +NV  LRE IG+VSQEPVLF  TI ENI+ G
Sbjct: 432  GKSTTVQLMQRLYDPTEGMVSVDGQDIRTINVRFLREIIGVVSQEPVLFATTIAENIRYG  491

Query: 492  NEHATHDQVVEACKMANANDFIKRLPDGYGTRVGEKGVQLSGGQKQRIAIARALVKNPKI  551
             E+ T D++ +A K ANA DFI +LP  + T VGE+G QLSGGQKQRIAIARALV+NPKI
Sbjct: 492  RENVTMDEIEKAVKEANAYDFIMKLPHKFDTLVGERGAQLSGGQKQRIAIARALVRNPKI  551

Query: 552  LLLDEATSALDTEAEREVQGALDQAQAGRTTIIVAHRLSTIRNVDRIFVFKAGNIVESGS  611
             LLLDEATSALDTE+E  VQ ALD+A+ GRTTI++AHRLST+RN D I  F G IVE G+
Sbjct: 552  LLLDEATSALDTESEAVVQVALDKARKGRTTIVIAHRLSTVRNADVIAGFDDGVIVEKGN  611
```

-continued

```
Query: 612  HEELMSKQGIFYDMTQAQVVRQQ--------QQEAGKDIEDTISESAHSHLRSKSSTRSA  663
            H+ELM ++GI++ +    Q     +        + ++  D  +   S  + S L RK STR +
Sbjct: 612  HDELMKEKGIYFKLVTMQTAGNEVELENAADESKSEIDALEMSSNDSRSSLIRKRSTRRS  671

Query: 664  I--SIATSIHQLAEEVEECKAPPTSMFKIFKFNGDKVGWFIGGIFGAFIFGSVTPVFALV  721
            +  S A        +E  +    PP S ++I K N   +   +F+ G+F A I G + P FA++
Sbjct: 672  VRGSQAQDRKLSTKEALDESIPPVSFWRIMKLNLTEWPYFVVGVFCAIINGGLQPAFAII  731

Query: 722  YAEIFNVYSLPAD--QMQANVYFWCGMFVLMGITFFVGFFTSANCLGRCGESLTMKLRFE  779
            +++I  V++   D    + N   +  +F+ +GI  F+ FF       G+ GE LT +LR+
Sbjct: 732  FSKIIGVFTRIDDPETKRQNSNLFSLLFLALGIISFITFFLQGFTFGKAGEILTKRLRYM  791

Query: 780  AFKNLLRQDIAFYDDLRHGTGKLCTRFATDAPNVR-YVFTRLPVVLASIVTICGALGIGF  838
             F+++LRQD++++DD ++ TG L TR A DA  V+  + +RL V+  +I  +   + I F
Sbjct: 792  VFRSMLRQDVSWFDDPKNTTGALTTRLANDAAQVKGAIGSRLAVITQNIANLGTGIIISF  851

Query: 839  YYGWQLALILVVMVPLLVMGGYFEMQMRFGKQIRDTQLLEEAGKVASQAVEHIRTVHSLN  898
             YGWQL L+L+ +VP++ + G  EM+M  G+ ++D + LE AGK+A++A+E+ RTV SL
Sbjct: 852  IYGWQLTLLLLAIVPIIAIAGVVEMKMLSGQALKDKKELECAGKIATEAIENFRTVVSLT  911

Query: 899  RQEQFHFTYCEYLREPFNTNLKHAHTYGAVFAFSQSLIFFMYAAAFYLGSIFVNQQAMQP  958
            ++++F   Y + L+ P+  +L+ AH +G  F+F+Q++++F YA  F  G+  V  + M
Sbjct: 912  QEQKFEHMYAQSLQVPYRNSLRKAHIFGITFSFTQAMMYFSYAGCFRFGAYLVAHKLMSF  971

Query: 959  IDVYRVFFAISFCGQMIGNTTSFIPDVVKARLAASLLFYLIEHPTPIDSLSDSGIV-KPI 1017
             DV  VF A+ F    +G  +SF PD  KA+++A+ +  +IE    IDS S  G++    +
Sbjct: 972  EDVLLVFSAVVFGAMAVGQVSSFAPDYAKAKISAAHIIMIIEKTPLIDSYSTEGLMPNTL 1031

Query: 1018 TGNISIRNVFFNYPTRKDTKVLQGFTLDIKAGKTVALVGHSGCGKSTIMGLLERFYNQDK 1077
             GN++  V FNYPTR D  VLQG +L++K G+T+ALVG SGCGKST++ LLERFY+
Sbjct: 1032 EGNVTFGEVVFNYPTRPDIPVLQGLSLEVKKGQTLALVGSSGCGKSTVVQLLERFYDPLA 1091

Query: 1078 GMIMIDGDNIRNLNISSLREQVCIVSQEPTLFDCTIGENICYGTN-RNVTYQEIVEAAKM 1136
            G +++DG  I+ LN+  LR  + IVSQEP LFDC+I ENI YG N R V+ +EIV AAK
Sbjct: 1092 GKVLLDGKEIKRLNVQWLRAHLGIVSQEPILFDCSIAENIAYGDNSRVVSQEEIVRAAKE 1151

Query: 1137 ANIHNFILGLPDGYDTHVGEKGTQLSGGQKQRIAIARALVRSPSVLLLDEATSALDTESE 1196
            ANIH FI  LP+ Y T VG+KGTQLSGGQKQRIAIARALVR P +LLLDEATSALDTESE
Sbjct: 1152 ANIHAFIESLPNKYSTKVGDKGTQLSGGQKQRIAIARALVRQPHILLLDEATSALDTESE 1211

Query: 1197 KIVQEALDAAKQGRTCLVIAHRLSTIQNSDVIAIVSEGKIVEKGTHDELIRKSEIY 1252
            K+VQEALD A++GRTC+VIAHRLSTIQN+D+I +   G++ E GTH +L+ +  IY
Sbjct: 1212 KVVQEALDKAREGRTCIVIAHRLSTIQNADLIVVFQNGRVKEHGTHQQLLAQKGIY 1267

Score = 379 bits (1280), Expect = e-103
Identities = 238/622 (38%), Positives = 367/622 (58%), Gaps = 25/622 (4%)

Query: 18   RSHSSDSSIDESTVKLTNYGIFYYTQGVDLLLLITGTVAAVIHGAGFPLLAIVLGGMTTV 77
            R S+ ++DES   ++ + I       +     + G   A+I+G   P  AI+  + V
Sbjct: 680  RKLSTKEALDESIPPVSFWRIMKLNL-TEWPYFVVGVFCAIINGGLQPAFAIIFSKIIGV 738

Query: 78   FLRAQNSDFVVGVDNVNPEGLVPISLDEFNSEVVKYCIYYLVLGVLMFFTSYVQIACFES 137
            F R + +      N+                    + + +L LG++ F T ++Q   F
Sbjct: 739  FTRIDDPETKRQNSNL-------------------FSLLFLALGIISFITFFLQGFTFGK 779

Query: 138  YAERLVHKLRQNYLKAILRQQIQWFD--KQQTGNLTARLTDDLERVREGLGDKFALLVQM 195
              E L  +LR    +++LRQ + WFD  K  TG LT RL +D  +V+  +G + A++ Q
Sbjct: 780  AGEILTKRLRYMVFRSMLRQDVSWFDDPKNTTGALTTRLANDAAQVKGAIGSRLAVITQN 839

Query: 196  FAAFLAGYGVGFFYSWSMTLVMMGFAPLIVLSGAKMSKSMATRTRVEQETYAVAGAIAEE 255
            A    G  + F Y W +TL+++  P+I ++G   K ++ +  +++   AG IA E
Sbjct: 840  IANLGTGIIISFIYGWQLTLLLLAIVPIIAIAGVVEMKMLSGQALKDKKELEGAGKIATE 899

Query: 256  TFSSIRTVHSLNGHKRELDRFYNALEVGRQTGIVKYCYMGIGVGFSNLCMYSSYALAFWY 315
              + RTV SL  ++     +  +L+V  +  + K   GI  F+   MY SYA  F +
Sbjct: 900  AIENFRTVVSLTQEQKFEHMYAQSLQVPYRNSLRKAHIFGITFSFTQAMMYFSYAGCFRF 959

Query: 316  GSTLIINDPTFDRGLIFTVFFAVLSGSTSLGGALPHLASFGTARGAASTVLRVINSHPKI 375
            G+ L+ +       +  VF AV+ G+ ++G     + A+ +A+ ++ +I   P I
Sbjct: 960  GAYLVAHK-LMSFEDVLLVFSAVVFGAMAVGQVSSFAPDYAKAKISAAHIIMIIEKTPLI 101

Query: 376  DPYSLEGILVDNMKGDISFKDVHFRYPSRKDIHVLKGISLELKAGDKIALVGSSGCGKST 435
            D YS EG++  + ++G+++F +V F YP+R DI VL+G+SLE+K G  +ALVGSSGCGKST
Sbjct: 1019 DSYSTEGLMPNTLEGNVTFGEVVFNYPTRPDIPVLQGLSLEVKKGQTLALVGSSGCGKST 107

Query: 436  IVNLLQRFYDPTKGRVLIDGVDLREVNVHSLREQIGIVSQEPVLFDGTIYENIKMGNEH- 494
            +V LL+RFYDP  G+VL+DG +++ +NV  LR  +GIVSQEP+LFD +I ENI  G+
Sbjct: 1079 VVQLLERFYDPLAGKVLLDGKEIKRLNVQWLRAHLGIVSEQPILFDSCIAENIAYGDNSR 1138

Query: 495  -ATHDQVVEACKMANANDFIKRLPDGYGTRVGEKGVQLSGGQKQRIAIARALVKNPKILL 553
             + +++V A K AN + FI+ LP+ Y T+VG+KG QLSGGQKQRIAIARALV+ P ILL
Sbjct: 1139 VVSQEEIVRAAKEANIHAFIESLPNKYSTKVGDKGTQLSGGQKQRIAIARALVRQPHILL 119

Query: 554  LDEATSALDTEAEREVQGALDQAQAGRTTIIVAHRLSTIRNVDRIFVFKAGNIVESGSHE 613
            LDEATSALDTE+E+ VQ ALD+A+ GRT I++AHRLSTI+N D I VF+ G + E G+H+
Sbjct: 1199 LDEATSALDTESEKVVQEALDKAREGRTCIVIAHRLSTIQNADLIVVFQNGRVKEHGTHQ 125

Query: 614  ELMSKQGIFYDMTQAQVVRQQQ 635
            +L++++GI++ M  Q  ++Q
Sbjct: 1259 QLLAQKGIYFSMVSVQAGTKRQ 1280

Score = 327 bits (1104), Expect = 3e-88
Identities = 226/610 (37%), Positives = 342/610 (56%), Gaps = 27/610 (4%)

Query: 674  AEEVEECKAPPTSMFKIFKF-NGDKVGWFIGGIFGAFIFGSVTPVFALVYAEIFNVYSLP 732
            +E+ ++ K P  S+F +F++ N     + + G  A I G+  P+  LV+ E+ ++++
Sbjct: 23   SEKDKKEKKPTVSVFSMFRYSNWLDKLYMVVGTLAAIIHGAGLPLMMLVFGEMTDIFANA 82

Query: 733  AD---------------------QMQANVYFWCGMFVLMGITFFVGFFTSANCLGRCGES 771
            +                     ++ ++  +  +  +G  V  +  +
Sbjct: 83   GNLEDLMSNITNRSDINDTGFFMNLEEDMTRYAYYYSGIGAGVLVAAYIQVSFWCLAAGR 142

Query: 772  LTMKLRFEAFKNLLRQDIAFYDDLRHGTGKLCTRFATDAPNV-RYVFTRLPVVLASIVTI 830
               K+R + F  ++RQ+I ++D  H G+L TR  D  +   ++ +  S+ T
Sbjct: 143  QIHKIRKQFFHAIMRQEIGWFD--VHDVGELNTRLTDDVSKINEGIGDKIGMFFQSMATF 200
```

-continued

```
Query: 831  CGALGIGFYYGWQLALILVVMVPLLVMGGYFEMQMRFGKQIRDTQLLEEAGKVASQAVEH 890
                 +GF  GW+L L+++ + P+L +      ++      ++      +AG VA + +
 Sbjct: 201  FTGFIVGFTRGWKLTLVILAISPVLGLSAAVWAKILSSFTDKELLAYAKAGAVAEEVLAA 260

Query: 891  IRTVHSLNRQEQFHFTYCEYLREPFNTNLKHAHTYGAVFAFSQSLIFFMYAAAFYLGSIF 950
            IRTV +   Q++    Y + L E     +K A T        +  LI   YA AF+ G+
Sbjct: 261  IRTVIAFGGQKKELERYNKNLEEAKRIGIKKAITANISIGAAFLLIYASYALAFWYGTTL 320

Query: 951  VNQQAMQPIDVYRVFFAISFCGQMIGNTTSFIPDVVKARLAASLLFYLIEHPTPIDSLSD 1010
            V          V  VFF++      +G  +  I      AR AA  +F +I++   IDS S
Sbjct: 321  VLSGEYSIGQVLTVFFSVLIGAFSVGQASPSIEAFANARGAAYEIFKIIDNKPSIDSYSK 380

Query: 1011 SG-IVKPITGNISIRNVFFNYPTRKDTKVLQGFTLDIKAGKTVALVGHSGCGKSTIMGLL 1069
            SG     I GN+  RNV F+YP+RK+ K+L+G  L +++G+TVALVG+SGCGKST + L+
Sbjct: 381  SGHKPDNIKGNLEFRNVHFSYPSRKEVKILKGLNLKVQSGQTVALVGNSGCGKSTTVQLM 440

Query: 1070 ERFYNQDKGMIMIDGDNIRNLNISSLREQVCIVSQEPTLFDCTIGENICYGTNRNVTYQE 1129
            +R Y+  +GM+ +DG +IR +N+  LRE + +VSQEP LF  TI ENI YG   NVT  E
Sbjct: 441  QRLYDPTEGMVSVDGQDIRTINVRFLREIIGVVSQEPVLFATTIAENIRYG-RENVTMDE 499

Query: 1130 IVEAAKMANIHNFILGLPDGYDTHVGEKGTQLSGGQKQRIAIARALVRSPSVLLLDEATS 1189
            I +A K AN ++FI+ LP  +DT VGE+G QLSGGQKQRIAIARALVR+P +LLLDEATS
Sbjct: 500  IEKAVKEANAYDFIMKLPHKFDTLVGERGAQLSGGQKQRIAIARALVRNPKILLLDEATS 559

Query: 1190 ALDTESEKIVQEALDAAKQGRTCLVIAHRLSTIQNSDVIAIVSEGKIVEKGTHDELIRKS 1249
            ALDTESE +VQ ALD A++GRT +VIAHRLST++N+DVIA   +G IVEKG HDEL+++
Sbjct: 560  ALDTESEAVVQVALDKARKGRTTIVIAHRLSTVRNADVIAGFDDGVIVEKGNHDELMKEK 619

Query: 1250 EIYQKFCETQ 1259
             IY K    Q
Sbjct: 620  GIYFKLVTMQ 629
```

The following exemplary BLAST search illustrates how the searches were carried out and how the list of genes was annotated. The C34G6.4 blast analysis also identified the following related proteins.

| | | | |
|---|---|---|---|
| gi\|19743730\|gb\|AAL92458.1\| | (AY082609) ATP-binding cassette . . . | 963 | 0.0 |
| gi\|307180\|gb\|AAA59575.1\| | (M14758) P-glycoprotein [*Homo sapi* . . . | 961 | 0.0 |
| gi\|8926217\|gb\|AAF81747.1\| | (AF269224) his-tagged-multidrug r . . . | 959 | 0.0 |
| gi\|266517\|sp\|P21447\|MDR3_MOUSE | Multidrug resistance protein . . . | 958 | 0.0 |
| gi\|6755048\|ref\|NP_035206.1\| | (NM_011076) Abcb1a; P glycoprot . . . | 958 | 0.0 |
| gi\|126928\|sp\|P21449\|MDR2_CRIGR | Multidrug resistance protein . . . | 957 | 0.0 |
| gi\|4505769\|ref\|NP_000918.1\| | (NM_000927) ATP-binding cassett . . . | 957 | 0.0 |
| gi\|2149087\|gb\|AAB58489.1\| | (U78609) multidrug resistance pro . . . | 955 | 0.0 |
| gi\|2852441\|gb\|AAC02113.1\| | (AF045016) multidrug resistance p . . . | 954 | 0.0 |
| gi\|1269241\|sp\|P21448\|MDR1_CRIGR | Multidrug resistance protein . . . | 952 | 0.0 |
| gi\|833699\|gb\|AAA75000.1\| | (U17608) multidrug resistance prot . . . | 952 | 0.0 |
| gi\|7739773\|gb\|AAF69007.1\|AF257746_1 | (AF257746) multidrug re . . . | 952 | 0.0 |
| gi\|1362689\|pir\|\|S55692 | multidrug resistance protein homolog . . . | 952 | 0.0 |

When the most closely related human amino acid sequence (LOCUS: MDR1_HUMAN 1280 aa linear PRI 16-OCT-2001; DEFINITION: Multidrug resistance protein 1 (P-glycoprotein 1). ACCESSION P08183) was used as a query versus the Genbank wormpep database, the C34G6.4 transporter had the second highest homology score. (The top four homologs have nearly equivalent scores of about 1000 bits).

| Sequences producing significant alignments: | | (bits) | Value |
|---|---|---|---|
| gi\|17558664\|ref\|NP_507487.1\| | (NM_075086) multidrug resistan . . . | 1081 | 0.0 |
| gi\|17508505\|ref\|NP_491707.1\| | (NM_059306) abc transporter [*C* . . . | 1073 | 0.0 |
| gi\|17541710\|ref\|NP_502413.1\| | (NM_070012) multidrug resistan . . . | 1022 | 0.0 |
| gi\|462583\|sp\|P34712\|MDR1_CAEEL | Multidrug resistance protein . . . | 1021 | 0.0 |
| gi\|17569145\|ref\|NP_509902.1\| | (NM_077501) p-glycoprotein [*Ca* . . . | 902 | 0.0 |
| gi\|17569143\|ref\|NP_509901.1\| | (NM_077500) multidrug resistan . . . | 902 | 0.0 |
| gi\|462584\|sp\|P34713\|MDR3_CAEEL | Multidrug resistance protein . . . | 879 | 0.0 |
| gi\|17567265\|ref\|NP_510126.1\| | (NM_077725) p-glycoprotein (MD . . . | 824 | 0.0 |
| gi\|17567269\|ref\|NP_510128.1\| | (NM_077727) p-glycoprotein (MD . . . | 820 | 0.0 |
| gi\|17567267\|ref\|NP_510127.1\| | (NM_077726) p-glycoprotein (MD . . . | 766 | 0.0 |
| gi\|17569909\|ref\|NP_509812.1\| | (NM_077411) p-glycoprotein [*Ca* . . . | 752 | 0.0 |
| gi\|17569907\|ref\|NP_509813.1\| | (NM_077412) p-glycoprotein [*Ca* . . . | 735 | 0.0 |
| gi\|17550138\|ref\|NP_509810.1\| | (NM_077409) p-glycoprotein [*Ca* . . . | 704 | 0.0 |
| gi\|17569911\|ref\|NP_509811.1\| | (NM_077410) p-glycoprotein [*Ca* . . . | 697 | 0.0 |
| gi\|7508148\|pir\|\|T25082 | hypothetical protein T21E8.2 - *Caeno* . . . | 622 | e−178 |
| gi\|7508147\|pir\|\|T25083 | hypothetical protein T21E8.1 - *Caeno* . . . | 601 | e−172 |

-continued

| Sequences producing significant alignments: | | (bits) | Value |
|---|---|---|---|
| gi\|17567271\|ref\|NP_510129.1\| | (NM_077728) p-glycoprotein (MD . . . | 536 | e−152 |
| gi\|17532731\|ref\|NP_495674.1\| | (NM_063273) multidrug resistan . . . | 351 | 2e−96 |
| gi\|17543740\|ref\|NP_502776.1\| | (NM_070375) ABC transporter [*C* . . . | 347 | 3e−95 |
| gi\|17511077\|ref\|NP_491754.1\| | (NM_059353) transporter protei . . . | 339 | 7e−93 |
| gi\|7511165\|pir\|\|T32865 | hypothetical protein ZK484.2 - *Caeno* . . . | 339 | 8e−93 |
| gi\|7510080\|pir\|\|T31617 | hypothetical protein Y50E8A.m - *Caen* . . . | 331 | 2e−90 |

Interestingly, MDR1 has been implicated in mammalian lipid transport (van Helvoort et al., *Cell* 87:507–17, 1996). (MDR1 P-glycoprotein is a lipid translocase of broad specificity, while MDR3 P-glycoprotein specifically translocates phosphatidylcholine (van Helvoort A. et al., *Cell* 87:507–17, 1996). The ABC transporters are promising drug targets because their natural targets are small molecules, which represent good candidates for drug development. Drugs that inhibit ABC transporter activity, particularly with respect to the transport of fats and fat metabolites, could be identified using the methods of the invention.

F11E6.5 Mammalian Ortholog

Another RNAi clone that caused a reduced fat phenotype in wild-type nematodes, as well as in the increased fat mutant nematodes, e.g., tub-1, tph-1, daf-2, lpo-1, and lpo-6, was F11E6.5. F11E6.5 encodes a transmembrane protein that functions to elongate fatty acids. Epistasis analysis indicates that F11E6.5 acts at the same point in the pathway as the ABC transporter gene, C34G6.4. Blast analysis of F11E6.5 identified the following highly related proteins.

| | | | | |
|---|---|---|---|---|
| gi\|17539766\|ref\|NP_503114.1\| | (NM_070713) GNS1/SUR4 family [. | 496 | e−139 | . . . it self |
| gi\|8489829\|gb\|AAF75771.1\|AF265296_1 | (AF265296) putative mul. | 166 | 2e−40 | . . . *drosophila* noa gene |
| gi\|7294O75\|gb\|AAF49430.1\| | (AE003526) Baldspot gene product | 166 | 2e−40 | *drosophila* bald spot gene . . . same as noa above |
| gi\|17540336\|ref\|NP_500793.1\| | (NM_068392) integral membrane . . . | 160 | 1e−38 | |
| gi\|17540774\|ref\|NP_501689.1\| | (NM_069288) Yeast YJT6 like [*C* . . . | 158 | 5e−38 | |
| gi\|17540338\|ref\|NP_500797.1\| | (NM_068396) F41H10.8.p [*Caenor* . . . | 158 | 6e−38 | |
| gi\|17539514\|ref\|NP_501147.1\| | (NM_068746) D2024.3.p [*Caenorh* . . . | 147 | 8e−35 | |
| gi\|17454617\|ref\|XP_058360.1\| | (XM_058360) similar to CIG30 [. . . | 146 | 2e−34 | |
| gi\|18496985\|ref\|NP_569717.1\| | (NM_130450) long chain fatty a . . . | 145 | 3e−34 | |
| gi\|20137972\|sp\|Q9HB03\|ELO3 HUMAN | Elongation of very long ch . . . | 145 | 5e−34 | |
| gi\|13129088\|ref\|NP_076995.1 | (NM_024090) long-chain fatty-a . . . | 143 | 2e−33 | |
| gi\|11875973\|emb\|CAC18863.1\| | (AL499614) transmembrane protei . . . | 135 | 5e−31 | |
| gi\|16151801\|dbj\|BAB69888.1\| | (AB071986) fatty acid elongase . . . | 131 | 7e−30 | |

F11E6.5 blast analysis identified the most closely related human homologue as "Elongation of very long chain fatty acids protein 3 (Accession number: Q9HB03)." The human homolog is an integral membrane protein that is likely found in the endoplasmic reticulum where it has been implicated in the synthesis of very long chain fatty acids and sphingolipids; it may catalyze one or both of the reduction reactions required for fatty acid elongation, i.e., conversion of beta-ketoacyl CoA to beta-hydroxyacyl CoA or reduction of trans-2-enoyl CoA to the saturated acyl CoA derivative.

When this human homologue was blasted versus the *C. elegans* database, F11E6.5 was identified as the second most closely related protein ($e^{-35}$). The results of the blast analysis are shown below.

| Sequences producing significant alignments: | | (bits) | Value |
|---|---|---|---|
| gi\|17539514\|ref\|NP_501147.1\| | (NM_068746) D2024.3.p [*Caenorh* . . . | 164 | 3e−41 |
| gi\|17539766\|ref\|NP_503114.1\| | (NM_070713) GNS1/SUR4 family [ . . . | 143 | 8e−35 |
| gi\|17552588\|ref\|NP_499056.1\| | (NM_066655) Yeast hypothetical . . . | 141 | 3e−34 |
| gi\|17537431\|ref\|NP_497086.1\| | (NM_064685) Y53F4B.2.p [*Caenor* . . . | 134 | 5e−32 |
| gi\|17540338\|ref\|NP_500797.1\| | (NM_068396) F41H10.8.p [*Caenor* . . . | 129 | 2e−30 |
| gi\|17540774\|ref\|NP_501689.1\| | (NM_069288) Yeast YJT6 like [*C* . . . | 125 | 2e−29 |
| gi\|17540336\|ref\|NP_500793.1\| | (NM_068392) integral membrane . . . | 113 | 7e−26 |
| gi\|17540772\|ref\|NP_501691.1\| | (NM_069290) Yeast GNS1 like [*C* . . . | 101 | 3e−22 |

T14E8.3 Mammalian Ortholog

T14E8.3 encodes a G protein coupled receptor. T14E8.3 RNAi caused a reduced fat phenotype in wild-type nematodes, and in tub-1, tph-1, daf-2, lpo-1, and lpo-6 mutant nematodes. Blast analysis of the T14E8.3 amino acid sequence indicated that the most closely related mammalian proteins are dopamine D2 receptors.

| Sequences producing significant alignments: | | (bits) | Value | |
|---|---|---|---|---|
| gi\|17569809\|ref\|NP_509106.1\| | (NM_076705) G-protein coupled . . . | 1982 | 0.0 | |
| gi\|17562444\|ref\|NP_505478.1\| | (NM_073077) dopamine receptor . . . | 133 | 1e–29 | |
| gi\|1363347\|pir\|\|D56849 | dopamine receptor-like protein D222 . . . | 130 | 6e–29 | |
| gi\|7381416\|gb\|AAF61479.1\|AF176812_1 | (AF176812) dopamine rec . . . | 130 | 1e–28 | (Human) |
| gi\|17986270\|ref\|NP_057658.2\| | (NM_016574) dopamine receptor . . . | 130 | 1e–28 | |
| gi\|3820492\|gb\|AAC78779.1\| | (AF050737) dopamine D2 receptor [ . . . | 129 | 1e–28 | |
| gi\|4503385\|ref\|NP_000786.1\| | (NM_000795) dopamine receptor D . . . | 129 | 1e–28 | |
| gi\|405310\|gb\|AAB26819.1\| | (S62137) D2 dopamine receptor [*Hom* . . . | 129 | 1e–28 | |
| gi\|11344838\|gb\|AAG34495.1\| | (AF293962) dopamine D2 receptor . . . | 129 | 2e–28 | |
| gi\|1706283\|sp\|P52702\|D2DR_CERAE | D(2) dopamine receptor >gi\| . . . | 129 | 2e–28 | |
| gi\|203906\|gb\|AAA41075.1\| | (M36831) dopamine receptor subtype . . . | 129 | 2e–28 | |
| gi\|11344842\|gb\|AAG34497.1\| | (AF293964) dopamine D2 receptor . . . | 129 | 2e–28 | |
| gi\|1706284\|sp\|P53453\|D2DR_FUGRU | D(2)-LIKE DOPAMINE RECEPTOR . . . | 129 | 2e–28 | |
| gi\|6753680\|ref\|NP_034207.1\| | (NM_010077) dopamine receptor 2 . . . | 129 | 2e–28 | |
| gi\|11344837\|gb\|AAG34494.1\| | (AF293962) dopamine D2 receptor . . . | 129 | 2e–28 | |
| gi\|226700\|prf\|\|1603358B | D2 dopamine receptor 2in [*Rattus no* . . . | 128 | 3e–28 | |
| gi\|1363346\|pir\|\|C56849 | dopamine receptor-like protein D215 . . . | 128 | 4e–28 | |
| gi\|226699\|prf\|\|1603358A | D2 dopamine receptor 2in [*Bos taurus*] | 127 | 7e–28 | |
| gi\|118205\|sp\|P20288\|D2DR_BOVIN | D(2) dopamine receptor >gi\|7 . . . | 127 | 8e–28 | |
| gi\|10719976\|sp\|O73810\|D2DR_MELGA | D(2) dopamine receptor >gi . . . | 126 | 1e–27 | |
| gi\|17550186\|ref\|NP_508786.1\| | (NM_076385) C05E11.7.p [*Caenor* . . . | 126 | 2e–27 | |
| gi\|16445402\|ref\|NP_387512.1\| | (NM_033663) dopamine receptor . . . | 124 | 8e–27 | |
| gi\|16445398\|ref\|NP_387508.1\| | (NM_033659) dopamine receptor . . . | 123 | 1e–26 | |

The most closely related human homolog is a dopamine receptor, D2 longer (ACCESSION AAF61479). When this human amino acid sequence was blasted against the Wormpep database, it identified the original T14E8.3 as the second most closely related protein.

| Sequences producing significant alignments: | | (bits) | Value | |
|---|---|---|---|---|
| gi\|17562444\|ref\|NP_505478.1\| | (NM_073077) dopamine receptor . . . | 101 | 7e–22 | |
| gi\|17569809\|ref\|NP_509106.1\| | (NM_076705) G-protein coupled . . . | 99 | 5e–21 | this is T14E8.3 |
| gi\|17567023\|ref\|NP_508760.1\| | (NM_076359) G-protein coupled . . . | 93 | 3e–19 | |
| gi\|17569449\|ref\|NP_510535.1\| | (NM_078134) octopamine recepto . . . | 91 | 1e–18 | |
| gi\|7504744\|pir\|\|T29877 | hypothetical protein F59C12.2 - *Caen* . . . | 87 | 2e–17 | |
| gi\|7511648\|pir\|\|T37239 | serotonin receptor 5-HT2, short spli . . . | 87 | 3e–17 | |
| gi\|17569447\|ref\|NP_510684.1\| | (NM_078283) G-protein coupled . . . | 86 | 4e–17 | |
| gi\|17555606\|ref\|NP_497452.1\| | (NM_065051) Y22D7AR.13.p [*Caen* . . . | 86 | 5e–17 | |
| gi\|17568989\|ref\|NP_508839.1\| | (NM_076438) G-protein coupled . . . | 84 | 2e–16 | |
| gi\|20198773\|gb\|AAM15552.1\|U64603_2 | (U64603) Hypothetical pr . . . | 80 | 2e–15 | |
| gi\|17550264\|ref\|NP_508474.1\| | (NM_076073) G-protein coupled . . . | 80 | 2e–15 | |
| gi\|3025118\|sp\|Q19084\|YDBM_CAEEL | PROBABLE G PROTEIN-COUPLED . . . | 80 | 3e–15 | |
| gi\|17551400\|ref\|NP_509184.1\| | (NM_076783) G-protein coupled . . . | 80 | 3e–15 | |
| gi\|17551692\|ref\|NP_508947.1\| | (NM_076546) G-protein coupled . . . | 80 | 3e–15 | |

Without being bound to a particular theory, it is possible that this *C. elegans* receptor responds to a neurotransmitter that is regulated by or regulates metabolism and or fat levels. For example, this pathway may correspond to the nematode's autonomic nervous system. Interestingly, the Dopamine D2 receptor in humans has been implicated in obesity (Comings et al., *Biochem Med Metab Biol* 50:176–85, 1993; Contreras et al., *J Hum Hypertens,* 16 Suppl 1, S13-7, 2002) where it functions in the regulation of weight and height. Mutations in this gene may indicate an increased propensity to develop late-onset non-insulin-dependent diabetes mellitus.

*C. elegans* Provides A Useful System for Cholesterol-Lowering Drug Screens

Hydroxymethylglutary-CoA (HMG-CoA) reductase is a regulatory enzyme in cholesterol biosynthesis. Inhibitors of HMG-CoA reductase, such as lovastatin or mevinolin, are commonly used to lower human cholesterol. Lovastatin was tested for its effect on *C. elegans* fat accumulation. High fat lpo-1 mutant nematodes were grown on plates containing 200 μg/ml mevinolin, an HMG-CoA reductase inhibitor. Fat accumulation was then assessed using Nile Red staining, as previously described. As in humans, lovastatin decreased fat accumulation in *C. elegans*, indicating that *C. elegans* provides a facile, inexpensive, and efficient system in which to identify cholesterol lowering compounds. This experiment demonstrated that natural product libraries can be screened for fat modulators using the Nile Red protocol. Based on our RNAi studies, such fat modulators might target the active site of kinases and phosphatases, the dopamine D2 receptor, fatty acid elongases, and novel proteins.

Microarrays

The global analysis of gene expression using gene chips can provide insights into gene expression perturbations in tissues associated with obesity. Such studies can compare the expression profiles of mammalian fat metabolic regulator genes (e.g., those listed in Table IX, X, XI, XII, XIII, or XIV) in tissues, such as the hypothalamus or fat, of obese and wild-type mice. Genes identified using this method are expected to be fat-level-responsive genes. In fact, transcription factors constitute one class of genes identified via systematic Nile Red RNAi analysis in *C. elegans*. Those genes whose expression is modulated in the obese mice, relative to wild-type control mice, represent important therapeutic targets for further analysis. Such targets could be explored in cell culture models of fat deposition, as well as in obese or lipodystrophic variant humans.

Microarrays may be prepared, used, and analyzed using methods known in the art. (See, e.g., Brennan et al., U.S. Pat. No. 5,474,796; Schena et al., *Proc. Natl. Acad. Sci.* 93:10614, 1996; Baldeschweiler et al., PCT application WO95/251116, 1995; Shalon, D. et al., PCT application WO95/35505, 1995; Heller et al., *Proc. Natl. Acad. Sci.* 94:2150, 1997; and Heller et al., U.S. Pat. No. 5,605,662; MacBeath et al., *Science* 289:1760–1763, 2000; De Wildt et al., *Nature Biotechnol.* 18, 989–994, 2000; Fung et al., *Curr. Opin. Biotechnol.* 12:65–69, 2001).

siRNA

Short twenty-one to twenty-five nucleotide double stranded RNAs are effective at down-regulating gene expression in mammalian tissue culture cell lines (Elbashir et al., *Nature* 411:494–498, 2001 hereby incorporated by reference). Using such methods, the inactivation of mammalian orthologs (e.g., those listed in Table IX, X, XI, XII, XIII, or XIV) may be analyzed for fat phenotype. The nucleic acid sequence of mammalian fat metabolism regulator gene orthologs can be used to design small interfering RNAs (siRNAs) that will inactivate mammalian fat metabolism regulator genes for the treatment of obesity or obesity-related disease.

Given the sequence of a mammalian fat metabolism regulator gene, siRNAs may be designed to inactivate that gene. For example, for a gene that consists of 2000 nucleotides, 1,978 different twenty-two nucleotide oligomers could be designed; this assumes that each oligomer has a two base pair 3' overhang, and that each siRNA is one nucleotide residue from the neighboring siRNA. For RNAi, only a few of these twenty-two nucleotide oligomers would be needed; approximately one dozen siRNAs, evenly spaced across the 2,000 nucleotide gene, could be sufficient to significantly reduce mammalian gene activity. These siRNAs could be transferred into mammalian cells in culture, and the effect of the siRNAs on the cultured cells fat content would then be assayed using Nile Red, such methods are standard in the art and are described by Elbashir et al., (*Nature* 411:494–498, 2001, hereby incorporated by reference). Alternatively, siRNAs could be injected into an animal, for example, into the blood stream (McCaffrey et al., *Nature* 418:38–92002). Thus, based on the mammalian genes identified (e.g., those that encode the polypeptides listed in Table IX, X, XI, XII, XIII, or XIV), oligonucleotides may be designed to inhibit mammalian gene activity.

Those siRNAs that are effective in reducing the fat content of cultured cells can be used as therapeutics. The injection of siRNAs corresponding to the DNA sequences of novel mammalian fat metabolism regulator genes listed in XI would be expected to inactivate those genes, thereby reducing fat levels without adverse side-effects.

Druggable Targets

Enzymes with small molecule substrates have been traditional targets for drug development. Examples include kinases, phosphatases, lipases, synthases, ABC transporters, nuclear hormone receptors, small molecule receptors, and small molecule transporters. Many small molecule drugs have already been developed. The chemical backbone of drugs designed against a class of enzymes with small substrate molecules, e.g. kinases or nuclear hormone receptors, may be used as a starting point for developing and designing drug targets against other members within that class of enzymes. The genomic survey described herein has identified a number of enzymes with small molecule substrates that function in regulation of body fat content. The mammalian orthologs of these worm genes represent targets, in this case for regulation of body fat, that would traditionally be selected for development of small molecule drugs. The mammalian orthologs of the genes listed below appear in Tables XII, XIII, and XIV and are novel candidates for the development of drugs for the treatment of obesity and obesity-related diseases.

Inactivation of the mammalian orthologs of worm fat regulatory genes, for example, by pharmaceuticals that target proteins with small molecule binding sites or small active sites, such as phosphatases, or fatty acid metabolism enzymes, could lead to lower fat levels. For those fat regulatory genes that encode such enzymes, small molecule libraries could be used to screen for the increase or decrease of in vitro enzymatic activity of the isolated and purified proteins.

In one working example, a candidate compound that inactivates a kinase could be identified using standard methods to monitor the kinases biological activity, for example, substrate phosphorylation. A decrease in substrate phosphorylation in the presence of the candidate compound, as compared to substrate phosphorylation in the absence of the candidate compound, identifies that candidate compound as useful in the methods of the invention. In fact, it is reasonable to expect the substrate of that kinase to be present in the lists of fat regulatory genes provided herein, for example, in Tables XII, XIII, and XIV.

In another working example, the biochemical activity of a fatty acid elongase could be monitored in vitro using routine methods. A decrease in the biochemical activity of the elongase in the presence of a candidate compound, as compared to the activity of the elongase in the absence of the candidate compound, identifies the candidate compound as useful in the methods of the invention.

In addition to screening synthetic compound libraries, natural product libraries, for example, from fungi, could be screeened with isolated and purified proteins expressed in vitro. Lovastatin is one example of a natural product that demonstrates that such an approach is advantageous. It is reasonable to expect that fungi and bacteria might produce fat metabolism modulating compounds because they compete with animals for nutrients.

Desirable drug targets are those that have small active sites. These are the most advantageous for drug development, that is, represent druggable targets. Exemplary druggable targets are shown in Tables XVIII, IX, and XX. This list should not be construed as limiting; other exemplary druggable targets are shown in Tables XII, XIII, and XIV.

TABLE XVIII

RNAi Clones that Reduce Fat Content without Reducing Viability/Growth and have small molecule substrates and their mammalian orthologs are novel targets for drug development

| *C. elegans* Gene | Brief Description |
|---|---|
| AH10.1 | medium-chain acyl-CoA synthetase |
| B0285.8 | choline/ethanolamine kinase |
| C01C10.3 | phospholipid and glycerol acyltransferase |
| C06E7.3 | S-adenosylmethionine synthetase |
| C17C3.1 | long-chain acyl-coA thioesterase |
| C24A11.9 | trans-prenyltransferase |
| C31H2.3 | 4-hydroxyphenylpyruvate dioxygenase |
| C46H11.2 | flavin binding monooxygenase |
| E01A2.7 | glutamate-cysteine ligas/arylesterase |
| F11E6.5 | polyunsaturated fatty acid elongase |
| F13D11.1 | lysosomal acid phosphatase precursor |
| F23H11.9 | CDP-alcohol phosphatidyltransferas |
| F28H6.3 | 1-aminocyclopropane-1-carboxylic acid synthase |
| F43H9.2 | serine palmitoyltransferase II |
| F52B11.2 | phosphomannomutase 2 |
| K03B8.3 | neutral zinc metallopeptidases |
| K07C6.4 | cytochrome P450 2C2 (P450 PBC2) |
| K07C6.5 | cytochrome P450 2C2 (P450 PBC2) |
| K09D9.2 | cytochrome P450 |
| M28.6 | serine beta lactamase-like protein |
| T04A8.16 | calpain-type cystein-protease |
| T09B4.8 | alanine-glyoxylate aminotransferase 2 |
| T12A2.1 | chlorohydrolase/histidine degradation |
| W01C9.4 | mitochondrial Δ2,Δ4-dienoyl-CoA reductase |
| Y49A3A.1 | choline/ethanolaminephosphotransferas |
| Y6B3B.10 | lag1 (ceramide synthesis) |
| C37H5.3 | esterase/lipase |
| F13D12.6 | esterase/lipase/Serine carboxypeptidase (S10) |
| B0280.3 | nhr-10(ribose 5-phosphate ketol-isomerase) |
| C46E10.9 | zinc finger, C2H2 type |
| C47C12.3 | zinc finger, C2H2 type/mouse OPR |
| K08A2.b | hepatocyte nuclear factor 4 receptor type |
| T09F3.1 | zinc finger, C2H2 type |
| T23F11.4 | zinc finger, C2H2 type |
| W02C12.3 | microphthalmia transcription factor |
| Y116A8C.32 | Zn-finger CCHC type transcription factor/ZFM1 |
| ZK686.4 | zinc finger, C2H2 type |
| B0218.5 | serine/threonine kinase |
| C02F4.2 | serine/threonine protein phosphatase (PP2b) |
| C03D6.3 | dual specificity protein phosphatase |
| C06A1.3 | serine/threonine specific protein phosphatase |
| C16A11.3 | serine/threonine protein kinase |
| C44F1.5 | guanylate cyclase |
| C47D12.1 | phosphatidylinositol 3- and 4-kinase/EF-hand family |
| F41D9.1 | RabGAP/TBC domain/SH3 domain |
| F45H7.4 | pim1 serine/threonine-protein kinase |
| F46G11.3 | protein kinase |
| K10D3.5 | protein kinase/adaptor protein |
| M01B12.5 | tyrosine kinase catalytic domain |
| R107.4 | IKK-related kinase epsilon |
| T05C12.1 | serine/threonine protein kinase |
| T19D2.2 | dual specificity protein phosphatase family |
| Y53C12A.1 | serine/threonine protein kinase/membrane associated |
| ZC302.1 | serine/threonine specific protein phosphatase |
| ZC504.4 | Tyrosine kinase and serine/threonine protein kinase |
| ZK909.3 | guanosine-3',5'-bis(diphosphate)-pyrophosphohydrolase |
| ZK930.1 | serine/threonine protein kinase/Pl-3 |
| C38C10.1 | neurokinin-3 receptor |
| E02C12.3 | Rhodopsin-like GPCR superfamily |
| C32C4.1 | voltage-dependent potassium channel |
| C13D9.7 | sodium/calcium exchanger protein |
| C34G6.4 | ABC transporter |
| C37A5.1 | homology Best's ion exhangeer |

TABLE XVIII-continued

RNAi Clones that Reduce Fat Content without Reducing Viability/Growth and have small molecule substrates and their mammalian orthologs are novel targets for drug development

| *C. elegans* Gene | Brief Description |
|---|---|
| C46F11.1 | unc-93 protein/ABC-2 type transporter |
| F15H10.4 | lysosomal amino acid transporter |
| F23F1.6 | high affinity cationic amino acid permease |
| F59F5.1 | monocarboxylate transporter/XPCT |
| K04E7.2 | PepT1 oligopeptide symporters |
| K05F1.6 | organic solute carrier family 2/ (OCT1) |
| ZK682.2 | sugar transporter |
| H27A22.1 | glutaminyl cyclase |
| C15H9.7 | kynureninase |
| C33A12.1 | NADH-ubiquinone oxidoreductase B subunit |
| F14D12.2 | cytochrome c family heme-binding site |
| F20D1.9 | mitochondrial carrier proteins |
| F40H3.5 | heparan sulfate sulfotransferase |
| F11A5.3 | similarity to RAB2 |
| W03C9.3 | RAB7 |
| F21D5.5 | polynucleotide kinase 3' phosphatase |

TABLE XIX

RNAi Clones that Reduce Fat Content and Reduce Viability/Growth and have small molecule substrates and their mammalian orthologs are novel targets for drug development

| GENE NAME | BRIEF DESCRIPTION |
|---|---|
| Y37D8A.14 | Cytochrome c oxidase subunit Va |
| Y57G11C.12 | NADH-ubiquinone oxidoreductase |
| F28B3.1 | Cysteine proteases inhibitor |
| C23H3.4 | serine palmitoyltransferase |
| E04A4.7 | Cytochrome c family heme-binding |
| F01G10.1 | Transketolase |
| F46E10.1 | AMP-dependent synthetase and ligase |
| F57B9.2 | Proline-rich region• Glycosyl hydrolases family 5 |
| H14A12.2 | Fumarate lyase |
| K02F2.2 | S-adenosyl-L-homocysteine hydrolase |
| K06A4.5 | 3-hydroxyanthranilate 3,4-dioxygenase |
| T05H4.4 | Oxidoreductase/cytochrome B5 reductase |
| T05H4.5 | Oxidoreductase/cytochrome B5 reductase |
| B0285.1 | Eukaryotic protein kinase |
| C16C2.3 | inositol-1,4,5-triphosphate 5-phosphatase |
| F25H8.3 | Neutral zinc metallopeptidase |
| Y17G7A.2 | Zinc finger, C2H2 type |
| W06D12.2 | potassium channel, subfamily K |
| Y61A9LA_75.a | ABC transporters family |
| T23F2.1 | Glycosyl transferases group 1 |
| F41H10.7 | fatty acid elongase (ClG30/Fen1) |

TABLE XX

RNAi Clones that Increase Fat Content and have small molecule substrates and their mammalian orthologs are novel targets for drug development

| GENE NAME | BRIEF DESCRIPTION |
|---|---|
| C33A12.6 | UDP-glucoronosyl and UDP-glucosyl transferase |
| VF13D12L.1 | myo-inositol-1-phosphate synthase |
| C37F5.1 | elk-1 |
| C56C10.10 | aryl hydrocarbon receptor (Leber congenital amaurosis) |
| F16B4.9 | C4-type steroid receptor zinc finger |
| K10C3.6 | hepatocyte nuclear factor 4 receptor |
| R11H6.5 | interleukin enhancer binding factor 2 |
| C04G2.2 | serine/threonine protein kinase/tau tubulin kinase |

TABLE XX-continued

RNAi Clones that Increase Fat Content and have small molecule substrates and their mammalian orthologs are novel targets for drug development

| GENE NAME | BRIEF DESCRIPTION |
|---|---|
| C24F3.2 | glucokinase-associated dual specificity phosphatase |
| F39B1.1 | phosphoinositide 3-kinase |
| F46C5.6 | protein phosphatase PP2A subunit A |
| F56H11.6 | casein kinase/tau-tubulin kinase |
| R10D12.10 | casein kinase/tau-tubulin kinase |
| T04B2.2 | fms/fps protein kinase |
| T04C9.1 | oligophrenin-1 (focal adhesion GTPase) |
| W03A5.4 | guanylate kinase associated protein |
| ZC513.1 | permeability increasing/phospholipid transfer protein |
| C43H6.9 | glutamate receptor |
| ZC410.4 | potassium channel |
| C18H9.5 | sugar transporter |
| F14E5.1 | glucose transporter-3 |
| F52H2.2 | amino acid permease |

Transgenic Rodents

Yet another method for assessing the utility of targets, is the use of transgenic rodents that are widely used as mammalian models of obesity. Examples include the following trangenic/mutant mice: ob/ob, db/db, fat/fat, tubby/tubby, -5HTRc/5HTRc, MC3R/MC3R, MC4R/MC4R, BRC3/BRC3, 11-β-HSD-1/11-β-HSD-1, CYP19/CYP19, ADR3b/ADR3b, Ppara-α/Ppara-α, Esr-α/Esr-α, Pomc/Pomc, Fshr/Fshr, and agouti mice (Brockmann et al., *Trends in Genetics* 18: 367–376, 2002 and Butler et al., *Trends in Genetics* 17(10):S50–S54, 2001). These mice display hyperphagia and in some cases increased fat deposits. Mammalian fat metabolism regulator genes (e.g., those mammalian genes that encode the polypeptides listed in Table IX, X, XI, XII, XIII, or XIV) can be studied by assaying the fat phenotype of the obese mutant mice having a second mutation in a fat metabolism regulator gene, such as those identified herein (e.g., those novel mammalian genes that encode the polypeptides listed in Table IX, X, XI, XII, XIII, or XIV).

Alternatively, obese mice, such as: ob/ob, db/db, fat/fat, tubby/tubby, -5HTRc/5HTRc, MC3R/MC3R, MC4R/MC4R, BRC3/BRC3, 11-βHSD-1/11-β-HSD-1, CYP19/CYP19, ADR3b/ADR3b, Ppara-α/Ppara-α, Esr-α/Esr-α, Pomc/Pomc, Fshr/Fshr, and agouti mice, may be injected with an siRNA (for example, a twenty-one-nucleotide siRNA) that downregulates a mammalian gene identified herein (e.g., those novel mammalian genes that encode the polypeptides listed in Table XII, XIII, or XIV.

Human Genetics

The many genes that regulate *C. elegans* fat storage may correspond to loci that are variant in human obesity, obesity-related diseases, fat metabolism disorders, or lipodystrophy syndromes. Human obesity-related diseases include, but are not limited to, those diseases which are more common in over-weight individuals, for example, atherosclerosis, heart disease and stroke, noninsulin-dependent diabetes mellitus (type 2 diabetes), several types of cancer that occur in over-weight women, such as cancer of the uterus, gallbladder, cervix, ovary, breast, or colon, several types of cancer that occur in over-weight men, such as cancer of the colon, rectum, or prostate; joint diseases, such as osteoarthritis I, gout, gallbladder disease or gallstones.

Fat metabolism disorders or lipodystrophy syndromes, include, but are not limited to, diseases of cholesterol and lipid homeostasis (e.g., Tangier disease, familial HDL deficiency, progressive familial intrahepatic cholestasis type 2 and type 3, adrenoleukodystrophy, and sitosterolaemia).

The human orthologs of *C. elegans* fat metabolism regulator genes (e.g., those that encode the polypeptides listed in Table IX, X, XI, XII, XIII, or XIV) may be variant in affected individuals. Such genes could be studied by identifying mutations in the identified candidate genes (e.g., those that encode the polypeptides listed in Table IX, X, XI, XII, XIII, or XIV) in a population of variant humans. Such methods of identification are known to the skilled artisan, and are described Jackson et al. (*Nat. Genet.* 16:303–6. 1997, hereby incorporated by reference).

Isolation of Additional Fat Metabolism Regulator Genes

Based on the nucleotide and amino acid sequences described herein, the isolation and identification of additional coding sequences of genes regulating fat metabolism is made possible using standard strategies and techniques that are well known in the art.

In one example, fat metabolism regulator polypeptides disclosed herein (e.g., those listed in Tables XII, XIII, or XIV) are used to search a database, as described herein.

In another example, any organism that metabolizes fat can serve as the nucleic acid source for the molecular cloning of such a gene, and these sequences are identified as ones encoding a protein exhibiting structures, properties, or activities associated with fat metabolism regulation, such as the LPO-1, LPO-3, or fat metabolism regulator polypeptides disclosed herein (e.g., those listed in Tables XII, XIII, or XIV).

In one particular example of such an isolation technique, any one of the nucleotide sequences described herein, lpo-1, lpo-3, or a fat metabolism regulator gene disclosed herein (e.g., those that encode the polypeptides listed in Table XII, XIII, or XIV) may be used, together with conventional methods of nucleic acid hybridization screening. Such hybridization techniques and screening procedures are well known to those skilled in the art and are described, for example, in Benton and Davis (*Science* 196:180, 1977); Grunstein and Hogness (*Proc. Natl. Acad. Sci.,* USA 72:3961, 1975); Ausubel et al. (*Current Protocols in Molecular Biology,* Wiley Interscience, New York, 2001); Berger and Kimmel (*Guide to Molecular Cloning Techniques,* 1987, Academic Press, New York); and Sambrook et al., *Molecular Cloning: A Laboratory Manual*, Cold Spring Harbor Laboratory Press, New York. In one particular example, all or part of the lpo-1, lpo-3, or nucleic acid sequences that encode the polypeptides listed in Table XII, XIII, or XIV may be used as a probe to screen a recombinant DNA library for genes having sequence identity to the lpo-1, lpo-3 genes or those nucleic acid sequences that encode the polypeptides listed in Table XII, XIII, or XIV. Hybridizing sequences are detected by plaque or colony hybridization according to standard methods.

Alternatively, using all or a portion of the amino acid sequences of LPO-1, LPO-3, or those amino acid sequences listed in Table XII, XIII, or XIV, one may readily design gene-, or nucleic acid sequence specific oligonucleotide probes, including degenerate oligonucleotide probes (i.e., a mixture of all possible coding sequences for a given amino acid sequence). These oligonucleotides may be based upon the sequence of either DNA strand and any appropriate portion of the lpo-1 or lpo-3 nucleic acids, or nucleic acid sequences that encode the polypeptides listed in Table XII, XIII, or XIV sequences. General methods for designing and preparing such probes are provided, for example, in Ausubel et al. (supra), and Berger and Kimmel, (*Guide to Molecular Cloning Techniques,* 1987, Academic Press, New York). These oligonucleotides are useful for lpo-1 or lpo-3 gene isolation or for the isolation of a gene that encodes a polypeptide listed in Table XII, XIII, or XIV, either through their use as probes capable of hybridizing to lpo-1 or lpo-3 gene, or a gene those that encodes a polypeptide listed in Table XII, XIII, or XIV; or as complementary sequences or as primers for various amplification techniques, for example, polymerase chain reaction (PCR) cloning strategies. If desired, a combination of different, detectably-labelled oligonucleotide probes may be used for the screening of a recombinant DNA library. Such libraries are prepared according to methods well known in the art, for example, as described in Ausubel et al. (supra), or they may be obtained from commercial sources.

As discussed above, sequence-specific oligonucleotides may also be used as primers in amplification cloning strategies, for example, using PCR. PCR methods are well known in the art and are described, for example, in *PCR Technology,* Erlich, ed., Stockton Press, London, 1989*; PCR Protocols: A Guide to Methods and Applications*, Innis et al., eds., Academic Press, Inc., New York, 1990; and Ausubel et al. (supra). Primers are optionally designed to allow cloning of the amplified product into a suitable vector, for example, by including appropriate restriction sites at the 5' and 3' ends of the amplified fragment (as described herein). If desired, nucleotide sequences may be isolated using the PCR "RACE" technique, or Rapid Amplification of cDNA Ends (see, e.g., Innis et al. (supra)). By this method, oligonucleotide primers based on a desired sequence are oriented in the 3' and 5' directions and are used to generate overlapping PCR fragments. These overlapping 3'- and 5'-end RACE products are combined to produce an intact full-length cDNA. This method is described in Innis et al. (supra); and Frohman et al., (*Proc. Natl. Acad. Sci.* USA 85:8998, 1988).

Partial sequences, e.g., sequence tags, are also useful as hybridization probes for identifying full-length sequences, as well as for screening databases for identifying previously unidentified related virulence genes.

In general, the invention includes any nucleic acid sequence which may be isolated as described herein or which is readily isolated by homology screening or PCR amplification using any of the nucleic acid sequences disclosed herein (e.g., those listed in Table XII, XIII, or XIV).

It will be appreciated by those skilled in the art that as a result of the degeneracy of the genetic code, a multitude of polynucleotide sequences encoding LPO-1, LPO-3, or the genes that encode the polypeptides listed in Table XII, XIII, or XIV, some bearing minimal similarity to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally-occurring lpo-1, lpo-3, or those nucleic acid sequences that encode the polypeptides listed in Table XII, XIII, or XIV, and all such variations are to be considered as being specifically disclosed.

Although nucleotide sequences which encode LPO-1, LPO-3, or those polypeptides listed in Table XII, XIII, or XIV, or their variants are preferably capable of hybridizing to the nucleotide sequence of the naturally-occurring lpo-1, lpo-3, or those polypeptides listed in Table XII, XIII, or XIV under appropriately selected conditions of stringency, it may be advantageous to produce nucleotide sequences encoding LPO-1, LPO-3, or those polypeptides listed in Table XII, XIII, or XIV, or their derivatives possessing a substantially different codon usage, e.g., inclusion of non-naturally occurring codons. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding LPO-1, LPO-3, or those polypeptides listed in Table XII, XIII, or XIV and their derivatives without altering the encoded amino acid sequences include the production of RNA transcripts having more desirable properties, such as a greater half-life, than transcripts produced from the naturally occurring sequence.

The invention also encompasses production of DNA sequences which encode LPO-1, LPO-3, or those polypeptides listed in Table XII, XIII, or XIV, or fragments thereof generated entirely by synthetic chemistry. After production, the synthetic sequence may be inserted into any of the many available expression vectors and cell systems using reagents well known in the art. Moreover, synthetic chemistry may be used to introduce mutations into a sequence encoding any one of LPO-1, LPO-3, or those polypeptides listed in Table XII, XIII, or XIV, or any fragment thereof.

Also encompassed by the invention are polynucleotide sequences that are capable of hybridizing to the claimed polynucleotide sequences, and, in particular, to those that encode a polypeptide listed in Table XII, XIII, or XIV, and fragments thereof under various conditions of stringency. (See, e.g., Wahl, G. M. and S. L. Berger (1987) *Methods Enzymol.* 152:399; Kimmel, A. R. (1987) *Methods Enzymol.* 152:507) For example, stringent salt concentration will ordinarily be less than about 750 mM NaCl and 75 mM trisodium citrate, preferably less than about 500 mM NaCl and 50 mM trisodium citrate, and most preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and most preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 μg/ml denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

The washing steps which follow hybridization can also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include temperature of at least about 25° C., more preferably of at least about 42° C., and most preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a most preferred embodiment, wash steps will occur at 68° C. in 15 mM NaCl, 1.5 mM trisodium citrate, and 0.1% SDS. Additional variations on these conditions will be readily apparent to those skilled in the art.

Methods for DNA sequencing are well known in the art and may be used to practice any of the embodiments of the invention. The resulting sequences are analyzed using a variety of algorithms which are well known in the art. (See, e.g., Ausubel, F. M. (1997) *Short Protocols in Molecular Biology*, John Wiley & Sons, New York N.Y., unit 7.7)

Polypeptide Expression

In general, polypeptides of the invention (e.g., LPO-1, LPO-3, or those listed in Table XII, XIII, or XIV) may be produced by transformation of a suitable host cell with all or part of a polypeptide-encoding nucleic acid or fragment thereof in a suitable expression vehicle.

Those skilled in the field of molecular biology will understand that any of a wide variety of expression systems may be used to provide the recombinant protein. The precise host cell used is not critical to the invention. A polypeptide of the invention may be produced in a prokaryotic host (e.g., *E. coli*) or in a eukaryotic host (e.g., *Saccharomyces cerevisiae*, insect cells, e.g., Sf21 cells, or mammalian cells, e.g., NIH 3T3, HeLa, or preferably COS cells). Such cells are available from a wide range of sources (e.g., the American Type Culture Collection, Rockland, Md.; also, see, e.g., Ausubel et al., supra). The method of transformation or transfection and the choice of expression vehicle will depend on the host system selected. Transformation and transfection methods are described, e.g., in Ausubel et al. (supra); expression vehicles may be chosen from those provided, e.g., in Cloning Vectors: A Laboratory Manual (P. H. Pouwels et al., 1985, Supp. 1987).

One particular bacterial expression system for polypeptide production is the *E. coli* pET expression system (Novagen, Inc., Madison, Wis.). According to this expression system, DNA encoding a polypeptide is inserted into a pET vector in an orientation designed to allow expression. Since the gene encoding such a polypeptide is under the control of the T7 regulatory signals, expression of the polypeptide is achieved by inducing the expression of T7 RNA polymerase in the host cell. This is typically achieved using host strains which express T7 RNA polymerase in response to IPTG induction. Once produced, recombinant polypeptide is then isolated according to standard methods known in the art, for example, those described herein.

Another bacterial expression system for polypeptide production is the pGEX expression system (Pharmacia). This system employs a GST gene fusion system which is designed for high-level expression of genes or gene fragments as fusion proteins with rapid purification and recovery of functional gene products. The protein of interest is fused to the carboxyl terminus of the glutathione S-transferase protein from *Schistosoma japonicum* and is readily purified from bacterial lysates by affinity chromatography using Glutathione Sepharose 4B. Fusion proteins can be recovered under mild conditions by elution with glutathione. Cleavage of the glutathione S-transferase domain from the fusion protein is facilitated by the presence of recognition sites for site-specific proteases upstream of this domain. For example, proteins expressed in pGEX-2T plasmids may be cleaved with thrombin; those expressed in pGEX-3x may be cleaved with factor Xa.

Once the recombinant polypeptide of the invention is expressed, it is isolated, e.g., using affinity chromatography. In one example, an antibody (e.g., produced as described herein) raised against a polypeptide of the invention may be attached to a column and used to isolate the recombinant polypeptide. Lysis and fractionation of polypeptide-harboring cells prior to affinity chromatography may be performed by standard methods (see, e.g., Ausubel et al., supra).

Once isolated, the recombinant protein can, if desired, be further purified, e.g., by high performance liquid chromatography (see, e.g., Fisher, *Laboratory Techniques In Biochemistry And Molecular Biology*, eds., Work and Burdon, Elsevier, 1980).

Polypeptides of the invention, particularly short peptide fragments, can also be produced by chemical synthesis (e.g., by the methods described in *Solid Phase Peptide Synthesis,* 2nd ed., 1984 The Pierce Chemical Co., Rockford, Ill.). Also included in the invention are polypeptides which are modified in ways which do not abolish their biological activity (assayed, for example as described herein). Such changes may include certain mutations, deletions, insertions, or post-translational modifications, or may involve the inclusion of any of the polypeptides of the invention as one component of a larger fusion protein.

The invention further includes analogs of any naturally-occurring polypeptide of the invention. Analogs can differ from the naturally-occurring the polypeptide of the invention by amino acid sequence differences, by post-translational modifications, or by both. Analogs of the invention will generally exhibit at least 85%, more preferably 90%, and most preferably 95% or even 99% identity with all or part of a naturally-occurring amino acid sequence of the invention. The length of sequence comparison is at least 15 amino acid residues, preferably at least 25 amino acid residues, and more preferably more than 35 amino acid residues. Again, in an exemplary approach to determining the degree of identity, a BLAST program may be used, with a probability score between $e^{-3}$ and $e^{-100}$ indicating a closely related sequence. Modifications include in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs can also differ from the naturally-occurring polypeptides of the invention by alterations in primary sequence. These include genetic variants, both natural and induced (for example, resulting from random mutagenesis by irradiation or exposure to ethanemethylsulfate or by site-specific mutagenesis as described in Sambrook, Fritsch and Maniatis, *Molecular Cloning: A Laboratory Manual* (2d ed.), CSH Press, 1989, or Ausubel et al., supra). Also included are cyclized peptides, molecules, and analogs which contain residues other than L-amino acids, e.g., D-amino acids or non-naturally occurring or synthetic amino acids, e.g., β or γ amino acids.

In addition to full-length polypeptides, the invention also includes fragments of any one of the polypeptides of the invention. As used herein, the term "fragment," means at least 5, preferably at least 20 contiguous amino acids, preferably at least 30 contiguous amino acids, more preferably at least 50 contiguous amino acids, and most preferably at least 60 to 80 or more contiguous amino acids. Fragments of the invention can be generated by methods known to those skilled in the art or may result from normal protein processing (e.g., removal of amino acids from the nascent polypeptide that are not required for biological activity or removal of amino acids by alternative mRNA splicing or alternative protein processing events). The aforementioned general techniques of polypeptide expression and purification can also be used to produce and isolate useful peptide fragments or analogs (described herein).

Antibodies

The polypeptides disclosed herein or variants thereof or cells expressing them can be used as an immunogen to produce antibodies immunospecific for such polypeptides. "Antibodies" as used herein include monoclonal and polyclonal antibodies, chimeric, single chain, simianized antibodies and humanized antibodies, as well as Fab fragments, including the products of an Fab immunolglobulin expression library.

To generate antibodies, a coding sequence for a polypeptide of the invention may be expressed as a C-terminal fusion with glutathione S-transferase (GST) (Smith et al., *Gene* 67:31, 1988). The fusion protein is purified on glutathione-Sepharose beads, eluted with glutathione, cleaved with thrombin (at the engineered cleavage site), and purified to the degree necessary for immunization of rabbits. Primary immunizations are carried out with Freund's complete adjuvant and subsequent immunizations with Freund's incomplete adjuvant. Antibody titres are monitored by Western blot and immunoprecipitation analyses using the thrombin-cleaved protein fragment of the GST fusion protein. Immune sera are affinity purified using CNBr-Sepharose-coupled protein. Antiserum specificity is determined using a panel of unrelated GST proteins.

As an alternate or adjunct immunogen to GST fusion proteins, peptides corresponding to relatively unique immunogenic regions of a polypeptide of the invention may be generated and coupled to keyhole limpet hemocyanin (KLH) through an introduced C-terminal lysine. Antiserum to each of these peptides is similarly affinity purified on peptides conjugated to BSA, and specificity tested in ELISA and Western blots using peptide conjugates, and by Western blot and immunoprecipitation using the polypeptide expressed as a GST fusion protein.

Alternatively, monoclonal antibodies which specifically bind any one of the polypeptides of the invention are prepared according to standard hybridoma technology (see, e.g., Kohler et al., *Nature* 256:495, 1975; Kohler et al., *Eur. J. Immunol.* 6:511, 1976; Kohler et al., *Eur. J. Immunol.* 6:292, 1976; Hammerling et al., In *Monoclonal Antibodies and T Cell Hybridomas*, Elsevier, N.Y., 1981; Ausubel et al., supra). Once produced, monoclonal antibodies are also tested for specific recognition by Western blot or immunoprecipitation analysis (by the methods described in Ausubel et al., supra). Antibodies which specifically recognize the polypeptide of the invention are considered to be useful in the invention; such antibodies may be used, e.g., in an immunoassay. Alternatively monoclonal antibodies may be prepared using the polypeptide of the invention described above and a phage display library (Vaughan et al., *Nature Biotech* 14:309, 1996).

Preferably, antibodies of the invention are produced using fragments of the polypeptides disclosed herein which lie outside generally conserved regions and appear likely to be antigenic, by criteria such as high frequency of charged residues. In one specific example, such fragments are generated by standard techniques of PCR and cloned into the pGEX expression vector (Ausubel et al., supra). Fusion proteins are expressed in *E. coli* and purified using a glutathione agarose affinity matrix as described in Ausubel et al. (supra). To attempt to minimize the potential problems of low affinity or specificity of antisera, two or three such fusions are generated for each protein, and each fusion is injected into at least two rabbits. Antisera are raised by injections in a series, preferably including at least three booster injections.

Diagnostics

In another embodiment, antibodies which specifically bind any of the polypeptides described herein may be used for the diagnosis of obesity, an obesity-related disease, or a fat metabolism disorder. A variety of protocols for measuring such polypeptides, including immunological methods (such as ELISAs and RIAs) and FACS, are known in the art and provide a basis for diagnosing obesity, an obesity-related disease, or a fat metabolism disorder.

In another aspect, hybridization with PCR probes which are capable of detecting polynucleotide sequences, including genomic sequences, encoding lpo-1, lpo-3, or those encoding a polypeptide listed in Table IX, X, XI, XII, XIII, or XIV, or closely related molecules may be used to identify nucleic acid sequences which encode its gene product. The specificity of the probe, whether it is made from a highly specific region, e.g., the 5' regulatory region, or from a less specific region, e.g., a conserved motif, and the stringency of the hybridization or amplification (maximal, high, intermediate, or low), will determine whether the probe identifies only naturally occurring sequences encoding LPO-1, LPO-3, or a polypeptide listed in Table IX, X, XI, XII, XIII, or XIV allelic variants, or related sequences. Hybridization techniques may be used to identify mutations in fat metabolism regulator genes or may be used to monitor expression levels of these genes (for example, by Northern analysis, (Ausubel et al., supra).

In further embodiments, oligonucleotides or longer fragments derived from any of the polynucleotide sequences described herein may be used as targets in a microarray. The microarray can be used to monitor the expression level of large numbers of genes simultaneously and to identify genetic variants, mutations, and polymorphisms. This information may be used to determine gene function, to understand the genetic basis of a disorder, to diagnose a disorder, and to develop and monitor the activities of therapeutic agents. Microarrays may be prepared, used, and analyzed using methods known in the art. (See, e.g., Brennan et al., U.S. Pat. No. 5,474,796; Schena et al., *Proc. Natl. Acad. Sci.* 93:10614, 1996; Baldeschweiler et al., PCT application WO95/251116, 1995; Shalon, D. et al., PCT application WO95/35505, 1995; Heller et al., *Proc. Natl. Acad. Sci.* 94:2150, 1997; and Heller et al., U.S. Pat. No. 5,605,662.)

In yet another approach, mammals may be diagnosed for a propensity to a fat metabolism disease or disorder by direct analysis of the sequence of a fat metabolism regulator gene (for example, by sequence or mismatch detection assays). Exemplary candidates for use as reference wild-type sequences are listed in Table IX, X, XI, XII, XIII, or XIV.

Screening Assays

As discussed above, the identified fat metabolism regulator genes, lpo-1, lpo-3, or those that encode a polypeptide listed in Tables V, VI, VII, IX, X, XI, XII, XIII, and IV modulate the regulation of body fat. Based on this discovery, screening assays were developed to identify compounds that enhance or inhibit the action of a polypeptide or the expression of a nucleic acid sequence of the invention. The method of screening may involve high-throughput techniques. In addition, these screening techniques may be carried out in cultured cells or in animals (such as nematodes).

Any number of methods are available for carrying out such screening assays. In one working example, candidate compounds are added at varying concentrations to the culture medium of cultured cells expressing one of the nucleic acid sequences of the invention. Gene expression is then measured, for example, by standard Northern blot analysis (Ausubel et al., supra) or RT-PCR, using any appropriate fragment prepared from the nucleic acid as a hybridization probe. The level of gene expression in the presence of the candidate compound is compared to the level measured in a control culture medium lacking the candidate molecule. A compound which promotes an increase in the expression of lpo-1, lpo-3, or a nucleic acid that encodes a polypeptide listed in Tables V, VI, VII, IX, X, XI, XII, XIII, and IV or functional equivalent is considered useful in the invention; such a molecule may be used, for example, as a therapeutic to delay or ameliorate human diseases associated with obesity, an obesity-related disease, or a fat metabolism disorder. Such cultured cells include nematode cells (for example, *C. elegans* cells), mammalian, or insect cells.

In another working example, the effect of candidate compounds may be measured at the level of polypeptide production using the same general approach and standard immunological techniques, such as Western blotting or immunoprecipitation with an antibody specific for a fat metabolism regulator polypeptide, such as LPO-1, LPO-3, or a polypeptide listed in Table IX, X, XI, XII, XIII, or XIV. For example, immunoassays may be used to detect or monitor the expression of at least one of the polypeptides of the invention in an organism. Polyclonal or monoclonal antibodies (produced as described above) which are capable of binding to such a polypeptide may be used in any standard immunoassay format (e.g., ELISA, Western blot, or RIA assay) to measure the level of the polypeptide. A compound which promotes an increase in the expression of the polypeptide is considered particularly useful. Again, such a molecule may be used, for example, as a therapeutic to delay or ameliorate human diseases associated with excess body weight or obesity as is described above.

In yet another working example, candidate compounds may be screened for those which specifically bind to and agonize or antagonize LPO-1, LPO-3, or a polypeptide listed in Table V, VI, VII, IX, X, XI, XII, XIII, or XIV. The efficacy of such a candidate compound is dependent upon its ability to interact with LPO-1, LPO-3, or a polypeptide listed in Table V, VI, VII, IX, X, XI, XII, XIII, or XIV or a functional equivalent thereof. Such an interaction can be readily assayed using any number of standard binding techniques and functional assays (e.g., those described in Ausubel et al., supra). For example, a candidate compound may be tested in vitro for interaction and binding with a polypeptide of the invention and its ability to modulate body fat metabolism may be assayed by any standard assay (e.g., those described herein).

In one particular working example, a candidate compound that binds to a polypeptide (e.g, LPO-1, LPO-3, or a polypeptide listed in Table V, VI, VII, IX, X, XI, XII, XIII, or XIV) may be identified using a chromatography-based technique. For example, a recombinant polypeptide of the invention may be purified by standard techniques from cells engineered to express the polypeptide (e.g., those described above) and may be immobilized on a column. A solution of candidate compounds is then passed through the column, and a compound specific for the fat metabolism regulator polypeptide is identified on the basis of its ability to bind to the fat metabolism regulator polypeptide and be immobilized on the column. To isolate the compound, the column is washed to remove non-specifically bound molecules, and the compound of interest is then released from the column and collected. Compounds isolated by this method (or any other appropriate method) may, if desired, be further purified (e.g., by high performance liquid chromatography). In addition, these candidate compounds may be tested for their ability to affect fat metabolism (e.g., as described herein). Compounds isolated by this approach may also be used, for example, as therapeutics to delay or ameliorate human diseases associated with excess body weight or obesity. Compounds which are identified as binding to fat metabolism regulator polypeptides with an affinity constant less than or equal to 10 mM are considered particularly useful in the invention.

Potential agonists and antagonists include organic molecules, peptides, peptide mimetics, polypeptides, nucleic acids, and antibodies that bind to a nucleic acid sequence or polypeptide of the invention (e.g, fat metabolism regulator polypeptides) and thereby increase its activity. Potential agonists also include small molecules that bind to and occupy the binding site of the polypeptide thereby preventing binding to cellular binding molecules, such that normal biological activity is prevented.

Each of the DNA sequences provided herein may also be used in the discovery and development of fat metabolism regulator compounds. The encoded protein, upon expression, can be used as a target for the screening of fat metabolism regulating drugs. Additionally, the DNA sequences encoding the amino terminal regions of the encoded protein or Shine-Delgamo or other translation facilitating sequences of the respective mRNA can be used to construct antisense sequences to control the expression of the coding sequence of interest. Such sequences may be isolated by standard techniques (Ausubel et al., supra).

The antagonists and agonists of the invention may be employed, for instance, to delay or ameliorate human diseases associated with obesity, an obesity-related disease, or a fat metabolism disorder.

Optionally, compounds identified in any of the above-described assays may be confirmed as useful in delaying or ameliorating human diseases associated with excess body weight or obesity, an obesity-related disease, or a fat metabolism disorder in either standard tissue culture methods (e.g. Nile Red staining of fat storage in cultured cells) or animal models (e.g., naturally occurring rodent mutants such as, for example, Ob (leptin), db (leptin receptor), fat-1 (carboxypeptidase E), 5-HTR (serotonin receptor) and tubby and, if successful, may be used as therapeutics for the treatment of obesity or disorders related to fat metabolism.

Small molecules of the invention preferably have a molecular weight below 2,000 daltons, more preferably between 300 and 1,000 daltons, and most preferably between 400 and 700 daltons. It is preferred that these small molecules are organic molecules.

Test Compounds and Extracts

In general, compounds capable of delaying or ameliorating human diseases associated with obesity, an obesity-related disease, or a fat metabolism disorder are identified from large libraries of both natural product or synthetic (or semi-synthetic) extracts or chemical libraries according to methods known in the art. Those skilled in the field of drug discovery and development will understand that the precise source of test extracts or compounds is not critical to the screening procedure(s) of the invention. Compounds used in screens may include known compounds (for example, known therapeutics used for other diseases or disorders). Alternatively, virtually any number of unknown chemical extracts or compounds can be screened using the methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods. Furthermore, if desired, any library or compound is readily modified using standard chemical, physical, or biochemical methods.

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their fat metabolism regulating activity should be employed whenever possible.

When a crude extract is found to have a fat metabolism regulating activity, or a binding activity, further fractionation of the positive lead extract is necessary to isolate chemical constituents responsible for the observed effect. Thus, the goal of the extraction, fractionation, and purification process is the careful characterization and identification of a chemical entity within the crude extract having fat metabolism regulating activity. Methods of fractionation and purification of such heterogenous extracts are known in the art. If desired, compounds shown to be useful agents to delay or ameliorate human diseases associated with obesity, an obesity-related disease, or a fat metabolism disorder are chemically modified according to methods known in the art.

RNA Interference

RNAi is a form of post-transcriptional gene silencing initiated by the introduction of double-stranded RNA (dsRNA). Elbashir et al. reported that twenty-one-nucleotide RNA duplexes introduced into cultured mammalian cells could elicit gene-specific silencing (*Nature* 411:494–498, 2001). Based on these results, one would predict that a double stranded RNA corresponding to one of the fat metabolism regulator genes described herein (e.g., those that encode a polypeptide listed in Table XII, XIII, or XIV) could be used to specifically silence fat metabolism regulator gene expression. To this end, the nucleic acids described herein are contemplated to be employed as double-stranded RNA molecules.

Pharmaceutical Therapeutics

The invention provides a simple means for identifying compounds (including peptides, small molecule inhibitors, and mimetics) capable of delaying or ameliorating human diseases associated with obesity, an obesity-related disease, or a fat metabolism disorder. Accordingly, a chemical entity discovered to have medicinal value using the methods described herein is useful as a drug or as information for structural modification of existing fat metabolism regulating compounds, e.g., by rational drug design. Such methods are useful for screening compounds having an effect on a variety of conditions involving the dysregulation of body weight, fat metabolism, energy metabolism, obesity, including, but not limited to, atherosclerosis, type II diabetes mellitus, osteoarthritis of body joints, diseases of cholesterol and lipid homeostasis (e.g., Tangier disease, familial HDL deficiency, progressive familial intrahepatic cholestasis type 2 and type 3, adrenoleukodystrophy, and sitosterolaemia).

For therapeutic uses, the compositions or agents identified using the methods disclosed herein may be administered systemically, for example, formulated in a pharmaceutically-acceptable buffer such as physiological saline. Treatment may be accomplished directly, e.g., by treating the animal with antagonists which disrupt, suppress, attenuate, or neutralize the biological events associated with a fat metabolism regulator polypeptide. Preferable routes of administration include, for example, subcutaneous, intravenous, interperitoneally, intramuscular, or intradermal injections that provide continuous, sustained levels of the drug in the patient. Treatment of human patients or other animals will be carried out using a therapeutically effective amount of a fat metabolism regulator agent in a physiologically-acceptable carrier. Suitable carriers and their formulation are described, for example, in Remington's Pharmaceutical Sciences by E. W. Martin. The amount of the fat metabolism regulator agent to be administered varies depending upon the manner of administration, the age and body weight of the patient, and with the type of disease and extensiveness of the disease. Generally, amounts will be in the range of those used for other agents used in the treatment of other diseases associated with fat metabolism or obesity, although in certain instances lower amounts will be needed because of the increased specificity of the compound. A compound is administered at a dosage that inhibits obesity, an obesity-related disease, or a fat metabolism disorder Use of Transgenic and Knockout Animals in Diagnosis or Drug Screening The present invention also includes transgenic and knockout animals that may be used as research tools to determine genetic and physiological features of obesity, an obesity-related disease, or a fat metabolism disorder, and for identifying compounds that can affect such diseases or disorders. Such animals may include, for example, transgenic or knockout nematodes or rodents. Knockout animals include, for example, mutant animals that are either homozygous or heterozygous, for a deletion in a fat metabolism regulator gene (e.g., a gene listed in Tables V—XIV). Knockout animals also include animals where this normal gene has been inactivated or removed and replaced with a known polymorphic or other mutant allele of this gene. These animals can serve as a model system for the risk of acquiring a disease that is associated with a particular allele. In general, the method of identifying a fat metabolism regulator gene involves comparing the presence, absence, or level of expression of genes, either at the RNA level or at the protein level, in tissue from a transgenic or knock-out animal and in tissue from a matching non-transgenic or knock-out animal. Standard techniques for detecting RNA expression, e.g., by Northern blotting, or protein expression, e.g., by Western blotting, are well known in the art. Differences between animals such as the presence, absence, or level of expression of a gene indicate that the expression of the gene is a marker associated with a disorder. Identification of such markers are useful since they are candidate therapeutic targets. Identification of markers can take several forms.

One method by which molecular markers may be identified is by use of directed screens. Patterns of accumulation of a variety of molecules can be surveyed using immunohistochemical methods. Screens directed at analyzing expression of specific genes or groups of molecules implicated in obesity, an obesity-related disease, or a fat metabolism disorder can be continued during the life of the transgenic or knockout animal. Expression can be monitored by immunohistochemistry as well as by protein and RNA blotting techniques.

Alternatively, molecular markers may be identified using genomic screens. For example, tissue can be recovered from young transgenic or knockout animals and older transgenic or knockout animals, and compared with similar material recovered from age-matched normal littermate controls to catalog genes that are induced or repressed as obesity, an obesity-related disease, or a fat metabolism disorder is initiated, and as obesity, an obesity-related disease, or a fat metabolism disorder progresses to its final stages. These surveys will generally include cellular populations present in the affected tissue.

This analysis can also be extended to include an assessment of the effects of various treatments on differential gene expression (DGE). The information derived from the surveys of DGE can ultimately be correlated with obesity, an obesity-related disease, or a fat metabolism disorder initiation and progression in the transgenic or knockout animals.

To assess the effectiveness of a treatment paradigm, a transgene, such as a mutant of any of the nucleic acid sequences described herein, may be conditionally expressed (e.g., in a tetracycline sensitive manner). For example, the promoter for this gene may contain a sequence that is regulated by tetracycline and expression of the gene product ceases when tetracycline is administered to the mouse. In this example, a tetracycline-binding operator, tetO, is regulated by the addition of tetracycline, or an analog thereof, to the organism's water or diet. The tetO may be operably-linked to a coding region, for example, a wild-type or mutant nucleic acid sequence described herein. The system also may include a tetracycline transactivator (tTA), which contains a DNA binding domain that is capable of binding the tetO as well as a polypeptide capable of repressing transcription from the tetO (e.g., the tetracycline repressor (tetR)), and may be further coupled to a transcriptional activation domain (e.g., VP16). When the tTA binds to the tetO sequences, in the absence of tetracycline, transcription of the target gene is activated. However, binding of tetracycline to the tTA prevents activation. Thus, a gene operably-linked to a tetO is expressed in the absence of tetracycline and is repressed in its presence. Alternatively, this system could be modified such that a gene is expressed in the presence of tetracycline and repressed in its absence. Tetracycline regulatable systems are well known to those skilled in the art and are described in, for example, WO 94/29442, WO 96/40892, WO 96/01313, and Yamamoto et al. (*Cell* 101:57–66,2000).

In addition, the knockout organism may be a conditional, i.e., somatic, knockout. For example, FRT sequences may be introduced into the organism so that they flank the gene of interest. Transient or continuous expression of the FLP protein may then be used to induce site-directed recombination, resulting in the excision of the gene of interest. The use of the FLP/FRT system is well established in the art and is described in, for example, U.S. Pat. No. 5,527,695, and in Lyznik et al. (*Nucleic Acid Research* 24:3784–3789, 1996).

Conditional, i.e., somatic knockout organisms may also be produced using the Cre-lox recombination system. Cre is an enzyme that excises DNA between two recognition sites termed loxP. The cre transgene may be under the control of an inducible, developmentally regulated, tissue specific, or cell-type specific promoter. In the presence of Cre, the gene, for example a nucleic acid sequence described herein, flanked by loxP sites is excised, generating a knockout. This system is described, for example, in Kilby et al. (*Trends in Genetics* 9:413–421, 1993).

Particularly desirable is a mouse model wherein an altered nucleic acid sequence described herein is expressed in specific cells of the transgenic mouse such that the transgenic mouse develops obesity, an obesity-related disease, or fat metabolism disorder. In addition, cell lines from these mice may be established by methods standard in the art.

Construction of transgenes can be accomplished using any suitable genetic engineering technique, such as those described in Ausubel et al. (Current Protocols in Molecular Biology, John Wiley & Sons, New York, 2000). Many techniques of transgene construction and of expression constructs for transfection or transformation in general are known and may be used for the disclosed constructs.

One skilled in the art will appreciate that a promoter is chosen that directs expression of the chosen gene in the tissue in which a disease or disorder is expected to develop. For example, as noted above, any promoter that regulates expression of a nucleic acid sequence described herein can be used in the expression constructs of the present invention. One skilled in the art would be aware that the modular nature of transcriptional regulatory elements and the absence of position-dependence of the function of some regulatory elements, such as enhancers, make modifications such as, for example, rearrangements, deletions of some elements or extraneous sequences, and insertion of heterologous elements possible. Numerous techniques are available for dissecting the regulatory elements of genes to determine their location and function. Such information can be used to direct modification of the elements, if desired. It is desirable, however, that an intact region of the transcriptional regulatory elements of a gene is used. Once a suitable transgene construct has been made, any suitable technique for introducing this construct into embryonic cells can be used.

Animals suitable for transgenic experiments can be obtained from standard commercial sources such as Taconic (Germantown, N.Y.). Many strains are suitable, but Swiss Webster (Taconic) female mice are desirable for embryo retrieval and transfer. B6D2F (Taconic) males can be used for mating and vasectomized Swiss Webster studs can be used to stimulate pseudopregnancy. Vasectomized mice and rats are publicly available from the above-mentioned suppliers. However, one skilled in the art would also know how to make a transgenic mouse or rat. An example of a protocol that can be used to produce a transgenic animal is provided below.

Production Of Transgenic Mice And Rats

The following is but one desirable means of producing transgenic mice. This general protocol may be modified by those skilled in the art.

Female mice six weeks of age are induced to superovulate with a 5 IU injection (0.1 cc, IP) of pregnant mare serum gonadotropin (PMSG; Sigma) followed 48 hours later by a 5 IU injection (0.1 cc, IP) of human chorionic gonadotropin (hCG, Sigma). Females are placed together with males immediately after hCG injection. Twenty-one hours after hCG injection, the mated females are sacrificed by $CO_2$ asphyxiation or cervical dislocation and embryos are recovered from excised oviducts and placed in Dulbecco's phosphate buffered saline with 0.5% bovine serum albumin (BSA, Sigma). Surrounding cumulus cells are removed with hyaluronidase (1 mg/ml). Pronuclear embryos are then washed and placed in Earle's balanced salt solution containing 0.5% BSA (EBSS) in a 37.5° C. incubator with humidified atmosphere at 5% $CO_2$, 95% air until the time of injection. Embryos can be implanted at the two-cell stage.

Randomly cycling adult female mice are paired with vasectomized males. Swiss Webster or other comparable strains can be used for this purpose. Recipient females are mated at the same time as donor females. At the time of embryo transfer, the recipient females are anesthetized with an intraperitoneal injection of 0.015 ml of 2.5% avertin per gram of body weight. The oviducts are exposed by a single midline dorsal incision. An incision is then made through the body wall directly over the oviduct. The ovarian bursa is then torn with watchmakers forceps. Embryos to be transferred are placed in DPBS (Dulbecco's phosphate buffered saline) and in the tip of a transfer pipet (about 10 to 12 embryos). The pipet tip is inserted into the infundibulum and the embryos are transferred. After the transferring the embryos, the incision is closed by two sutures.

A desirable procedure for generating transgenic rats is similar to that described above for mice (Hammer et al., *Cell* 63:1099–112, 1990). For example, thirty-day old female rats are given a subcutaneous injection of 20 IU of PMSG (0.1 cc) and 48 hours later each female placed with a proven, fertile male. At the same time, 40–80 day old females are placed in cages with vasectomized males. These will provide the foster mothers for embryo transfer. The next morning females are checked for vaginal plugs. Females who have mated with vasectomized males are held aside until the time of transfer. Donor females that have mated are sacrificed ($CO_2$ asphyxiation) and their oviducts removed, placed in DPBA (Dulbecco's phosphate buffered saline) with 0.5% BSA and the embryos collected. Cumulus cells surrounding the embryos are removed with hyaluronidase (1 mg/ml). The embryos are then washed and placed in EBSs (Earle's balanced salt solution) containing 0.5% BSA in a 37.5° C. incubator until the time of microinjection.

Once the embryos are injected, the live embryos are moved to DPBS for transfer into foster mothers. The foster mothers are anesthetized with ketamine (40 mg/kg, IP) and xulazine (5 mg/kg, IP). A dorsal midline incision is made through the skin and the ovary and oviduct are exposed by an incision through the muscle layer directly over the ovary. The ovarian bursa is torn, the embryos are picked up into the transfer pipet, and the tip of the transfer pipet is inserted into the infundibulum. Approximately 10 to 12 embryos are transferred into each rat oviduct through the infundibulum. The incision is then closed with sutures, and the foster mothers are housed singly.

Generation Of Knockout Mice

The following is but one example for the generation of a knockout mouse and the protocol may be readily adapted or modified by those skilled in the art.

Embryonic stem cells (ES), for example, $10^7$ AB1 cells, may be electroporated with 25 μg targeting construct in 0.9 ml PBS using a Bio-Rad Gene Pulser (500 μF, 230 V). The cells may then be plated on one or two 10-cm plates containing a monolayer of irradiated STO feeder cells. Twenty-four hours later, they may be subjected to G418 selection (350 μg/ml, Gibco) for 9 days. Resistant clones may then be analyzed by Southern blotting after Hind III digestion, using a probe specific to the targeting construct. Positive clones are expanded and injected into C57BL/6 blastocysts. Male chimeras may be back-crossed to C57BL/6 females. Heterozygotes may be identified by Southern blotting and intercrossed to generate homozygotes.

The targeting construct may result in the disruption of the gene of interest, e.g., by insertion of a heterologous sequence containing stop codons, or the construct may be used to replace the wild-type gene with a mutant form of the same gene, e.g. a "knock-in." Furthermore, the targeting construct may contain a sequence that allows for conditional expression of the gene of interest. For example, a sequence may be inserted into the gene of interest that results in the protein not being expressed in the presence of tetracycline. Such conditional expression of a gene is described in, for example, Yamamoto et al. (*Cell* 101:57–66, 2000)).

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

What is claimed is:

1. A method of identifying a candidate compound that modulates fat metabolism, said method comprising a) contacting a mammalian cell or a nematode cell with a candidate compound;

b) obtaining mRNA from said mammalian cell or said nematode cell;

c) contacting a microarray with said mRNA, wherein said microarray consists of at least two mammalian or nematode fat metabolism regulator nucleic acids or fragment thereof, wherein said fragment encodes at least 50 contiguous amino acids of a fat metabolism polypeptide, and wherein inactivation of each of said mammalian or nematode fat metabolism regulator nucleic acids results in an alteration in fat content of an organism compared to a control organism; and d) detecting an alteration in cellular mRNA levels of at least two fat metabolism regulator nucleic acid molecules in said mammalian cell or said nematode cell contacted with said candidate compound compared to a control cell, wherein said alteration identifies the candidate compound as a candidate compound that modulates fat metabolism.

2. The microarray of claim 1, wherein said mammalian cell is contacted with said candidate compound and said microarray consists of at least two mammalian fat metabolism regulator nucleic acids.

3. The microarray of claim 1, wherein said nematode cell is contacted with said candidate compound and said microarray consists of at least two nematode fat metabolism regulator nucleic acids.

* * * * *

UNITED STATES PATENT AND TRADEMARK OFFICE

CERTIFICATE OF CORRECTION

PATENT NO. : 7,175,999 B2
APPLICATION NO. : 10/617351
DATED : February 13, 2007
INVENTOR(S) : Gary Ruvkun and Kaveh Ashrafi It is certified that error appears in the above-identified patent and that said Letters Patent is hereby corrected as shown below:

Column 180, line 55, in claim 2, replace “microarray of claim 1” with --method of claim 1--; and Column 180, line 59, in claim 3, replace “microarray of claim 1” with --method of claim 1--.

Signed and Sealed this

Fourteenth Day of October, 2008

JON W. DUDAS
*Director of the United States Patent and Trademark Office*